(12) United States Patent
Petkoska et al.

(10) Patent No.: US 11,576,853 B2
(45) Date of Patent: Feb. 14, 2023

(54) ANTIOXIDANT COMPOSITIONS AND METHODS OF PROTECTING SKIN, HAIR AND NAILS AGAINST HIGH ENERGY BLUE-VIOLET LIGHT

(71) Applicants: Anka T Petkoska, Skopje (MK); Anita T Broach, Christiansburg, VA (US)

(72) Inventors: Anka T Petkoska, Skopje (MK); Anita T Broach, Christiansburg, VA (US)

(73) Assignee: CSI: Create.Solve. Innovate. LLC, Christiansburg, VA (US)

(*) Notice: Subject to any disclaimer, the term of this patent is extended or adjusted under 35 U.S.C. 154(b) by 0 days.

(21) Appl. No.: 15/141,542

(22) Filed: Apr. 28, 2016

(65) Prior Publication Data

US 2016/0346191 A1 Dec. 1, 2016

Related U.S. Application Data

(60) Provisional application No. 62/154,228, filed on Apr. 29, 2015.

(51) Int. Cl.
| | |
|---|---|
| *A61K 8/92* | (2006.01) |
| *A61K 8/9789* | (2017.01) |
| *A61K 8/9794* | (2017.01) |
| *A61Q 17/04* | (2006.01) |

(52) U.S. Cl.
CPC .............. *A61K 8/922* (2013.01); *A61K 8/927* (2013.01); *A61K 8/9789* (2017.08); *A61K 8/9794* (2017.08); *A61Q 17/04* (2013.01); *A61K 2800/592* (2013.01); *A61K 2800/5922* (2013.01)

(58) Field of Classification Search
CPC . A61K 8/922; A61K 2800/5922; A61Q 17/04
See application file for complete search history.

(56) References Cited

U.S. PATENT DOCUMENTS

| | | | |
|---|---|---|---|
| 4,393,043 A | 7/1983 | Koulbanis |
| 4,737,360 A | 4/1988 | Allen |
| 6,280,751 B1 | 8/2001 | Fletcher |
| 7,060,306 B2 | 6/2006 | Springstead |
| 7,763,289 B2 | 7/2010 | Bommarito |
| 7,883,726 B2 | 2/2011 | Crutchfield |
| 7,897,194 B2 | 3/2011 | Leonard |
| 7,943,182 B2 | 5/2011 | Heeg |
| 8,501,248 B1 | 8/2013 | Sugerman |
| 8,986,748 B2 | 3/2015 | Ge |

(Continued)

FOREIGN PATENT DOCUMENTS

| | | |
|---|---|---|
| EP | 0953337 | 11/1999 |
| WO | 2008015575 | 2/2008 |

(Continued)

OTHER PUBLICATIONS

IPRP for PCT/US16/29845 dated Sep. 15, 2016.

*Primary Examiner* — Bethany P Barham
*Assistant Examiner* — Barbara S Frazier
(74) *Attorney, Agent, or Firm* — Rhodes IP PLC; Christopher Rhodes

(57) ABSTRACT

Compositions and methods of using them for protecting skin, hair and nails against exposure to high energy visible light are described. The compositions can include one or more natural oils or extracts which are effective to absorb the high energy visible light at least to some degree.

16 Claims, 93 Drawing Sheets

(56) References Cited

U.S. PATENT DOCUMENTS

| | | |
|---|---|---|
| 8,986,755 B1 | 3/2015 | Raymond-Coblantz |
| 9,101,657 B2 | 8/2015 | Minami |
| 9,289,374 B2 | 3/2016 | Chevreau |
| 2002/0106337 A1 | 8/2002 | Deckers |
| 2003/0091518 A1* | 5/2003 | Pauly .................. A61K 8/97 424/59 |
| 2004/0101507 A1 | 5/2004 | Predovan |
| 2004/0258783 A1* | 12/2004 | Millou .................. A61K 8/11 424/778 |
| 2005/0084470 A1 | 4/2005 | Abbas |
| 2007/0224229 A1 | 9/2007 | Gibbons |
| 2007/0281044 A1 | 12/2007 | Mueller |
| 2008/0014153 A1 | 1/2008 | Schwarz |
| 2008/0118450 A1 | 5/2008 | Bibb |
| 2008/0286390 A1 | 11/2008 | Tanyani |
| 2009/0035228 A1 | 2/2009 | Modak |
| 2009/0123578 A1 | 5/2009 | Crutchfield |
| 2009/0130220 A1 | 5/2009 | Johnson |
| 2009/0189090 A1 | 7/2009 | Meyer |
| 2009/0208431 A1 | 8/2009 | Bommarito |
| 2009/0304603 A1 | 12/2009 | Crutchfield |
| 2009/0317502 A1 | 12/2009 | Crutchfield |
| 2009/0324705 A1 | 12/2009 | Vikhrieva |
| 2010/0111884 A1 | 5/2010 | Acker |
| 2010/0166687 A1 | 7/2010 | Golz-Berner |
| 2010/0166891 A1 | 7/2010 | Schmidt |
| 2011/0008474 A1 | 1/2011 | Boegli |
| 2012/0308586 A1 | 12/2012 | Garcia Villarrubia |
| 2013/0078205 A1 | 3/2013 | Dayan |
| 2013/0095196 A1 | 4/2013 | Raymond-Coblantz |
| 2013/0309183 A1 | 11/2013 | Vuong |
| 2014/0056829 A1* | 2/2014 | Pather .................. A61K 31/12 424/59 |
| 2014/0179747 A1 | 6/2014 | Lewis |
| 2014/0193480 A1 | 7/2014 | McWherter |
| 2014/0243426 A1 | 8/2014 | Gurge |
| 2014/0315995 A1 | 10/2014 | Dreher |
| 2015/0086498 A1 | 3/2015 | Lerebour |
| 2015/0216791 A1 | 8/2015 | Lerebour |
| 2015/0374614 A1 | 12/2015 | Pegeon |
| 2016/0000685 A1 | 1/2016 | Saquet-Gouville |
| 2016/0033538 A1 | 2/2016 | Meyer |
| 2016/0106654 A1 | 4/2016 | Lewis |
| 2016/0129063 A1 | 5/2016 | Malkmus |
| 2016/0206549 A1 | 7/2016 | Lewis |
| 2016/0296438 A1 | 10/2016 | Modepalli |

FOREIGN PATENT DOCUMENTS

| | | |
|---|---|---|
| WO | 2011092368 | 8/2011 |
| WO | 2011112414 | 9/2011 |
| WO | 2013149323 | 10/2013 |
| WO | 2014095049 | 6/2014 |
| WO | 2016070194 | 5/2016 |
| WO | 2016164744 | 10/2016 |

\* cited by examiner

| Active ingredient | UV <400nm | HEV 400-440nm | HEV 440-500nm |
|---|---|---|---|
| feverfew oil | xxx | x | |
| castor oil | xx | x | |
| yellow marigold oil | xxx | x | |
| Helichrysum oil | xxx | | |
| cinnamon bark oil | xxx | | |
| ginger oil | xxx | x | |
| pomegranate oil | xx | xx | x |
| rosemary oil | x | | |
| soybean oil | xx | | |
| sea buckthorn oil | x | xxx | xxx |
| evening primrose oil | xxx | xx | x |
| red raspberry oil | xxx | xx | x |
| acai berry oil | xx | xx | |
| turmeric oil | xxx | xx | |
| sesame oil | xxx | xx | x |
| avocado oil | xxx | x | |
| tea tree oil | xx | x | |
| meadowfoam oil | xx | x | |
| hemp seed oil | xx | xxx | xx |
| rosehip oil | xx | xxx | xxx |
| marula oil | xxx | xx | x |
| flax seed oil | x | xxx | xxx |
| cumin oil | xxx | xxx | xx |
| pumpkin seed oil | xx | xxx | x |
| extra virgin olive oil (EVOO) | xx | xxx | xxx |
| wheat germ oil | xx | xxx | xxx |
| carrot seed oil | xx | xxx | x |
| aloe vera oil | xx | x | |
| sunflower oil | xxx | xx | xx |
| jojoba oil | xxx | xxx | x |
| apricot seed oil | xx | xx | xx |
| Egyptian germanium oil | xxx | x | |
| eucaliptus oil | x | | |
| argan oil | xx | xx | xx |
| coconut oil | xx | x | |
| brocolli oil | x | xxx | xxx |
| clove oil | xxx | | |
| cranberry oil | xx | xxx | xxx |
| Frankincense oil | xx | | |
| grapeseed oil | xxx | xx | |
| hazelnut oil | xx | x | |
| ricebran oil | xxx | xx | x |
| black rasberry oil | xxx | xxx | xx |
| grapefruit seed oil | xxx | xx | |
| chia seed oil | xxx | xx | x |
| chaga extract / oil | xxx | xx | x |
| oregano oil | xxx | xx | x |
| St John's worth/olive oil | xxx | xx | x |
| shea butter | xx | xxx | xx |
| bee wax | xxx | xx | |

FIG. 3

| Group A | UV <400nm | HEV 400-440nm | HEV 440-500nm |
|---|---|---|---|
| hemp seed oil | xx | xxx | xx |
| rosehip oil | xx | xxx | xxx |
| flax seed oil | x | xxx | xxx |
| cumin oil | xxx | xxx | xx |
| pumpkin seed oil | xx | xxx | x |
| extra virgin olive oil (EVOO) | xx | xxx | xxx |
| wheat germ oil | xx | xxx | xxx |
| carrot seed oil | xx | xxx | x |
| black raspberry oil | xxx | xxx | xx |
| sea buckthorn oil | x | xxx | xxx |
| red raspberry oil | xxx | xx | x |
| broccoli seed oil | x | xxx | xxx |
| cranberry oil | xx | xxx | xxx |
| jojoba oil | xxx | xxx | x |
| sunflower oil | xxx | xx | xx |
| sesame oil | xxx | xx | x |

FIG. 4

| Group B | UV <400nm | HEV 400-440nm | HEV 440-500nm |
|---|---|---|---|
| Helichrysum oil | xxx | | |
| cinnamon bark oil | xxx | | |
| ginger oil | xxx | | |
| turmeric oil | xxx | x | |
| grapeseed oil | xxx | xx | |
| clove oil | xxx | xx | |
| feverfew oil | xxx | x | |
| yellow marigold oil | xxx | x | |
| grapefruit seed oil | xxx | xx | |

FIG. 6Y

| Type I (strong HEV + good UVA) | 420nm/380nm > 0.8 | 460nm/380nm > 0.3 | 500nm/380nm |
| --- | --- | --- | --- |
| extra virgin olive oil (EVOO) | 1.45 | 1.02 | 0.52 |
| seabuckthorn berry oil | 2.26 | 3.08 | 1.26 |
| seabuckthorn seed oil | 2.38 | 3.70 | 2.13 |
| hemp seed oil | 1.49 | 0.79 | 0.26 |
| flax seed oil | 1.19 | 1.27 | 0.45 |
| wheat germ oil | 1.38 | 1.82 | 0.90 |
| broccoli seed oil | 1.63 | 1.89 | 0.70 |
| cranberry oil | 1.50 | 1.22 | 0.47 |
| cumin (black seed) oil | 0.83 | 0.48 | 0.15 |
| rosehip oil | 0.99 | 1.28 | 0.87 |
| pomegranate oil | 0.76 | 0.64 | 0.28 |
| black raspberry oil | 0.83 | 0.65 | 0.30 |
| carrot seed oil | 0.97 | 0.35 | 0.16 |
| apricot kernel oil | 0.94 | 1.12 | 0.56 |
| argan oil | 0.76 | 0.76 | 0.31 |
| pumpkin seed oil | 1.61 | 0.31 | 0.05 |
| jojoba oil | 0.92 | 0.33 | 0.05 |

FIG. 9

| Type II (good HEV+good UVA protection) | 420nm/380nm = 0.3 - 0.8 | 460nm/380nm = 0.1 - 0.3 | 500nm/380nm |
|---|---|---|---|
| red raspberry oil | 0.63 | 0.38 | 0.17 |
| sunflower oil | 0.70 | 0.75 | 0.38 |
| sesame oil | 0.53 | 0.27 | 0.13 |
| aloe vera oil | 0.39 | 0.17 | 0.05 |
| avocado oil | 0.33 | 0.12 | 0.02 |
| chia seed oil | 0.56 | 0.48 | 0.14 |
| evening primrose oil | 0.56 | 0.31 | 0.12 |
| grapeseed oil | 0.46 | 0.15 | 0.05 |
| ricebran oil | 0.37 | 0.16 | 0.04 |
| hazelnut oil | 0.37 | 0.18 | 0.05 |
| avocado oil | 0.33 | 0.12 | 0.02 |
| marula oil | 0.60 | 0.32 | 0.12 |
| meadowfoam oil | 0.43 | 0.17 | 0.05 |
| coconut oil | 0.38 | 0.18 | 0.06 |
| chaga extract | 0.55 | 0.25 | 0.10 |
| chaga oil | 0.50 | 0.15 | 0.04 |
| oregano extract | 0.29 | 0.16 | 0.04 |
| oreganol | 0.72 | 0.38 | 0.16 |
| soyabean oil | 0.43 | 0.21 | 0.08 |
| castor oil | 0.44 | 0.20 | 0.09 |

FIG. 10

| Type III (strong UVA protection) | 420nm/380nm | 460nm/380nm | 500nm/380nm |
|---|---|---|---|
| Helicrysum oil | 0.10 | 0.01 | 0.00 |
| ginger oil | 0.14 | 0.06 | 0.01 |
| cinamon bark oil | 0.04 | 0.01 | 0.00 |
| turmeric oil | 0.20 | 0.05 | 0.01 |
| clove oil | 0.07 | 0.03 | 0.01 |
| grapefruit seed oil | 0.34 | 0.11 | 0.03 |
| Frankincense oil | 0.23 | 0.12 | 0.00 |
| yellow marigold oil | 0.26 | 0.08 | 0.03 |
| Egyptian germanium | 0.24 | 0.07 | 0.02 |
| tea tree oil | 0.28 | 0.10 | 0.03 |
| eucaliptus oil | 0.20 | 0.08 | 0.02 |

FIG. 11

| Group FA-1 | n-6/n-3 <10 | Group FA-2 | n-6/n-3 = 10-150 | Group FA-3 | n-6/n-3 > 150 |
|---|---|---|---|---|---|
| EVOO | 7.05 | argan oil | 98.90 | walnut oil | 1208 |
| chia seed oil | 0.31 | pumpkin seed oil | 127.00 | almond oil | 171 |
| flax seed oil | 0.27 | sesame oil | 81.90 | grapeseed oil | 210 |
| cranberry oil | 1.38 | cumin oil | 146.25 | | |
| soybean oil | 6.72 | sunflower oil | 135.00 | | |
| turmeric oil | 2.30 | carrot seed oil | 24.50 | | |
| rosehip oil | 1.38 | avocado oil | 20.10 | | |
| blueberry oil | 1.70 | apricot kernel oil | 29.30 | | |
| red raspberry oil | 1.61 | tomato seed oil | 25.90 | | |
| black raspberry oil | 1.71 | milk thistle seed oil | 74.72 | | |
| broccoli oil | 1.93 | wheat germ oil | 11.30 | | |
| hemp seed oil | 3.41 | borage oil | 100 | | |
| seabuckthorn seed oil | 1.06 | | | | |
| seabuckthorn berry oil | 2.34 | | | | |
| rapeseed oil | 1.80 | | | | |
| black currant oil | 4.10 | | | | |
| evening primrose oil | 6.90 | | | | |

FIG. 12

| Active ingredient | ΣSFA | ΣMUFA n-9 | ΣPUFA | ΣPUFA n-3 | ΣPUFA n-6 | ΣSFA/ΣPUFA | n-6/n-3 |
|---|---|---|---|---|---|---|---|
| red raspberry seed oil | 3.4 | 11.4 | 71.3 | 22-29 | 52-55 | 0.048 | 2.1 |
| black raspberry seed oil | 1.4 | | 87.5 | 29.5 | 50.5 | 0.016 | 1.71 |
| clove oil | 18 | 39.7 | 42.1 | | | 0.428 | |
| blackberry seed oil | 6.4 | 18 | 78.6 | | | 0.081 | |
| carrot seed oil | 3.9 | 68.4 | | | | | |
| chia seed oil | 11.5 | 8.36 | 79.83 | 60.9 | 10.8 | 0.144 | 54 |
| EVOO | 17.5/ | 76.3 | 6.28 | 0.78 | 18.7 | | 0.31 |
| cranberry seed oil | 7 | 22.5 | 65 | 29 | 5.5 | 0.108 | 7.05 |
| flax seed oil | 9.2 | 20.6 | 70.2 | 55.2 | 40 | 0.131 | 1.38 |
| omegranate seed oil | 6.45 | 5.1 | 68.34 | | 15 | 0.094 | 0.27 |
| argan oil | 19.2 | 45.8 | 35 | 0.35 | 34.6 | 0.549 | 98.9 |
| avocado oil | 19.2 | 65.3 | 15.5 | 0.73 | 14.7 | 1.239 | 20.1 |
| rosehip oil | 6.9 | 15.3 | 70.2 | 32.5 | 44.7 | | 1.38 |
| turmeric oil | 22.5 | 56 | 26.5 | 5 | 11.5 | 0.849 | 2.3 |
| cumin (black seed) | 18.1 | 23.8 | 58.1 | 0.4 | 58.5 | 0.312 | 146.25 |
| brocolli seed oil | 3.25 | 52.25 | | 9 | 17.4 | | |
| hemp seed oil | 10 | 12.5 | 76 | 17 | 58 | 0.132 | 3.41 |
| apricot oil | 7.1 | 70.4 | 21.2 | 0.7 | 20.5 | 0.335 | 29.3 |
| seabuck seed | 15.89 | 18.58 | 65.53 | | | 0.242 | 1.06 |
| seabuck pulp | 40.56 | 53.96 | 5.47 | | | 7.415 | 5.05 |
| seabuck berry | 37.87 | 53.22 | 8.91 | | | 4.250 | 2.34 |
| milk thistle oil | 19.53 | 22.92 | 57.55 | 0.76 | 56.79 | 0.339 | 74.72 |
| pumpkin seed oil | 20.2 | 24.7 | 55.1 | 0.43 | 54.7 | 0.367 | 127 |
| soybean oil | 13.5 | 24.5 | 62 | 8.03 | 54 | 0.218 | 6.72 |
| grapeseed oil | 12.7 | 17.7 | 69.6 | 0.33 | 69.3 | 0.182 | 210 |
| sesame oil | 16.4 | 41.4 | 42.3 | 0.51 | 41.8 | 0.388 | 81.9 |
| walnut oil | 13.3 | 26.6 | 60.4 | 0.05 | 60.4 | 0.220 | 1208 |
| sunflower oil | 8.65 | 53.2 | 38.1 | 0.28 | 37.8 | 0.227 | 135 |
| wheat germ oil | 26.1 | 16.2 | 57.7 | 4.68 | 53 | 0.452 | 11.3 |
| almond oil | 8.79 | 67.1 | 24 | 0.14 | 23.9 | 0.366 | 171 |
| black currant oil | | 11 | 81 | 15 | 65 | | 4.1 |
| rapeseed oil | | 60 | 36 | 13 | 23 | | 1.8 |
| borage oil | | 17 | 71 | | 66 | | 100 |
| evening primrose | | 8 | 63 | | 85 | | 100 |

FIG. 13

| Group X | total TP > 800 (mg/kg) | Group Y | total TP < 800 (mg/kg) |
|---|---|---|---|
| seabuckthorn oil | 1000-3000 | coconut oil | 30 |
| wheat germ oil | 2050 | sesame oil | 620 |
| cranberry oil | 2380 | blueberry oil | 111 |
| soybean oil | 829 | EVOO | 177 |
| walnut oil | 1600 | cumin oil | 362 |
| red rasberry oil | 890 | black rasberry oil | 132 |
| hemp seed oil | 800 | sunflower oil | 615 |
| pumpkin seed oil | 850 | flax seed oil | 658 |
| corn oil | 829 | rapeseed oil | 430 |
| rosehip oil | 1125 | apricot kernel oil | 475 |
| clove oil | 908 | grape seed oil | 121 |
|  |  | peanut oil | 226 |
|  |  | milk thistle oil | 464 |

FIG. 14

| Active ingredient | total phenols [mg GAE/100 g] |
|---|---|
| oils | |
| pumpkin seed oil | 68 |
| EVOO | 342 |
| seabuckthorn oil | 400-700 |
| cumin oil | 11-31. |
| flax seed oil | 28.5 |
| sunflower oil | 193 |
| palm oil | 3.2 |
| rapeseed oil | 156 |
| chaga extract | 14950 |
| red raspberry seed oil | 200 |
| onion seed oil | 340 |
| extacts | |
| cinnamon | 4533 |
| cloves | 16550 |
| cumin seeds | 849 |
| oregano | 3789 |
| rosemary | 4980 |
| turmeric | 2754 |

FIG. 15

| Active ingredient | total phenols [mg CAE/100 g] |
|---|---|
| pumpkin seed oil | 2.45 |
| flax seed oil | 1.14 |
| ricebran oil | 1.44 |
| hemp seed oil | 2.45 |
| soybean oil | 1.48 |

FIG. 16

| Active ingredient | total carotenoids [mg/kg] |
|---|---|
| pumpkin seed oil | 150 |
| blueberry oil | 1.4 |
| red raspberry oil | 0.2 |
| EVOO | 596 |
| seabuckthorn seed oil | 200-850 |
| seabuck pulp oil | 300-20,000 |
| cumin oil | 89 |
| flax seed oil | 150 |
| rosehip oil | 108 |
| sunflower oil | 7.6 |
| soybean oil | 27 |
| rapeseed oil | 81 |

FIG. 17

| Active ingredient | total sterols [mg/100 g] |
|---|---|
| pumpkin seed oil | 294 |
| EVOO | 180-260 |
| seabuckthorn oil | 1200-2300 |
| cumin oil | 209 |
| hemp seed oil | 279 |
| flax seed oil | 512 |
| cranberry oil | 345 |
| carrot seed oil | 245 |
| sesame oil | 500 |
| rosehip seed oil | 649 |
| sunflower oil | 410 |
| soybean | 460 |
| corn oil | 970 |
| rapeseed oil | 374 |

FIG. 18

| Active ingredient | mmol Trolox/liter |
|---|---|
| cumin oil | 21.02 |
| flax seed oil | 2.38 |
| soybean oil | 3.96 |
| sunflower oil | 2.22 |
| canola oil | 2.01 |
| pumkin seed oil | 3.42 |
| sesame oil | 2.32 |
| pomegrante oil | 12.9 |
| red rasberry oil | 12.6 |
| black rasberry oil | 19.17 |
| grape seed oil | 2.32 |
| EVOO | 6.2 |

FIG. 19A

| Active ingredient | mmol Trolox/kg |
|---|---|
| chaga extract | 5,146 |
| seabuckthorn seed | 324.2 |
| avocado oil | 0.58 |
| sesame oil | 1.38 |
| macadamia oil | 0.17 |
| saflower oil | 1.77 |
| pumkin seed oil | 1.44 |
| rosehip oil | 2.32 |
| linola oil | 1.68 |
| flax seed oil | 1.58 |
| walnut oil | 1.28 |
| hemp oil | 1.74 |
| poppy oil | 0.72 |
| milk thistle oil | 1.7 |

FIG. 19B

| Active ingredient | ORAC value |
|---|---|
| clove oil | 1,078.70 |
| coriander oil | 298.3 |
| clary sage oil | 221 |
| German chamomile oil | 218.6 |
| cedarwood oil | 169 |
| rose oil | 160.4 |
| marjoram oil | 130.9 |
| ylang ylang | 130 |
| palmarosa | 127.8 |
| rosewood oil | 113.2 |
| geranium oil | 101 |
| ginger oil | 99.3 |
| eucaliptus oil | 83 |
| cumin oil | 82.4 |
| blue cypress | 73 |
| limette oil | 69.2 |
| pepermint oil | 37.3 |
| mandarin oil | 26.5 |
| lime oil | 26.2 |
| cypress oil | 24.3 |
| grapefruit oil | 22.6 |
| thyme oil | 15.96 |
| oregano oil | 15.3 |
| sage oil | 11.3 |
| cinnamon bark oil | 7.1 |
| valerian oil | 3.86 |
| orange oil | 1.89 |
| lemongrass oil | 1.78 |
| Helichrusym oil | 1.74 |
| lemon oil | 0.66 |
| Frankincese oil | 0.63 |
| spearmint oil | 0.54 |
| lavender oil | 0.36 |
| rosemary oil | 0.33 |
| juniper oil | 0.25 |
| Roman chamomile oil | 0.24 |

FIG. 20

| "Boosters" | compounds/enzyme of interest |
|---|---|
| chaga extract | SOD (enzymatic AO) |
| cumin oil | thymoquinone |
| seabuckthorn oil / extract | omega-7 & SOD |
| pomegranate seed oil | omega-5 |
| turmeric | curcumins / curcuminoids |
| green tea extract | gallates |
| berry extracts / oils | anthocyanidins |
| rosehip oil | vitamin C |
| cranberry oil | vitamin C & proanthocyanins |
| broccoli seed oil | vitamin C |
| grape seed extract / oil | proanthocyanidins |
| EVOO | squalene, oleoeuropein |
| clove oil | eugenol |
| cinnamon bark oil | eugenol |

FIG. 21

| ID | Active ingredients | % (by volume) |
|---|---|---|
| A1 | EVOO/Helicrysum | 50/50 |
| A2 | EVOO/Helicrysum/cumin | 33.3/33.3/33.3 |
| B1 | hemp/cinnamon | 50/50 |
| B2 | hemp/cinnamon/wheat germ | 33.3/33.3/33.3 |
| C1 | carrot seed/flax seed | 50/50 |
| C2 | carrot seed/flax seed/cinnamon | 33.3/33.3/33.3 |
| D1 | EVOO/turmeric | 50/50 |
| D2 | EVOO/turmeric/pumkin seed | 33.3/33.3/33.3 |
| E1 | turmeric/cumin | 50/50 |
| E2 | turmeric/curmin/pumkin seed | 33.3/33.3/33.3 |
| F1 | rosehip/hemp | 50/50 |
| F2 | rosehip/hemp/Helicrycum | 37.5/37.5/25 |
| G1 | cumin/flax seed | 50/50 |
| G2 | cumin/flax seed/turmeric | 37.5/37.5/25 |
| H1 | cumin/hemp | 50/50 |
| H2 | cumin/hemp/flax seed | 37.5/37.5/25 |
| I1 | cumin/EVOO | 50/50 |
| I2 | cumin/EVOO/cinnamon | 25/25/50 |
| J1 | cumin/pumkin seed | 50/50 |
| J2 | cumin/pumkin seed/wheatgerm | 33.3/33.3/33.3 |
| K1 | cumin/hemp/wheatgerm | 33.3/33.3/33.3 |
| K2 | cumin/hemp/EVOO | 33.3/33.3/33.3 |
| K3 | cumin/EVOO/wheatgerm | 33.3/33.3/33.3 |
| K4 | cumin/hemp/EVOO/wheat | 33.3/33.3/16.7/16.7 |
| K5 | cumin/hemp/pumkin seed | 33.3/33.3/33.3 |
| L1 | jojoba/hemp | 50/50 |
| L2 | jojoba/hemp/cumin | 25/25/50 |
| L3 | jojoba/hemp/cumin/wheatgerm | 16.7/16.7/33.3/33.3 |
| M1 | jojoba/cumin | 50/50 |
| M2 | jojoba/cumin/flax seed | 33.3/33.3/33.3 |
| M3 | jojoba/cumin/flax seed | 55.5/22.2/22.2 |
| N1 | jojoba/rosehip | 50/50 |
| N2 | jojoba/rosehip/cumin | 25/25/50 |
| N3 | rosehip/cumin | 50/50 |
| N4 | rosehip/cumin/turmeric | 33.3/33.3/33.3 |
| O1 | EVOO/cranberry | 50/50 |
| O2 | EVOO/cranberry/broccoli | 33.3/33.3/33.3 |
| O3 | EVOO/cranberry/broccoli/black raspberry | 25/25/25/25 |
| O4 | EVOO/cranberry/broccoli/black raspberry/rosehip | 20/20/20/20/20 |
| P1 | carrot/rosehip | 50/50 |
| P2 | carrot/rosehip/cranberry | 33.3/33.3/33.3 |
| P3 | carrot/rosehip/cranberry/broccoli | 25/25/25/25 |
| P4 | carrot/rosehip/cranberry/broccoli/seabuckthorn seed | 22.2/22.2/22.2/22.2/11.2 |
| Q1 | black raspberry/jojoba | 50/50 |
| Q2 | black raspberry/jojoba/red raspberry | 33.3/33.3/33.3 |
| Q3 | black raspberry/jojoba/red raspberry/rosehip | 25/25/25/25 |
| Q4 | black raspberry/jojoba/red raspberry/rosehip/hemp | 20/20/20/20/20 |
| R1 | pumpkin seed/broccoli | 50/50 |
| R2 | pumpkin seed/broccoli/rosehip | 33.3/33.3/33.3 |
| R3 | pumpkin seed/broccoli/rosehip/turmeric | 28.6/28.6/28.6/14.2 |
| R4 | pumpkin seed/broccoli/rosehip/turmeric/joboba | 22.2/22.2/22.2/22.2/11.2 |

FIG. 22A

| ID | Active ingredients | % (by volume) |
|---|---|---|
| AA1 | cumin/turmeric/EVOO/wheat/hemp | 25/12.5/12.5/25/25 |
| AA2 | cumin/turmeric/EVOO/hemp/wheat | 16.6/8.3/8.3/16.6/50.2 |
| AA3 | cumin/turmeric/EVOO/wheat/hemp/rosehip | 16.6/8.3/8.3/16.6/16.6/33.6 |
| AA4 | cumin/turmeric/EVOO/wheat/hemp/rosehip | 44.5/5.5/5.5/11/11/22.4 |
| BB1 | cumin/wheatgerm/hemp | 33.3/33.3/33.3 |
| BB2 | cumin/wheatgerm/hemp/cinnamon/Helicrysum | 28.6/28.6/28.6/7.1/7.1 |
| BB3 | cumin/wheatgerm/hemp/cinnamon/Helicrysum | 29.6/29.6/29.6/5.6/5.6 |
| BB4 | cumin/wheatgerm/hemp/cinnamon/Helicrysum | 32/32/32/2/2 |
| CC1 | cumin/pumkin seed | 50/50 |
| CC2 | cumin/pumkin seed/turmeric | 44.5/44.5/11 |
| CC3 | cumin/pumkin seed/turmeric | 48.1/48.1/3.8 |
| DD1 | cumin/wheat germ | 50/50 |
| DD2 | cumin/wheat germ/hemp | 33.3/33.3/33.3 |
| DD3 | cumin/wheat germ/hemp/rosehip | 28.6/28.6/28.6/14.2 |
| EE1 | cumin/pumkin seed/turmeric | 48.3/48.3/3.4 |
| EE2 | cumin/pumkin seed/turmeric | 51.4/45.7/2.9 |
| EE3 | cumin/hemp/wheat germ/rosehip | 30.8/30.8/30.8/7.7 |
| CH | cinnamon/Helicrysum | 50/50 |
| FF1 | turmeric/brocolli/cranberry | 40/20/40 |
| FF2 | turmeric/brocolli/cranberry/seabuckthorn | 33.3/16.7/33.3/16.7 |
| FF3 | turmeric/brocolli/cranberry/seabuckthorn/Helicrysum | 28.6/14.3/28.6/14.3/14.3 |
| FF4 | turmeric/brocolli/cranberry/seabuckthorn/Helicrysum | 44.4/11.1/22.2/11.1/11.1 |
| FF5 | turmeric/brocolli/cranberry/seabuckthorn/Helicrysum | 33.3/16.7/25/8.3/16.7 |

FIG. 22B formulation L1 formulation L2 formulation L3

| HEV-1 group | HEV/VIS ≥ 1.5 |
|---|---|
| jojoba oil | 2.079 |
| sunflower oil | 1.654 |
| sesame oil | 1.775 |
| rosehip oil | 2.241 |
| carrot seed oil | 1.600 |
| wheat germ oil | 2.502 |
| pumpkin seed oil | 1.963 |
| cumin oil | 2.361 |
| hemp seed oil | 1.677 |
| flax seed oil | 2.062 |
| turmeric oil | 1.496 |
| chaga extract | 1.604 |
| oreganol | 1.543 |
| black raspberry oil | 2.000 |
| cranberry oil | 2.345 |
| broccoli seed oil | 2.368 |
| seabuckthorn berry oil | 2.574 |
| EVOO | 1.974 |
| pomegranate oil | 1.619 |
| red raspberry oil | 1.876 |

FIG. 33A

| HEV-2 group | 1.0 < HEV/VIS < 1.5 |
|---|---|
| grape seed oil | 1.489 |
| yellow marigold oil | 1.253 |
| feverfew oil | 1.357 |
| soyabean oil | 1.114 |
| Egypt. germanium oil | 1.146 |
| aloe vera oil | 1.117 |
| apricot kernel oil | 1.364 |
| argan oil | 1.325 |
| meadowfoam oil | 1.140 |
| marula oil | 1.309 |
| grapefruit seed oil | 1.205 |
| chia seed oil | 1.270 |
| ricebran oil | 1.139 |
| hazelnut oil | 1.113 |
| evening primrose oil | 1.392 |
| castor oil | 1.291 |

FIG. 33B

| UVA group | HEV/VIS ≤ 1.0 |
|---|---|
| coconut oil | 1.078 |
| avocado oil | 1.066 |
| eucaliptus oil | 1.029 |
| tea tree oil | 1.061 |
| clove oil | 1.022 |
| frankincense oil | 1.014 |
| Helichrysum oil | 1.036 |
| ginger oil | 1.064 |
| cinnamon bark oil | 0.874 |

FIG. 33C

| ID | HEV/VIS ratio | ID | HEV/VIS ratio | ID | HEV/VIS ratio | ID | HEV/VIS ratio |
|---|---|---|---|---|---|---|---|
| A1 | 1.474 | K1 | 2.511 | P1 | 1.571 | CC1 | 1.758 |
| A2 | 1.406 | K2 | 1.996 | P2 | 1.949 | CC2 | 1.694 |
| B1 | 1.104 | K3 | 2.109 | P3 | 1.980 | CC3 | 1.656 |
| B2 | 1.299 | K4 | 2.279 | P4 | 2.507 | DD1 | 2.369 |
| C1 | 2.201 | K5 | 2.132 | Q1 | 1.672 | DD2 | 2.218 |
| C2 | 1.150 | L1 | 1.730 | Q2 | 1.901 | DD3 | 2.256 |
| D1 | 1.680 | L2 | 1.960 | Q3 | 1.496 | EE1 | 1.558 |
| D2 | 1.909 | L3 | 2.625 | Q4 | 2.208 | EE2 | 1.715 |
| E1 | 1.777 | M1 | 1.865 | R1 | 2.553 | EE3 | 1.980 |
| E2 | 1.710 | M2 | 2.681 | R2 | 2.556 | FF1 | 1.752 |
| F1 | 2.140 | M3 | 2.394 | R3 | 1.661 | FF2 | 2.549 |
| F2 | 1.665 | N1 | 2.271 | R4 | 2.216 | FF3 | 2.059 |
| G1 | 1.845 | N2 | 2.597 | AA1 | 1.824 | FF4 | 2.276 |
| G2 | 2.144 | N3 | 2.261 | AA2 | 1.909 | FF5 | 2.427 |
| H1 | 2.138 | N4 | 1.668 | AA3 | 1.905 | CS1-1 | 1.715 |
| H2 | 2.281 | O1 | 1.975 | AA4 | 1.982 | CS1-2 | 1.980 |
| I1 | 2.031 | O2 | 2.101 | BB1 | 1.944 | CS1-3 | 2.574 |
| I2 | 2.003 | O3 | 2.047 | BB2 | 1.483 | CS1-4 | 2.427 |
| J1 | 2.094 | O4 | 1.594 | BB3 | 1.620 | CS1-5 | 1.604 |
| J2 | 1.866 | CH | 0.925 | BB4 | 1.642 | CS1-6 | 1.691 |

FIG. 34

ANTIOXIDANT COMPOSITIONS AND METHODS OF PROTECTING SKIN, HAIR AND NAILS AGAINST HIGH ENERGY BLUE-VIOLET LIGHT

PRIORITY APPLICATION

This application claims priority to, and the benefit of, U.S. Provisional Application No. 62/154,228 filed on Apr. 29, 2015, the entire disclosure of which is hereby incorporated herein by reference for all purposes.

TECHNOLOGICAL FIELD

This application is related to compositions and methods of using them to protect a user's skin, nails, and hair from exposure to high energy violet or blue visible light. In certain instances, the compositions are effective to absorb light in the 380-500 nm range or in the 400-500 nm range to protect the skin of the user. The compositions may be present in a cosmetic formulation or as a lotion or other configurations that permits placement and/or retention on the skin, hair, and nails.

BACKGROUND

Many new indoor compact fluorescent light (CFL) bulbs and light-emitting diodes (LEDs) can emit light in the 380-500 nm range. These wavelengths of light can cause damage to the skin of a user positioned under or near the CFL and LED bulbs. Also, solar radiation reaching the Earth consists approximately 25-30% light in this range. Conventional sunscreen compositions are designed to absorb light at wavelengths below 380 nm and provide no protection against longer wavelength solar radiation (>380 nm), as well as CFL- and LED-light exposure above 380 nm. Electronic device screens and displays having LED backlights emit light in 400-500 nm range, and thus, present danger for the user, as well.

SUMMARY

In a first aspect, a method of protecting cellular damage of an animal cell from exposure to incident high energy light comprising a wavelength of about 380 nm to about 500 nm is described. In certain instances, the method comprises topically administering a composition to the animal cell comprising at least one natural oil or extract present in an effective amount to provide a HEV/VIS ratio of greater than or equal to 1.5 at an area of the animal cell where the composition has been topically administered.

In some configurations, the method comprises the natural oil or extract from the group consisting of extra virgin olive oil, wheat germ oil, sunflower oil, flax seed oil, rosehip oil, carrot seed oil, apricot seed oil, pumpkin seed oil, hemp oil, jojoba oil, argan oil, cranberry oil, broccoli seed oil, pomegranate oil, evening primrose oil, red raspberry oil, black raspberry oil, sea buckthorn berry oil, sea buckthorn seed oil, sesame oil, turmeric oil, cumin oil, marula oil, chia seed oil, shea butter, chaga extract and bees wax. In other configurations, the method comprises configuring the composition to comprise at least two natural oils or extracts or their combination. In some examples, the method comprises selecting each of the two natural oils or extract to independently be one of extra virgin olive oil, wheat germ oil, sunflower oil, flax seed oil, rosehip oil, carrot seed oil, apricot seed oil, pumpkin seed oil, hemp oil, jojoba oil, argan oil, cranberry oil, broccoli seed oil, pomegranate oil, evening primrose oil, red raspberry oil, black raspberry oil, sea buckthorn oil, sesame oil, turmeric oil, cumin oil, marula oil, chia seed oil, shea butter, chaga extract and bees wax, wherein the two natural oils are different oils and wherein the amount of each of the two natural oils is selected so the composition absorbs about 30% of the incident high energy light. In other instances, the method comprises configuring the composition to comprise at least three natural oils or extracts or their combination. In some embodiments, the method comprises selecting each of the three natural oils or extracts to independently be one of extra virgin olive oil, wheat germ oil, sunflower oil, flax seed oil, rosehip oil, carrot seed oil, apricot seed oil, pumpkin seed oil, hemp oil, jojoba oil, argan oil, cranberry oil, broccoli seed oil, pomegranate oil, evening primrose oil, red raspberry oil, black raspberry oil, sea buckthorn oil, sesame oil, turmeric oil, cumin oil, marula oil, chia seed oil, shea butter, chaga extract and bees wax, wherein the three natural oils are different oils and wherein the amount of each of the three natural oils is selected to provide a HEV/VIS ratio for the total composition of greater than or equal to 1.5 at an area of the animal cell where the composition has been topically administered. In certain examples, the method comprises configuring the composition to comprise at least four natural oils or extracts or their combination. In other examples, the method comprises selecting each of the four natural oils or extracts to independently be one of extra virgin olive oil, wheat germ oil, sunflower oil, flax seed oil, rosehip oil, carrot seed oil, apricot seed oil, pumpkin seed oil, hemp oil, jojoba oil, argan oil, cranberry oil, broccoli seed oil, pomegranate oil, evening primrose oil, red raspberry oil, black raspberry oil, sea buckthorn oil, sesame oil, turmeric oil, cumin oil, marula oil, chia seed oil, shea butter, chaga extract and bees wax, wherein the four natural oils are different oils and wherein the amount of each of the four natural oils is selected to provide a HEV/VIS ratio for the total composition of greater than or equal to 1.5 at an area of the animal cell where the composition has been topically administered. In other examples, the method comprises configuring the composition to comprise at least one Group A natural oil and at least one Group B natural oil. In some embodiments, the method comprises selecting the at least one natural oil from Type I oils. In further examples, the method comprises configuring the composition with at least one Type II oil. In some embodiments, the method comprises configuring the composition with at least one Type III oil. In certain examples, the method comprises configuring the composition with at least one booster. In some embodiments, the booster is selected from the group consisting of chaga extract, cumin oil, seabuckthorn oil/extract, pomegranate seed oil, turmeric oil, green tea extracts, berry extracts/oils, rosehip oil, cranberry oil, broccoli seed oil, grape seed extract/oil, extra virgin olive oil, clove oil and cinnamon bark oil. In certain embodiments, the method comprises configuring the composition with at least one carrier, e.g., natural or non-natural carrier compounds, effective to permit topical administration of the composition. In some embodiments, the method comprises configuring the carrier to enhance transport of the composition into cells. In additional examples, the method comprises configuring the composition with a first natural oil that absorbs about 30%, 40%, 50% or more of the incident high energy light having a wavelength of about 380-400 nm that is incident on the area of the animal cell where the composition has been topically administered. In further examples, the method comprises configuring the composition with a second natural oil that absorbs at least 30%, 40%, 50% or more of the incident high energy light having a wavelength of about 400-440 nm that is incident on the area of the animal cell where the composition has been topically administered. In some embodiments, the method comprises configuring the composition with a third natural oil that absorbs at least 30%, 40%, 50% or more of the incident high energy light having a wavelength of about 440-500 nm that is incident on the area of the animal cell where the composition has been topically administered. In some examples, the method comprises configuring the composition with at least one of (i) an additional component effective to absorb incident light having a wavelength below 380 nm, (ii) a booster effective to reduce reactive oxygen species or (iii) particles effective to scatter light comprising a wavelength of about 380 nm to about 500 nm.

In another aspect, a method of simultaneously reducing the level of reactive oxygen species in an external animal cell and protecting the animal cell from exposure to incident light comprising a wavelength of about 380 nm to about 500 nm is disclosed. In certain instanced, the method comprises topically administering a composition comprising at least one natural oil or extract, wherein the natural oil or extract is present in an effective amount in the composition to reduce reactive oxygen species in the external animal cell by at least 10% after topical application of the composition to the external animal cell, and wherein the composition comprises a HEV/VIS ratio of at least 1.5 where the compositions has been topically applied.

In certain configurations, the method comprises selecting the at least one natural oil as a Group A oil or a Type I oil. In other examples, the method comprises configuring the composition with at least one additional oil which is a Group B, Type II or Type III oil. In some embodiments, the method comprises configuring the composition with at least one booster. In further examples, the method comprises selecting the booster as one or more of chaga extract, cumin oil, seabuckthorn extract/oil, pomegranate seed oil, turmeric oil, green tea extracts, berry extracts/oils, rosehip oil, cranberry oil, broccoli seed oil, grape seed extract/oil, extra virgin olive oil, clove oil and cinnamon bark oil. In other examples, the method comprises configuring the composition with at least two, three, four or more different natural oils or extracts or their combination. In certain embodiments, the method comprises configuring the composition with a first natural oil that absorbs at least 50% of the incident light comprising a wavelength of about 380-400 nm that is incident on the external mammalian cell where the composition has been topically administered. In some examples, the method comprises configuring the composition with a second natural oil that absorbs at least 30% of the incident light comprising a wavelength of about 400-440 nm that is incident on the external mammalian cell where the composition has been topically administered. In some embodiments, the method comprises configuring the composition with a third natural oil that absorbs at least 30% of the incident high energy light comprising a wavelength of about 440-500 nm that is incident on the external mammalian cell where the composition has been topically administered. In some examples, the method comprises configuring the composition with at least one of (i) an additional component effective to absorb incident light having a wavelength below 380 nm, (ii) a booster effective to reduce reactive oxygen species or (iii) particles effective to scatter light comprising a wavelength of about 380 nm to about 500 nm.

In another aspect, a method of simultaneously reducing cellular aging, reducing free radical species and providing visible light protection to mammalian skin, hair or nails is provided. In certain examples, the method comprises topically administering a composition comprising an effective amount of a natural oil which (i) absorbs at least 30% of incident light comprising a wavelength of about 380 nm to about 500 nm which is incident on the mammalian skin, hair or nails and (ii) prevents the generation of reactive oxygen species in the skin due to light exposure during and after the topical administration of the composition on the mammalian skin, hair or nails by at least 20%.

In certain examples, the method comprises selecting the at least one natural oil as a Group A oil or a Type I oil. In other examples, the method comprises configuring the composition with at least one additional oil which is a Group B, Type II or Type III oil. In some embodiments, the method comprises configuring the composition with at least one booster. In certain examples, the method comprises selecting the booster as one or more of chaga extract, cumin oil, seabuckthorn oil/extract, pomegranate seed oil, turmeric oil, green tea extracts, berry extracts/oils, rosehip oil, cranberry oil, broccoli seed oil, grape seed extract/oil, extra virgin olive oil, clove oil and cinnamon oil. In some examples, the method comprises configuring the composition with at least two, three, four or more different natural oils or extracts or their combination. In certain embodiments, the method comprises configuring the composition with a first natural oil that absorbs at least 30% of the incident light comprising a wavelength of about 380-400 nm that is incident on the external mammalian cell where the composition has been topically administered. In some examples, the method comprises configuring the composition with a second natural oil that absorbs at least 30% of the incident light comprising a wavelength of about 400-440 nm that is incident on the external mammalian cell where the composition has been topically administered. In other examples, the method comprises configuring the composition with a third natural oil that absorbs at least 30% of the incident high energy light comprising a wavelength of about 440-500 nm that is incident on the external mammalian cell where the composition has been topically administered. In certain embodiments, the method comprises configuring the composition to comprise substantially no absorption of light having a wavelength below about 380 nm. In some examples, the method comprises configuring the composition with at least one of (i) an additional component effective to absorb incident light having a wavelength below 380 nm, (ii) a booster effective to reduce reactive oxygen species or (iii) particles effective to scatter light comprising a wavelength of about 380 nm to about 500 nm.

In an additional aspect, a method of reducing skin, hair or nail damage associated with exposure to light comprising a wavelength of about 380 nm to about 500 nm is disclosed. In certain examples, the method comprises providing a composition comprising at least one natural oil or extract present in an effective amount to absorb at least 30% of the incident light comprising the wavelength of 380 nm to about 500 nm when the composition is topically administered to the skin, hair or nails, wherein the composition comprises a HEV/VIS ratio of at least 1.5.

In certain embodiments, the method comprises selecting the natural oil or extract from the group consisting of extra virgin olive oil, wheat germ oil, sunflower oil, flax seed oil, rosehip oil, carrot seed oil, apricot seed oil, pumpkin seed oil, hemp oil, jojoba oil, argan oil, cranberry oil, broccoli seed oil, pomegranate oil, evening primrose oil, red raspberry oil, black raspberry oil, sea buckthorn oil, sesame oil, turmeric oil, cumin oil, marula oil, chia seed oil, shea butter, chaga extract and bees wax, and wherein the amount of the natural oil in the composition is selected to absorb at least 30% of the incident light, e.g., with a wavelength of about 380 nm to about 500 nm, that is incident on the skin, hair or nails where the composition has been topically administered. In other embodiments, the method comprises configuring the composition to comprise at least two natural oils or extracts or their combination. In some instances, the method comprises selecting each of the two natural oils to independently be one of extra virgin olive oil, wheat germ oil, sunflower oil, flax seed oil, rosehip oil, carrot seed oil, apricot seed oil, pumpkin seed oil, hemp oil, jojoba oil, argan oil, cranberry oil, broccoli seed oil, pomegranate oil, evening primrose oil, red raspberry oil, black raspberry oil, sea buckthorn oil, sesame oil, turmeric oil, cumin oil, marula oil, chia seed oil, shea butter, chaga extract and bees wax, wherein the two natural oils are different oils and wherein the amount of each of the two natural oils is selected so the composition absorbs at least 30% of the incident light, e.g., with a wavelength of about 380 nm to about 500 nm, that is incident on the skin, hair or nails where the composition has been topically administered. In further examples, the method comprises configuring the composition to comprise at least three natural oils or extracts or their combination. In some examples, the method comprises each of the three natural oils or extracts to independently be one of extra virgin olive oil, wheat germ oil, sunflower oil, flax seed oil, rosehip oil, carrot seed oil, apricot seed oil, pumpkin seed oil, hemp oil, jojoba oil, argan oil, cranberry oil, broccoli seed oil, pomegranate oil, evening primrose oil, red raspberry oil, black raspberry oil, sea buckthorn oil, sesame oil, turmeric oil, cumin oil, marula oil, chia seed oil, shea butter, chaga extract and bees wax, wherein the three natural oils are different oils and wherein the amount of each of the three natural oils is selected so the composition absorbs at least 30% of the incident light, e.g., with a wavelength of about 380 nm to about 500 nm, that is incident on the skin, hair or nails where the composition has been topically administered. In some examples, the method comprises configuring the composition to comprise at least four natural oils or extracts or their combination. In other embodiments, the method comprises selecting each of the four natural oils or extract to independently be one of extra virgin olive oil, wheat germ oil, sunflower oil, flax seed oil, rosehip oil, carrot seed oil, apricot seed oil, pumpkin seed oil, hemp oil, jojoba oil, argan oil, cranberry oil, broccoli seed oil, pomegranate oil, evening primrose oil, red raspberry oil, black raspberry oil, sea buckthorn oil, sesame oil, turmeric oil, cumin oil, marula oil, chia seed oil, shea butter, chaga extract and bees wax, wherein the four natural oils are different oils and wherein the amount of each of the four natural oils is selected so the composition absorbs at least 30% of the incident light, e.g., with a wavelength of about 380 nm to about 500 nm, that is incident on the skin, hair or nails where the composition has been topically administered. In some instances, the method comprises configuring the composition to comprise at least one Group A natural oil and at least one Group B natural oil. In other examples, the method comprises selecting the at least one natural oil from Type I oils. In some instances, the method comprises further configuring the composition with at least one Type II oil. In certain examples, the method comprises further configuring the composition with at least one Type III oil. In some embodiments, the method comprises configuring the composition with at least one booster. In certain examples, the booster is selected from the group consisting of chaga extract, cumin oil, seabuckthorn oil/ extract, pomegranate seed oil, turmeric oil, green tea extracts, berry extracts/oils, rosehip oil, cranberry oil, broccoli seed oil, grape seed extract oil, extra virgin olive oil, clove oil and cinnamon bark oil. In other instances, the method comprises configuring the composition with at least one carrier effective to permit topical administration of the composition. In some examples, the method comprises configuring the carrier to enhance transport of the composition into cells. In other examples, the method comprises configuring the composition with a first natural oil that absorbs at least 30% of incident high energy light comprising a wavelength of about 380-400 nm that is incident on the skin, hair or nails where the composition has been topically administered. In certain embodiments, the method comprises configuring the composition with a second natural oil that absorbs at least 30% of the incident high energy light having a wavelength of about 400-440 nm that is incident on the skin, hair or nails where the composition has been topically administered. In other instances, the method comprises configuring the composition with a third natural oil that absorbs at least 50% of the incident high energy light having a wavelength of about 400-440 nm that is incident on the skin, hair or nails where the composition has been topically administered. In some embodiments, the method comprises selecting the composition to comprise a composition that has substantially no absorption of light having a wavelength below about 380 nm. In some examples, the method comprises configuring the composition with at least one of (i) an additional component effective to absorb incident light having a wavelength below 380 nm, (ii) a booster effective to reduce reactive oxygen species or (iii) particles effective to scatter light comprising a wavelength of about 380 nm to about 500 nm.

In another aspect, a method of protecting human skin from light comprising a wavelength from about 380 nm to about 500 nm is described. In certain examples, the method comprises providing a composition comprising at least one natural oil or extract present in an effective amount to provide a HEV/VIS ratio of at least 1.5 where the composition is topically administered to the skin, and providing instructions for topically administering the composition on the skin.

In certain embodiments, the method comprises selecting the natural oil or extract and its concentration to provide a HEV/VIS ratio of at least 1.75. In other examples, the method comprises selecting the natural oil or extract and its concentration to provide a HEV/VIS ratio of at least 2.0. In some embodiments, the method comprises selecting the natural oil or extract and its concentration to provide a HEV/VIS ratio of at least 2.25. In certain examples, the method comprises selecting the composition to comprise two natural oils or extracts or their combination each present in an effective amount to provide a HEV/VIS ratio of at least 1.5 for the composition. In other examples, the method comprises selecting the two natural oils or extracts or their combination and their concentrations to provide a HEV/VIS ratio of at least 2.0 for the composition. In some embodiments, the method comprises selecting the composition to comprise three natural oils or extracts or their combination each present in an effective amount to provide a HEV/VIS ratio of at least 1.5 for the composition. In other examples, the method comprises selecting the three natural oils or extracts or their combination and their concentrations to provide a HEV/VIS ratio of at least 2.0 for the composition. In some examples, the method comprises selecting the composition to comprise four natural oils or extracts or their combination each present in an effective amount to provide a HEV/VIS ratio of at least 1.5 for the composition. In certain instances, the method comprises selecting the four natural oils or extracts or their combination and its concentration to provide a HEV/VIS ratio of at least 2.0 for the composition. In some examples, the method comprises configuring the composition with at least one of (i) an additional component effective to absorb incident light having a wavelength below 380 nm, (ii) a booster effective to reduce reactive oxygen species or (iii) particles effective to scatter light comprising a wavelength of about 380 nm to about 500 nm.

In another aspect, a composition comprising at least one natural oil or extract present in an effective amount to provide a HEV/VIS ratio of greater than or equal to 1.5 at an area of an animal where the composition has been topically administered, and a carrier combinable with the natural oil or extract to permit topical application of the natural oil or extract to the skin, hair or nails, e.g., a natural or non-natural carrier or excipient can be present.

In certain embodiments, the natural oil or extract and its concentration is present in an effective amount to provide a HEV/VIS ratio of at least 1.75. In other embodiments, the natural oil or extract and its concentration is present in an effective amount to provide a HEV/VIS ratio of at least 2.0. In certain examples, the natural oil or extract and its concentration is present in an effective amount to provide a HEV/VIS ratio of at least 2.25. In some instances, the composition comprises two natural oils or extracts or their combination, wherein the two natural oils or extracts are each present in an effective amount to provide a HEV/VIS ratio of at least 1.5 for the composition. In other instances, the two natural oils or extracts or their combination and their concentrations are selected to provide a HEV/VIS ratio of at least 2.0 for the composition. In some embodiments, the composition comprises three natural oils or extracts or their combination, wherein the two natural oils or extracts are each present in an effective amount to provide a HEV/VIS ratio of at least 1.5 for the composition. In some examples, the three natural oils or extracts or their combination and their concentrations are selected to provide a HEV/VIS ratio of at least 2.0 for the composition. In other examples, the composition comprises four natural oils or extracts or their combination each present in an effective amount to provide a HEV/VIS ratio of at least 1.5 or at least 2.0 for the composition. In some embodiments, the composition comprises at least one of (i) an additional component effective to absorb incident light having a wavelength below 380 nm, (ii) a booster effective to reduce reactive oxygen species or (iii) particles effective to scatter light comprising a wavelength of about 380 nm to about 500 nm.

In an additional aspect, a composition comprising at least one natural oil or extract, wherein the natural oil or extract is present in an effective amount in the composition to reduce reactive oxygen species in an external animal cell by at least 10% after topical application of the composition to the external animal cell, and wherein the composition comprises an effective amount of the oil to provide a HEV/VIS ratio of at least 1.5 where the compositions has been topically applied, and a carrier combinable with the natural oil or extract to permit topical application of the natural oil or extract to the external animal cell is provided.

In certain instances, the natural oil or extract and its concentration is present in an effective amount to provide a HEV/VIS ratio of at least 1.75 or at least 2.0 or at least 2.25. In other examples, the composition comprises at least two natural oils or extracts, wherein the two natural oils or extracts or their combination and each is present in an effective amount to provide a HEV/VIS ratio of at least 1.5 or at least 2.0 for the composition. In some examples, the composition comprises at least three natural oils or extracts, wherein the three natural oils or extracts or their combination and each is present in an effective amount to provide a HEV/VIS ratio of at least 1.5 or at least 2.0 for the composition. In other examples, the composition comprises at least three natural oils or extracts, wherein the three natural oils or extracts or their combination and each is present in an effective amount to provide a HEV/VIS ratio of at least 1.5 or at least 2.0 for the composition. In some examples, the composition comprises at least one of (i) an additional component effective to absorb incident light having a wavelength below 380 nm, (ii) a booster effective to reduce reactive oxygen species or (iii) particles effective to scatter light comprising a wavelength of about 380 nm to about 500 nm.

In another aspect, a composition comprising an effective amount of a natural oil or extract which simultaneously (i) absorbs at least 30% of incident light comprising a wavelength of about 380 nm to about 500 nm which is incident on the mammalian skin, hair or nails and (ii) prevents future generation of additional reactive oxygen species in the skin during and after the topical administration of the composition on the mammalian skin, hair or nails for at least 20%, and a carrier combinable with the natural oil or extract to permit topical application of the natural oil or extract to the external animal cell is described.

In certain embodiments, the natural oil or extract is selected from the group consisting of Group A oils, Type I oils and HEV-1 group oils. In other embodiments, the composition comprises at least two natural oils or extracts each present in an effective amount to provide the composition which simultaneously (i) absorbs at least 30% of incident light comprising the wavelength of about 380 nm to about 500 nm which is incident on the mammalian skin, hair or nails and (ii) prevents future generation of additional reactive oxygen species in the skin during and after the topical administration of the composition on the mammalian skin, hair or nails for at least 20%. In some examples, at least one of the natural oils or extracts is selected from the group consisting of Group A oils, Type I oils and HEV-1 group oils, and the other natural oil or extract is selected from the group consisting of Group A oils, Group B oils, Type I oils, Type II oils, Type III oils, HEV-1 group oils, HEV-2 group oils and UVA group oils. In some embodiments, the composition comprises at least three natural oils or extracts each present in an effective amount to provide the composition which simultaneously (i) absorbs at least 30% of incident light comprising the wavelength of about 380 nm to about 500 nm which is incident on the mammalian skin, hair or nails and (ii) prevents the generation of reactive oxygen species in the skin due to light exposure during and after the topical administration of the composition on the mammalian skin, hair or nails for at least 20%. In certain examples, at least one of the natural oils or extracts is selected from the group consisting of Group A oils, Type I oils and HEV-1 group oils, and the other two natural oils or extracts are each independently selected from the group consisting of Group A oils, Group B oils, Type I oils, Type II oils, Type III oils, HEV-1 group oils, HEV-2 group oils and UVA group oils. In some instances, the composition comprises at least four natural oils or extracts each present in an effective amount to provide the composition which simultaneously (i) absorbs at least 30% of incident light comprising the wavelength of about 380 nm to about 500 nm which is incident on the mammalian skin, hair or nails and (ii) prevents the generation of reactive oxygen species in the skin due to light exposure during and after the topical administration of the composition on the mammalian skin, hair or nails for at least 20%. In some embodiments, at least one of the natural oils or extracts is selected from the group consisting of Group A oils, Type I oils and HEV-1 group oils, and the other three natural oils or extracts are each independently selected from the group consisting of Group A oils, Group B oils, Type I oils, Type II oils, Type III oils, HEV-1 group oils, HEV-2 group oils and UVA group oils. In other embodiments, the carrier comprises at least one of liposomes, lipids, micelles, and particles. In some instances, the composition comprises at least one of (i) an additional component effective to absorb incident light having a wavelength below 380 nm, (ii) a booster effective to reduce reactive oxygen species or (iii) particles effective to scatter light comprising a wavelength of about 380 nm to about 500 nm.

In another aspect, a composition comprises at least one natural oil present in an effective amount to absorb at least 30% of the incident light comprising the wavelength of 380 nm to about 500 nm when the composition is topically administered to the skin, hair or nail of a mammal, wherein the composition comprises a HEV/VIS ratio of at least 1.5, and a carrier combinable with the natural oil or extract to permit topical application of the natural oil or extract to the external animal cell. In some embodiments, the natural oil or extract is selected from the group consisting of Group A oils, Type I oils and HEV-1 group oils. In other embodiments, the composition comprises at least two natural oils or extracts or their combination. In some examples, at least one of the natural oils or extracts is selected from the group consisting of Group A oils, Type I oils and HEV-1 group oils, and the other natural oil or extract is selected from the group consisting of Group A oils, Group B oils, Type I oils, Type II oils, Type III oils, HEV-1 group oils, HEV-2 group oils and UVA group oils. In other examples, the composition comprises at least three natural oils or extracts or their combination. In certain embodiments, at least one of the natural oils or extracts is selected from the group consisting of Group A oils, Type I oils and HEV-1 group oils, and the other two natural oils or extracts are each independently selected from the group consisting of Group A oils, Group B oils, Type I oils, Type II oils, Type III oils, HEV-1 group oils, HEV-2 group oils and UVA group oils. In other examples, the composition comprises at least four natural oils or extracts or their combination. In some instances, at least one of the natural oils or extracts is selected from the group consisting of Group A oils, Type I oils and HEV-1 group oils, and the other three natural oils or extracts are each independently selected from the group consisting of Group A oils, Group B oils, Type I oils, Type II oils, Type III oils, HEV-1 group oils, HEV-2 group oils and UVA group oils. In certain examples, the carrier comprises at least one of liposomes, lipids, micelles, and particles. In other examples, the composition comprises at least one of (i) an additional component effective to absorb incident light having a wavelength below 380 nm, (ii) a booster effective to reduce reactive oxygen species or (iii) particles effective to scatter light comprising a wavelength of about 380 nm to about 500 nm.

In another aspect, a composition comprising a plurality of natural oils or extracts or their combination each present in an effective amount in the composition so the composition comprises a HEV/VIS ratio of at least 1.5 is provided.

In certain examples, the natural oils or extracts or combination are each independently selected from the group consisting of Group A oils, Type I oils and HEV-1 group oils. In other instances, the composition comprise a booster. In some instances, at least one of the natural oils or extracts or combinations is selected from the group consisting of Group A oils, Type I oils and HEV-1 group oils, and the other natural oils or extracts is selected from the group consisting of Group A oils, Group B oils, Type I oils, Type II oils, Type III oils, HEV-1 group oils, HEV-2 group oils and UVA group oils. In other instances, the composition comprises a booster and light scattering particles. In some examples, at least one of the natural oils or extracts is selected from the group consisting of Group A oils, Type I oils and HEV-1 group oils, and the other natural oils or extracts are each independently selected from the group consisting of Group A oils, Group B oils, Type I oils, Type II oils, Type III oils, HEV-1 group oils, HEV-2 group oils and UVA group oils. In some embodiments, the composition comprises at least four natural oils or extracts or their combination. In certain examples, at least one of the natural oils or extracts is selected from the group consisting of Group A oils, Type I oils and HEV-1 group oils, and the other three natural oils or extracts are each independently selected from the group consisting of Group A oils, Group B oils, Type I oils, Type II oils, Type III oils, HEV-1 group oils, HEV-2 group oils and UVA group oils. In some examples, the composition comprises a carrier comprising at least one of liposomes, lipids, micelles, and particles. In certain embodiments, the composition comprises at least one additional component effective to absorb incident light having a wavelength below 380 nm. In some embodiments, the composition further comprises an additional component effective to absorb incident light having a wavelength below 380 nm.

In another aspect, a kit comprising a composition comprising at least one natural oil or extract present in an effective amount to provide a HEV/VIS ratio of at least 1.5 where the composition is topically administered to the skin, hair or nails of a mammal, and instructions for topically administering the composition to the skin, hair or nails of a mammal is provided.

In certain examples, the natural oil or extract is selected from the group consisting of Group A oils, Type I oils and HEV-1 group oils. In other examples, the kit comprises a composition comprising at least two natural oils or extracts or their combination in the composition. In some examples, at least one of the natural oils or extracts is selected from the group consisting of Group A oils, Type I oils and HEV-1 group oils, and the other natural oil or extract is selected from the group consisting of Group A oils, Group B oils, Type I oils, Type II oils, Type III oils, HEV-1 group oils, HEV-2 group oils and UVA group oils. In other examples, the kit comprises a composition comprising at least three natural oils or extracts or their combination in the composition. In some instances, at least one of the natural oils or extracts is selected from the group consisting of Group A oils, Type I oils and HEV-1 group oils, and the other two natural oils or extracts are each independently selected from the group consisting of Group A oils, Group B oils, Type I oils, Type II oils, Type III oils, HEV-1 group oils, HEV-2 group oils and UVA group oils. In other examples, the kit comprises a composition comprising at least four natural oils or extracts or their combination in the composition. In some embodiments, at least one of the natural oils or extracts is selected from the group consisting of Group A oils, Type I oils and HEV-1 group oils, and the other three natural oils or extracts are each independently selected from the group consisting of Group A oils, Group B oils, Type I oils, Type II oils, Type III oils, HEV-1 group oils, HEV-2 group oils and UVA group oils. In other examples, the kit comprises a carrier which comprises at least one of liposomes, lipids, micelles, and particles. In some instances, the kit comprises at least one of (i) an additional component effective to absorb incident light having a wavelength below 380 nm, (ii) a booster effective to reduce reactive oxygen species or (iii) particles effective to scatter light comprising a wavelength of about 380 nm to about 500 nm.

In another aspect, a method of protecting mammalian hair, skin, nails or fur from generation of infrared radiation induced reactive oxygen species is disclosed. In certain examples, the method comprises topically administering a composition to the mammalian hair, skin, nails or fur comprising at least one natural oil or extract present in an effective amount to absorb at least about 25% of incident light comprising a wavelength of about 380 nm to about 500 nm, and wherein the natural oil or extract and the effective amount is selected to prevent generation of infrared radiation induced reactive oxygen species in the hair, skin, nail or fur comprising the topically administered composition is provided.

Additional embodiments, aspects, configurations and features are described in more detail below.

BRIEF DESCRIPTION OF THE FIGURES

Certain illustrative compositions and their use are described below with reference to the following figures in which:

FIG. 3 is a table showing the absorption characteristics of numerous oils, in accordance with certain examples;

FIG. 4 is another table showing the absorption characteristics of numerous oils, in accordance with certain examples;

FIG. 9 is a table showing various absorbance ratios for certain Type I oils;

FIG. 10 is a table showing various absorbance ratios for certain Type II oils;

FIG. 11 is a table showing various absorbance ratios for certain Type III oils;

FIG. 12 is a table showing various absorbance ratios for certain Type FA-1 oils;

FIG. 13 is a table showing the fatty acid content for certain oils;

FIG. 14 is a table showing certain oil groupings (X and Y) and the phenol contents;

FIG. 15 is a table showing the phenol content of certain oils;

FIG. 16 is another table showing the phenol content of certain oils;

FIG. 17 is a table showing the carotenoid content of certain oils;

FIG. 18 is a table showing the sterol content of certain oils;

FIG. 19A-19B are tables showing Trolox values for certain oils;

FIG. 20 is a table showing ORAC values for certain oils;

FIG. 21 is a table that lists certain boosters which can be included in the compositions;

FIGS. 22A and 22B are tables listing various oil combinations and their percent by volume;

FIGS. 33A-33C are tables showing HEV/VIS ratios for various oils; and

FIG. 34 is a table showing various HEV/VIS ratios for certain formulations.

DETAILED DESCRIPTION

Figure 1:
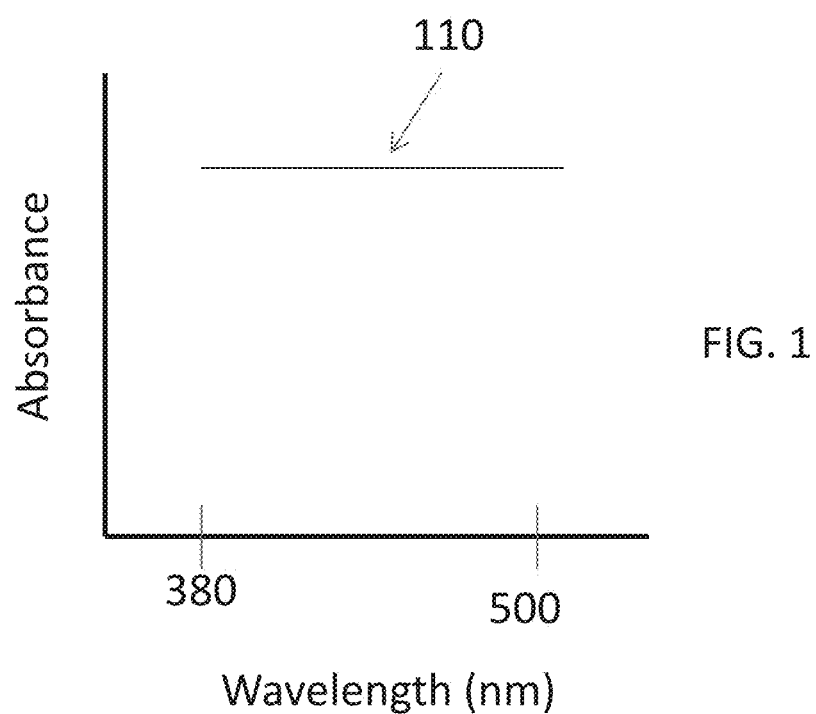
FIG. 1 is a graph showing absorbance versus wavelength, in accordance with certain examples.

Certain aspects, embodiments and examples described herein are directed to skin, hair and nail care product compositions, which can protect the skin, hair and nails from harmful energetic portions of the visible light spectrum, i.e. violet-blue light part (380-500 nm or 400-500 nm also referred to herein as high energy visible (HEV) light). Certain compositions protect the skin, nail and hair from the light originated from the sun and artificial light sources, such as fluorescent bulbs, compact fluorescent lights (CFLs), light-emitting diode (LED) lights, high-intensity discharge (HID) bulbs, metal halide lights, as well as the radiation coming out from electronic devices' monitors, displays, TV screens, etc. The sun, light sources and electronic screens emit significant light portion in the violet and blue spectral range (380-500 nm or 400-500 nm). While there are available kinds of UV light protections, e.g. broad band sunscreen lotions or glass envelopes around certain light bulbs, which significantly cut the UV light penetration into the skin or hair, there is no a product on the market that protects the skin, hair and nails from the harmful violet-blue visible light. Embodiments described herein relate to topically-applied compositions, which have one or more of violet-blue light blocking functionality, anti-oxidant and anti-inflammatory activity in addition to some other functionalities as described herein.

In certain configurations, the compositions are formulated in such a way to provide the right amount and type of essential fatty acids (FAs), tocopherols, polyphenols and other ingredients present in the oils used. By example only, EVOO and argan oil can be combined in certain ratios to provide sufficient amount of tocopherol to be effective against oxygen- and nitrogen-radicals, respectively. A proper combination of saturated (SFA) and unsaturated FAs (MUFA and PUFA) can be selected for each composition in order to provide the sufficient amount of phytonutrients, but also tailoring the consistency (viscosity) of each formulation depending on its final application as a cream, lotion, balm, spray, aerosol or oil. The compositions described herein can be considered multi-functional in that they provide a barrier/protective coating (film) that can shield the skin, hair and nails from the harmful UV, violet and blue light as well as providing additional functionalities such as anti-aging, rejuvenating, moisturizing, nourishing, anti-photoaging and others. In another embodiment, the proposed compositions can be tailored to provide the maximum protection for each skin type against UVA, violet and blue spectral rays. Depending on the melanin level in each particular skin tone, the relative ratio of the ingredients in the skin composition can be adjusted for each skin tone.

In other instances, the compositions described herein can protect, e.g., provide full protection or partial protection from generation of new reactive oxygen species (ROS) due to HEV light exposure. The compositions may also reduce existing ROS within a cell in addition to preventing further ROS generation. Where the description below refers to a reduction in ROS, this reduction may be based on prevention of additional ROS within the cell and/or reduction of an existing amount of ROS within the cell.

While various compositions described herein may be designed to absorb substantially all light within a selected wavelength range, to provide protective effects it may not be necessary to absorb 100% of the light. For example, a 20%, 30%, 40% or even 50% reduction in the amount of light in the 380-500 nm range or the 400-500 nm range which reaches the skin can provide beneficial results as well. The particular amount of light to be absorbed can be tailored or tuned by adjusting the relevant weight percentages of the components and/or by including different components with each other. For example, it may be desirable to include a plurality of different components whose peak absorbance is different over the wavelength range of 380-500 nm or 400-500 nm. Inclusion of these different components can flatten out the overall absorbance curve such that substantial absorbance of the blue-violet light occurs over the desired wavelength range. For example and referring to FIG. 1, an ideal absorbance spectrum is shown where the absorbance (A), which is labeled as line 110 in FIG. 1, of the composition is substantially constant with a change in wavelength ($\lambda$), or $dA/d\lambda$=substantially constant over 380-500 nm or 400-500 nm or even 380-450 nm or 450-500 nm depending on the particular wavelengths of light that a user is exposed. While FIG. 1 shows the slope as being zero, i.e., a constant absorbance over the wavelength range, the absorbance of the compositions described herein may fluctuate, for example, by 2-20% from an average absorbance over a desired wavelength range. In some instances, the fluctuation may be more than 20% or less than 2% depending on the exact components present in the composition.

In certain configurations, UVC light is blocked by the ozone layer, UVA, UVB, visible and IR light portions from the solar irradiation reach the Earth's surface. The visible part of the solar radiation has approximately 25-30% violet-blue light. Also, the light originating from the artificial indoor and outdoor light sources, especially the newest types, claimed to be energy-efficient, are emitting significant amounts of high energy violet-blue light. Some of the light manufactures, viz. those of compact fluorescent lights or CFLs, are already using double glass cover layers (envelopes) around the bulbs, which only "cut" the UV fraction of the emitted light, but do not filter the violet-blue fraction. Another energy-efficient light source are the light-emitting diodes or LEDs, which are quickly becoming very popular for indoor and outdoor lighting due to their "efficiency"—they use 85% less energy than the traditional bulbs and can last up-to 10 years. In the EU by law, by 2016, traditional incandescent light sources will be replaced, and LEDs may become the major light sources. In 2014, traditional incandescent light sources were banned in USA. For comparative purposes, approx. 26% of the light from the popular CFLs is in the violet-blue portion of the spectrum, and approx. 35% of the radiation from the energy-efficient cool white LEDs is violet-blue. The conventional incandescent lamps emitted very little violet-blue light (about 3%). In addition, the light irradiated from various electronic devices, such as computer monitors, cell phone screens, TV screens, laptop and tablet displays, PDAs, digital and video cameras and so on, also have pronounced violet-blue light fraction. Depending on the backlight source used in the electronic device (LED, or OLED, or quantum dots backlight source), the 400-500 nm light coming from these devices can have negative effects in the users. Increased alertness level, insomnia, eye strain, headaches, blurred vision, fatigue and even some serious diseases, among others, have been noticed and reported for the users of electronic devices. The origin of these undesirable effects have been associated to disturbed circadian rhythms, which is mostly affected by the blue light fraction emitted from these devices. Also, many smartphones may use white LEDs, while others may use OLEDs as a backlight. Regardless of what type of device it is—laptop, tablet, cell phone, TV screen, camera, or video game—all of these products have a significant emission peak in 450-500 nm. Moreover, the statistics shows that people spend in average 9 hours in front of some kind of screen/display during the day which emits these light wavelengths.

While certain embodiments and formulations refer to the ability to block or absorb some percentage of HEV light, the compositions may also be effective against the harmful effects of IR radiation. It is known that IR light can also generate ROS in the skin, which may result from the heating effects from the IR radiation. The compositions described herein can also be used to reduce the ROS generated by the IR portion of the incident light (if any) due to the existence of oils, extracts, antioxidants and other components in the compositions.

In certain instances, the compositions described herein may be added topically to cells. For example, the compositions can be applied to external animal cells, e.g., external mammalian cells, such as, for example, the dermis, nails, hair, fur and other external cells of mammals which can be exposed to visible light. While the efficacy of certain illustrative formulations are tested below using fish embryos, other studies have shown that results obtained from fish embryo testing are similar to results obtained from human cell testing. See, for example, Wenjau Lee et al Ecotoxicology and Environmental Safety 108 (2014) 187-194 and Takako YASUDA et al J. Radiat. Res., 47, 295-303 (2006).

The compositions described herein can be particularly effective at absorbing HEV light when applied to the skin, hair or nails of animals including mammals and non-mammals. For example, the compositions may be applied to those mammals in the genera *Afrosoricida, Artiodactyla, Carnivora, Cetacea, Chiroptera, Cingulata, Dasyuromorphia, Dermoptera, Didelphimorphia, Diprotodontia, Eulipotyphla, Hyracoidea, Lagomorpha, Macroscelidea, Microbiotheria, Monotremata, Notoryctemorphia, Paucituberculata, Peramelemorphia, Perissodactyla, Pholidota, Pilosa,* Primates such as *Homo, Proboscidea, Rodentia, Scandentia, Sirenia,* and *Tubulidentata.* In certain instances, the compositions may be particularly desirable for use on the hair, skin and nails of human species, equine species, canine species, porcine species, bovine species, feline species and other animals commonly found in zoological settings or encountered in veterinary practices, e.g., dogs, cats, horses, cattle, pigs, rodents, etc.

In certain examples, the skin is the largest organ of the body, and its main role is to act as a barrier and protect the internal organs against the deleterious effects of various harmful substances, predominantly environmental pollutants and solar ultraviolet (UV) radiation. UV radiation has been proven to be harmful for humans and animals. The skin is made up of several different layers, each with particular properties and function. The major layers are the epidermis and the dermis. The dominant cell type of the epidermis is the keratinocytes, which account for more than 90% of the cells in the epidermal layer. Among the many environmental factors, the exposure of the skin to solar radiation is a key factor in the initiation of various skin disorders, such as wrinkling, hypopigmentation and hyperpigmentation, as well as skin cancer. Statistically, the average annual UV dose that an average American receives in a year is about 2.5-3.3 $J/cm^2$ with an additional exposure of about 0.8 $J/cm^2$ during a vacation period. Sunlight is a major source of UV radiation, which consists of: long-wave UVA (320-400 nm), mid-wave UVB (290-320 nm), and short-wave UVC (200-290 nm). The UV spectrum which reaches the surface of the Earth consists of approximately 5% UVB and 95% UVA. Most of the UVC fraction of solar UV spectrum is blocked by the Earth's stratospheric ozone layer. However, the UV fraction from the sun constitutes only 5% of the electromagnetic spectrum that reaches the Earth's surface, while about 50% of the solar radiation reaching the Earth is the visible light. Shorter wavelength visible light (violet, indigo, blue) is the most energetic part of the visible portion and the most detrimental for the skin, hair and nails. This light can result in photoaging, generation of reactive oxygen species or reactive nitrogen species, oxidative damage and potentially immune suppression and nucleic acid damage. UVA radiation can penetrate deeper into the epidermis and dermis of the skin compared to the UVB radiation. Extensive exposure of the skin to UVA can lead to benign tumor formation. In particular, exposure of the skin to UVA induces the generation of singlet oxygen and hydroxyl free radicals, which can cause damage to cellular macromolecules, such as proteins, lipids, and DNA. UVA-induced oxidative stress can enhance the process of photo-aging in the form of skin sagging and wrinkling and also can suppress some immunological functions. UVB radiations are mutagenic and carcinogenic in nature and are responsible for a variety of skin diseases. UVB radiation can penetrate inside the epidermis of the skin and can induce oxidative stress, immunosuppression, DNA damage, premature aging of the skin and skin cancers including the melanoma and non-melanoma.

Skin cancer, including melanoma and non-melanoma, represents a major public health problem as the incidence of skin cancer is equivalent to the incidence of cancers in all other organs combined. The chronic exposure of the skin to solar ultraviolet (UV) radiation is a major etiologic factor for initiation of skin cancers. Skin cancers are by far the most common malignancy of humans, particularly in the white population, with over a million cases detected each year. Skin cancers are named according to the cell from which they arise and the clinical behavior. The three commonest types are basal cell carcinomas (BCCs), and squamous cell carcinomas (SCCs) (both also referred as non-melanocytic skin cancers—NMSC) and cutaneous malignant melanomas (CMs) (also known as malignant melanoma of the skin or melanoma). U.S. estimates consider that approximately 1 in 5 Americans will develop skin cancer. They account for nearly 15 thousand deaths and more than three billion dollars per year in medical costs in the U.S.A. [M. C. F. Simoes et al., Skin cancer and new treatment perspectives: A review, Cancer Letters, 2014].

A widely accepted action of UVA radiation is production of reactive oxygen and nitrogen species (radicals) resulting in damage to DNA, lipids and proteins. In particular, exposure to UV irradiation due to energy absorption of UV photons and consequent generation of reactive oxygen species (ROS) lead to alterations of skin cells, which contribute to clinical manifestations such as wrinkle formation, laxity, leathery appearance, fragility, impaired wound healing and higher vulnerability.

The light effects on the skin are largely dependent on the type of light (i.e. the amount and intensity of light or total energy), and the stage at which the cells on the skin are in during their normal division and renewal process. The light can produce a number of effects within the cell including specific types of DNA damage in skin cells and, with extreme high energy light exposure, cell death. Some of these types of oxidative DNA and nucleotide damage, and failure of the cells to repair this damage can prompt cells to mutate, leading to the development of skin cancers. Also, Sun exposure that doesn't result in burning may still damage the skin cells. Research suggests that regular exposure to UV radiation year after year can also lead to skin cancer.

The exposure to sunlight leads to a series of biochemical events. As a primary reaction, light of an appropriate wavelength interacts with a suitable chromophore(s) in the skin. Many chromophores capable of absorbing UV light in the skin exist, but DNA and urocanic acid have been identified as being biologically important; the first leading to UV-induced DNA mutations. Also, skin chromophores, e.g., melanin, riboflavin, bilirubin, protoporphyrin IX, oxyhemoglobin, etc., exist which absorb light in the violet-blue visible part of the spectrum. The chromophore upon exposure may be directly damaged or might act as a photosensitizer for subsequent reactions. Moreover, photo-oxidative processes are initiated in the presence of oxygen which is found in all light-exposed tissues.

In certain embodiments, exposure of the skin to visible light, e.g., violet-blue visible light, can also have very similar effects on the skin like the effects caused by UVA radiation [M. M. Kleinpenning et al., Clinical and histological effects of blue light on normal skin, Photodermatology, Photoimmunology & Photomedicine, 26, 16-21, 2010]. Violet-blue light (400-500 nm), in particular, penetrates deeper than UVA through the dermis into the sub-dermis, the follicles of the scalp, the circulation vessels and the lymphatic vessels. For instance, light with wavelength of 400 nm penetrates 250 µm in the skin compared to 100 µm skin penetration by UV light at 300 nm. 50% of skin aging has been attributed to the effects of visible light. Violet-blue light part of the solar spectrum promotes the DNA damage via free radical and reactive oxygen species, displays toxic effects and can induce cellular dysfunction and cell death. This light also promotes degradation of collagen and elastin resulting in the formation of glycation wrinkles and advances premature aging. It also generates uneven pigmentation through lipid peroxidation forming lipofuscin age spots.

For example, the visible blue light spectrum ranges from 400 nm to 475 nm, peaking at 420 nm. Various biological effects have been shown to be exerted by visible light wavelengths (400-700 nm), including erythema, pigmentation and generation of reactive oxygen species. Due to the sequential position along the electromagnetic radiation (EMR) spectrum, blue light (400-475 nm) biological effects could be theoretically compared to the UVA ones. [G. Monfrecola et al., The effect of visible blue light on the differentiation of dendritic cells in vitro, Biochimie 101 (2014) 252-255].

Visible light was found to be genotoxic on human keratinocytes and CHO cells through oxidative stress mechanisms similar to the ones induced by UVA radiation. The level of DNA breakage induced by visible light was 50% of the one generated by UVA/visible irradiation. However, UVA radiations were 10 times more effective than visible radiations to produce DNA single-strand breaks (SSB). [C. Botta et al., Genotoxicity of visible light (400-800 nm) and photoprotection assessment of ectoin, L.-ergothioneine and mannitol and four sunscreens, Journal of Photochemistry and Photobiology B: Biology 91 (2008) 24-34]. Solar radiation gives rise to DNA damage in mammalian cells not only directly by excitation of DNA, which generates predominantly pyrimidine dimers, but also indirectly by the excitation of endogenous photosensitizers, which causes oxidative DNA modifications. These results indicate that oxidative damage generated by endogenous photosensitizers in mammalian cells is genotoxic. The relative contribution of this type of damage to the adverse effects of solar radiation could be significant for repeated irradiations at low doses, in deeper layers of the skin and in cells defective in the repair of oxidative DNA damage. [S. Hoffmann-D¨orr et al., Visible light (>395 nm) causes micronuclei formation in mammalian cells without generation of cyclobutane pyrimidine dimers, Mutation Research 572 (2005) 142-149].

In contrast to ultraviolet and infrared irradiation, which are known to facilitate cutaneous photoaging, immunosuppression, or tumor emergence due to formation of free radicals and reactive oxygen species, potentially similar effects of visible light on the human skin are still poorly characterized. The dose-dependent significant degradation of carotenoids was measured to be 13.5% and 21.2% directly after irradiation at 50 J/cm2 and 100 J/cm2. The degradation of cutaneous carotenoids indirectly shows the amount of generated free radicals and especially reactive oxygen species in human skin. In all volunteers the cutaneous carotenoid concentration dropped down in a manner similar to that caused by the infrared or ultraviolet irradiations, leading to the conclusion that also blue-violet light at high doses could represent a comparably adverse factor for human skin. This study demonstrated that visible blue-violet light also induces free radicals in human skin in vivo. [S. Vandersee et al. Blue-Violet Light Irradiation Dose Dependently Decreases Carotenoids in Human Skin, Which Indicates the Generation of Free Radicals, Oxidative Medicine and Cellular Longevity, 2015, Article ID 579675].

Energy from the shorter-wavelength UVB is absorbed in greater amounts by the epidermis and by keratinocyte DNA, compared with the energy from UVA, which penetrates more deeply into the dermal layers of the skin. Visible and IR light wavelengths penetrate deep into the dermis and have been thought to, following absorption, only produce heat. In contrast to the extensive research on the damaging effect of UV, few studies have looked at the effects of visible light on skin. Daily skin exposure to solar radiation causes cells to produce reactive oxygen species (ROS), which are a primary factor in skin damage. Irradiation of human skin equivalents with visible light induced production of ROS, pro-inflammatory cytokines, and matrix metalloproteinase (MMP)-1 expression. It was found in this study that antioxidants reduce the ROS, cytokine, and MMP production induced by visible light. A 50 J/cm2 dose at 150 mW/cm2 of visible light was able to significantly increase the amount of free radicals by 85.8% over baseline measurements. The addition of antioxidants to the sunscreen was able to significantly reduce the free radicals by 54%. These results are consistent with the in vitro ROS results and clearly demonstrate that visible light exposure induces free-radical production in the skin. The findings suggest that other portions of the solar spectrum aside from UV, particularly visible light, may also contribute to signs of premature photoaging in skin. Thus, even though visible light photons are less energetic than UV photons, due to the deeper dermal penetration visible light may still have a substantial effect on skin. Taken together, these results demonstrate that visible light exposure can induce ROS, which can lead to the release of pro-inflammatory cytokines and MMPs in the skin, similar to the effects of UV, and therefore visible light may contribute to the signs of premature aging in the skin. [F. Liebel et al., Irradiation of Skin with Visible Light Induces Reactive Oxygen Species and Matrix-Degrading Enzymes, Journal of Investigative Dermatology (2012) 132, 1901-1907]

Irradiation of skin cells with visible light, in doses comparable to 15-90 min of sunlight exposure, elicited a skin response similar to that induced by UV radiation, i.e., inflammation, ROS production, and the release of matrix-degrading enzymes. 8-oxo-guanosin formation was found by Kielbassa et al. after irradiation of Chinese hamster cells with visible light. Maximum DNA damage occurred between 400 and 450 nm. More research is needed to investigate the exact contribution of visible light to DNA damage as most of the earlier studies were carried out with mixtures of UV and visible radiation. [L. Kolbe, How Much Sun Protection Is Needed?: Are We on the Way To Full-Spectrum Protection?, The Journal of Investigative Dermatology (2012), Volume 132, 1756-1757]

The damage of human skin by solar radiation is not caused by UV light only. One study found that irradiation with blue light (410, 420 nm) led to intracellular oxidative stress and toxic effects in a dose and wavelength dependent manner. No toxicity was observed using light at 453 nm and 480 nm. Furthermore, blue light (410, 420, 453 nm) at low doses reduced the anti-oxidative capacity of fibroblasts. At non-toxic doses, irradiations at 410, 420 and 453 nm reduced proliferation indicating a higher susceptibility of proliferating fibroblasts to blue light. The results showed that blue light at different wavelengths may induce varying degrees of intracellular oxidative stress with different physiological outcome, which could contribute to premature skin photoaging. A significant increase of intracellular oxidants in blue light exposed cells was observed with 410 nm and 420 nm in comparison to the control, whereas irradiation with 453 nm and 480 nm showed no significant effect. Blue light induced cell toxicity at 410 nm and 420 nm is partly caused by generation of singlet oxygen. [C. Opländer et al., Effects of blue light irradiation on human dermal fibroblasts, Journal of Photochemistry and Photobiology B: Biology 103 (2011) 118-125].

To induce biological activity, light must be absorbed by certain molecules (photoacceptors), transforming them to an excited state; the molecules then affect secondary targets inside the cell, transducing the light signal into a molecular Response. In addition, it has been shown that UVA light is capable of releasing bioactive nitric oxide (NO) from nitrite and nitrosated proteins found in high concentrations in the human skin, which makes these classes of molecules photoacceptors as well. Irradiation with wavelengths of 412, 419, and 426 nm at high fluences (66-100 J/cm2) and 453 nm wavelength at very high fluences (4500 J/cm2) was found to be cytotoxic for skin-derived endothelial cells, as well as keratinocytes. The shorter the wavelength, the more harm on living cells was observed. Also, the endothelial cells suffered in a greater extent than the keratinocytes. [J. Liebmann et al., Blue-Light Irradiation Regulates Proliferation and Differentiation in Human Skin Cells, Journal of Investigative Dermatology (2010) 130, 259-269]

Experimental evidence suggests that the creation of free radicals—mainly reactive oxygen species (ROS)—is the common photobiological answer to the skin-sunlight interaction. The free radical action spectrum (wavelength dependency) for ultraviolet and visible light (280-700 nm) has been determined by quantitative ESR spectroscopy. Visible light produces around 50% of the total oxidative stress caused by sunlight. Reactive species like *O, *OH and *CHR are generated by visible light. The amount of ROS correlates with the visible light intensity (illuminance). It was also demonstrated the creation of excess free radicals by near-infrared light (NIR, 700-1600 nm). Free radical generation does not depend exclusively on the NIR irradiance, but also on the NIR initiated skin temperature increase. The temperature dependence follows the physiological fever curve. The results indicate that the complex biological system skin creates the same type of free radicals over the entire active solar spectrum. This general response will make it possible to define the beneficial or deleterious action of sunlight on human skin by introduction of a free radical threshold value. [L. Zastrow et al., UV, visible and infrared light. Which wavelengths produce oxidative stress in human skin?, Hautarzt, 2009 April; 60(4):310-317].

The recent European recommendation on the efficacy of sunscreen products requests now a minimum ratio of UVA/UVB protection. However, the visible and the infrared (IR) parts of the sun spectrum have received little attention concerning their possible contribution to skin damage. A common biophysical answer for the different wavelengths of the sun spectrum can be found in the creation of excess free radicals—mainly reactive oxygen species (ROS). Thanks to electron spin resonance spectroscopy applied to skin biopsies, it was determined for the first time the free radical action spectrum covering UV and visible light (280-700 nm). Convolution of the action spectrum with sunlight spectral irradiance showed that 50% of the total skin oxidative burden was generated by visible light. Creation of ROS by visible light was experimentally confirmed by varying the illuminance of a spotlight. It was also evidenced the creation of excess free radicals by near-IR radiation. In that case, free radical generation does not depend exclusively on the dose, but also on the skin temperature increase initiated by near-IR light. Some phenomena which are still unclear, such as the question about the deleterious or beneficial role of sunlight, are reviewed, implying the research on new protection strategies for the prevention of skin cancer. [L. Zastrow et al., The missing link—light-induced (280-1,600 nm) free radical formation in human skin, Skin Pharmacol Physiol. 2009; 22(1):31-44].

Visible light can induce cellular dysfunction and cell death both in vitro and in vivo. The violet-blue region (400-500 nm) of the visible spectrum is likely to be particularly important because it has a relatively high energy, can penetrate tissue(s), and is associated with the occurrence of malignant melanoma in animal models. Irradiation of mammalian cells with visible light induces cellular damage primarily via reactive oxygen species (ROS). ROS such as the hydroxyl radical, superoxide anion, and singlet oxygen can be produced when visible light excites cellular photosensitizers. The interaction of these chromophores with light can generate ROS, which in turn can damage lipids, proteins, and DNA. Exposure of lipofuscin-containing cells to visible light caused an increase in both mitochondrial and nuclear DNA lesions compared with non-pigmented cells. We conclude that visible light can cause cell dysfunction through the action of reactive oxygen species on DNA and that this may contribute to cellular aging, age-related pathologies, and tumorigenesis. Our results demonstrate that exposure of non-pigmented epithelial cells to blue light causes mitochondrial dysfunction and mtDNA damage and that such effects are mediated by the action of reactive oxygen species. We have further identified that the ROS primarily responsible for blue light-induced mtDNA damage is the superoxide radical [B. F. Godley et al., Blue Light Induces Mitochondrial DNA Damage and Free Radical Production in Epithelial Cells, THE JOURNAL OF BIOLOGICAL CHEMISTRY Vol. 280, No. 22, Issue of June 3, pp. 21061-21066, 2005].

Radical production by UV (wavelengths>400 nm) and visible components (>400 nm) was −67% and 33% respectively. Radical protection by a four star-rated sunscreen (with UVA protection) was optimal when applied as a thin film, but less so when rubbed into the skin, possibly due to cream filling crevices, which reduced film thickness. Visible light contribution to radical production, and loss of protection when sunscreen is rubbed into skin, has implications for sunscreen design and use for the prevention of free-radical damage. [R. Haywood, Relevance of Sunscreen Application Method, Visible Light and Sunlight Intensity to Free-radical Protection: A Study of ex vivo Human Skin, Photochemistry and Photobiology, 2006, 82: 1123-1131].

Every day, during the day and evening hours, indoors and outdoors, the skin, hair and fur of people and pets are exposed to the danger of the natural and artificial light and are not properly protected. While the windows in residential and office buildings, as well as windshields and side windows in vehicles, partially protect from UV rays, they do not protect from energetic violet-blue portion of the light spectrum. Even staying indoors, humans and pets are not protected from the energetic visible light portion from the sun, which is passing through the windows, as well as from the light coming from certain light sources, such as CFLs and LEDs. Moreover, light emitted from the electronic devices' screens and displays is adding more violet-blue light exposure to our skin, especially to faces and hands.

The cosmetic industry has developed a variety of skin-, hair- and nail-care products claiming to protect from UVB or UVA or both UV portions. Some of the current commercially-available "broad-band" sunscreens claiming to block UVB and UVA light are combining various chemicals to provide the broad spectral coverage. Besides the fact that it was known much earlier that UVA light is the problem, it was not until 2011 that the US Food and Drug Administration (FDA) issued new guidelines mandating that a sunscreen must filter both UVA and UVB radiation in order for manufacturers to put a SPF (sun protection factor) rating on their labels. The newer formulated sunscreens are termed "broad spectrum," as they are now required to filter both UVB and UVA solar rays.

SPF itself is a measurement of sunscreen's effectiveness against UVB rays only and is not related to UVA rays in any way. Moreover, as SPF increases, e.g. above 30, the UVB protection increases insignificantly. Even today, many sunscreens do not protect from UVA rays. But even those which claim that they do protect from UVA—they only protect from short-wave UVA and do not provide protection from the long-wave UVA waves. As mentioned in the text above, UVA is causing significant issues in the skin, most of them leading to premature skin aging, DNA damage etc. Even when a given sunscreen blocks the whole UVA+UVB spectral range, which represents only 5% of the solar radiation, the skin is not protected from the remaining 95% of the Sun light. And the most damaging effects from these 95% are coming from the higher energy violet-blue visible light in the spectrum.

Regarding the current sunscreen compositions, they are made of multiple components. Since each chemical in the sunscreen covers only a specific portion of the electromagnetic spectrum, several chemicals must be combined to provide UVA and UVB to be filtered. This combining chemicals creates diverse problems and reports on the stability of these combinations under Sun are contradictory. Ironically, there are reports that many sunscreen ingredients degrade under the Sun, sometimes in a matter of minutes or hours, and then let the UV radiation penetrates through to the skin. FDA has not proposed requirements for sunscreen stability yet.

Figure 2A:
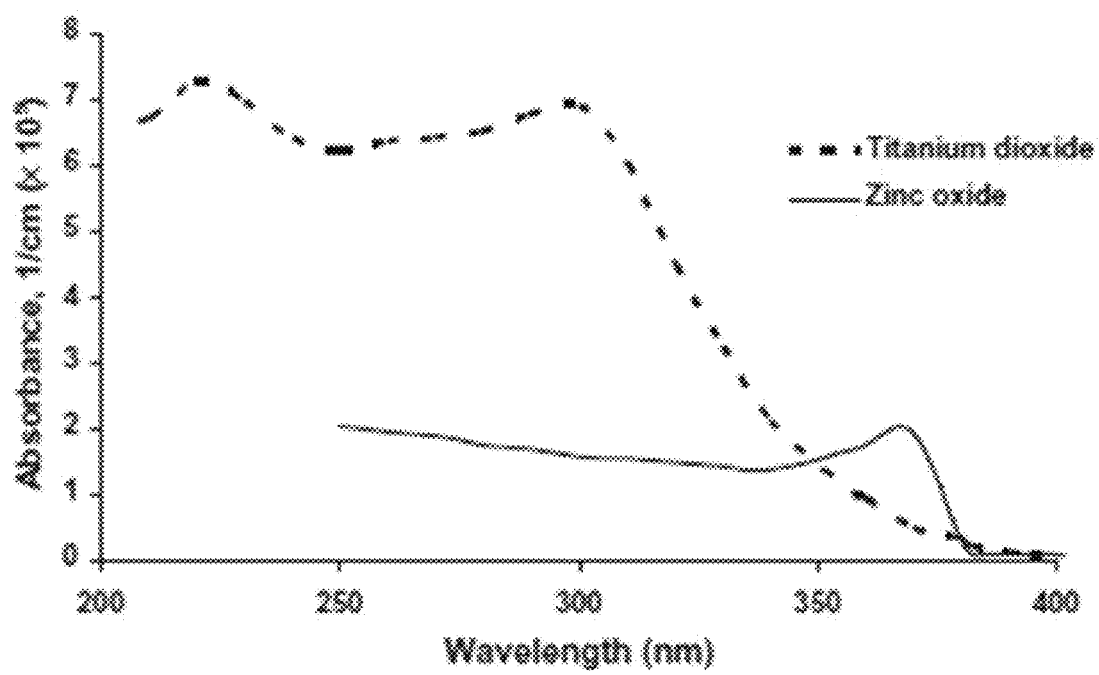
FIG. 2A is a graph showing the absorbance of some conventional sunblock components as a function of wavelength.
Figure 2B:
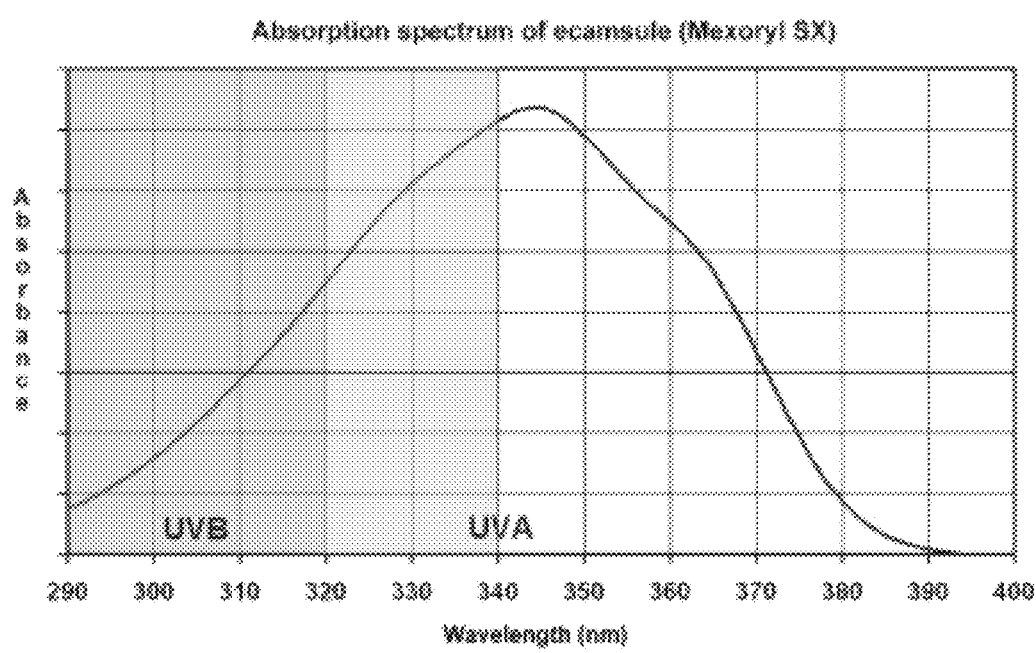
FIG. 2B is a graph showing various the absorbance of certain UV blockers.

Currently, the newer sunscreen formulations use ZnO and TiO2 nanoparticles as physical blockers of UV light. The absorbance spectra of these sunscreens containing physical UV blockers are shown in FIG. 2A [T. G. Smijs and S. Pavel: Titanium dioxide and zinc oxide nanoparticles in sunscreens: focus on their safety and effectiveness, Nanotechnology, Science and Applications, 2011:4 95-112]. Also, chemical UV blockers are used in sunscreens. The absorption spectrum of such chemical UV blocker is shown in FIG. 2B [Fourtanier et al.: Sunscreens containing the broad-spectrum UVA absorber, Mexoryl SX, prevent the cutaneous detrimental effects of UV exposure: a review of clinical study results, Photodermatology, Photoimmunology & Photomedicine 24, 164-174, 2008]. As can be seen from FIG. 2A and FIG. 2B, conventional sunscreens have little or no absorption at wavelengths larger than 380 nm. There is also an increased concern that these sunscreen nanoparticles can be absorbed by the skin and harm the living skin tissues, or can even penetrate deeper in the body. Many contradictory reports regarding this issue can be found in literature. The International Agency for Research on Cancer (IARC) has recently classified TiO2 as an IARC group 2B carcinogen, possibly carcinogenic to humans. The IARC conclusions are based on evidence showing that high concentrations of pigment-grade and ultrafine TiO2 dust cause respiratory tract cancer in rats. ZnO, on the other hand, is by the FDA "generally recognized as safe" when used as a UV filter. Although both the US Environmental Protection Agency and the European Community have taken actions to manage nanoparticle risks, there are still no official safety regulations for using nanoparticles in particular. For instance, it has been reported TiO2 nanoparticles create cellular damage due to the impairment of cell function, as the nanoparticles can cause decreased cell proliferation, decreased mobility, decreased ability to contract collagen, can create oxidative stress, reduce glutathione and increase hydroperoxide levels, kill epidural cells, cross both cell and nuclear membranes, damage DNA and disrupt normal cell division, cross the protective blood-brain barrier, create reactive oxygen species (ROS) that result in brain neuron death, etc.

To-date, there is no skin, hair or nail product that protects from the visible light in 380-500 nm range or the 400-500 nm spectral range. The FDA has approved sunscreen lotions recommended as broad-band (UVA+UVB protection), but there is no any protection from the energetic visible light portion. Therefore, there is a need for a protection in a form of cream, lotion, spray oil and so on, that can be applied easily on the hair, skin and nails and shield them from the harmful violet-blue visible light to which humans and pets are exposed indoors and outdoors.

Many types of free radicals exist, but oxygen-derived radicals, known as Reactive Oxygen Species (ROS) are the most concerning for the skin, and the health, in general. ROS are chemically-reactive molecules derived from oxygen and include superoxide and hydroxyl radicals and non-radical species (e.g. hydrogen peroxide and singlet oxygen).

ROS are generated as secondary products of cellular metabolism, as well as due to induced oxidative stress by external factors, such as solar radiation, pollutants, smoke, etc. ROS can readily react with many molecules including biomolecules, starting a chain reaction of free radical formation. In fact, ROS attack the vital biological molecules, such as lipids, proteins, and DNA. They cause proteins to link together to make skin leathery and they deplete the collagen that makes skin smooth and supple. The damage caused results in wrinkling, age spots, and cancer. A subtraction of a hydrogen atom from a macromolecule, viz. an enzyme, a protein, DNA or a lipid, forming as a result, a new free radical, which will lead to radical intermediate compounds with high toxicity.

The intrinsic aging of skin and other organs suffer from increased oxidative stress by accumulated ROS. Intracellular ROS can be eliminated by multiple antioxidant systems. When there is an overproduction of free radicals (ROS) and cells are not able to neutralize them by their own antioxidant mechanisms, then oxidative stress occurs. Oxidative stress is thought to be involved in the aetiology of a wide variety of diseases, including atherosclerosis, diabetes, neurodegenerative diseases, chronic inflammatory diseases, cancer and in aging.

Oxidative stress in the skin plays a major role in the aging process. This is true for intrinsic aging and even more for extrinsic aging. Although the results are quite different in dermis and epidermis, extrinsic aging is driven to a large extent by oxidative stress caused by Sun UV irradiation, and in the past several years, more and more scientific evidence is suggesting that HEV light is a significant contributor to the oxidative stress, as well.

An imbalance between ROS and the skin's own antioxidant protection mechanisms leads to oxidation of macromolecules, including DNA, lipids, and proteins, resulting in loss of structural and/or functional integrity of key components of the epidermal barrier. It has been shown, in fact, that photoaged skin exhibits high levels of different markers of oxidative stress, including the accumulation of lipid peroxides, glycation end-products, and oxidized proteins.

As one ages, the protective antioxidants found in the different layers of the skin are greatly reduced, leading to pathological effects in the upper and lower layers of the skin. Cross-linked or glycated proteins are classic characteristics of skin aging. Cross-linked proteins in the skin result in stiffening, wrinkling, and the unsightly leathery appearance of the skin with age. The cross-linking of the proteins occurs because of oxidation of some of the amino acids in susceptible proteins such as collagens and elastins. In extreme cases, direct and indirect DNA damage occurs. This oxidation can be prevented (or reduced) by antioxidants, leading to reduced cross-linked protein formation in aged skin.

Oxidative stress is caused by an imbalance between the production of reactive oxygen species (ROS) and the ability of a biological system to eliminate ROS or repair the resulting damage. An imbalance between ROS and the skin's own antioxidant protection mechanisms leads to oxidation of macromolecules, including DNA, lipids, and proteins, resulting in loss of structural and/or functional integrity of key components of the epidermal barrier. It has been shown, in fact, that photoaged skin exhibits high levels of different markers of oxidative stress, including the accumulation of lipid peroxides, glycation end-products, and oxidized proteins.

Human skin is equipped with an array of antioxidants and enzyme systems to protect the cells from damaging effects of ROS including, but not limited to, vitamin C, glutathione, lipoic acid, vitamin E, uric acid, carotenoids, superoxide dismutase, catalase, glutathione peroxidase, glutathione-S-peroxidase, etc. Antioxidant molecules such as vitamin A, vitamin C, and vitamin E slow the process of aging either by preventing free radicals from oxidizing sensitive biological molecules or by reducing the formation of free radicals and quenching the already formed ROS. In addition, enzymes such as superoxide dismutase (SOD), catalase, and glutathione (GSH) biosynthesizing enzymes protect the tissues from free radicals. However, the levels of these antioxidants, as well as antioxidant enzymes, are reduced by age and various environmental stresses, such as Sun exposure, pollutants, smoke, etc.

Endogenous nonenzymatic antioxidants include hydrophobic antioxidants, such as Vitamins A and E that protect the membranes from free radical attack and hydrophilic antioxidants, such as Vitamin C that interacts with free radicals and neutralizes them. Endogenous enzymatic antioxidants include superoxide dismutase (SOD), catalase and glutathione peroxidase.

Exogenous antioxidants can be introduced topically or via diet to mitigate and/or suppress the damage caused by ROS and can be used to complement the endogenous protection against skin damage. These antioxidants (AOs) can be classified as primary and secondary AO. Primary or free radical scavenging antioxidants inhibit oxidation via chain terminating reactions. Examples of primary antioxidant molecules include GSH, vitamin E, and vitamin C. GSH and ascorbic acid are water-soluble antioxidants, whereas vitamin E is membrane-bound and capable of intercepting free radical-mediated chain reactions. They can also regenerate one another, thereby providing synergistic combinations (e.g. vitamin C and vitamin E) when applied topically. Secondary antioxidants are often used in combination with primary antioxidants to yield synergistic stabilization effects. They can regenerate the primary antioxidants and protect them from degradation. In human skin lipoic acid, which is an essential cofactor for many enzyme complexes, can be considered as a secondary antioxidant. With age and environmental influences, the skin's endogenous anti-oxidative system weakens and the production of ROS increases. A study of photoaged skin has shown a significant depletion of antioxidant enzyme expression within the stratum corneum and in the epidermis. An excess of free radicals will perturb cellular metabolism, affect biological macromolecules directly and lead to cell damage, functional impairment, necrosis or apoptosis. Visible signs of such oxidative damage are numerous skin disorders, immunosuppression, premature aging of the skin and development of melanoma and non-melanoma skin cancers.

Well characterized antioxidants that may be useful in the treatment of skin conditions, either cosmetically or therapeutically, include vitamin E, ferulic acid, coenzyme Q10 (ubiquinone), lycopene, curcumin, vitamin C (ascorbic acid), glutathione, green tea, silymarin, resveratrol, grape seeds extract, alpha lipoic acid, genistein and melatonin. Other antioxidants include extracts or pure compounds of coffee, polypodium leucotomes, pomegranate, pycnogenol, dehydroepiandrosterone, selenium, quercetin and rosemarinic acid.

Harman's free radical theory of aging (given in 1956) provides much support for ROS, such as superoxide, hydrogen peroxide and hydroxyl radicals, playing a role in the initiation and progression of the aging process. Therefore, it is well-established that oxidative stress in skin plays a major role in the aging process. This is true for intrinsic aging and even more due to extrinsic aging. Although the results are quite different in dermis and epidermis, extrinsic aging is driven to a large extent by oxidative stress caused by UV irradiation, and in most recent decade, there is an evidence that HEV light can cause oxidative stress and consequences associated with it in similar manner as the UVA radiation.

Intrinsic aging is described as a result of genetic factors and changes that occur during the normal aging process, whereas extrinsic aging focuses on aging process accelerated by environmental influences. It was proposed that only 3% of all aging factors have a genetic background. Aging leads to a thinning of epidermal as well as dermal skin layers. The skin also loses sensibility due to decreased number of nerve-endings. In addition, the skin gets dryer and gradually loses the function to serve as a first barrier against the environment. In contrast, extrinsic aging caused thicker and completely changes its composition. Extrinsic aging is synonymous with photoaging as UV- and HEV-radiation have severe consequences for the exposed skin. However, there are many more environmental factors influencing skin aging, such as pollutants, smoking, chemicals, etc.

In response to the attack of ROS, the skin has developed a complex antioxidant defense system including, among others, the manganese-superoxide dismutase (MnSOD). MnSOD is the mitochondrial enzyme that disposes of superoxide generated by respiratory chain activity. Importantly, an accumulation of oxidatively modified proteins was found specifically within the upper dermis of photoaged skin. Upon acute ultraviolet exposure, depleted catalase expression and increased protein oxidation was reported. Not all skin cells are exposed to the same level of oxidative stress. Superoxide anion levels are much higher in keratinocytes, and keratinocytes display much higher lipid peroxidation level and a lower reduced glutathione/oxidized glutathione ratio. Destruction of collagen is another hallmark of photoaging. The major enzyme responsible for collagen 1 digestion is matrix metallo-proteinase-1 (MMP-1). Skin fibroblasts produce MMP-1 in response to UVB irradiation, and keratinocytes play a major role through an indirect mechanism involving the release of epidermal cytokine after UVB exposure. Furthermore, oxidative stress induces a cellular redox imbalance which has been found to be present in various cancer cells compared with normal cells; the redox imbalance thus may be related to oncogenic stimulation. DNA mutation is a critical step in carcinogenesis and elevated levels of oxidative DNA lesions (8-OH-G) have been noted in various tumors, strongly implicating such damage in the etiology of cancer. It appears that the DNA damage is predominantly linked with the initiation process. The oxidative stress is a problem for the skin cells and the body in general; endogenous as well as exogenous antioxidants could play an important role in decreasing this stress. To protect them from oxidative stress, cells possess multiple anti-oxidative defense systems. Among the enzymatic AOs, superoxide dismutase (SOD) plays a central role in anti-oxidative system. There are three isozymes of SOD: the copper/zinc superoxide dismutase (SOD1) is localized in the cytoplasm; the manganese superoxide dismutase (SOD2) is distributed in the mitochondrial matrix; and the extracellular superoxide dismutase (SOD3) is secreted in extracellular plasma. SOD1-deficiency led to skin atrophy associated with collagen malformation. One study with SOD1-deficient mice showed various aging phenotypes, such as age-related macular degeneration, and skin atrophy accompanied by the degeneration of collagen and elastic fibers, which resembled the physiological aging in humans.

Vitamin E is the generic term for four tocopherols and four tocotrienols. The family of four tocopherols are alpha, beta, gamma, and delta tocopherol and four tocotrienols (alpha, beta, gamma and delta). Normal human epidermis contains 87% alpha-tocopherol, 9% gamma-tocopherol, 3% gamma-tocotrienol and 1% alpha-tocotrienol. Natural sources of vitamin E include vegetables, oils, seeds, nuts, soy, etc. Vitamin E has been used in the healing of wounds of skin, photoprotection such as sunburn, photocarcinogenesis, photoimmunoinhibition, and changes in the dermal matrix i.e. wrinkles. Alpha-tocopherol is quantitatively the most important vitamin E isoform and comprises the bulk of first line free radical defense in the lipid compartment. It removes free radical intermediates and prevents oxidation reactions, by reacting with lipid radicals produced in the lipid peroxidation chain reaction.

Alpha-tocopherol is the name of the most active form of vitamin E in human. It reacts with fatty acid peroxyl radicals, the primary products of lipid peroxidation, intercepting the chain reaction, and shows, in vitro, pro-oxidative effects. Vitamin E benefits are due to the antioxidant properties: it helps to stabilize cell membranes and protects the biological tissues which are more sensitive to oxidation. Vitamin E also protects the skin from deleterious effects due to its exposure to exogeneous toxic agents such as pollutants, chemical and sunrays, preventing the propagation of free-radicals.

A series of studies investigating non-enzymatic stratum corneum antioxidants have demonstrated that vitamin E might be the dominant physiological barrier antioxidant in human skin. There are different benefits of vitamin E on the skin including but not limited to reduction of stretch mark appearance, reduction of age spot appearance, reduction of trans-epidermal water loss, strengthening of the skin, etc., and this is the main reason that it is very popular in numerous skin care products. In the field of skin care, there is a large body of experimental evidence pointing to vitamin E photoprotective effects. A key function of vitamin E is deactivating free radicals with its antioxidant properties. It provides one of its electrons to the electron deficient free radical and makes it more stable. Both, the natural (alcohol form d-a-tocopherol) and the synthetic form (dl-tocopherol acetate), possess antioxidant activity, but the natural form of vitamin E is more readily and effectively absorbed by the skin. The synthetic one does not penetrate the skin's surface well and provides less of the benefits of vitamin E such as antioxidant activity for the skin.

Moreover, recent studies indicate that the use of vitamin E may provide dermatological benefits that surpass the purpose of cosmetics and may extend into an area that has been termed cosmeceuticals. It is known that vitamin E is used in the treatment of aging. In fact, vitamin E helps skin look younger by reducing the appearance of wrinkles and fine lines whose appearance is a natural sign of aging. The antioxidant action of alpha-tocopherol is due to its reaction with fatty acid peroxyl radicals, the primary products of lipid peroxidation to interrupt the chain propagation reaction. The alpha-tocopherol reaction with the peroxyl radical is faster than that of peroxyl radicals with any other compounds. Moreover, alpha-tocopherol removes the radical character from the oxidizing fatty acid preventing further radical reactions and producing a stable radical (tocopheroxyl radical) that, under normal circumstances, it will react with another radical, a tocopheroxyl radical or a fatty acid peroxyl radical, to form stable non-radical products.

Vitamin C is a cofactor for several enzymes participating in the post-translational hydroxylation of collagen, in the biosynthesis of carnitine, in the conversion of the neurotransmitter dopamine to norepinephrine, in peptide amidation and in tyrosine metabolism. The prolonged deprivation of vitamin C generates defects in the post-translational modification of collagen that cause scurvy.

Vitamin C is a water-soluble antioxidant acting as scavenger of the superoxide radical anion, hydrogen peroxide, hydroxyl radical and the singlet oxygen. It contributes to the formation of skin barrier function by enhancing epidermal differentiation. Vitamin C is also required for the production of collagen fibers to maintain connective tissue in its normal state, as necessary for efficient wound healing. It is the most known for its role in preventing scurvy, and has anti-inflammatory activities, as well.

It plays a fundamental role in regenerating vitamin E from the tocopheryl radical, and promotes higher rates of collagen synthesis and cell proliferation in skin fibroblasts, as well as is required for efficient wound healing.

Vitamin C is capable of reducing DNA damage and erythema formation, which is attributed to the scavenging of reactive species generated as a direct or indirect result of exposure to UV radiation. Clinical studies showed that vitamin C increased the synthesis of collagen, reduced facial wrinkles, increased the number of dermal papillae and improved the overall aspect of the skin. Vitamin C displays a skin lightening effect via the inhibition of tyrosinase activity in melanocytes. The effectiveness of topical application of vitamin C is limited due to its reduced stability in aqueous solution and poor penetration of the skin. In recent years, different stable derivatives of ascorbic acid have been synthesized and some have already been employed in a variety of cosmetic and pharmaceutical formulations. To improve stability and increase skin permeation, vitamin C has been formulated in multiple emulsions and microemulsions or encapsulated in micro- and nano-particles.

However, the effectiveness of topical formulations incorporating vitamin C is mainly challenged by its intrinsic lack of stability and its poor penetration of the skin. In recent years, this has prompted efforts to utilize novel delivery systems, as well as to use derivatives of vitamin C.

When vitamin C and vitamin E coexist in the system, they demonstrate synergistic effects. The proposed mechanism of action is that when vitamin E intercepts a radical, thus forming a complex alpha-tocopheroxyl-radical, it can be reduced back to alpha-tocopherol by vitamin C or other agents, thus attenuating the propagation of free radical reactions. Vitamin C prevents the pro-oxidant activity of vitamin E by decreasing the activity of the tocopheroxyl radical to alpha-tocopherol, thereby contributing to increased total antioxidant status and reducing oxidative stress. Moreover, whilst vitamin E protects lipid structures including membranes, vitamin C acts complimentary—protecting the aqueous environment. U.S. Pat. No. 7,897,194B2 describes the synergistic effect of oil mixtures.

A wide variety of plant-derived polyphenols have been reported to possess substantial skin photoprotective effects. Polyphenolic compounds include tannins (gallic acid esters of glucose and other sugars) and phenylpropanoids such as lignins, flavonoids, and condensed tannins. The largest and best studied polyphenols are the flavonoids, which include several thousand compounds, among them the flavonols, flavones, catechins, flavanones, anthocyanidins, and isoflavonoids. Polyphenols can be found in many natural products including fruits, vegetables, nuts, seeds, flowers, and bark. Various studies confirm significant polyphenols' anti-inflammatory, antioxidant and anti-DNA damaging effects. Most of the natural polyphenols are pigments, typically yellow, red or purple, and can absorb UV and partially visible light. Therefore, when applied topically, they can prevent penetration of these light wavelengths into the skin. This ability of natural polyphenols to act as sunscreens can reduce inflammation, oxidative stress and DNA damaging effects of UV radiation in the skin. Thus, the observed photoprotective effects of topically-applied polyphenols are due in part to this sunscreen effect.

Proanthocyanidins are naturally occurring compounds that are widely found in fruits, vegetables, nuts, seeds, flowers and bark. They are a class of phenolic compounds that take the form of oligomers or polymers of polyhydroxy flavan-3-ol units, such as (+)-catechin and (−)-epicatechin. These compounds are mostly found in pine bark, grape seed and red wines. However, bilberry, cranberry, black currant, green tea, black tea, and other plants also contain these flavonoids. The seeds of the grape are particularly rich source of proanthocyanidins, which have been shown to be potent free radical scavengers, and to have anti-inflammatory and anti-carcinogenic activity in cutaneous system. Proanthocyanidins are found in the form of dimers, trimers, and polymerized oligomers of monomeric catechins. Highly effective antioxidant carotenoids are capable of neutralizing singlet oxygen and peroxyradicals, frequently formed during photo-oxidative processes. Pheophytins showed strong anti-oxidant activity. They can prevent oxidative DNA damage and lipid peroxidation both by reducing reactive oxygen species, and by chelation of metal ions, such as Fe(II), which can form reactive oxygen species, as well.

In order to reduce the barrier capability of the stratum corneum, chemical enhancers, physical and electrical methods, can be employed. Chemical enhancers are substances that alter the skin barrier function to permit a faster and better drug permeation through the skin. Many enhancers, such as azone, DMSO, alcohols, fatty acids and terpenes, have been shown to increase permeability by disordering or fluidizing the lipid structure of the stratum corneum. Enhancer molecules can form microcavities within the lipid bilayers hence increasing the diffusion of the drug. In some cases, the enhancers can penetrate into and mix homogeneously with the lipids.

In summary, the skin is an organ with high metabolic activity that is highly exposed to oxidative stress risk due to ROS and sun radiation, and in the recent decades to harmful energy-efficient light sources and electronic displays and screens. Such stress determines modifications of collagen and elastin and pigment accumulation typical of aging, as lipofuscin and ceroids that are formed due to the oxidative polymerization of skin lipids. Besides the premature aging signs, the tumor risk is increased, as well. Moreover, in some cases of sensitive skin types or aged skin or skin exposed to excess environmental insults, the skin's antioxidant defenses are not sufficient to protect against prolonged exposure to Sun rays and other insults. For instance, 30 min of solar ray exposure reduces by 50-60% the skin alpha-tocopherol content. Thus, one reasonable strategy to prevent ROS-mediated damage to the skin would be to support skin's antioxidant defense systems with exogenous antioxidants, as it is an objective of this invention. Besides the necessary essential fatty acid (EFA)-content, the present compositions are rich with cocktails of AOs exhibiting synergistic protection against ROS. A combination of various AOs can show synergism and strengthen the individual antioxidant effects. The presence of only one antioxidant would be much less effective, and in high doses could even cause contrary effects of pro-oxidation. Proper types and ratios of antioxidants in the skin will neutralize the ROS and protect the skin from photodamage.

The compositions described herein can be used in topically-applied formulations, as well as some of them can be further developed to be used as supplements in the diet, i.e. nutricosmetics supplements (Nutricosmetics are nutritional supplements with purpose to support the function and the structure of the skin). Further, certain embodiments described herein are directed to compositions for skin, hair and nail protection from the harmful visible light in the range 380-500 nm range or in the 400-500 nm. Various formulation described herein can protect skin, hair and nails from violet-blue light and may include one or more essential oils, botanical seed oils, vegetable oils, fruit-, leave-, herb- and spice-oils, and others and various combinations thereof, which are rich in saturated, monounsaturated and polyunsaturated fatty acids, various phenolic compounds, hydrocarbons, pigments, carotenoids, phospholipids, various forms of vitamin E (tocopherols), among the other ingredients. Some of these compounds, besides their violet-blue light blocking (filtering) capability, can function as excellent anti-oxidant, anti-microbial and anti-inflammatory agents. In certain instances, the compositions may be effective to absorb substantially all light in the 380-500 nm range or in the 400-500 nm range over an exposure period, e.g., up to about 4-6 hours. For example, the composition may absorb violet-blue light throughout a period where the compositions remain on the skin. While this period may vary depending on the user's activities, the period typically occurs immediately after application of the compositions to the skin and may last up to the composition is absorbed or removed from the skin. In other instances, the compositions need not absorb all the energy in the 380-500 nm range or the 400-500 nm range, but can instead reduce a person's exposure by absorbing some portion of the energy, e.g., 5%, 10%, 20%, 30%, 40%, 50%, 60%, 70%, 80% or 90% of the energy may be absorbed by the compositions.

In certain embodiments, the various components of the formulations may be grouped according to their ability to absorb violet-blue light. For example and referring to FIG. 3, various components of the formulations are shown which are ranked on a three point scale with xxx providing good protection, xx providing moderate protection and x providing weak protection within a particular wavelength range. This same three point scale is used in other figures described below. It may be desirable to combine two, three, four, five or more of these components such that substantial absorbance of light over the 380-500 nm range or 400-500 nm range occurs. As noted in more detail below, various combinations may also provide anti-oxidant protection and can generally reduce of prevent accumulation of reactive oxygen species, radical, etc. within cells.

In certain embodiments, a particular group of oils which provide good light absorbance over 400-500 nm are shown in FIG. 4 and FIG. 5. To provide a formulation which provides protection over the wavelength range from 400-500 nm, it may be desirable to combine two or more of these oils into a single composition. For example, hemp oil provides good absorption (xxx) from 400-440 nm, moderate absorption (xx) from 440-500 nm and moderate protection below 400 nm., and rosehip oil provides good absorption from 400-500 nm, especially around 460 nm range. A composition can be produced comprising both hemp oil and rosehip oil to provide protection from violet-blue light over the entire 400-500 nm range. Even where a single oil may provide good protection by itself from 400-500 nm, it may be desirable to combine the single oil with an additional oil or extract to increase the overall protection against generation of reactive oxygen species, photoaging, etc.

Referring now to FIG. 6, several components are shown which have good protection, e.g., high absorbance, in the 380-400 nm range but have weak (x) or moderate (xx) protection in the 400-440 nm range and no protection in the 440-500 nm range. Any one or more of these oils can be combined with one of the materials from FIG. 5 to provide good protection from 380-500 nm range. As noted herein, conventional sunscreen compositions do not absorb well or at all in the 380-400 nm range.

Figure 5A:
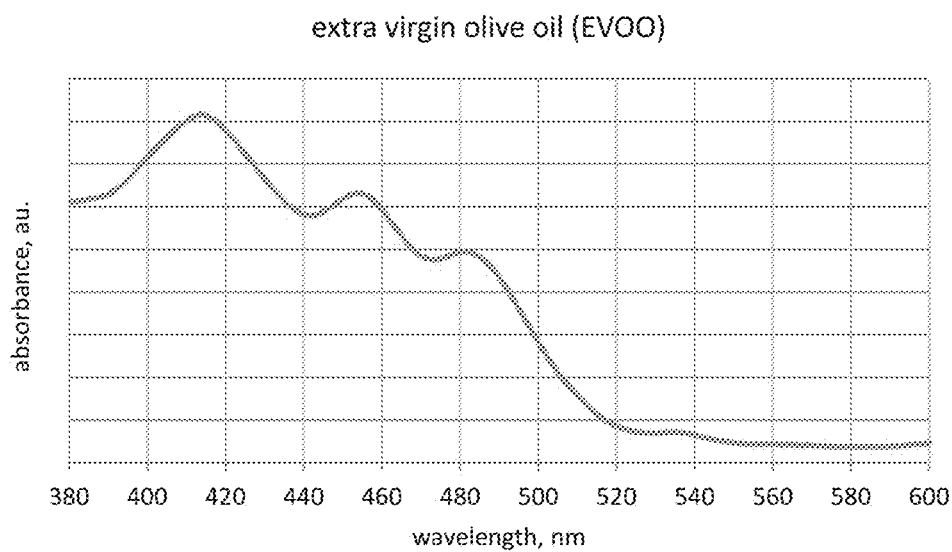
FIGS. 5A-5X are spectra showing the absorbance of various Group A oils at different wavelengths, in accordance with certain embodiments.
Figure 5B:
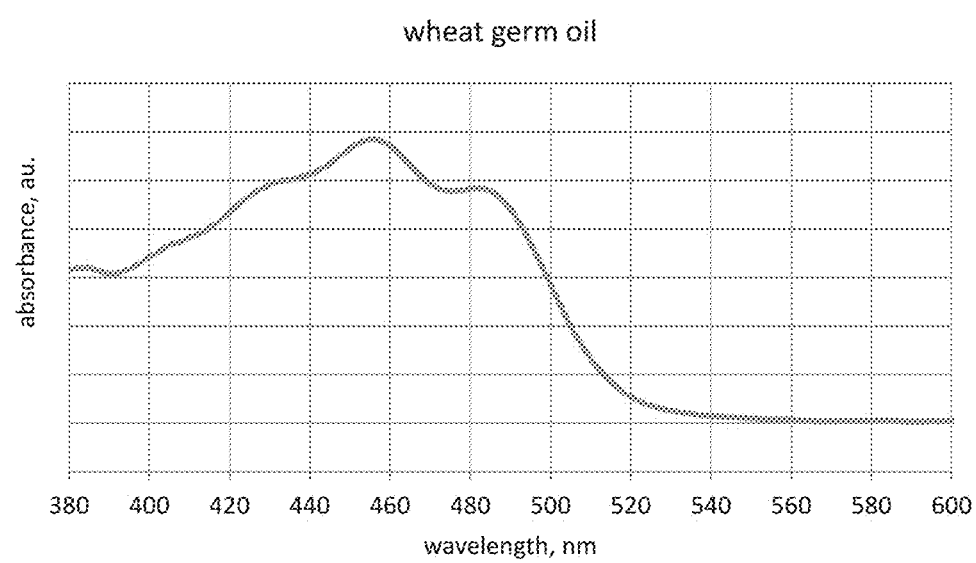
Figure 5C:
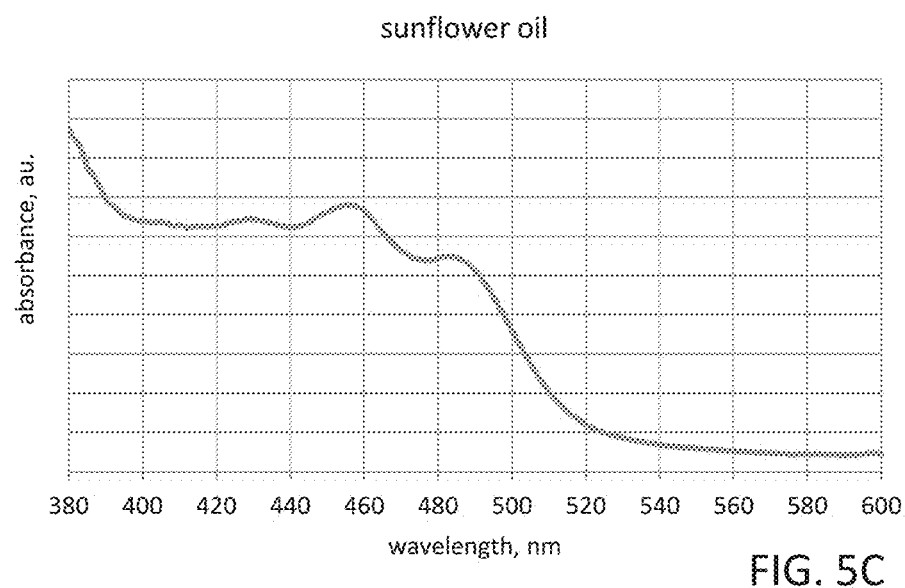
Figure 5D:
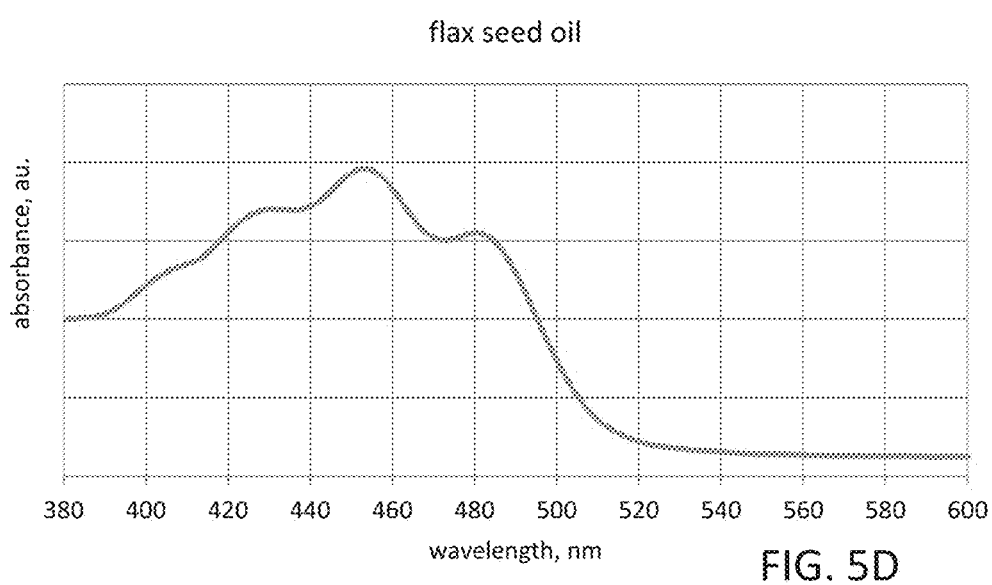
Figure 5E:
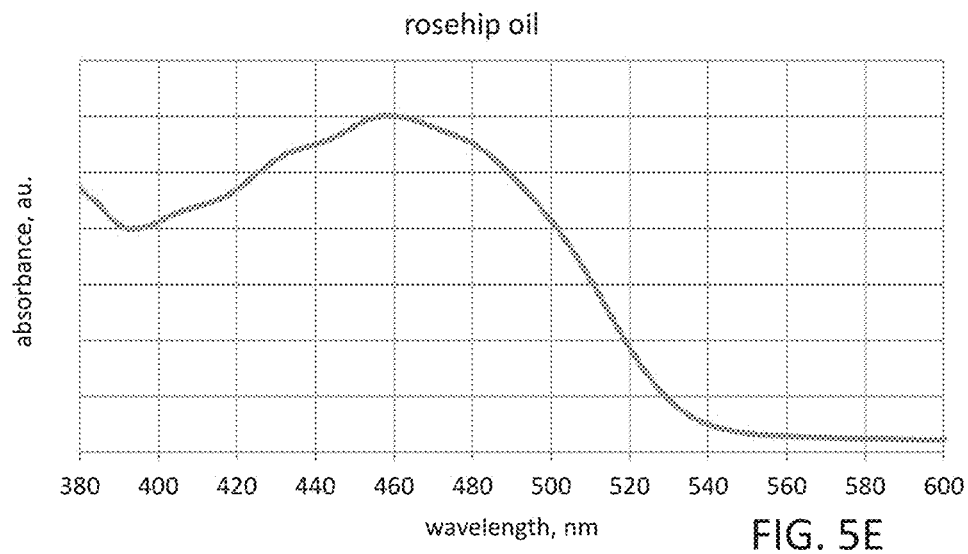
Figure 5F:
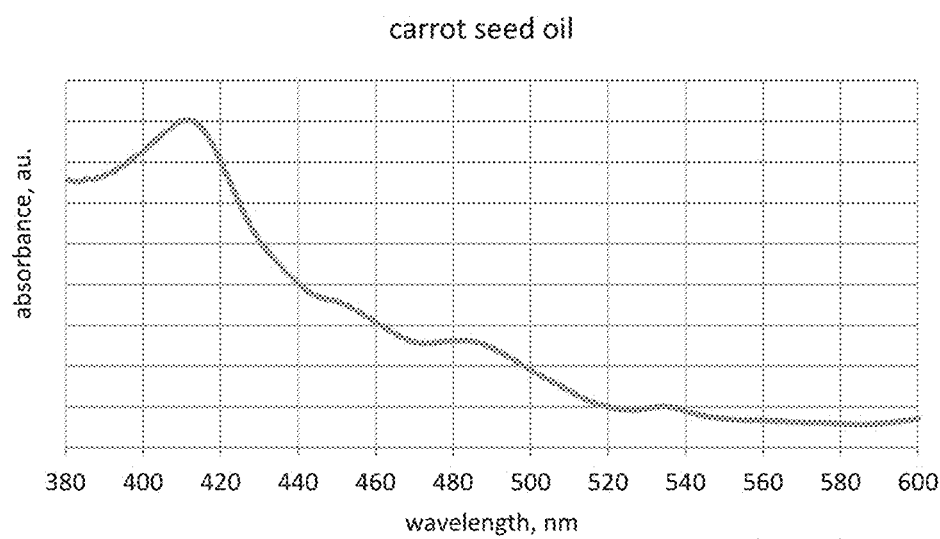
Figure 5G:
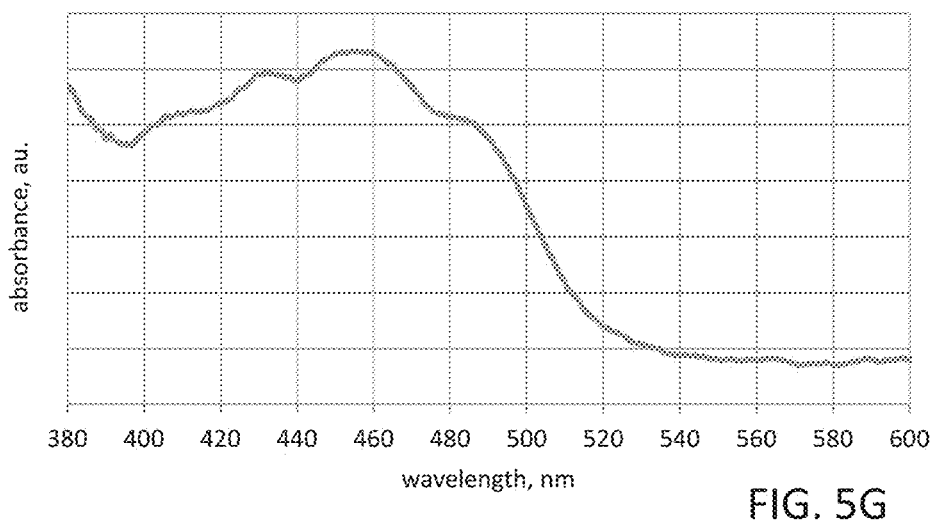
Figure 5H:
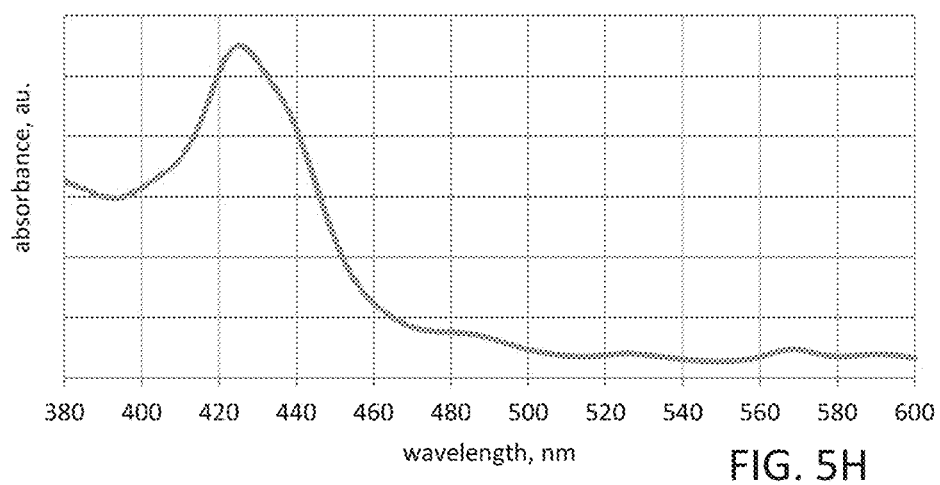
Figure 5I:
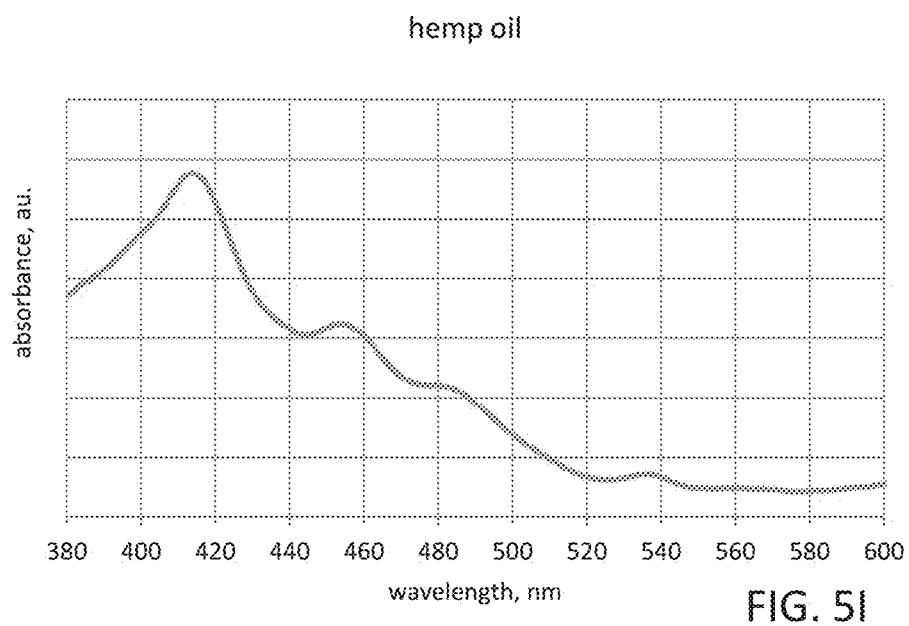
Figure 5J:
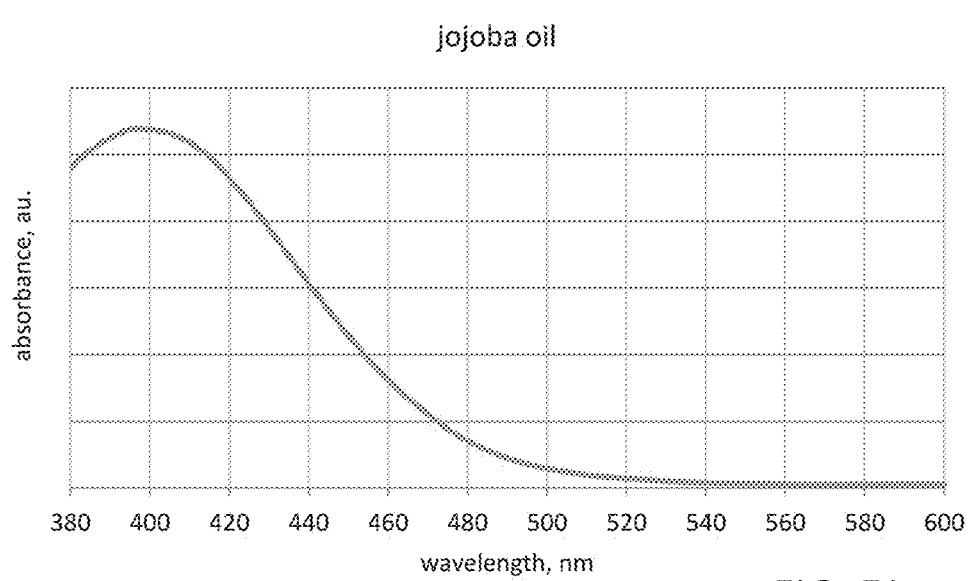
Figure 5K:
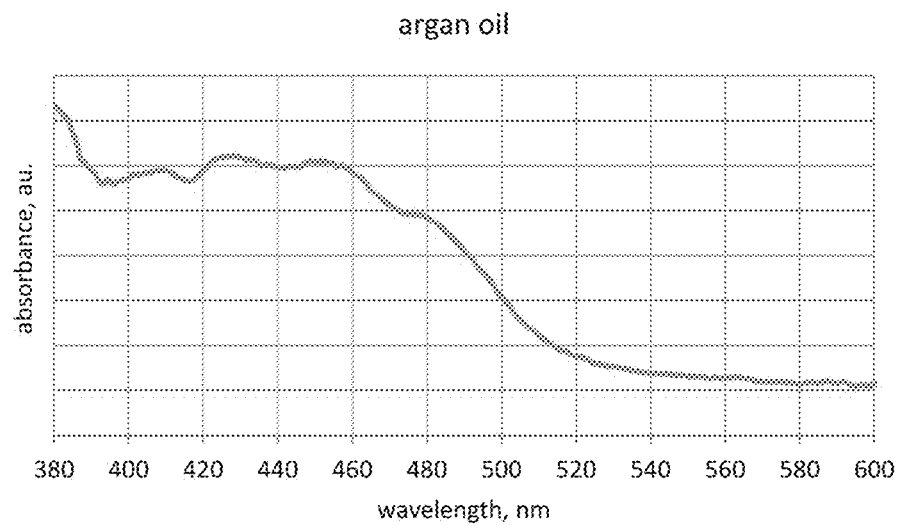
Figure 5L:
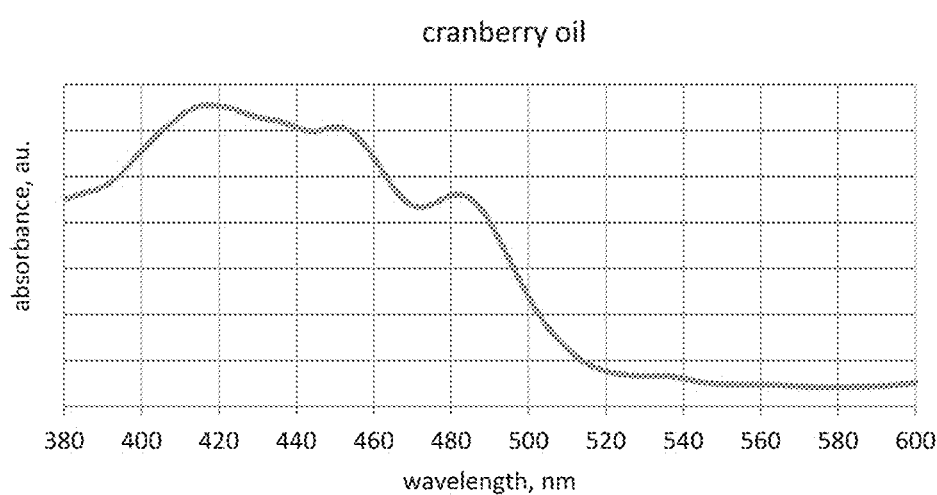
Figure 5M:
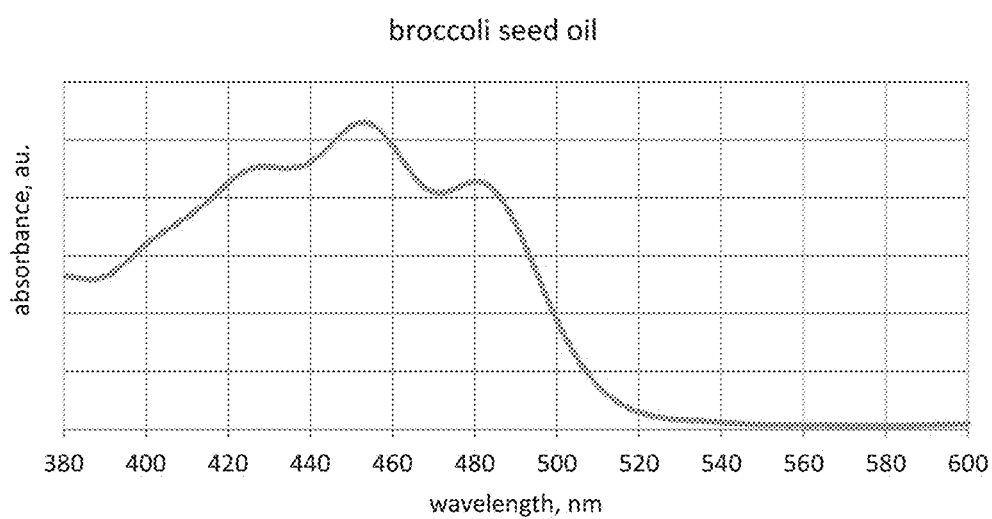
Figure 5N:
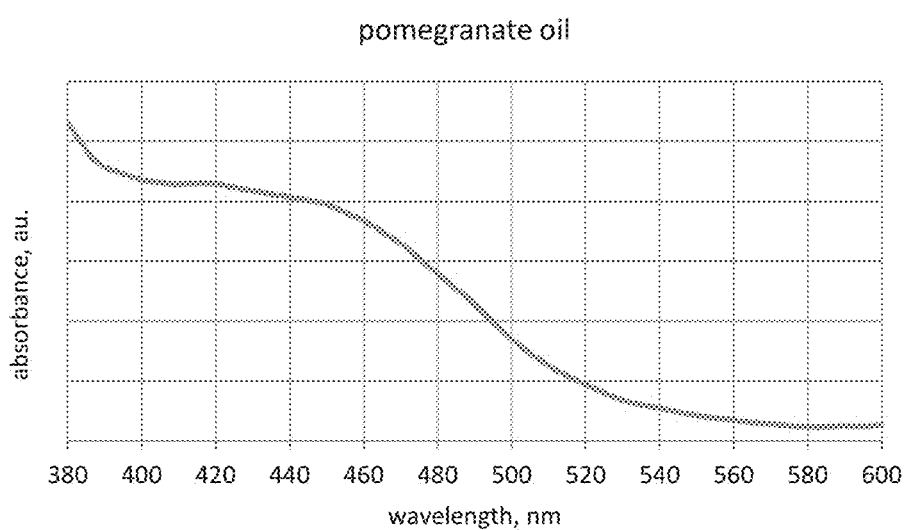
Figure 5O:
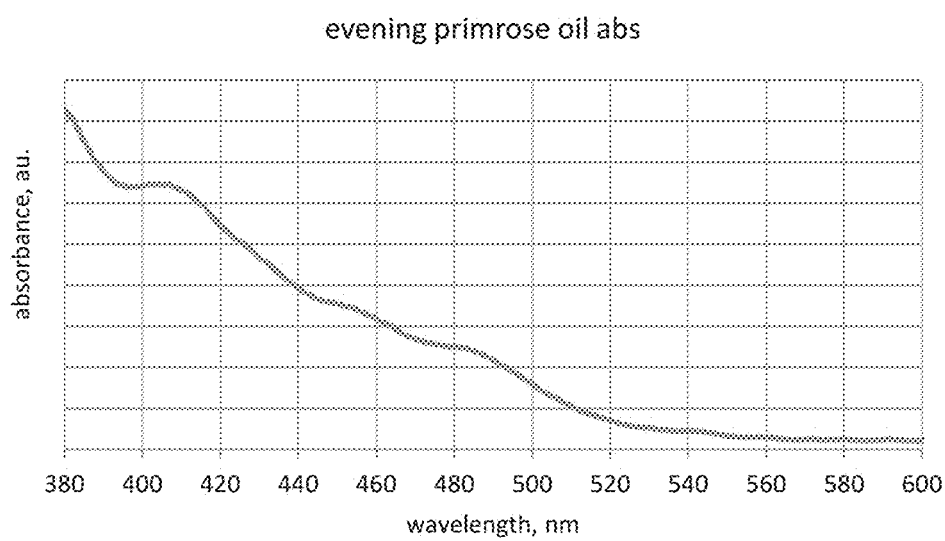
Figure 5P:
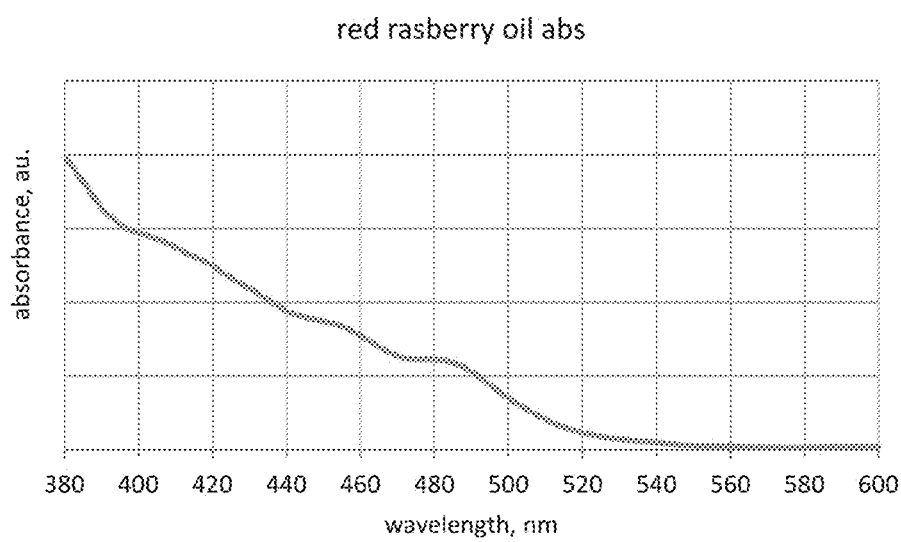
Figure 5Q:
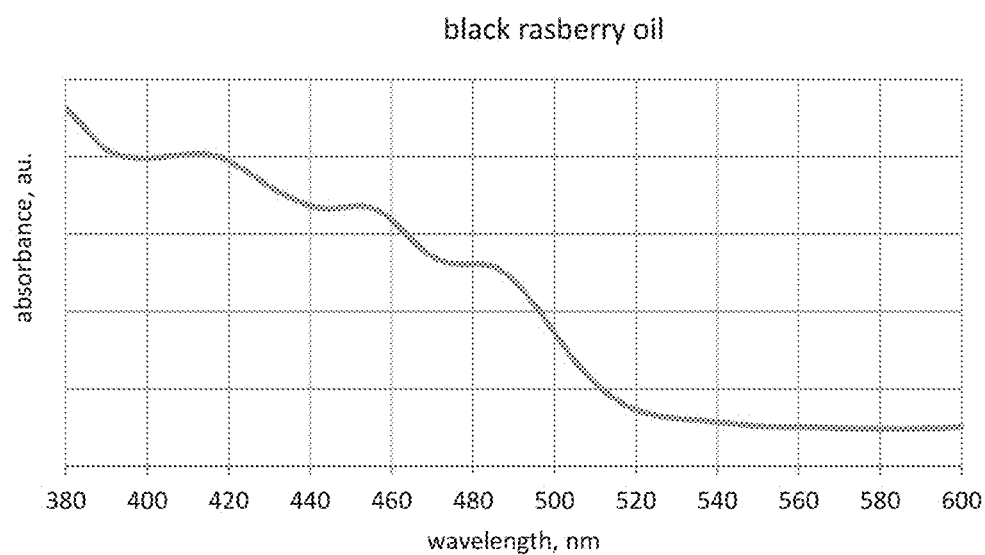
Figure 5R:
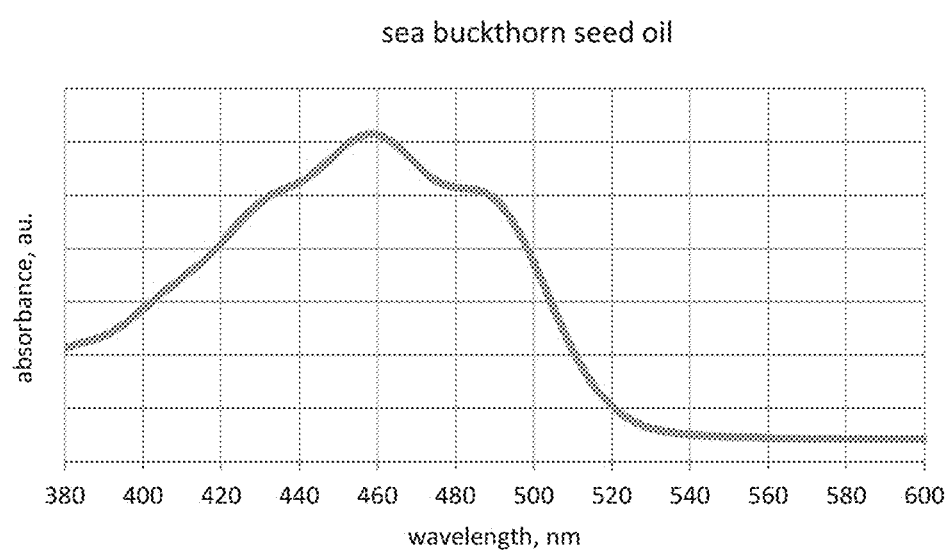
Figure 5S:
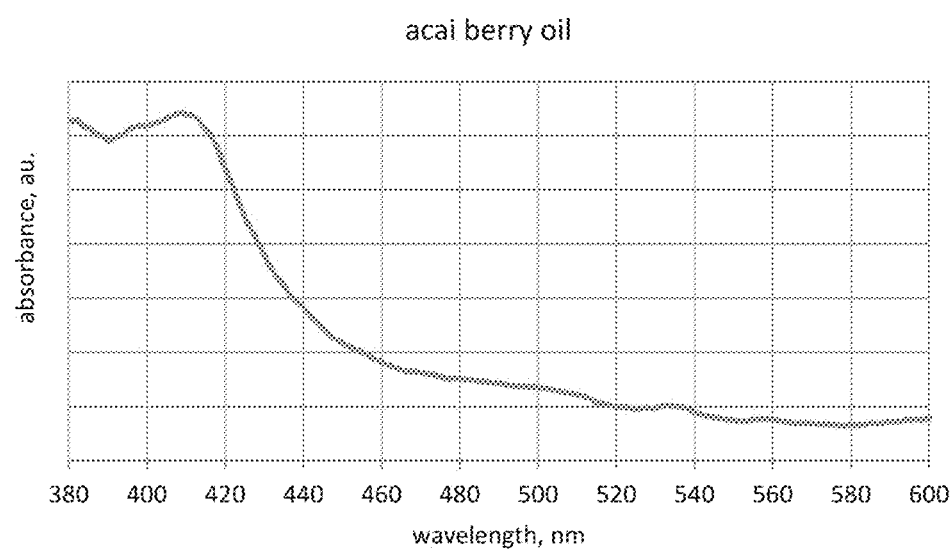
Figure 5T:
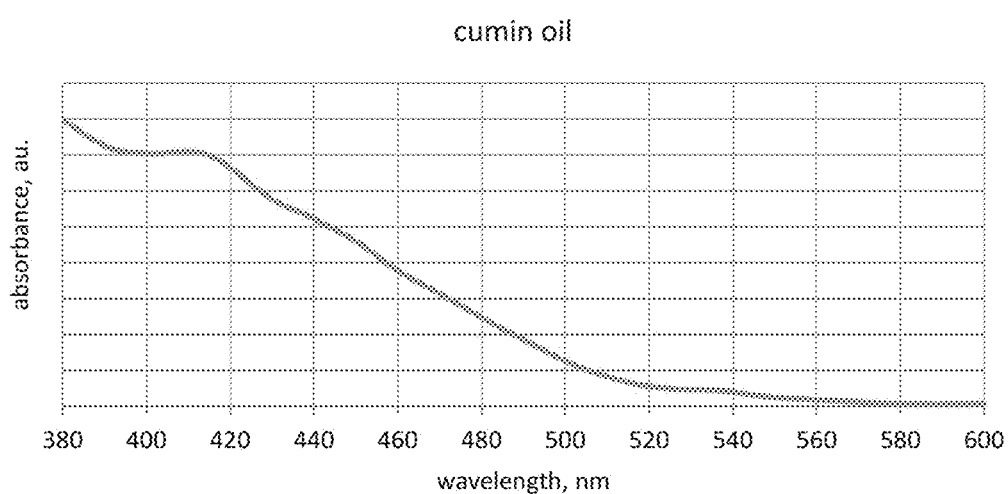
Figure 5U:
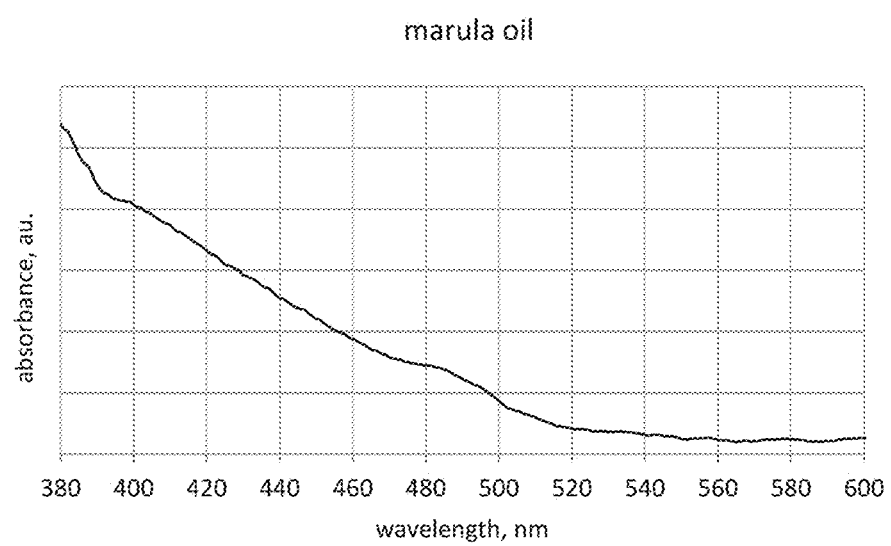
Figure 5V:
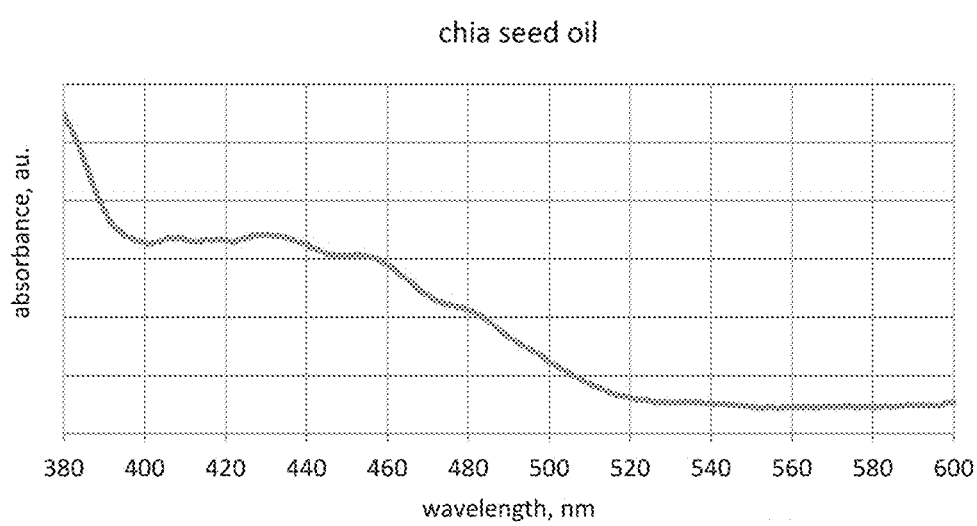
Figure 5W:
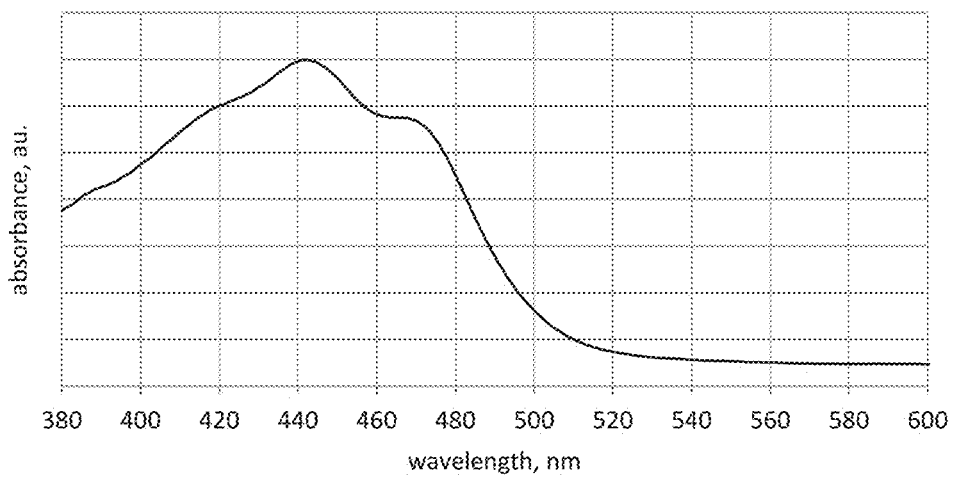
Figure 5X:
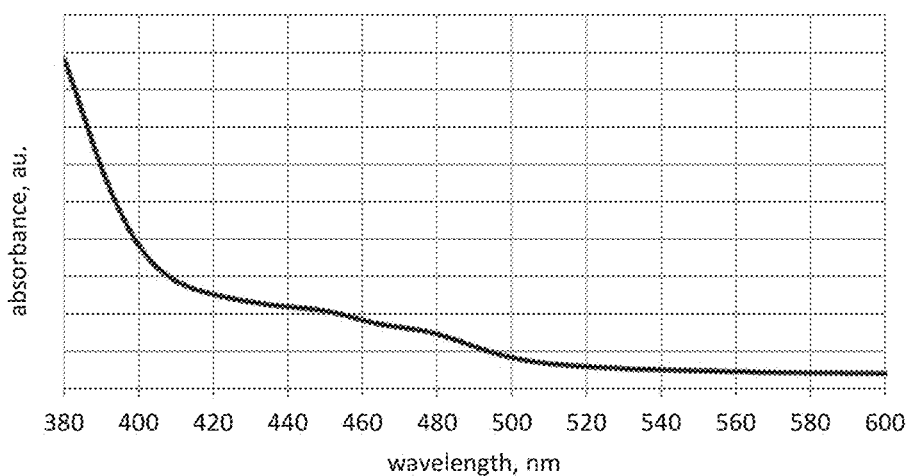

In certain instances, the compositions described herein comprise at least one oil or extract or combination selected from the group consisting of extra virgin olive oil (EVOO), jojoba oil, sesame oil, flax seed (linseed) oil, safflower oil, lavender oil, geranium oil, aloe vera juice and oil, sunflower oil, carrot seed oil, canola oil, palm kernel oil, coconut oil, walnut, almond, peanut and other nut oils, orange oil, lemon oil, pomace olive oil, apricot kernel (seed) oil, grape seed oil and extract, pomace grape seed oil, ylang-ylang oil, cactus fruit oil, sandalwood oil, rosewood oil, clary-sage oil, hydrangea oil, red clover oil, caper oil, soybean oil, clove oil, lily oil, green tea extract and oil, chamomile oil, rose oil, lavandin oil, rosmarin oil, marjoram oil, tea tree oil, pumpkin seed oil, eucalyptus oil, cotton seed oil, corn oil, hemp seed, lanolin oil, sea weed oil, evening primrose oil, tomato seed oil, turmeric oil, ginseng oil, ginger oil, rice bran oil, red raspberry seed oil, black raspberry seed oil, black tea oil, argan oil, lemon grass oil, rosemary oil, rosehip oil, avocado oil, cape jasmine oil, cumin (black seed) oil, peppermint oil, spearmint oil, broccoli seed oil, marula oil, lavender oil, coriander oil, valerian oil, citrus oil, juniper oil, cypress oil, cinnamon bark oil, myrrh oil, cedarwood oil, Helichrysum oil, oregano oil and extract, chaga extract, thyme oil, marigold oil, poppyseed extract and oil, seabuckthorn seed oil and extract, seabuckthorn berry oil and extract, cacao extract, coffee extract, cranberry oil and extract, meadowfoam oil, acai berry oil, goji berry extract, castor oil, borage oil, milk thistle oil and extract, dandelion extract, sugar cane extract, ginko extract, cucumber extract, calendula oil, berry seed extracts, rapeseed oil, Polypodium Leucotomos extract, fernblock extract, beeswax, rhea butter, orange peel, etc. The particular oil and extract amounts in any one composition can be selected to provide an absorption profile that is effective over a particular frequency range. For example, where the composition is designed to absorb light in the 380-500 nm range or 400-500 nm range, suitable amounts of two, three, four, five, six or more oils or extracts or their mixtures can be combined such that a desired absorption profile from 400-500 nm is achieved. The composition can be designed solely of one oil as the major component and may also be combined with one or more "boosters" (FIG. 21) as noted in more detail below. The UV-visible absorbance spectra of selected oils are shown in FIGS. 5A-5X. In the figures, the absorbance spectra represent extra virgin olive oil (FIG. 5A), wheat germ oil (FIG. 5B), sunflower oil (FIG. 5C), flax seed oil, (FIG. 5D), rosehip oil (FIG. 5E), carrot seed oil (FIG. 5F), apricot seed oil (FIG. 5G), pumpkin seed oil (FIG. 5H), hemp oil (FIG. 5I), jojoba oil (FIG. 5J), argan oil (FIG. 5K), cranberry oil (FIG. 5L), broccoli seed oil (FIG. 5M), pomegranate oil (FIG. 5N), evening primrose oil (FIG. 5O), red raspberry oil (FIG. 5P), black raspberry oil (FIG. 5Q), sea buckthorn oil (FIG. 5R), acai berry oil (FIG. 5S), cumin oil (FIG. 5T), marula oil (FIG. 5U), chia seed oil (FIG. 5V), shea butter (FIG. 5W) and bees wax (FIG. 5X). The oils and materials shown in FIGS. 5A-5X are referred to herein as "Group A" oils. As can be seen in these spectra, different Group A oils have peak absorptions of light in the 380-500 nm range. In certain instances, at least one of the Group A oils is present in the compositions described herein. In other instances, at least two different Group A oils are present in the compositions described herein. Where two different Group A oils are present, the oils selected desirably have different peak absorption values to "flatten" out the overall absorbance curve and provide for enhanced HEV protection. In some instances, at least three of the Group A oils are present in the compositions described herein. Where three different Group A oils are present, the oils selected desirably each have different peak absorption values to "flatten" out the overall absorbance curve provided by the combination of three oils. In some instances, the two or three Group A oils which are present are selected to provide at least 50% absorption of light (on average) over the 380-500 nm range or over the 400-500 nm range. As noted below, one or more boosters or enhancers can be used with the two or three Group A oils to provide for enhanced HEV protection and/or one or more of antioxidant protection, antiphotoaging protection or other desired protective effects.

In certain embodiments, the compositions described herein may comprise extra virgin olive oil (EVOO) by itself or in combination with one, two or more other Group A oils. Where EVOO is present by itself or in combination with one, two or more other Group A oils, the compositions desirably comprise a suitable amount of each oil to provide an average absorption of light over the 380-500 nm range or the 400-500 nm range of at least 30%, or at least 50%, or at least 70% or at least 80% over the 380-500 nm range or over the 400-500 nm range.

In other embodiments, the compositions described herein may comprise wheat germ oil by itself or in combination with one, two or more other Group A oils. Where wheat germ oil is present by itself or in combination with one, two or more other Group A oils, the compositions desirably comprise a suitable amount of each oil to provide an average absorption of light over the 380-500 nm range or the 400-500 nm range of at least 30%, or at least 50%, or at least 70% or at least 80%.

In certain embodiments, the compositions described herein may comprise sunflower oil by itself or in combination with one, two or more other Group A oils. Where sunflower oil is present by itself or in combination with one, two or more other Group A oils, the compositions desirably comprise a suitable amount of each oil to provide an average absorption of light over the 380-500 nm range or the 400-500 nm range of at least 30%, or at least 50%, or at least 70% or at least 80%.

In other embodiments, the compositions described herein may comprise flax seed oil by itself or in combination with one, two or more other Group A oils. Where flax seed oil is present by itself or in combination with one, two or more other Group A oils, the compositions desirably comprise a suitable amount of each oil to provide an average absorption of light over the 380-500 nm range or the 400-500 nm range of at least 30%, or at least 50%, or at least 70% or at least 80%.

In certain embodiments, the compositions described herein may comprise rosehip oil by itself or in combination with one, two or more other Group A oils. Where rosehip oil is present by itself or in combination with one, two or more other Group A oils, the compositions desirably comprise a suitable amount of each oil to provide an average absorption of light over the 380-500 nm range or the 400-500 nm range of at least 30%, or at least 50%, or at least 70% or at least 80%.

In other embodiments, the compositions described herein may comprise carrot seed oil by itself or in combination with one, two or more other Group A oils. Where carrot seed oil is present by itself or in combination with one, two or more other Group A oils, the compositions desirably comprise a suitable amount of each oil to provide an average absorption of light over the 380-500 nm range or the 400-500 nm range of at least 30%, or at least 50%, or at least 70% or at least 80%.

In certain embodiments, the compositions described herein may comprise apricot seed oil by itself or in combination with one, two or more other Group A oils. Where apricot seed oil is present by itself or in combination with one, two or more other Group A oils, the compositions desirably comprise a suitable amount of each oil to provide an average absorption of light over the 380-500 nm range or the 400-500 nm range of at least 30%, or at least 50%, or at least 70% or at least 80%.

In other embodiments, the compositions described herein may comprise pumpkin seed oil by itself or in combination with one, two or more other Group A oils. Where pumpkin seed oil is present by itself or in combination with one, two or more other Group A oils, the compositions desirably comprise a suitable amount of each oil to provide an average absorption of light over the 380-500 nm range or the 400-500 nm range of at least 50%, or at least 70% or at least 80%.

In certain embodiments, the compositions described herein may comprise hemp oil by itself or in combination with one, two or more other Group A oils. Where hemp oil is present by itself or in combination with one, two or more other Group A oils, the compositions desirably comprise a suitable amount of each oil to provide an average absorption of light over the 380-500 nm range or the 400-500 nm range of at least 30%, or at least 50%, or at least 70% or at least 80%.

In other embodiments, the compositions described herein may comprise jojoba oil by itself or in combination with one, two or more other Group A oils. Where jojoba oil is present by itself or in combination with one, two or more other Group A oils, the compositions desirably comprise a suitable amount of each oil to provide an average absorption of light over the 380-500 nm range or the 400-500 nm range of at least 30%, or at least 50%, or at least 70% or at least 80%.

In certain embodiments, the compositions described herein may comprise argan oil by itself or in combination with one, two or more other Group A oils. Where argan oil is present by itself or in combination with one, two or more other Group A oils, the compositions desirably comprise a suitable amount of each oil to provide an average absorption of light over the 380-500 nm range or the 400-500 nm range of at least 30%, or at least 50%, or at least 70% or at least 80%.

In other embodiments, the compositions described herein may comprise cranberry oil by itself or in combination with one, two or more other Group A oils. Where cranberry oil is present by itself or in combination with one, two or more other Group A oils, the compositions desirably comprise a suitable amount of each oil to provide an average absorption of light over the 380-500 nm range or the 400-500 nm range of at least 30%, or at least 50%, or at least 70% or at least 80%.

In certain embodiments, the compositions described herein may comprise broccoli seed oil by itself or in combination with one, two or more other Group A oils. Where broccoli oil is present by itself or in combination with one, two or more other Group A oils, the compositions desirably comprise a suitable amount of each oil to provide an average absorption of light over the 380-500 nm range or the 400-500 nm range of at least 30%, or at least 50%, or at least 70% or at least 80%.

In other embodiments, the compositions described herein may comprise pomegranate oil by itself or in combination with one, two or more other Group A oils. Where pomegranate oil is present by itself or in combination with one, two or more other Group A oils, the compositions desirably comprise a suitable amount of each oil to provide an average absorption of light over the 380-500 nm range or the 400-500 nm range of at least 30%, or at least 50%, or at least 70% or at least 80%.

In certain embodiments, the compositions described herein may comprise evening primrose oil by itself or in combination with one, two or more other Group A oils. Where evening primrose oil is present by itself or in combination with one, two or more other Group A oils, the compositions desirably comprise a suitable amount of each oil to provide an average absorption of light over the 380-500 nm range or the 400-500 nm range of at least 30%, or at least 50%, or at least 70% or at least 80%.

In other embodiments, the compositions described herein may comprise red raspberry oil by itself or in combination with one, two or more other Group A oils. Where red raspberry oil is present by itself or in combination with one, two or more other Group A oils, the compositions desirably comprise a suitable amount of each oil to provide an average absorption of light over the 380-500 nm range or the 400-500 nm range of at least 30%, or at least 50%, or at least 70% or at least 80%.

In certain embodiments, the compositions described herein may comprise black raspberry oil by itself or in combination with one, two or more other Group A oils. Where black raspberry oil is present by itself or in combination with one, two or more other Group A oils, the compositions desirably comprise a suitable amount of each oil to provide an average absorption of light over the 380-500 nm range or the 400-500 nm range of at least 30%, or at least 50%, or at least 70% or at least 80%.

In other embodiments, the compositions described herein may comprise sea buckthorn oil by itself or in combination with one, two or more other Group A oils. Where sea buckthorn oil is present by itself or in combination with one, two or more other Group A oils, the compositions desirably comprise a suitable amount of each oil to provide an average absorption of light over the 380-500 nm range or the 400-500 nm range of at least 30%, or at least 50%, or at least 70% or at least 80%.

In certain embodiments, the compositions described herein may comprise acai berry oil by itself or in combination with one, two or more other Group A oils. Where acai berry oil is present by itself or in combination with one, two or more other Group A oils, the compositions desirably comprise a suitable amount of each oil to provide an average absorption of light over the 380-500 nm range or the 400-500 nm range of at least 30%, or at least 50%, or at least 70% or at least 80%.

In other embodiments, the compositions described herein may comprise cumin oil by itself or in combination with one, two or more other Group A oils. Where cumin oil is present by itself or in combination with one, two or more other Group A oils, the compositions desirably comprise a suitable amount of each oil to provide an average absorption of light over the 380-500 nm range or the 400-500 nm range of at least 30%, or at least 50%, or at least 70% or at least 80%.

In certain embodiments, the compositions described herein may comprise marula oil by itself or in combination with one, two or more other Group A oils. Where marula oil is present by itself or in combination with one, two or more other Group A oils, the compositions desirably comprise a suitable amount of each oil to provide an average absorption of light over the 380-500 nm range or the 400-500 nm range of at least 30%, or at least 50%, or at least 70% or at least 80%.

In other embodiments, the compositions described herein may comprise chia seed oil by itself or in combination with one, two or more other Group A oils. Where chia seed oil is present by itself or in combination with one, two or more other Group A oils, the compositions desirably comprise a suitable amount of each oil to provide an average absorption of light over the 380-500 nm range or the 400-500 nm range of at least 30%, or at least 50%, or at least 70% or at least 80%.

In certain embodiments, the compositions described herein may comprise shea butter by itself or in combination with one, two or more other Group A oils. Where shea butter is present by itself or in combination with one, two or more other Group A oils, the compositions desirably comprise a suitable amount of each oil to provide an average absorption of light over the 380-500 nm range or the 400-500 nm range of at least 30%, or at least 50%, or at least 70% or at least 80%.

In other embodiments, the compositions described herein may comprise bees wax by itself or in combination with one, two or more other Group A oils. Where bees wax is present by itself or in combination with one, two or more other Group A oils, the compositions desirably comprise a suitable amount of each oil to provide an average absorption of light over the 380-500 nm range or the 400-500 nm range of at least 30%, or at least 50%, or at least 70% or at least 80%.

Certain specific Group A oils and their beneficial properties are described in more detail below. Plant and seed oils, botanical oils, essential oils and plant extracts are rich with variety of fatty acids (FAs), especially EFAs, vitamins, phenolics and other antioxidants (AOs). However, a single type of oil, seed or extract may or may not provide the "perfect" combination of all the compounds with biologically important functions. Therefore, their mixing may be desired in the final composition to provide a desired ratio of nutrients and "protective compounds" for the skin, and the body in general. Furthermore, using multiple types of AOs can result in super-potent AO-mixtures, where cooperative effects (synergistic effects) have been observed.

When possible, cold-pressed oils are preferred for making the compositions described herein. Cold pressing involves no thermal or chemical treatments and no refining. The cold-pressed oils can be produced from grains (including seeds), fruit, nuts or germs. Cold-pressed oils are free from chemicals associated with the refining processing and the oils contain most of the phytochemicals and natural antioxidants, which sometimes are being destroyed or removed by the chemical treatment refining. The modern technology of producing these oils through cold-pressing using nitrogen atmosphere or supercritical carbon dioxide extraction allows to retain the nutrients almost in an intact state, which is very important for some unstable antioxidant compounds. Cold-pressed oils depending on the source can provide a wide range of bioactive substances, such as tocopherols and tocotrienols, free and esterified sterols, FAs, hydrocarbons (squalene), triterpene alcohols, carotenoids and chlorophylls.

Various specific Group A oils and combinations thereof based on the following description can be produced which provide compositions for skin-, hair- and nail-protection exhibiting HEV light protection, anti-oxidative, anti-inflammatory and anti-aging functionalities.

Sea buckthorn oil is rich in fatty acids, carotenoids, sterols, and vitamins A, C, E, D, K, minerals, fibers and proteins. It contains over 190 valuable nutrients and phytonutrients. Particularly, sea buckthorn seed oil consists of 90% unsaturated fatty acids, including omega 3, 6, 7, and 9 EFAs; it's the only plant source that contains omega 3, 6, 9, and 7 FA. It's a rich source of the elusive essential fatty acid, omega-7—a rare EFA vital acid for collagen production and healthy skin, hair and nails. Omega-7, also known as palmitoleic acid (16:1 n-7 or 9-hexadecenic acid) is very close to human sebum, in chemical profile. The oil content in seeds of sea buckthorn is on average 7-11% while oil content of pulp is around 1.5-3%. Oils from sea buckthorn seeds and pulp differ considerably in fatty acid composition. While linoleic acid and α-linolenic acid are the major fatty acids in seed oil, sea buckthorn pulp oil contains approximately 65% combined of the monounsaturated fatty acid, palmitoleic acid, and the saturated fatty acid, palmitic acid. Particularly, linoleic (18:2n-6) and alpha-linolenic acids (18:3n-3) comprise about 70% of seed oil fatty acids. Palmitoleic acid (16:1n-7), practically absent in the seed oil, comprised 12-39% of oil in pulp/peel and 9-31% of that in the whole berries. Both oils also contain high amounts of tocopherols, tocotrienols, and plant sterols, while carotenoids are more present in pulp and berry oil. Sea buckthorn oil is rich with variety of antioxidants, including: vitamin C in amount 12 times higher content than that of an orange, vitamin E as much as the wheat germ oil, vitamin A in quantity of three times more than carrots, and superoxide dismutase (SOD) in amount of four times more than ginseng.

Alpha-Tocopherol is the major vitamin E compound in sea buckthorn counting for 70-80% of the total tocopherols and tocotrienols. Seed oil also contains considerable amounts of gamma-tocopherol. The total amount of tocopherols and tocotrienols in seed oil is roughly 100-300 mg/100 g and in pulp oil 100-200 mg/100 g of oil.

Carotenoids, the pigments that give sea buckthorn berry its distinctive color, are present in high amounts, especially in the pulp oil. The total content of carotenoids varies (300-2000 mg/100 g) greatly between different growth locations and subspecies. In general, the main carotenoids present in pulp oil are Beta-carotene, zeaxanthin and lycopene. Total phenolic content is ca. 60-70%, among which flavonoids, such as quercetin, kaempferol, isorhamnetin, myricetin and proanthocyanidins are the most present.

Both seabuckthorn seed and pulp oil also contain considerable amounts of plant sterols. Total sterol content is between 1.0-2.9%, and Beta-sitosterol is the major sterol compound throughout the berry which constitutes 57-83% of total sterols.

The synergistic effect of sea buckthorn's essential fatty acids, including Omega 3, 6, 9, and 7, as well as its vast array of vitamins A, C, E, K, minerals, and anti-oxidants, makes it an outstanding protection for the skin and appropriate to use for various health issues. It also provides trace elements including iron, zinc, calcium, copper, manganese, selenium and iodine which are easy to absorb without any hormones. All this coupled with very high absorption of seabuckthorn oil in the violet-blue spectral range makes it an ideal candidate in this invention. Therefore, seabuckthorn oil is a preferred oil in this invention—can be used alone or in combination with other plant or seed oils and extracts to shield the skin from harmful HEV light, while providing the necessary nutrients for the skin and body.

Extra virgin olive oil (Olea Europaea) is olive oil (extra virgin olive oil, EVOO) has protective action towards the skin, as well as a preventive activity towards aging and chronic degenerative diseases. This is due to its balanced fatty acid composition which has an ideal ratio between n-6 and the n-3 series (ca. 7:1), and its low saturated and high monounsaturated oleic acid (18:1 n-9) content. In fact EVOO contains: palmitic acid (C16:0) up to 20%, palmitoleic acid (C16:1 n-7) and stearic acid (C18:0) up-to 5% each, oleic acid (C18:1, n-9) 55-83%, linoleic acid (C18:2 n-6) 3.5-21% and alpha-linolenic acid (C18:3 n-3) up-to 1.5%. Its greatest health action however can be due to the numerous minor components of notable biological value, such as vitamin E, polyphenols, carotenoids, triterpene hydrocarbons, phospholipids, phytosterols, and numerous aromatic compounds. Among them of most interest are phenolic compounds that, besides preventing peroxidative risk, offer numerous other useful protections for the body. Among the phenolics found in EVOO are the following: phenolic acids: cinnamic acid, ferulic acid, caffeic acid, coumaric acid, gallic acid, lignans including pinoresinol and acetoxypinoresinol, flavones including apigenin and luteolin, secoiridoids including oleoerupein and its derivatives, phenolic alcohols, etc. Antioxidants in EVOO can be liposoluble or hydrosoluble, and therefore, can act both in lipophilic compartments (biologic membrane and lipoproteins) and in hydrophilic compartments (blood and tissues). EVOO is the only dietary and topical "fat" that has both liposoluble and hydrosoluble polyphenols. Olive oil can be considered to be a perfect natural lubricant due to linoleic acid, which the human body doesn't produce and prevents water from evaporating. The topical use of olive oil also can inhibit the neoplastic risk activating onco-suppressor protein p53. Among the antioxidants in EVOO of particular importance are: Vitamin E (alpha-tocopherol). Tocopherol contained in olive oil is of the alpha-form, the only form used by the body. EVOO contains 150-200 mg/l of α-tocopherol, with an optimum relationship with the PUFA present. Particularly, the ratio of vitamin E (alpha-tocopherol) to PUFA should never be inferior to 0.5 and in olive oil it is 1.5. EVOO contains (even if in limited amounts) some carotenoids that gives the oil a yellowish color. Among these are in particular Beta-carotene that protects the skin, lycopene and lutein, which are highly active against skin photo-aging. Lutein has been found to act in synergy with lycopene. Phenolics are present in considerable quantities in EVOO. The most biologically important are hydroxytyrosol and oleoeuropein, both with an anti-inflammatory action that inhibits phospholipase A (that releases AA), cyclo-oxygenase and lipo-oxygenase. Other phenolics present in a lesser quantity are caffeic acid, ferulic acid, vanillic acid, verbascoside and lignans.

Squalene is a component of sebum that has activity against solar radiation by filtering singlet oxygen. It is present in a high quantity in EVOO (400450 mg/100 g) and in lesser amounts in refined olive oil and seed oils. If consumed, it is distributed ubiquitously in all tissues where it acts as an anti-tumor agent, but the greatest concentration is found in the skin where it integrates into the stratum corneum, reinforcing the structural equilibrium of the lipidic film necessary for the skin barrier function.

In order to perform the above-mentioned protective activity against oxygen singlets it therefore needs the simultaneous presence of antioxidants such as alpha-tocopherol and polyphenols; exactly the situation that is present in EVOO. The most important aspect of EVOO is the presence of antioxidant agents. Exposure to solar radiation determines, in fact, a serious loss of antioxidant protection in the skin. In particular, it has been observed that after 30 minutes of UV exposure, the skin's alpha-tocopherol content is reduced by 50-60%. Topical application of alpha-tocopherol clearly reduces the damage. Overall, the antioxidants contained in olive oil may be present in relatively low concentrations, but their activity is notably effective due to the synergistic action among the single components that increase the anti-oxidative potential with respect to that observed when the same components are tested singularly.

Besides the EVOO, there are commercial products which are actually isolated and concentrated active components derived from olive oil. Such product is the Fitoderm™ Squalene which is high purity botanical lipid duplicate in molecular structure to human lipids and produced from olives. Squalene is an unsaturated hydrocarbon (C30H50). It is found in human sebum at a level of 12% and it is believed that the sebum helps keep the skin supple and moisturized and to form a protective coat against fungi and bacteria on the skin. Fitoderm™ Squalene has a defined molecular structure and is an ideal emollient for skin care products, because it is present in nature and in human skin.

Other concentrated olive oil products are those offered by Natac, such as Natac OLIOL with min. 16% Hydroxytyrosol, Natac OLIVE (dry extract) with 20% oleuropein (topical oleoeuropein has a potent antioxidant activity by acting directly in the skin as a free radical scavenger) and Natac AllOlive with approx. 20% oleuropein, 10% Beta-sitosterol, 3% alpha-tocopherol, 3% hydroxytyrosol among others.

EVOO's protective action is linked to the antioxidant action of its minor components (alpha-tocopherol, carotenoids, polyphenols) and to its balanced acidic composition which, besides an adequate amount of linoleic and alpha-linolenic acids, has oleic acid resistant to peroxidative risk. EVOO, therefore, acts against skin aging and reduces the risk of skin cancer. Therefore, it is a preferred active ingredient in the proposed formulations, used alone or in a combination with other active ingredients (oils, extracts, etc.).

Figure 7A:
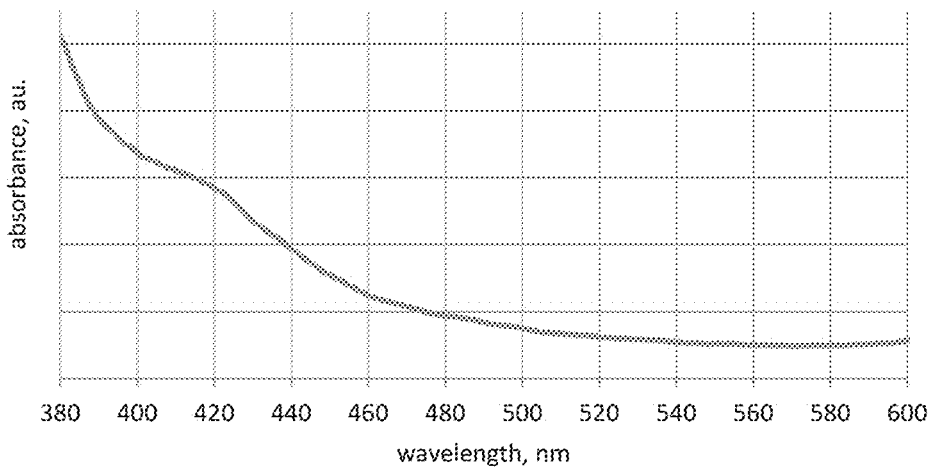
FIGS. 7A-7D are absorbance spectra or extracts.
Figure 7B:
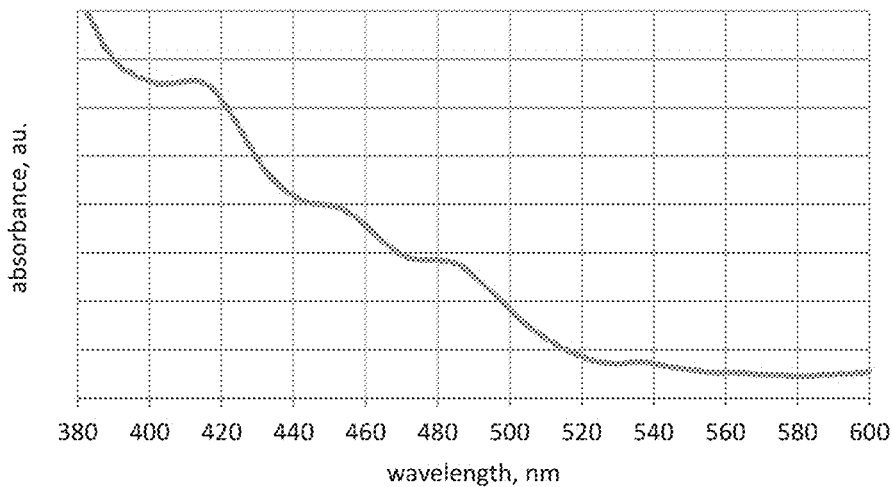
Figure 7C:
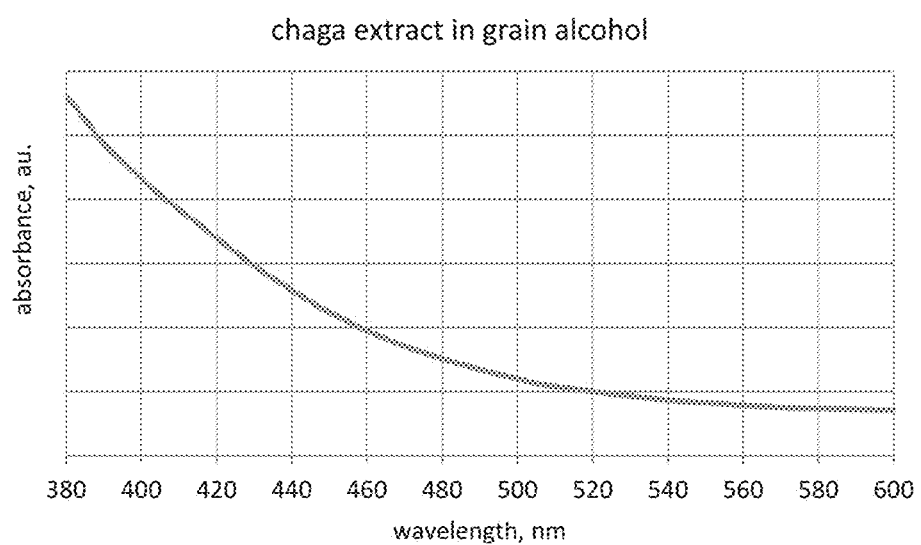

In other instances, the Group A oil may comprise Chaga extracts which can be aqueous or oil based (FIG. 7A and FIG. 7C). Chaga mushroom extracts are isolated from Innotus Obliquus mushroom. Among hundreds of other phytochemicals and phytonutrients, chaga mushroom extract contains: SOD (superoxide dismutase)—a powerful, super-antioxidant enzyme, Beta-glucans—healing polysaccharides that enhance immune system response, variety of flavonoids—strong antioxidant compounds, B-vitamins—play an important role in cell metabolism, minerals—necessary for some vital metabolic enzymes, plant sterols—showing LDL cholesterol lowering effects, melanin—needed for nourishment of the hair, skin and nails, betulin and betulinic acid—possess anti-viral, anti-inflammatory and anti-cancer properties, germanium—improves tissue function and immune function, superoxide dismutase (SOD) is a vital enzyme that catalyzes the breakdown of superoxide radicals, the most common and destructive free radicals in the body, into components consisting of oxygen and hydrogen peroxide. SOD also is neutralizing the resulting by-products of this process to protect cells and tissue from further damage. High SOD levels have been associated with long life spans. Several studies on aging have found that animals that produce the highest levels of SOD have the longest life spans. Normally SOD is created by the body, but by ages 25-30 the levels of enzymes needed to create SOD in any significant amount have diminished. Wild-harvested chaga mushrooms have the highest levels of SOD content of any known food or extract. In fact, it is clinically proven to be one of nature's safest and most powerful medicinal herbs. Chaga extract contains 25-50 times more SOD antioxidants than the antioxidant powers of vitamin C, Co Q10, fish oils, many essential oils and others. In addition, low molecular weight polyphenols, triterpenoids and steroids are found in the aqueous extracts of chaga mushroom. Chaga extract also consists of a folate derivative, pterolyglutamic acid, and aromatic substances, including aromatic vanillic acid, syringic acid and gamma-hydroxybenzoic acid.

Chaga components have been found to possess protective effects against hydrogen peroxide-induced apoptosis and premature senescence in human fibroblasts. In addition, chaga can suppress UV-induced morphologic skin changes, such as skin thickening and wrinkle formation. Increased collagen synthesis through inhibition of MMP-1 and MMP-9 activities in hydrogen peroxide-treated human fibroblasts was found in hairless mice in vivo. Taken together, these results demonstrate that chaga can prevent the aging process by attenuating oxidative stress in a model of stress-induced premature senescence.

Due to its high level of the enzymatic antioxidant SOD, chaga extract is a preferred ingredient in this invention. Together with other ingredients, rich in non-enzymatic antioxidants, it is an ideal candidate for the proposed compositions with HEV protection and anti-oxidant benefits.

In certain instances, the Group A oil can be black cumin seed oil (*Nigella sativa*), also called Black coriander oil or black oil or cumin oil which is isolated from the *Nigella Sativa* plant. It consists of about 35% carbohydrates, 21% protein and 35-38% fats. Cumin oil is a great source of essential fatty acids (EFA) as it contains 70-80% of these highly desirable fatty acids. It has a high level of linoleic and smaller amounts of oleic, palmitic and stearic acids. Most of the therapeutic properties of this oil are due to the presence of some phenolic compounds especially thymoquinone, which is major bioactive component of the cumin essential oil. Other very active functional components in cumin oil are thymohydroquinone, Beta-sisterol, nigellone, p-cumene, thymol, carvacol, alpha- and beta-pinene and so on. The oil also contains selenium, iron, arginine, carotene, calcium, potassium, zinc and phosphorus. Cumin oil exhibits very high permeability through the stratum corneum. Black seed oil is also used for skin problems like eczema and psoriasis. It helps sooth inflammation and improve the speed and which skin heals. It is also used topically in some cultures to naturally soften, strengthen and firm skin and help increase hair growth. Some studies even suggest that it may be a very useful remedy against scars and to prevent scar formation on wounds. Due to its highly anti-oxidant and other benefits, as well as pronounced long wavelength UVA and higher energy violet visible light absorbance, cumin oil is desirable for use in the compositions described herein.

In certain instances, turmeric oil can be used in the compositions described herein. Turmeric oil (*Curcuma longa* L.) is usually obtained from the rizome of *Curcuma longa* L. herb. Various sources of turmeric oils have been reported with various chemical composition ascribed to different cultivars, different soil and climate, and age of plants that influenced the composition. Curcumin (1, 7-bis (4-hydroxy-3-methoxyphenyl)-1,6-heptadiene-3,5-dione) and curcuminoids are the most important compounds in turmeric oil. In an in vitro test, curcumin significantly inhibited the generation of reactive oxygen species (ROS) such as superoxide anions and H2O2, as well as reactive nitric species (RNS), which play an important role in inflammation. In another study, curcumin exerted powerful inhibitory effect against H2O2-induced damage in human keratinocytes and fibroblasts. Curcumin can reduce the inflammatory response and can help maintain the membrane structure integrity and function. Curcumin also acts as a potent anticarcinogenic compound. The antioxidant capacity of curcumin is attributed to its unique conjugated structure, which exists in an equilibrium between the two forms that are strongly favored by intramolecular H-bonding. The three curcuminoids present in turmeric oil are the polyphenol curcumin (diferuloymethane) which is the main and most active constituent, demethoxy-curcumin, and bisdemethoxycurcumin. This oil is also rich in sesquiterpenes, among which turmerone account for nearly 50% of the oil. In summary, turmeric oil is capable of affecting many of the anti-inflammatory pathways, as well as can regulate anti-oxidative and anti-carcinogenic pathways. These properties contribute to its great potential to prevent conditions such as different types of cancer, skin conditions, heart diseases, neurological diseases, arthritis, acne, psoriasis and photoaging to mention a few. It has been described that when absorbed, it can affect more than 100 different molecular targets. Due to its significant UVA absorbance, anti-cancer, anti-oxidant and anti-inflammatory character, turmeric oil is a desired component to be used in combination with other oils or extracts in the compositions described herein.

In some examples, the compositions described herein may comprise wheat germ oil. Wheat germ oil (*Triticum vulgare*), also known as wheat oil, is extracted from the germ of the wheat kernel. It has many health benefits. It's full of A, B, D and E vitamins, fibers, proteins and other natural antioxidants. Wheat germ oil, with its high vitamin E content (255 mg/100 g oil) is considered to be one of the richest oils and foods (food that has not undergone prior preparation or vitamin fortification) with this vitamin. Wheat germ oil also contains biologically important components, such as selenium, zinc, calcium, manganese and copper. Wheat germ oil contains linoleic (n-6) acid ca. 55%, palmitic acid 16%, oleic acid 14% and linoleic acid (n-3) 7%. Wheat germ oil is particularly high in octacosanol—a long-chain saturated primary alcohol found in a number of different vegetable waxes and beeswax, which has been reported to lower plasma cholesterol in humans. Wheat-germ oil is readily absorbed by human skin, which makes it an effective moisturizer and an appropriate topical treatment. When applied to the skin, wheat-germ oil delivers a healthy infusion of vitamin A, vitamin D, B vitamins, antioxidants and fatty acids. These nutrients not only moisturize and heal dry or cracked skin, they also help prevent scarring. In particular, wheat-germ oil is a rich source of vitamin E, which helps reduce skin damage, fight free radicals, support healthy collagen formation and maintain even skin tone. Its richness in vitamin E coupled with essential FA, as well as its strong HEV absorbance, put the wheat germ oil on the list of preferred oils in this invention. It can be used alone or in combination with other oils and extracts in the compositions described herein.

In some embodiments, flax seed oil can be used in the compositions described herein. Flax seed or linseed oil (*Linum usitatissimum*), is considered to be nature's richest source of n-3 fatty acids. It also contains n-6 and n-9 essential fatty acids, B vitamins, potassium, lecithin, magnesium, fiber, protein, and zinc. Flax oil contains high quantities of biologically active compounds such as unsaturated fatty acids (mostly alpha-linolenic acid and linoleic acid) and several components from isoprenoid pathway, such as squalene, phytosterols (mostly campesterol, stigmasterol, and Beta-sitosterol), carotenoids (lutein), tocochromanols (tocopherols and plastochromanol-8), lignans and squalene with anti-inflammatory properties. Due to its n-6/n-3 ratio and pronounced absorbance in HEV spectral range, flax seed oil is desirable for use alone or in combination with other oils and extracts used in the compositions described herein.

In another embodiment, the compositions described herein may comprise pumpkin seed oil. Pumpkin seed oil (*Cucurbita Pepo*) contains various carotenoids, mostly Beta-carotene and lutein and is considered to have the highest amount of Beta-carotene among the seed oils. There is also a high level of oil content (as high as 50%). The four fatty acids which comprise 98% of pumpkin seed oil are palmitic, stearic, linoleic, and oleic acids. Palmitic acid works to promote natural oil regeneration, which is an important component for the skin to retain its protective barrier. Stearic acid acts primarily as a lubricant. It allows the skin to retain the proper moisture balance vital for good health. Linoleic acid is one step far for the manufacture of prostaglandins, which decrease inflammation in the body. Linoleic acid helps maintain smooth skin, and will help repair flaky, itchy, or rough skin. Oleic acid is another fatty acid found in pumpkin seed oil. It works to replenish and maintain skin's moisture and lubrication. It is an omega-9 acid and has similar health benefits (both general for the health and to the skin) as the more present n-3 and n-6 EFA. Also, great skin benefits of pumpkin seed oil are result of its high levels of the natural antioxidants. Pumpkin seed oil is especially high in alpha-tocopherol form of Vitamin E, which is a powerful antioxidant and works by stabilizing the free radical, which renders the free radical harmless, and helps the skin retain its normal structure. Pumpkin seed oil also contains phytosterols and a wide variety of nutrients ranging from magnesium and manganese to copper, protein and zinc. Overall, pumpkin seed oil, rich in vitamin E, zinc, omega-3, -6, and -9 FA and other antioxidants, offers tremendous benefits for the skin in terms of retaining moisture, fighting ROS and maintaining a youthful skin appearance, help wounds heal more rapidly, fight acne and help with skin renewal. Pumpkin seed oil is desirable for use either alone or in combinations with other oils and extracts in the compositions described herein.

In certain instances, the compositions described herein may comprise hemp seed oil. Hemp seed oil (*Cannabis sativa*) or simply hemp oil is cold pressed from the *Cannabis sativa* plant. Hemp seed oil also provides an adequate supply of antioxidants (Vitamin E), carotene (precursor to Vitamin A), vitamin D, phytosterols, phospholipids and a number of minerals including calcium, magnesium, sulfur, potassium, phosphorus, along with modest amounts of iron and zinc. Hemp seed oil also provides a good source of chlorophyll. The hemp oil contains a number of fatty acids. About 30-35% of the weight of hempseed is an edible oil that contains about 80% as essential fatty acids (EFAs); i.e., linoleic acid, n-6 (LA, 55%), alpha-linolenic acid, omega-3 (ALA, 22%), in addition to gamma-linolenic acid, n-6 (GLA, 1-4%) and stearidonic acid, n-3 (SDA, 0-2%). It is considered to be nature's perfect oil besides the EVOO, with the ideal ratio of n-6/n-3 EFAs. Hemp seed oil, alone or in combination with other oils and extracts, is desired for use in the compositions described herein due to its pronounced absorbance in HEV spectral range coupled with its proven anti-oxidant and anti-inflammatory properties.

In some embodiments, the compositions described herein may comprise clove oil. Clove oil (*Syzygium aromaticum*) is a good source of essential fatty acids and lipid-soluble bioactives. The high linoleic and oleic acid contents, tocopherols and phenolics present in the clove oil, make it nutritionally valuable for the skin. The present antioxidants react directly and quench the free radicals, thus, preventing lipid peroxidation. Clove oil also contain a variety of potentially bioactive compounds such as sesquiterpenes, tannins, and triterpenoids. The main aroma constituent of clove oil is a result of eugenol (4-allyl-2-methoxyphenol, 75-85%) that has been reported to have many biological activities. Eugenol is anti-inflammatory, and antimicrobial and anti-fungal agent and a very powerful fat-soluble antioxidant. Clove oil has the highest antioxidant value (Trolox/ORAC-values) among all the oils. The strong antioxidant behavior of clove oil might be due to the diversity in structural characteristics of phenolics presents and the synergism of different AO with other active components.

In other embodiments, the compositions described herein comprise cranberry seed oil (*Vaccinium macrocarpon*). Cranberry seed oil is cold pressed oil from the seeds of cranberry contains a very high essential fatty acid profile with approx. 1:1 ratio of omega 3 to omega 6 EFA, along with a good mixture of tocopherols and tocotrienols, Vitamins A, C and K, high phytosterols level and other phytonutrients. Cranberry seed oil has one of the highest antioxidant phytosterols content of all oils and a high absorbance in the HEV spectral range, making it a good natural protection product that prevents photo-damage. Cranberry seed oil easily penetrates the skin and is highly moisturizing. It can aid in the relief of itchy, scaly, irritated skin conditions such as eczema and psoriasis. Its strong antioxidant properties and stable shelf life can help to extend the life of more fragile ingredients included within the same formulation.

In some examples, the compositions described herein comprise broccoli seed oil. Broccoli seed oil (*Brassica Oleraceae Italica*) contains a fatty acid profile mainly composed of erucic acid (omega-9), oleic acid (omega-9) and linoleic acid (omega-6) that yield its excellent absorption properties while offering significant film forming properties on the skin and hair. Broccoli seed oil has another essential fatty acid, arachidonic acid, which is the second most abundant polyunsaturated fatty acid in the epidermis. The excellent anti-oxidant profile makes it an easy substitute for the activity of silicones where the film forming activity results in a natural shine of the skin and hair. Broccoli seed oil is full of vitamins C, A and K and other nutrients. Besides being strong antioxidant, broccoli seed oil is very good oil for eczema, psoriasis, and inflammatory skin conditions.

In certain instances, the compositions described herein comprise argan oil. Argan oil (*Argania spinosa*) is cold pressed from the nuts of organic *Argania spinosa*. With its unique composition of unsaturated fatty acids, carotenoids, tocopherols, plant sterols, polyphenols, ferulic acid, vitamin E and squalene, it delivers a therapeutic profile that offers regenerative and restructuring activity to the skin. Argan oil contains essential unsaturated fatty acids in abundance. It contains as much as 80% of essential fatty acids in its overall composition. FAs present in the argan oil have antioxidant and moisturizing properties and are vital for regeneration and repairing cell membranes, and thus help prevention of premature aging signs. The major natural phenols in argan oil are caffeic acid, oleuropein, vanillic acid, tyrosol, catechol, resorcinol, ferulic acid epicatechin and catechin. Among them, the ferulic acid is the most abundant phenolic compound present in this oil and its antioxidant potency increases on exposure to UV radiations, thus it is a very potent barrier against the damaging effects of UV radiation. The chemical structure of plant sterols and human sterols is strikingly similar. Therefore, the sterols present in argan oil work in a harmony with the human skin. They perform a multitude of functions like keeping structural integrity of cell membrane, reducing inflammation, improving skin metabolism process and moisture retention. They are the primary component of the outermost layer of human skin and functions like an optimal barrier. Sterols are very easily absorbable and penetrable in the skin.

In other examples, the compositions described herein comprise black raspberry seed oil. Black raspberry seed oil (*Rubus occidentalis*) contains high level of essential fatty acids with a perfect n-6/n-3 ratio. The oil is an exceptionally potent antioxidant and is useful as a free radical scavenger. Antioxidant constituents include tocopherols, tocotrienols, tannins and lutein. Black raspberry seed oil has strong absorbance in UVA and HEV range and have been shown to reverse environmental damage, therefore it is great for natural sun protection products. Black raspberry seed oil is a light oil that quickly penetrates the skin. Rich in phytonutrients, black raspberry seed oil is a desirable ingredient in formulations for healing and treatment of skin conditions such as eczema and psoriasis.

In some embodiments, the compositions described herein comprise red raspberry seed oil (*Rubus idaeus*). Red raspberry seed oil is highly moisturizing and emollient. It possesses an exceptionally high proportion of alpha- and gamma-tocopherols, polyphenols and other antioxidants. It is also rich in vitamin A and contains up to 83% omega-3 and omega-6 fatty acids. Red raspberry seed oil has more pronounced anti-inflammatory properties than avocado, grapeseed, hazelnut and wheat germ oils and may prove to be the most effective oil to use in the treatment of eczema, psoriasis and other skin conditions. Red raspberry seed oil also offers the skin broad spectrum protection from damaging UV and HEV rays. It contains elegiac acid, a compound that has been shown to reduce the destruction of collagen. This oil is rich in phytosterols which antioxidant activity prevents skin damage, encourages healthy skin growth and may protect against cancer.

In some embodiments, the compositions described herein comprise chia seed oil. Chia seed oil (*Salvia hispanica*) offers at 3:1 balance of omega-3 to omega-6 essential fatty acids for optimum skin nourishment. In fact, chia seed is considered the richest botanical source of omega-3 fatty acids found in nature, offering more than flax seed or fish oil. These fatty acids support the formation of collagen and elastin, which in turn supports skin structure and discourages sagging and bagging. They also help strengthen the epidermis and maintain moisture levels. Chia seed oil is clinically proven to significantly increase skin hydration, reduce trans-epidermal water loss and increase skin barrier function. Besides being a powerful source of alpha lipoic acid (ALA), chia seed oil is also a great source of vitamin B3, a natural anti-inflammatory agent, and zinc, which helps reduce skin oil production and appearance of acne. Among the antioxidants, it has chlorogenic acid and caffeic acid, as well as myricetin, quercetin, and kaempferol flavonoids. These components have strong free-radical fighting capabilities, and inhibit the oxidation of fats in the skin. The antioxidants in chia seed oil have shown to be even stronger than vitamin C and vitamin E. This oil has excellent anti-inflammatory properties. Being an important source of protein and zinc, chia seeds can help stimulating healthy hair growth.

In other instances, the compositions described herein may comprise pomegranate oil (*Punica granatum*). Pomegranate oil is cold-pressed from the seeds found in the red arils of the fruit. It is rich with the rare omega-5 essential fatty acid, also known as punicic acid, one of the most potent antioxidants known to modern science, and a natural phytoestrogen (plant-based estrogen). Omega 5 (9cis, 11trans, 13cis-conjugated linolenic acid] is an 18-carbon fatty acid possessing three double bonds and have been found to be at least six times more potent antioxidant than those in grape seed extract. It is a high-energy molecule that interferes with the production of inflammatory prostaglandins and leukotrienes. It also "mimics" the behavior of non-steroidal anti-inflammatory drugs like aspirin, but without the side effects. The conjugated molecular structure makes it highly compatible with and easily absorbed by skin. Acting as a delivery system, it helps channel nutrients directly to the cell, accelerating the process of cellular regeneration and rejuvenation. Pomegranate oil contains essential vitamins and minerals (B1, B2, C, potassium, and magnesium).

In some examples, the compositions described herein may comprise carrot seed oil. Carrot seed oil (*Daucus carota*) is one of the highest natural sources of Beta-carotene and vitamin E, resulting in its high anti-oxidant activity. It is also high in essential fatty acids and phytosterols (luteolins). Due to its high level of antioxidants and its absorption in UV and shorter wavelength HEV range, it can protect the skin from environmental assaults like sun rays, pollution, and stress. In fact, carrot seed oil may be added to sunscreen formulas because it is reputed to protect from free radicals produced by these assaults, and thus, reduce the skin damage.

In other embodiments, the compositions described herein may comprise macadamia nut oil. Macadamia nut oil (*Macadamia integrifolia*) is one of the richest sources of omega-7 essential fatty acid, palmitoleic acid, which is usually found in animal oils. This oil is considered to be the best plant alternative to animal based oils, i.e. oil of choice to replace the activity of mink oil and shark liver oil. Omega-7 level in macadamia nut oil can be as high as 21%—concentration that is rarely found in vegetable oils. This fatty acid is secreted by young children's sebaceous glands giving them pulp and dewy skin. It almost disappears from the sebum by aging. Therefore, it helps to add this oil in a potential skincare product. Macadamia nut oil also contains vitamins A1, B1, B2, niacin and essential elements such as calcium, iron, phosphorus, magnesium and potassium. The oil is a triglyceride oil and contains primarily monounsaturated fats up to 80-84%. Macadamia nut oil is also a rich source of squalene—a naturally occurring antioxidant present in human skin surface lipids that protects from sun-induced lipid peroxidation. Also, the presence of palmitoleic acid in this oil plays a role in the lipid protection.

Therefore, the use of macadamia nut oil protect the skin, especially the photo-damaged skin or skin exposed to excessive sunlight.

In some examples, the compositions described herein may comprise apricot seed (kernel) oil. Apricot kernel oil (*Prunus armeniaca*) is obtained from the kernels (seeds) of apricots. It is rich in gamma linoleic acid (GLA), which helps skin to maintain moisture balance. GLA also plays a role in firming and toning the skin. Additionally, it contains vitamins A and E, which is antioxidant and soothe the skin and slow down the signs of aging. The nourishing properties of apricot kernel seed oil have an anti-inflammatory effect and may soothe minor skin conditions such as eczema. Apricot kernel oil is one of the best carrier oils. It penetrates easily into the skin and also improves the delivery of essential oils and other herbal agents. This oil is also good for infusing with herbs and extracts.

In other embodiments, the compositions described herein may comprise jojoba oil (*Simmondsia chinensis*). Jojoba oil is actually a mixture of long chain monounsaturated liquid wax esters. They are structurally different from triglycerides, which are what most of the other seed oils are made of. It is extracted from the seeds of jojoba plant. What makes it so unique compared to other seed oils is that jojoba oil is structurally and chemically very similar to the human sebum. This is because sebum is also largely comprised of wax mono esters, the primary constituent of jojoba oil. It does not clog pores and does not cause any allergic reactions. It contains many different varieties of tocopherols and many other natural minerals, which make this oil anti-oxidant and antibacterial.

In certain examples, the compositions described herein may comprise marula oil. Marula oil (*Sclerocarya birrea*) is extracted from the kernels (nuts) of marula tree. It is rich in essential fatty acids omega-9-oleic and omega-6-linoleic that deeply hydrate and improve skin elasticity. It helps reduce transepidermal water loss and increases the smoothness of skin. Easily absorbed, it supports the natural buildup of the skin's lipid layers and possesses anti-inflammatory properties. Marula oil also contains high levels of important antioxidants including vitamin C, tocopherols, tochotrienols, phenolic compounds, essential amino acids, procyanidin, galattotannin, catechins and other flavonoids that help cells renew and resist damaging effects of the environment. The large proportion of monounsaturated fatty acids and natural antioxidants makes the oil very stable. Marula oil can deliver advanced protection against photo-aging—neutralizing free radicals, helps build healthy collagen, and provides antioxidant protection.

In other examples, the compositions described herein may comprise sesame oil. Sesame oil (*Sesamum indicum*) is composed of the following fatty acids: linoleic acid (41%), oleic acid (39%), palmitic acid (8%), stearic acid (5%) and others in small amounts. It is naturally antibacterial for common skin pathogens, antiviral and anti-inflammatory agent. Sesame oil is rich in two compounds, sasamine and sasamoline, that together with beta-sitosterol and high levels of essential fatty and polyunsaturated acids gives this oil the anti-oxidant activity. The oil also contains an antioxidant called sesamol which effectively prevents the appearances of wrinkles and fine lines. Research shows that sesame seed oil is a highly potent antioxidant. In the tissues beneath the skin, this oil will neutralize oxygen radicals. It penetrates into the skin quickly and enters the blood stream through the capillaries. Sesame oil has traditionally been used to improve the health of hair. It can help to darken hair color and also eliminate hair loss. Furthermore, the anti-bacterial effects of sesame oil can help to eliminate any of the pathogens or foreign bodies that can attack your scalp or hair. Sesame oil contains vitamin E in abundance along with vitamin B complex and vitamin A. Other beneficial nutrients in sesame oil include phosphorus, copper, calcium, zinc and magnesium. It can increase skin elasticity and smoothness, helping to reduce the appearance of age spots and eliminate skin conditions, including premature aging. Although sesame oil is fairly thick and sticky, it is easily absorbed by the skin and is often used as carrier oil or base oil. Sesame oil can also be used as a sunscreen because it creates a protective layer on the skin, which is another way of protecting the body from foreign substances or toxins that get in through the skin.

In certain embodiments, the compositions described herein may comprise avocado oil. Avocado oil (*Persea americana*) is rich in monounsaturated fats and vitamins A, B1, B2, D, and E. Almost 70% of avocado oil consists of oleic acid, a monounsaturated omega-9 fatty acid and low level of omega-6. Avocado oil is a relatively good source of lutein. The vitamins and minerals in avocado oil are not only nourishing, they can also "feed" the body from the outside in. The vitamin E, potassium, and lecithin which are the primary skin-feeding nutrients in the oil are all easily absorbed through the epidermis and into the dermis, where they provide energy for the growth and health of new skin fostering collagen production, as well as fortification of existing cells. Avocado oil is high in sterolins and sterols. Sterolin is extremely moisturizing to the skin and helps reduce fine lines and wrinkles. The same nutrients in avocado oil which make it ideal for moisturizing and feeding skin are also exceptionally nourishing for the hair. Due to its high concentration of anti-inflammatory oleic acid, avocado oil can be applied topically to ease discomfort caused by certain skin conditions, including but not limited to dandruff, cracked eels, keratosis pilaris, insect bites and stings, sunburn, eczema, and psoriasis.

In other embodiments, the compositions described herein may comprise castor oil. Castor oil (*Ricinus commumis*) is a highly stable oil and one of the thickest of all oil carriers. It is also one of the most moisturizing oils, by providing a sufficient barrier locking moisture in the skin.

In some instances, the compositions described herein may comprise borage seed oil (*Borago officinalis*). Borage seed oil contains one of the highest levels of gamma-linolenic acid GLA, (16-26%), which is needed for healthy skin cell membranes. In the body, gamma linolenic acid is converted into prostaglandin 1, which helps heal inflammation of the skin and promotes skin health. In herbal medicine, borage seed oil has been used for skin disorders such as eczema, seborrheic dermatitis, and neurodermatitis.

In other instances, the compositions described herein may comprise evening primrose oil (*Oenothera biennis*). Evening primrose oil is valuable for its rich source of unsaturated fatty acids, in particular its high gamma-linolenic acid (GLA) content. It is a good choice for mature skin, where it offers support, for healthy skin physiology, relief for dry skin, and improves circulation.

In some examples, the compositions described herein may comprise palm oil. Palm oil (*Elaeis guineensis*) contains about 50% saturated fat (majority of which is oleic acid), 40% monounsaturated fatty acids (MUFAs), and 10% polyunsaturated fatty acid (PUFAs). Palm oil gets its reddish color from the carotenes (β-carotene and lycopene), which levels are 15 times higher than carrots and 300 times higher than tomatoes. Palm oil also contains 20 other carotenes, as well as vitamin E, particularly tocotrienol, vitamin K, CoQ10, squalene, phytosterols, flavonoids, phenolic acids, and glycolipids.

In other examples, the compositions described herein may comprise rapeseed oil (*Brassica campestris*). Rapeseed oil contains omega-3 and omega-6 fatty acids, among which is alpha-linolenic acid (ALA). Rapeseed oil has a favorable balance of fatty acids—less saturated acids, high in mono-unsaturated fats (~60%), while PUFA's is ~30%. It is also a rich source of vitamin E (alpha-, gamma-, delta-tocopherols), vitamin K and sterols (stigmasterols, beta-sitosterol, campesterol).

In additional examples, the compositions described herein may comprise rosehip oil (*Rosa aff. rubiginosa* or *Rosa moschata*). Rosehip oil is composed of many powerful nutrients and antioxidant, such as linoleic acid (~50%), oleic acid (~14%), lycopene, β-carotene (pro-vitamin A) and Vitamin C. The essential fatty acids in rose hip seed oil can help reduce scarring and promote skin regeneration. They are emollients, which improve skin flexibility and permeability. Vitamin A helps delay the effects of skin aging and also assists with cell regeneration; together with vitamin C promotes collagen and elastin levels to increase. The oil can penetrate due to the vitamin A, which has small enough molecules to go deeper into the skin.

In further examples, the compositions described herein may comprise sunflower oil (*Helianthus annuus*). Sunflower oil is very high in antioxidants, particularly vitamins A, C and E. It also contains other nutrients such as: palmitic acid, stearic acid, lecithin, tocopherols, carotenoids, selenium, proteins, copper, iron, zinc, calcium, and others. Folate or folic acid, present in sunflower oil, helps the body in the manufacture of new cells.

In some examples, the compositions described herein may comprise helichrysum oil (*Helichrysum italicum*). The Helichrysum plant, also known by other names, including "everlasting", "immortelle" or "curry plant" is used for making Helichrysum oil. Helichrysum's flavonoids and terpene compounds were effective against bacteria and fungus growth that can cause various skin irritations, including rashes, infections and delayed wound healing. Helichrysum can help hydrate burnt skin and relieve the pain following sunburns. It can also decrease signs of aging on the skin and block UV-light damage that can eventually lead to formation of skin cancer. Helichrysum oil has strong antibiotic and antimicrobial properties that make it a great natural cure for acne, for it works without drying the skin or causing redness and other unwanted side effects. Overall, Helichrysum oil has multiple effects that occur at the same time—inhibiting inflammatory enzymes, scavenging free radicals, and a third effect that resembles how corticosteroids work in taming inflammation. This three-pronged approach helps to calm, protect, and heal skin that is inflamed, damaged, or stressed and is perfect for anti-aging skin products.

In other instances, the compositions described herein may comprise oregano oil (*Origanum vulgare*). Oregano oil is high in phenols—natural phytochemical compounds with beneficial antioxidant effects. The two most abundant phenols in it are: thymol—a natural fungicide with antiseptic properties, which helps prevent tissue damage and encourages healing, and carvacrol, which is found to be effective against various bacteria. Nutrients like vitamins A, C, and E, calcium, magnesium, zinc, iron, potassium, manganese, copper, boron, and niacin are also found in oregano oil.

In further examples, the compositions described herein may comprise ginger oil. Ginger oil (*Zingiber officinale*) benefits mostly come from its powerful mono- and sesquiterpenoids, alpha-pinene, Beta-pinene, camphene, linalool, borneol, nerol, gingerol, and others. It contains vitamins, zinc and phosphorus. It is restorative oil for the skin as well as stimulates hair growth via increasing blood circulation in the scalp. It provides efficient UV ray protection.

In some examples, the compositions described herein may comprise cinnamon oil. Cinnamon oil (*Cinnamomum zeylanicum*) contains 68-87% eugenol, which is the primary ingredient in clove oil. Cinnamon bark oil contains approx. 40-50% aldehydes (cinamaldehyde cinnamic aldehyde, which give the aroma and calming effect), while the cinnamon leaf oil contains approx. 80% phenols. This oil promotes circulation when applied to the skin and is excellent protection against UV rays.

In other instances, the compositions described herein may comprise shea butter (*Butyrospermum parkii*). Shea butter is a skin superfood that comes from the seeds of the fruit of the Shea tree. Shea butter extract is a complex fat that in addition to many nonsaponifiable components contains the following fatty acids: oleic acid (40-60%), stearic acid (20-50%), linoleic acid (3-11%), palmitic acid (2-9%), linolenic acid (<1%) and arachidic acid (<1%). It nourishes the skin with vitamins A, E and F. Vitamin F consists of two vital fatty acids namely linoleic acid and alpha-linoleic acid. Due to its cinnamic acid and other compounds, shea butter is anti-inflammatory. Particularly, lupeol cinnamate was found to reduce skin inflammation and even potentially help avoid skin mutations. Shea butter aids in the skin's natural collagen production and its fatty acids protect and nourish the skin to prevent drying It also has emollient and humectant properties. Shea butter has been used as a sunblocking lotion and has a limited capacity to absorb ultraviolet radiation. It offers UV and HEV protection and provides the skin with essential fatty acids and the nutrients necessary for collagen production.

In some examples, the compositions described herein may comprise green tea extract (*Camellia sinensis*). Green tea extract is made from unfermented leaves of the plant *Camellia sinensis* and is rich in polyphenols (catechins), which are potent antioxidant flavonoids. Epigallocatechin gallate is particularly abundant in green tea and biologically active. It is considered that green tea polyphenols offer protection against UV-induced stress via both interacting with UVB-induced reactive oxygen species and attenuating mitochondrion-mediated apoptosis.

In other embodiments, the compositions described herein may comprise grape seed oil and/or extract (*Vitis vinefera*). Grape seed oil is usually cold-pressed from the seeds of grapes. It contains more linoleic acid than many other carrier oils (~70%), oleic acid (~16%), palmitic acid (7%), stearic acid (4%) among the others. Grape seed oil and extract are rich in phenolics and steroids (campesterol, beta-sitosterol, stigmasterol) and contains small amounts of vitamin E. They contain polyphenolic proanthocyanidins and procyanidins, which have strong antioxidant effects. They can facilitate skin wound healing and protect collagen and elastin from degradation.

Figure 6A:
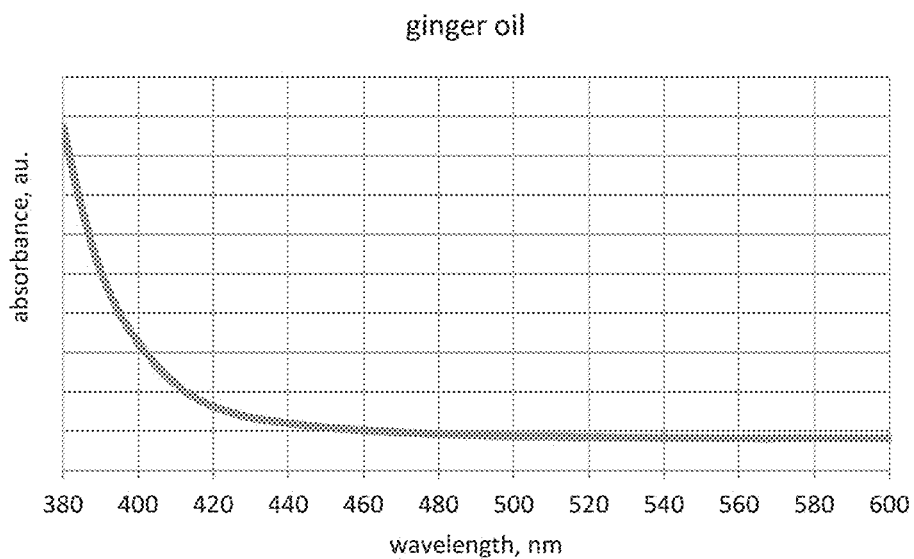
FIGS. 6A-6X are spectra showing the absorbance of various Group A oils at different wavelengths, in accordance with certain embodiments.
Figure 6B:
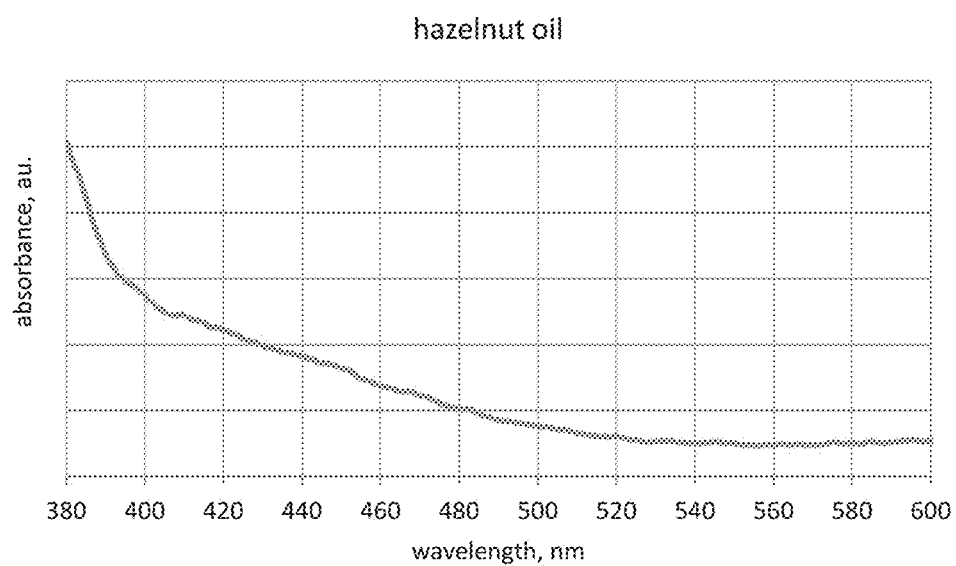
FIG. 6Y is a table showing the absorption characteristics of certain Group B oils.
Figure 6C:
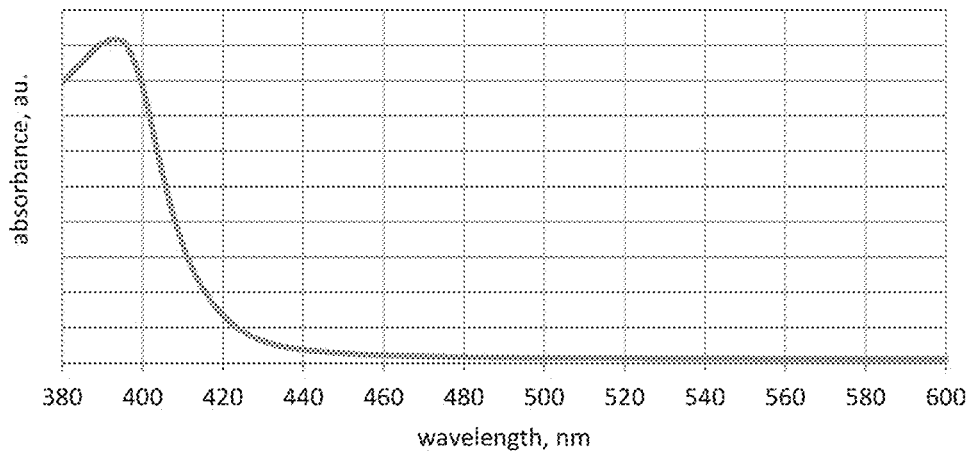
Figure 6D:
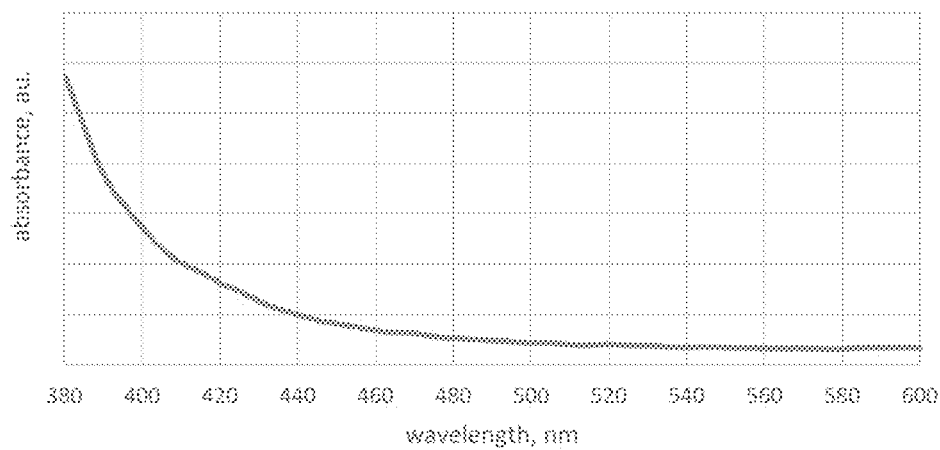
Figure 6E:
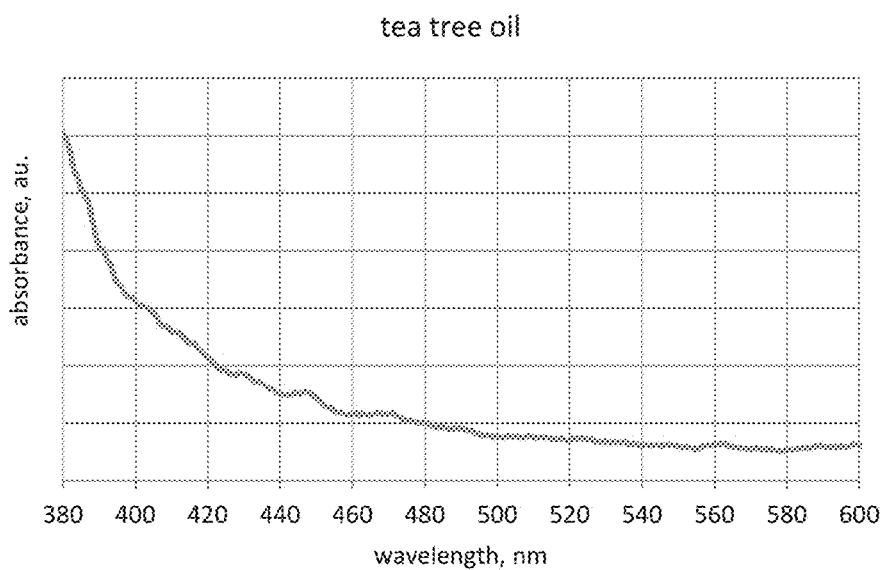
Figure 6F:
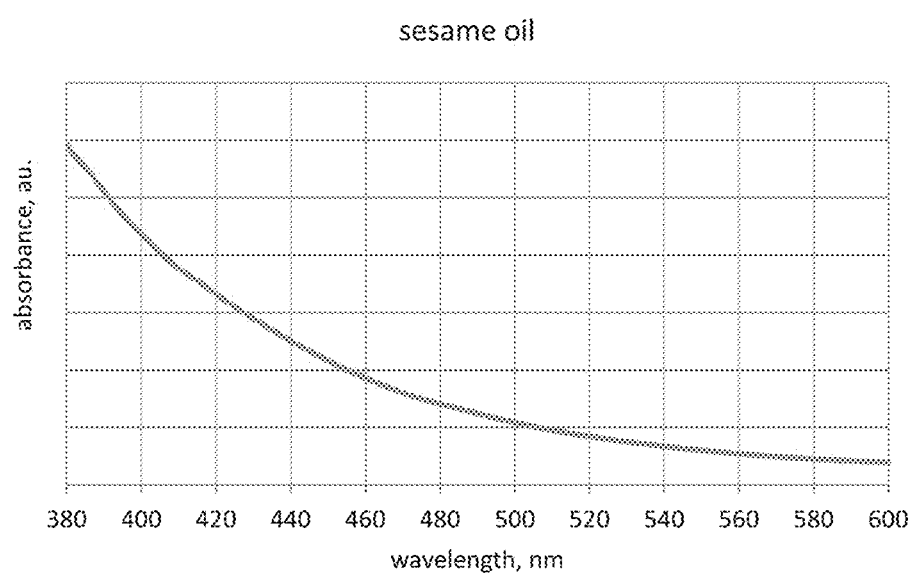
Figure 6G:
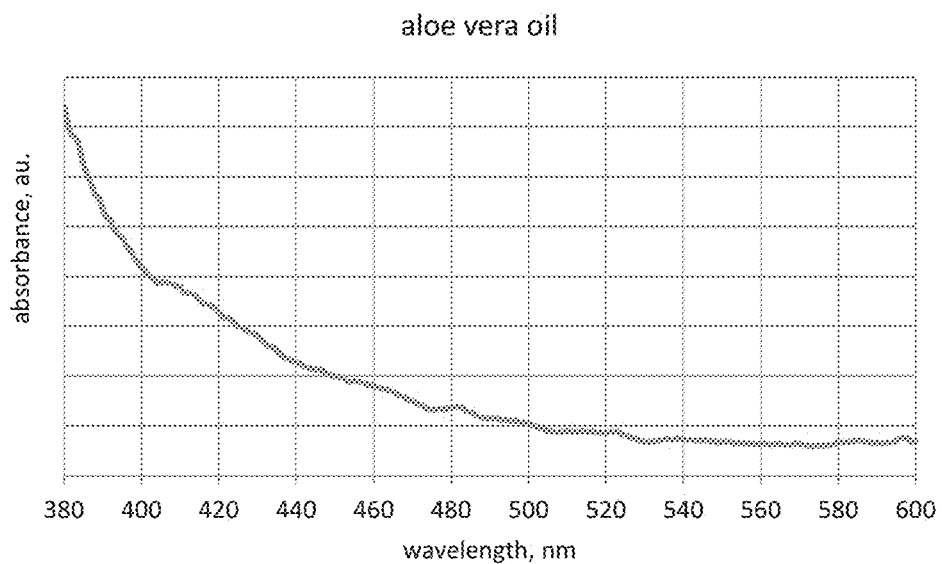
Figure 6H:
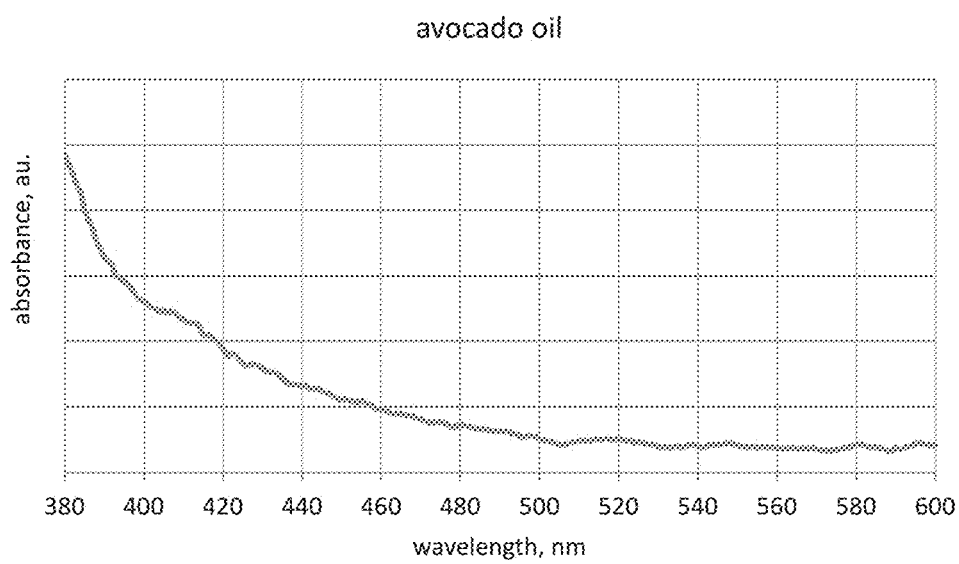
Figure 6I:
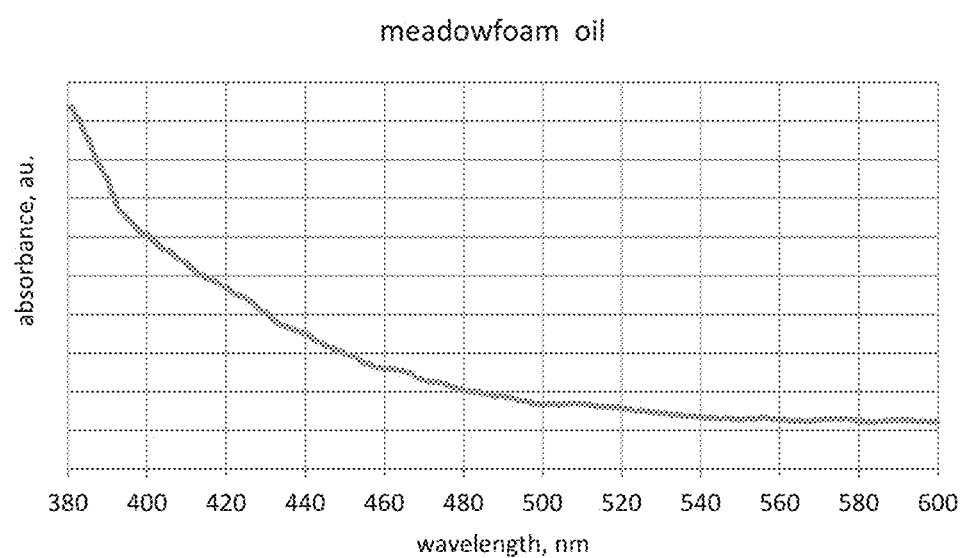
Figure 6J:
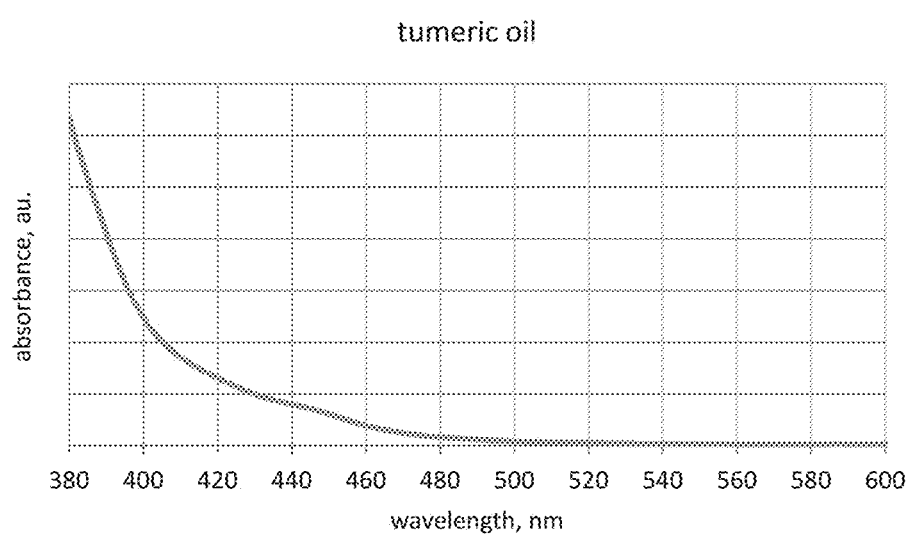
Figure 6K:
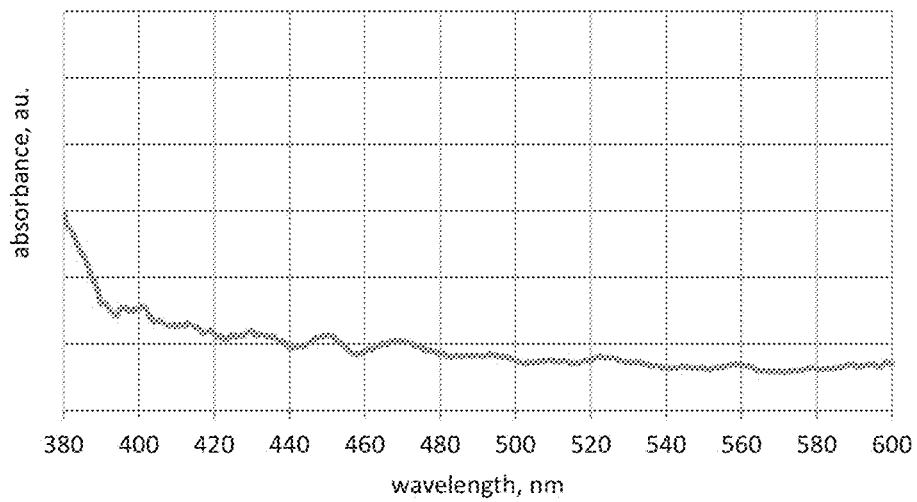
Figure 6L:
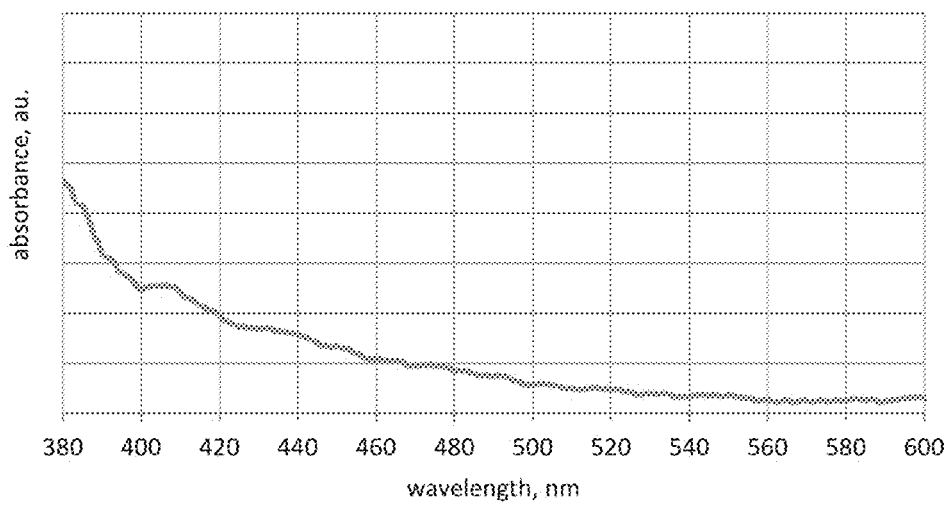
Figure 6M:
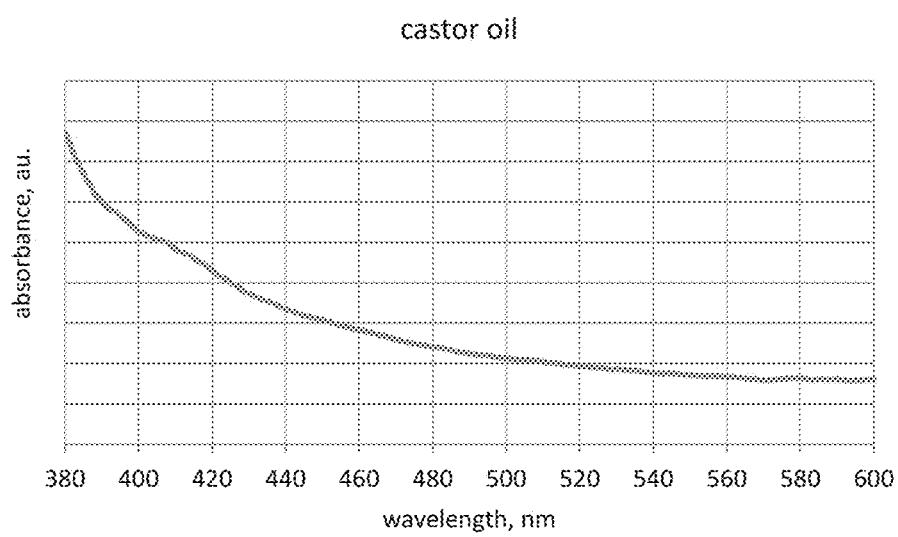
Figure 6N:
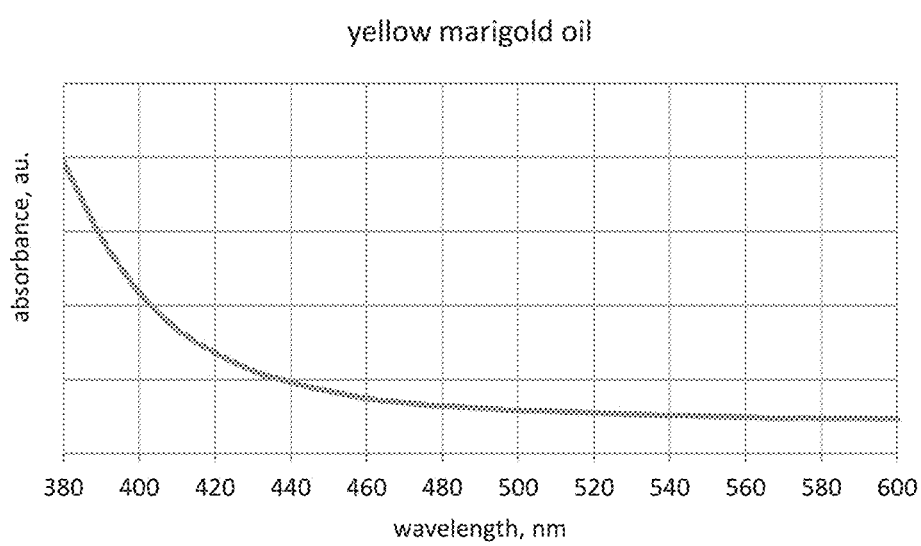
Figure 6O:
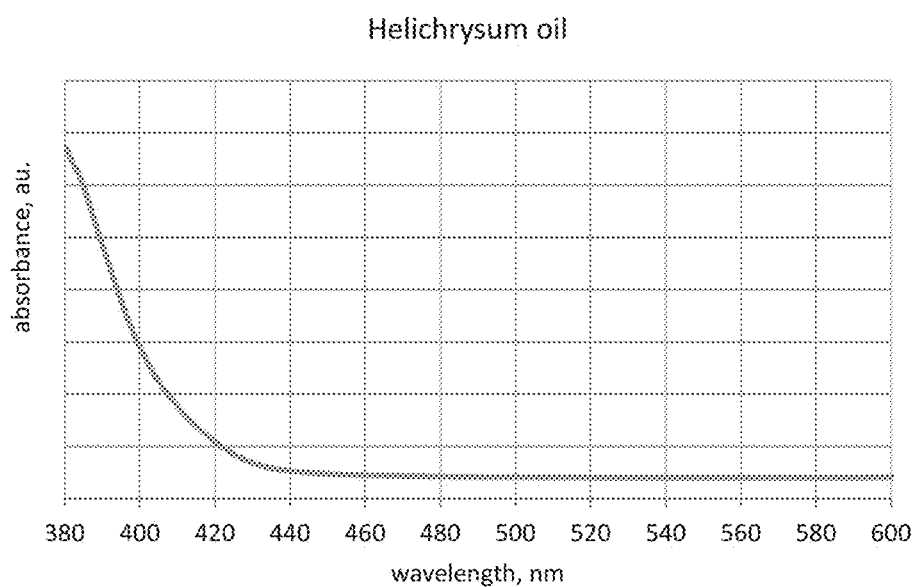
Figure 6P:
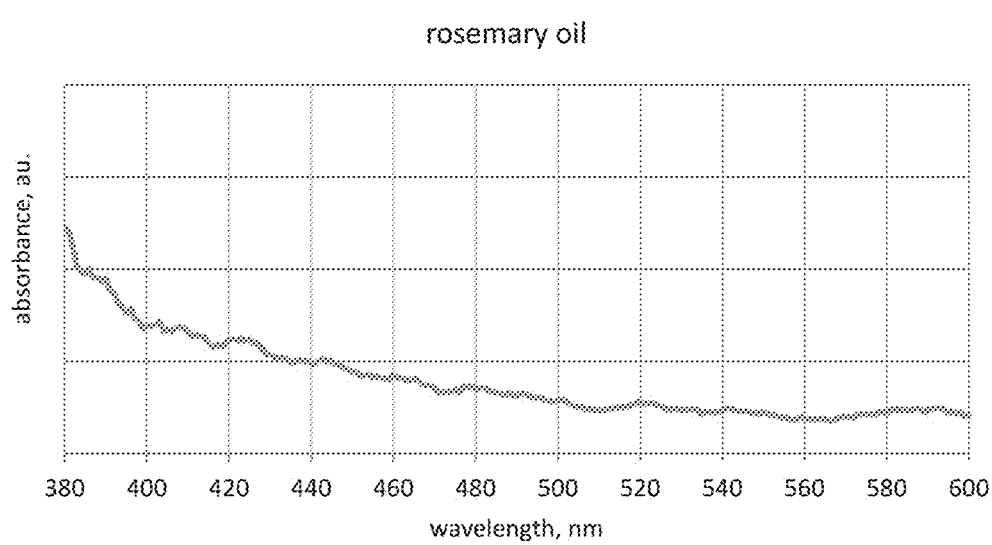
Figure 6Q:
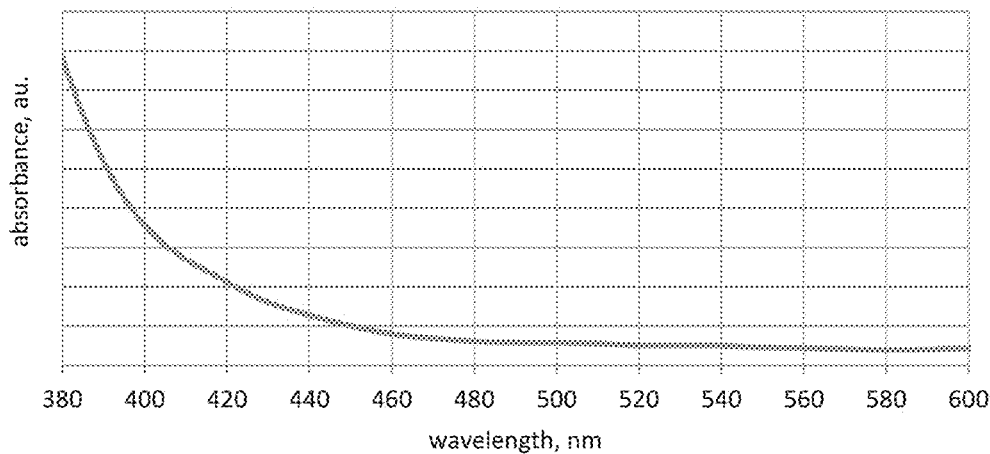
Figure 6R:
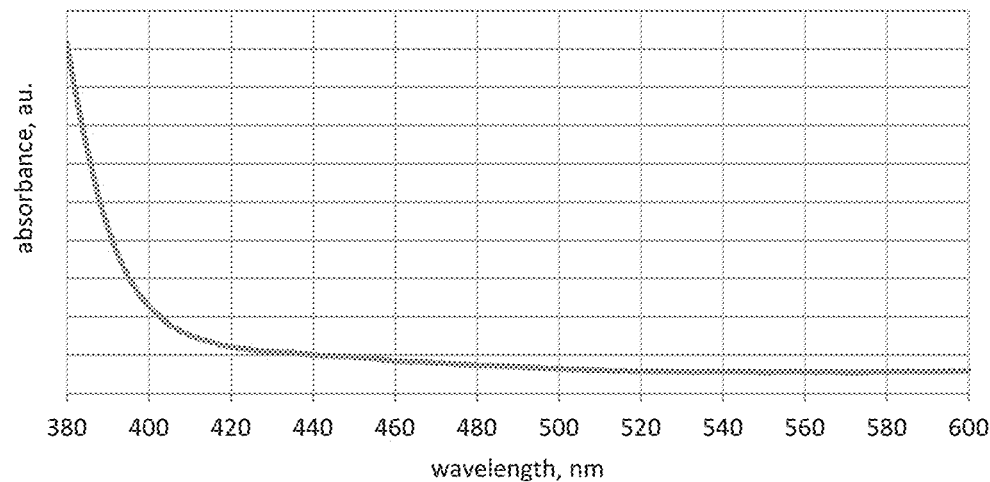
Figure 6S:
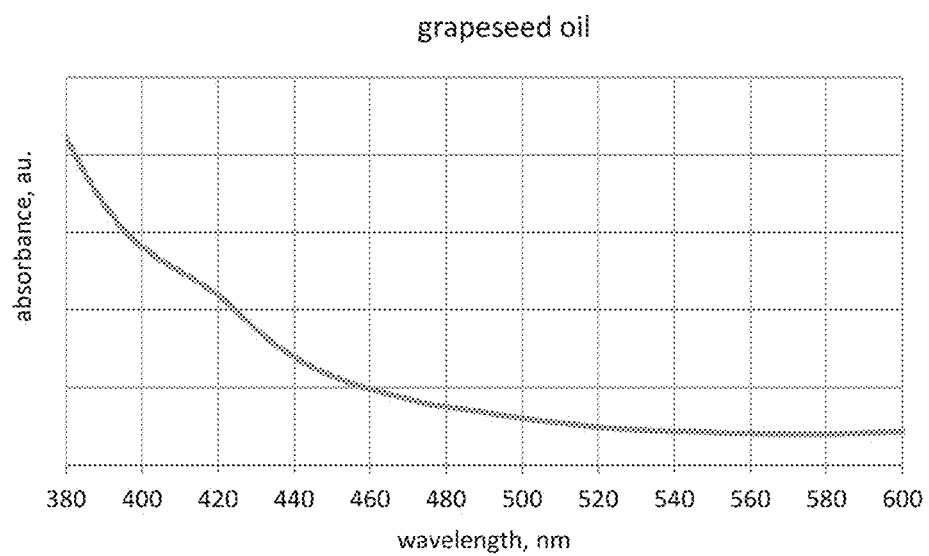
Figure 6T:
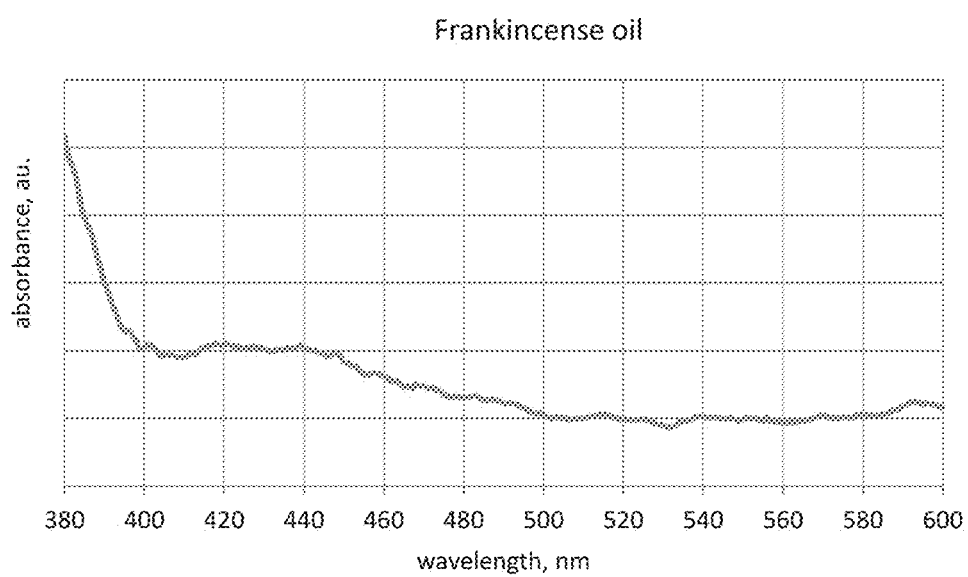
Figure 6U:
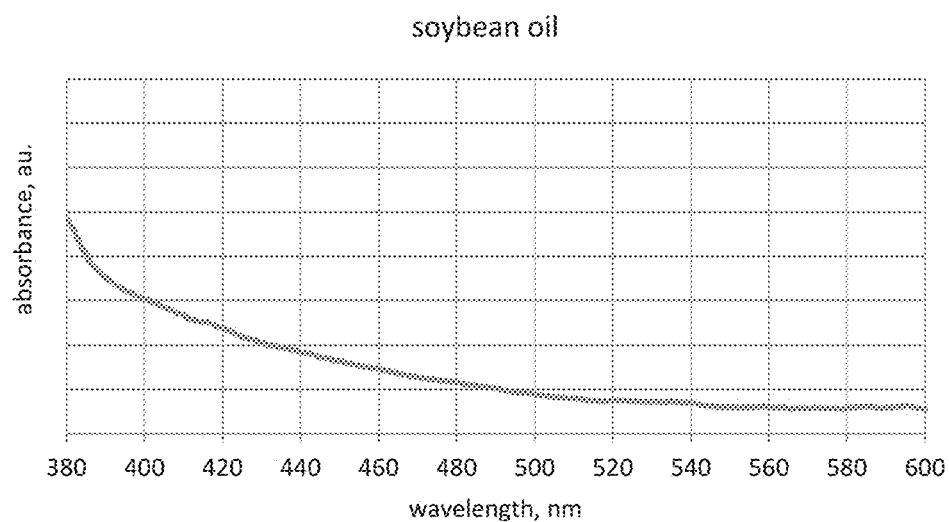
Figure 6V:
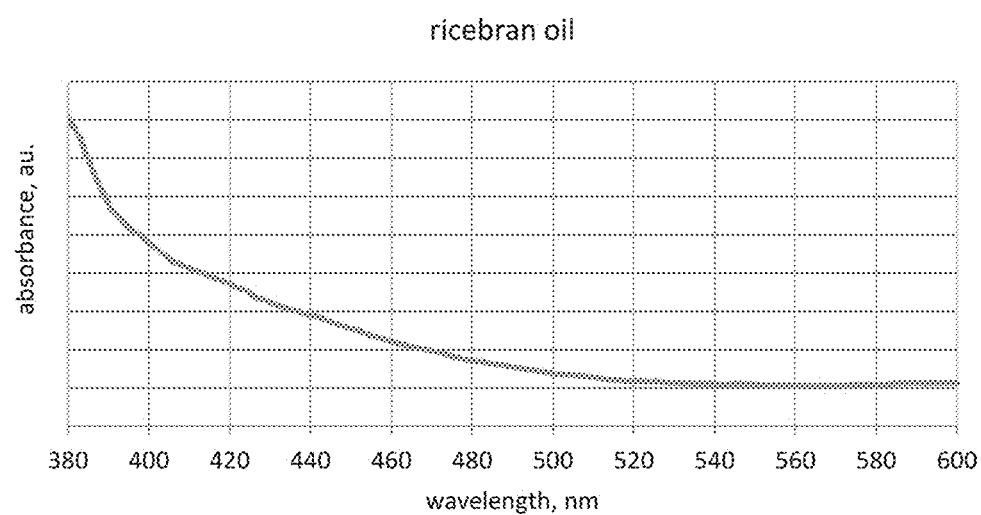
Figure 6W:
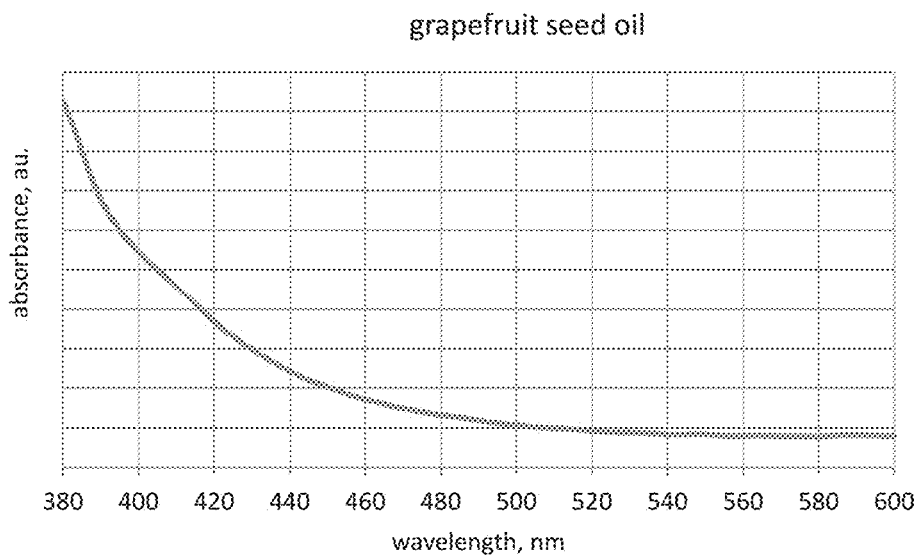
Figure 6X:
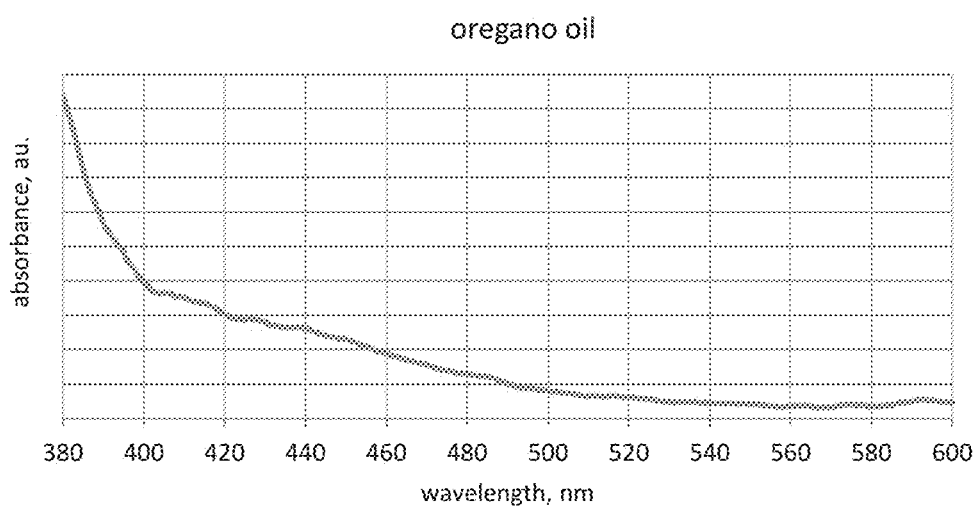

In certain embodiments, the absorbance spectra of certain materials, e.g., oils, that absorb well in the 380-400 nm range are shown in FIGS. 6A-6X. These oils include ginger oil (FIG. 6A), hazelnut oil (FIG. 6B), cinnamon bark oil (FIG. 6C), Egyptian germanium oil (FIG. 6D), tea tree oil (FIG. 6E), sesame oil (FIG. 6F), aloe vera oil (FIG. 6G), avocado oil (FIG. 6H), meadowfoam oil (FIG. 6I), turmeric oil (FIG. 6J), eucalyptus oil (FIG. 6K), coconut oil (FIG. 6L), castor oil (FIG. 6M), yellow marigold oil (FIG. 6N), Helichrysum oil (FIG. 6O), rosemary oil (FIG. 6P), feverfew oil (FIG. 6Q), clove oil (FIG. 6R), grapeseed oil (FIG. 6S), frankincense oil (FIG. 6T), soybean oil (FIG. 6U), rice bran oil (FIG. 6V), grapefruit seed oil (FIG. 6U) and oregano oil (FIG. 6X). These oils are referred to as "Group B" oils. While these oils have a high absorption from 380-400 nm, they have little or no absorption from 450-500 nm. It may be desirable to combine one or more of the oils from Group A oils with one or more of the oils from Group B oils to provide a composition which has a good average absorbance, e.g., 50% absorption or greater, over the entire 380-500 nm or the 400-500 nm range. In some instances, a Group A oil is used in combination with a Group B oil, optionally along with other components, to provide a composition with an average absorbance of about 75% (compared to baseline) over the 380-500 nm range or over the 400-500 nm range.

In certain instances, the compositions described herein comprise ginger oil in combination with one, two, three or more Group A oils and optionally in combination with one, two or three other Group B oils. Where ginger oil is present in combination with one, two or more other Group A oils, the compositions desirably comprise a suitable amount of each oil to provide an average absorption of light over the 380-500 nm range or the 400-500 nm range of at least 30%, or at least 50%, or at least 70% or at least 80%.

In certain instances, the compositions described herein comprise hazelnut oil in combination with one, two, three or more Group A oils and optionally in combination with one, two or three other Group B oils. Where hazelnut oil is present in combination with one, two or more other Group A oils, the compositions desirably comprise a suitable amount of each oil to provide an average absorption of light over the 380-500 nm range or the 400-500 nm range of at least 30%, or at least 50%, or at least 70% or at least 80%.

In other instances, the compositions described herein comprise cinnamon bark oil in combination with one, two, three or more Group A oils and optionally in combination with one, two or three other Group B oils. Where hazelnut oil is present in combination with one, two or more other Group A oils, the compositions desirably comprise a suitable amount of each oil to provide an average absorption of light over the 380-500 nm range or the 400-500 nm range of at least 30%, or at least 50%, or at least 70% or at least 80%.

In other instances, the compositions described herein comprise Egyptian germanium oil in combination with one, two, three or more Group A oils and optionally in combination with one, two or three other Group B oils. Where Egyptian germanium oil is present in combination with one, two or more other Group A oils, the compositions desirably comprise a suitable amount of each oil to provide an average absorption of light over the 380-500 nm range or the 400-500 nm range of at least 30%, or at least 50%, or at least 70% or at least 80%.

In other instances, the compositions described herein comprise tea tree oil in combination with one, two, three or more Group A oils and optionally in combination with one, two or three other Group B oils. Where tea tree oil is present in combination with one, two or more other Group A oils, the compositions desirably comprise a suitable amount of each oil to provide an average absorption of light over the 380-500 nm range or the 400-500 nm range of at least 30%, or at least 50%, or at least 70% or at least 80%.

In certain instances, the compositions described herein comprise sesame oil in combination with one, two, three or more Group A oils and optionally in combination with one, two or three other Group B oils. Where sesame oil is present in combination with one, two or more other Group A oils, the compositions desirably comprise a suitable amount of each oil to provide an average absorption of light over the 380-500 nm range or the 400-500 nm range of at least 30%, or at least 50%, or at least 70% or at least 80%.

In certain instances, the compositions described herein comprise aloe vera oil in combination with one, two, three or more Group A oils and optionally in combination with one, two or three other Group B oils. Where aloe vera oil is present in combination with one, two or more other Group A oils, the compositions desirably comprise a suitable amount of each oil to provide an average absorption of light over the 380-500 nm range or the 400-500 nm range of at least 30%, or at least 50%, or at least 70% or at least 80%.

In other instances, the compositions described herein comprise avocado oil in combination with one, two, three or more Group A oils and optionally in combination with one, two or three other Group B oils. Where avocado oil is present in combination with one, two or more other Group A oils, the compositions desirably comprise a suitable amount of each oil to provide an average absorption of light over the 380-500 nm range or the 400-500 nm range of at least 30%, or at least 50%, or at least 70% or at least 80%.

In additional instances, the compositions described herein comprise meadowfoam oil in combination with one, two, three or more Group A oils and optionally in combination with one, two or three other Group B oils. Where meadowfoam oil is present in combination with one, two or more other Group A oils, the compositions desirably comprise a suitable amount of each oil to provide an average absorption of light over the 380-500 nm range or the 400-500 nm range of at least 30%, or at least 50%, or at least 70% or at least 80%.

In additional instances, the compositions described herein comprise turmeric oil in combination with one, two, three or more Group A oils and optionally in combination with one, two or three other Group B oils. Where turmeric oil is present in combination with one, two or more other Group A oils, the compositions desirably comprise a suitable amount of each oil to provide an average absorption of light over the 380-500 nm range or the 400-500 nm range of at least 30%, or at least 50%, or at least 70% or at least 80%.

In additional instances, the compositions described herein comprise eucalyptus oil in combination with one, two, three or more Group A oils and optionally in combination with one, two or three other Group B oils. Where eucalyptus oil is present in combination with one, two or more other Group A oils, the compositions desirably comprise a suitable amount of each oil to provide an average absorption of light over the 380-500 nm range or the 400-500 nm range of at least 30%, or at least 50%, or at least 70% or at least 80%.

In other instances, the compositions described herein comprise coconut oil in combination with one, two, three or more Group A oils and optionally in combination with one, two or three other Group B oils. Where coconut oil is present in combination with one, two or more other Group A oils, the compositions desirably comprise a suitable amount of each oil to provide an average absorption of light over the 380-500 nm range or the 400-500 nm range of at least 30%, or at least 50%, or at least 70% or at least 80%.

In additional instances, the compositions described herein comprise castor oil in combination with one, two, three or more Group A oils and optionally in combination with one, two or three other Group B oils. Where castor oil is present in combination with one, two or more other Group A oils, the compositions desirably comprise a suitable amount of each oil to provide an average absorption of light over the 380-500 nm range or the 400-500 nm range of at least 30%, or at least 50%, or at least 70% or at least 80%.

In other instances, the compositions described herein comprise yellow marigold oil in combination with one, two, three or more Group A oils and optionally in combination with one, two or three other Group B oils. Where yellow marigold oil is present in combination with one, two or more other Group A oils, the compositions desirably comprise a suitable amount of each oil to provide an average absorption of light over the 380-500 nm range or the 400-500 nm range of at least 30%, or at least 50%, or at least 70% or at least 80%.

In some examples, the compositions described herein comprise Helichrysum oil in combination with one, two, three or more Group A oils and optionally in combination with one, two or three other Group B oils. Where Helichrysum oil is present in combination with one, two or more other Group A oils, the compositions desirably comprise a suitable amount of each oil to provide an average absorption of light over the 380-500 nm range or the 400-500 nm range of at least 30%, or at least 50%, or at least 70% or at least 80%.

In some examples, the compositions described herein comprise rosemary oil in combination with one, two, three or more Group A oils and optionally in combination with one, two or three other Group B oils. Where rosemary oil is present in combination with one, two or more other Group A oils, the compositions desirably comprise a suitable amount of each oil to provide an average absorption of light over the 380-500 nm range or the 400-500 nm range of at least 30%, or at least 50%, or at least 70% or at least 80%.

In certain examples, the compositions described herein comprise clove oil in combination with one, two, three or more Group A oils and optionally in combination with one, two or three other Group B oils. Where clove oil is present in combination with one, two or more other Group A oils, the compositions desirably comprise a suitable amount of each oil to provide an average absorption of light over the 380-500 nm range or the 400-500 nm range of at least 30%, or at least 50%, or at least 70% or at least 80%.

In certain examples, the compositions described herein comprise grapeseed oil or extract in combination with one, two, three or more Group A oils and optionally in combination with one, two or three other Group B oils. Where grapeseed oil is present in combination with one, two or more other Group A oils, the compositions desirably comprise a suitable amount of each oil to provide an average absorption of light over the 380-500 nm range or the 400-500 nm range of at least 30%, or at least 50%, or at least 70% or at least 80%.

In certain examples, the compositions described herein comprise frankincense oil in combination with one, two, three or more Group A oils and optionally in combination with one, two or three other Group B oils. Where frankincense oil is present in combination with one, two or more other Group A oils, the compositions desirably comprise a suitable amount of each oil to provide an average absorption of light over the 380-500 nm range or the 400-500 nm range of at least 30%, or at least 50%, or at least 70% or at least 80%.

In some examples, the compositions described herein comprise soybean oil in combination with one, two, three or more Group A oils and optionally in combination with one, two or three other Group B oils. Where soybean oil is present in combination with one, two or more other Group A oils, the compositions desirably comprise a suitable amount of each oil to provide an average absorption of light over the 380-500 nm range or the 400-500 nm range of at least 30%, or at least 50%, or at least 70% or at least 80%.

In certain examples, the compositions described herein comprise rice bran oil in combination with one, two, three or more Group A oils and optionally in combination with one, two or three other Group B oils. Where rice bran oil is present in combination with one, two or more other Group A oils, the compositions desirably comprise a suitable amount of each oil to provide an average absorption of light over the 380-500 nm range or the 400-500 nm range of at least 30%, or at least 50%, or at least 70% or at least 80%.

In some examples, the compositions described herein comprise grapefruit seed oil in combination with one, two, three or more Group A oils and optionally in combination with one, two or three other Group B oils. Where grapefruit seed oil is present in combination with one, two or more other Group A oils, the compositions desirably comprise a suitable amount of each oil to provide an average absorption of light over the 380-500 nm range or the 400-500 nm range of at least 30%, or at least 50%, or at least 70% or at least 80%.

In some examples, the compositions described herein comprise oregano oil in combination with one, two, three or more Group A oils and optionally in combination with one, two or three other Group B oils. Where oregano oil is present in combination with one, two or more other Group A oils, the compositions desirably comprise a suitable amount of each oil to provide an average absorption of light over the 380-500 nm range or the 400-500 nm range of at least 30%, or at least 50%, or at least 70% or at least 80%.

In certain embodiments, FIG. 6Y shows a table listing certain oils and materials which can be combined together to provide a composition that provides good absorbance over the 380-500 nm range or the 400-500 nm range. In some examples, the composition comprises two or more of the materials listed in FIG. 6Y, e.g., 3, 4, 5, 6 or more of the materials listed in FIG. 6Y.

Figure 7D:
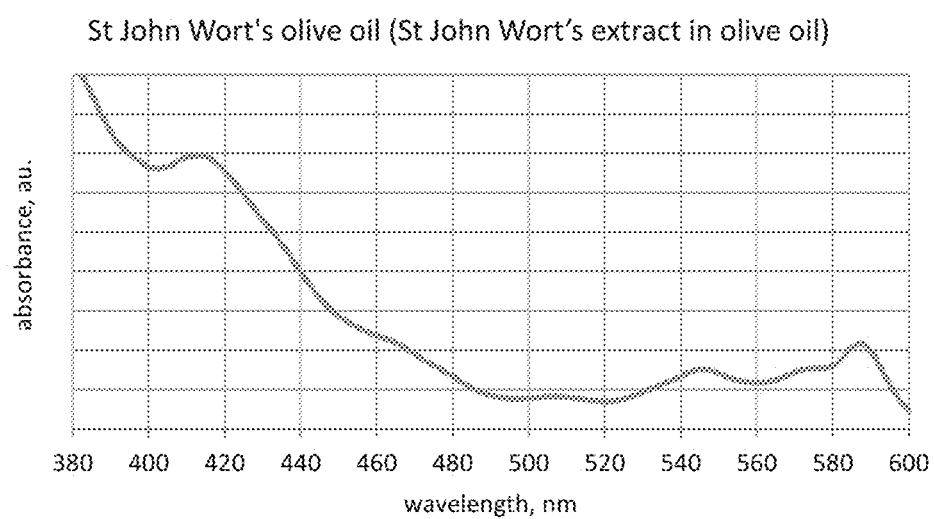

Certain oil combinations and their absorption curves are shown in FIGS. 7A-7F. These combinations include chaga mushroom extract in olive oil (FIG. 7A), oregano extract in olive oil (FIG. 7B), chaga extract in grain alcohol (FIG. 7C) and St. John's wort extract in olive oil (FIG. 7D). By combining two oils, the overall absorption curve flattens out, e.g., the slope decreases compared to the slope where only one oil is present, which results in enhanced protective effects from 38-500 nm. Additional combinations of two or more Group A and Group B oils are described below in the Examples appended hereto.

Figure 8A:
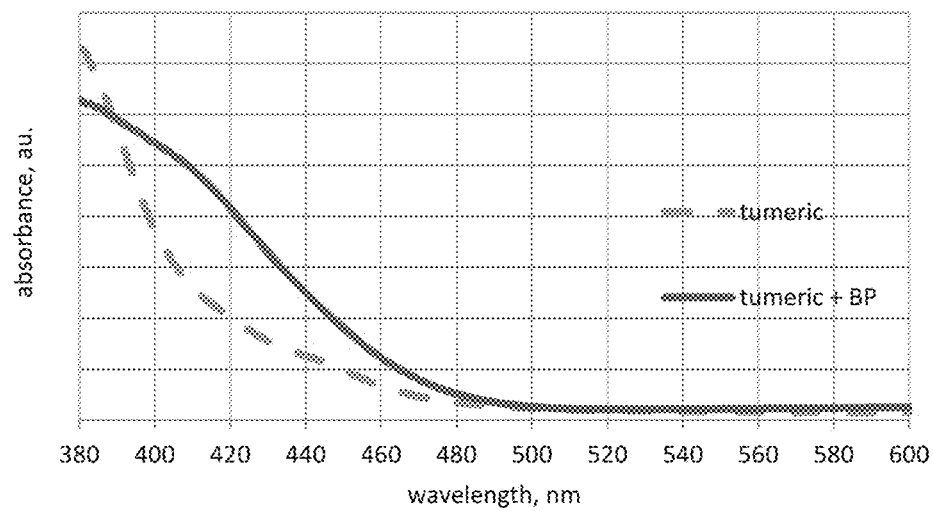
FIG. 8A shows turmeric oil and turmeric oil in combination with blue-reflecting/scattering microparticles.
Figure 8B:
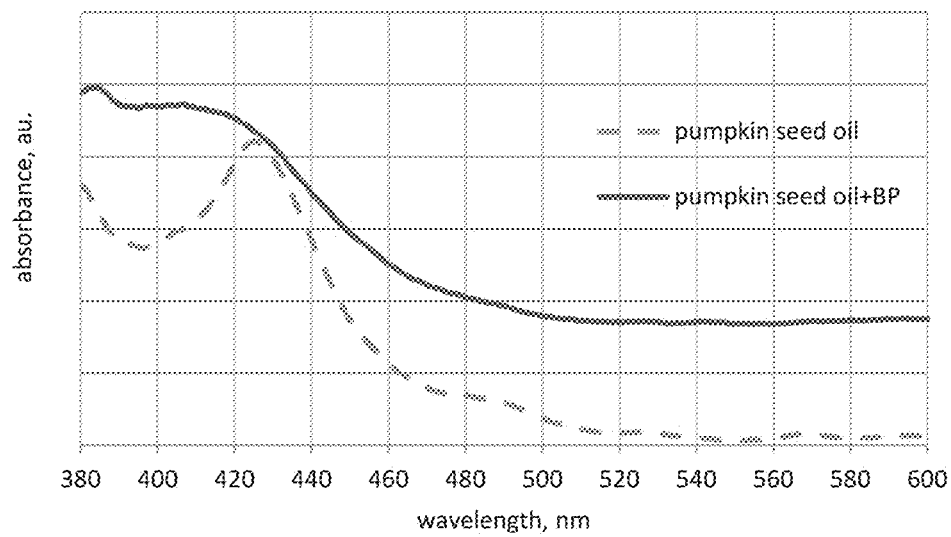
FIG. 8B shows pumpkin seed oil and pumpkin seed oil in combination with the blue-reflecting/scattering microparticles.

In certain instances, it may be desirable to include microparticles, nanoparticles, etc. in combination with one or more of the oils and extracts to further enhance the protective effects described herein. For example, microparticles or nanoparticles which can scatter violet-blue light and/or red shift the light to lower energy wavelengths may be desirable to enhance the protective effects of the compositions. FIG. 8A shows turmeric oil and turmeric oil in combination with blue-reflecting/scattering microparticles, and FIG. 8B shows pumpkin seed oil and pumpkin seed oil in combination with the blue-reflecting/scattering microparticles. As an example only, TechPolymer micron-size polymer particles, viz. grade XX-3541Z and grade XX-3542Z (Sekisui Plastics Co., Ltd), can be used. The exact amount and type of microparticles and nanoparticles may vary, and illustrative amounts include, but are not limited to, about 1% to about 20% by weight of the composition.

In certain embodiments and referring to FIG. 9, the various materials of the compositions may be classified according to their 420 nm/380 nm ratio. For example, it may be desirable to select one oil of the composition based on it having a 420/380 ratio of about 0.8 or higher. Illustrative oils with a 420/380 ratio of at least 0.8 include extra virgin olive oil, seabuckthorn berry oil, seabuckthorn seed oil, hemp seed oil, flax seed oil, wheat germ oil, broccoli oil, cranberry oil, cumin (black seed) oil, rosehip oil, pomegranate oil, black raspberry oil, carrot seed oil, apricot kernel oil and argan oil. Oils with a 420/380 ratio of at least 0.8 and a 460/380 ratio of at least 0.3 are referred to herein as Type I oils. Any of these Type I oils can be selected and used in combination with a Group A oil, a Group B oil or both in some instances, it may be desirable to select various combinations of Type I oils which have high absorbance ratios over the 420-500 nm range. For example, a first Type I oil can be selected with a high 420/380 nm ratio, e.g., above 0.8, a second Type I oil can be selected with a high 460/380 nm ratio, e.g., above 0.4 and a third Type I oil can be selected with a high 500/380 nm ratio, e.g., above 0.2, to provide a "flat" absorption curve over the 420-500 nm range. In some instances, a Type I oil with a 420/380 ratio of 1 or more can be combined with a Type 1 oil with a 460/380 ratio of 1 or more and/or with a Type 1 oil with a 500/380 ratio or 1 or more. By selecting Type I oil combinations whose ratios exceed 1 of these three ratio values, the overall protective effects of the oil combination can be increased. In certain instances, a Type I oil with a 420/380 ratio of 1 or more, a 460/380 ratio of 0.5 or more and a 500/380 ratio or 0.25 or more can be combined with a Group B oil to provide protective effects over the 380-500 nm range.

In certain examples, the compositions described herein comprise EVOO by itself or in combination with one, two or three other Type I oil. Where EVOO is present by itself or in combination with one, two or more other Type I oils, the compositions desirably comprise a suitable amount of each oil to provide an average absorption of light over the 380-500 nm range or the 400-500 nm range of at least 30%, or at least 50%, or at least 70% or at least 80%

In certain examples, the compositions described herein comprise seabuckthorn berry oil by itself or in combination with one, two or three other Type I oils. Where seabuckthorn berry oil is present by itself or in combination with one, two or more other Type I oils, the compositions desirably comprise a suitable amount of each oil to provide an average absorption of light over the 380-500 nm range or the 400-500 nm range of at least 30%, or at least 50%, or at least 70% or at least 80%.

In certain examples, the compositions described herein comprise seabuckthorn seed oil by itself or in combination with one, two or three other Type I oils. Where seabuckthorn seed oil is present by itself or in combination with one, two or more other Type I oils, the compositions desirably comprise a suitable amount of each oil to provide an average absorption of light over the 380-500 nm range or the 400-500 nm range of at least 30%, or at least 50%, or at least 70% or at least 80%.

In certain examples, the compositions described herein comprise hemp seed oil by itself or in combination with one, two or three other Type I oils. Where hemp seed oil is present by itself or in combination with one, two or more other Type I oils, the compositions desirably comprise a suitable amount of each oil to provide an average absorption of light over the 380-500 nm range or the 400-500 nm range of at least 50%, or at least 70% or at least 80%.

In certain examples, the compositions described herein comprise flax seed oil by itself or in combination with one, two or three other Type I oils. Where flax seed oil is present by itself or in combination with one, two or more other Type I oils, the compositions desirably comprise a suitable amount of each oil to provide an average absorption of light over the 380-500 nm range or the 400-500 nm range of at least 30%, or at least 50%, or at least 70% or at least 80%.

In certain examples, the compositions described herein comprise wheat germ oil by itself or in combination with one, two or three other Type I oils. Where wheat germ oil is present by itself or in combination with one, two or more other Type I oils, the compositions desirably comprise a suitable amount of each oil to provide an average absorption of light over the 380-500 nm range or the 400-500 nm range of at least 30%, or at least 50%, or at least 70% or at least 80%.

In certain examples, the compositions described herein comprise broccoli seed oil by itself or in combination with one, two or three other Type I oils. Where broccoli seed oil is present by itself or in combination with one, two or more other Type I oils, the compositions desirably comprise a suitable amount of each oil to provide an average absorption of light over the 380-500 nm range or the 400-500 nm range of at least 30%, or at least 50%, or at least 70% or at least 80%.

In certain examples, the compositions described herein comprise cranberry oil by itself or in combination with one, two or three other Type I oils. Where cranberry oil is present by itself or in combination with one, two or more other Type I oils, the compositions desirably comprise a suitable amount of each oil to provide an average absorption of light over the 380-500 nm range or the 400-500 nm range of at least 30%, or at least 50%, or at least 70% or at least 80%.

In certain examples, the compositions described herein comprise cumin oil by itself or in combination with one, two or three other Type I oils. Where cumin oil is present by itself or in combination with one, two or more other Type I oils, the compositions desirably comprise a suitable amount of each oil to provide an average absorption of light over the 380-500 nm range or the 400-500 nm range of at least 30%, or at least 50%, or at least 70% or at least 80%.

In certain examples, the compositions described herein comprise rosehip oil by itself or in combination with one, two or three other Type I oils. Where rosehip oil is present by itself or in combination with one, two or more other Type I oils, the compositions desirably comprise a suitable amount of each oil to provide an average absorption of light over the 380-500 nm range or the 400-500 nm range of at least 30%, or at least 50%, or at least 70% or at least 80%.

In certain examples, the compositions described herein comprise pomegranate oil by itself or in combination with one, two or three other Type I oils. Where pomegranate oil is present by itself or in combination with one, two or more other Type I oils, the compositions desirably comprise a suitable amount of each oil to provide an average absorption of light over the 380-500 nm range or the 400-500 nm range of at least 30%, or at least 50%, or at least 70% or at least 80%.

In certain examples, the compositions described herein comprise black raspberry oil by itself or in combination with one, two or three other Type I oils. Where black raspberry oil is present by itself or in combination with one, two or more other Type I oils, the compositions desirably comprise a suitable amount of each oil to provide an average absorption of light over the 380-500 nm range or the 400-500 nm range of at least 30%, or at least 50%, or at least 70% or at least 80%.

In certain examples, the compositions described herein comprise carrot seed oil by itself or in combination with one, two or three other Type I oils. Where carrot seed oil is present by itself or in combination with one, two or more other Type I oils, the compositions desirably comprise a suitable amount of each oil to provide an average absorption of light over the 380-500 nm range or the 400-500 nm range of at least 30%, or at least 50%, or at least 70% or at least 80%.

In certain examples, the compositions described herein comprise apricot kernel oil by itself or in combination with one, two or three other Type I oils. Where apricot kernel oil is present by itself or in combination with one, two or more other Type I oils, the compositions desirably comprise a suitable amount of each oil to provide an average absorption of light over the 380-500 nm range or the 400-500 nm range of at least 30%, or at least 50%, or at least 70% or at least 80%.

In certain examples, the compositions described herein comprise argan oil by itself or in combination with one, two or three other Type I oils. Where argan oil is present by itself or in combination with one, two or more other Type I oils, the compositions desirably comprise a suitable amount of each oil to provide an average absorption of light over the 380-500 nm range or the 400-500 nm range of at least 30%, or at least 50%, or at least 70% or at least 80%.

In certain examples, the compositions described herein comprise EVOO by itself or in combination with one, two or three Group B oils. Where EVOO is present by itself or in combination with one, two or more Group B oils, the compositions desirably comprise a suitable amount of each oil to provide an average absorption of light over the 380-500 nm range or the 400-500 nm range of at least 30%, or at least 50%, or at least 70% or at least 80%.

In certain examples, the compositions described herein comprise seabuckthorn berry oil by itself or in combination with one, two or three Group B oils. Where seabuckthorn berry oil is present by itself or in combination with one, two or more Group B oils, the compositions desirably comprise a suitable amount of each oil to provide an average absorption of light over the 380-500 nm range or the 400-500 nm range of at least 30%, or at least 50%, or at least 70% or at least 80%.

In certain examples, the compositions described herein comprise seabuckthorn seed oil by itself or in combination with one, two or three Group B oils. Where seabuckthorn seed oil is present by itself or in combination with one, two or more Group B oils, the compositions desirably comprise a suitable amount of each oil to provide an average absorption of light over the 380-500 nm range or the 400-500 nm range of at least 30%, or at least 50%, or at least 70% or at least 80%.

In certain examples, the compositions described herein comprise hemp seed oil by itself or in combination with one, two or three Group B oils. Where hemp seed oil is present by itself or in combination with one, two or other Group B oils, the compositions desirably comprise a suitable amount of each oil to provide an average absorption of light over the 380-500 nm range or the 400-500 nm range of at least 30%, or at least 50%, or at least 70% or at least 80%.

In certain examples, the compositions described herein comprise flax seed oil by itself or in combination with one, two or three Group B oils. Where flax seed oil is present by itself or in combination with one, two or more Group B oils, the compositions desirably comprise a suitable amount of each oil to provide an average absorption of light over the 380-500 nm range or the 400-500 nm range of at least 30%, or at least 50%, or at least 70% or at least 80%.

In certain examples, the compositions described herein comprise wheat germ oil by itself or in combination with one, two or three Group B oils. Where wheat germ oil is present by itself or in combination with one, two or more Group B oils, the compositions desirably comprise a suitable amount of each oil to provide an average absorption of light over the 380-500 nm range or the 400-500 nm range of at least 30%, or at least 50%, or at least 70% or at least 80%.

In certain examples, the compositions described herein comprise broccoli seed oil by itself or in combination with one, two or three Group B oils. Where broccoli oil is present by itself or in combination with one, two or more Group B oils, the compositions desirably comprise a suitable amount of each oil to provide an average absorption of light over the 380-500 nm range or the 400-500 nm range of at least 30%, or at least 50%, or at least 70% or at least 80%.

In certain examples, the compositions described herein comprise cranberry oil by itself or in combination with one, two or three Group B oils. Where cranberry oil is present by itself or in combination with one, two or more Group B oils, the compositions desirably comprise a suitable amount of each oil to provide an average absorption of light over the 380-500 nm range or the 400-500 nm range of at least 30%, or at least 50%, or at least 70% or at least 80%.

In certain examples, the compositions described herein comprise cumin oil by itself or in combination with one, two or three Group B oils. Where cumin oil is present by itself or in combination with one, two or more Group B oils, the compositions desirably comprise a suitable amount of each oil to provide an average absorption of light over the 380-500 nm range or the 400-500 nm range of at least 30%, or at least 50%, or at least 70% or at least 80%.

In certain examples, the compositions described herein comprise rosehip oil by itself or in combination with one, two or three Group B oils. Where rosehip oil is present by itself or in combination with one, two or more Group B oils, the compositions desirably comprise a suitable amount of each oil to provide an average absorption of light over the 380-500 nm range or the 400-500 nm range of at least 30%, or at least 50%, or at least 70% or at least 80%.

In certain examples, the compositions described herein comprise pomegranate oil by itself or in combination with one, two or three Group B oils. Where pomegranate oil is present by itself or in combination with one, two or more other Group B oils, the compositions desirably comprise a suitable amount of each oil to provide an average absorption of light over the 380-500 nm range or the 400-500 nm range of at least 30%, or at least 50%, or at least 70% or at least 80%.

In certain examples, the compositions described herein comprise black raspberry oil by itself or in combination with one, two or three Group B oils. Where black raspberry oil is present by itself or in combination with one, two or more Group B oils, the compositions desirably comprise a suitable amount of each oil to provide an average absorption of light over the 380-500 nm range or the 400-500 nm range of at least 30%, or at least 50%, or at least 70% or at least 80%.

In certain examples, the compositions described herein comprise carrot seed oil by itself or in combination with one, two or three Group B oils. Where carrot seed oil is present by itself or in combination with one, two or more Group B oils, the compositions desirably comprise a suitable amount of each oil to provide an average absorption of light over the 380-500 nm range or the 400-500 nm range of at least 30%, or at least 50%, or at least 70% or at least 80%.

In certain examples, the compositions described herein comprise apricot kernel oil by itself or in combination with one, two or three Group B oils. Where apricot kernel oil is present by itself or in combination with one, two or more Group B oils, the compositions desirably comprise a suitable amount of each oil to provide an average absorption of light over the 380-500 nm range or the 400-500 nm range of at least 30%, or at least 50%, or at least 70% or at least 80%.

In certain examples, the compositions described herein comprise argan oil by itself or in combination with one, two or three Group B oils. Where argan oil is present by itself or in combination with one, two or more Group B oils, the compositions desirably comprise a suitable amount of each oil to provide an average absorption of light over the 380-500 nm range or the 400-500 nm range of at least 30%, or at least 50%, or at least 70% or at least 80%.

In certain embodiments, the oils may be classified according to the absorption ratios where oils considered to be Type II oils generally have a 420/380 ratio less than 0.8 but greater than 0.3 and a 460/380 ratio of less than 0.3 but greater than 0.10. FIG. 10 shows a list of Type II oils which include, but are not limited to, pumpkin seed oil, jojoba oil, red raspberry oil, sunflower oil, sesame oil, aloe vera oil, avocado oil, chia seed oil, evening primrose oil, grapeseed oil, rice bran oil, hazelnut oil, avocado oil, marula oil, meadowfoam oil, coconut oil, chaga extract, chaga oil, oregano extract, oregano, soybean oil, and castor oil.

In certain examples, the compositions described herein comprise pumpkin seed oil in combination with one, two or three Type I oils or Group A oils. Where pumpkin seed oil is present in combination with one, two or more other Type I oils or Group A oils, the compositions desirably comprise a suitable amount of each oil to provide an average absorption of light over the 380-500 nm range or the 400-500 nm range of at least 30%, or at least 50%, or at least 70% or at least 80%.

In certain examples, the compositions described herein comprise jojoba oil in combination with one, two or three Type I oils or Group A oils. Where jojoba oil is present in combination with one, two or more Type I oils or Group A oils, the compositions desirably comprise a suitable amount of each oil to provide an average absorption of light over the 380-500 nm range or the 400-500 nm range of at least 30%, or at least 50%, or at least 70% or at least 80%.

In certain examples, the compositions described herein comprise red raspberry oil in combination with one, two or three Type I oils or Group A oils. Where red raspberry oil is present in combination with one, two or more Type I oils or Group A oils, the compositions desirably comprise a suitable amount of each oil to provide an average absorption of light over the 380-500 nm range or the 400-500 nm range of at least 30%, or at least 50%, or at least 70% or at least 80%.

In certain examples, the compositions described herein comprise sunflower oil in combination with one, two or three Type I oils or Group A oils. Where sunflower oil is present in combination with one, two or more Type I oils or Group A oils, the compositions desirably comprise a suitable amount of each oil to provide an average absorption of light over the 380-500 nm range or the 400-500 nm range of at least 30%, or at least 50%, or at least 70% or at least 80%.

In certain examples, the compositions described herein comprise sesame oil in combination with one, two or three Type I oils or Group A oils. Where sesame oil is present in combination with one, two or more Type I oils or Group A oils, the compositions desirably comprise a suitable amount of each oil to provide an average absorption of light over the 380-500 nm range or the 400-500 nm range of at least 30%, or at least 50%, or at least 70% or at least 80%.

In certain examples, the compositions described herein comprise aloe vera oil in combination with one, two or three Type I oils or Group A oils. Where aloe vera oil is present in combination with one, two or more Type I oils or Group A oils, the compositions desirably comprise a suitable amount of each oil to provide an average absorption of light over the 380-500 nm range or the 400-500 nm range of at least 30%, or at least 50%, or at least 70% or at least 80%.

In certain examples, the compositions described herein comprise avocado oil in combination with one, two or three Type I oils or Group A oils. Where avocado oil is present in combination with one, two or more Type I oils or Group A oils, the compositions desirably comprise a suitable amount of each oil to provide an average absorption of light over the 380-500 nm range or the 400-500 nm range of at least 30%, or at least 50%, or at least 70% or at least 80%.

In certain examples, the compositions described herein comprise chia seed oil in combination with one, two or three Type I oils or Group A oils. Where chia seed oil is present in combination with one, two or more Type I oils or Group A oils, the compositions desirably comprise a suitable amount of each oil to provide an average absorption of light over the 380-500 nm range or the 400-500 nm range of at least 30%, or at least 50%, or at least 70% or at least 80%.

In certain examples, the compositions described herein comprise evening primrose oil in combination with one, two or three Type I oils or Group A oils. Where evening primrose oil is present in combination with one, two or more Type I oils or Group A oils, the compositions desirably comprise a suitable amount of each oil to provide an average absorption of light over the 380-500 nm range or the 400-500 nm range of at least 30%, or at least 50%, or at least 70% or at least 80%.

In certain examples, the compositions described herein comprise grapeseed oil in combination with one, two or three Type I oils or Group A oils. Where grapeseed oil is present in combination with one, two or more Type I oils or Group A oils, the compositions desirably comprise a suitable amount of each oil to provide an average absorption of light over the 380-500 nm range or the 400-500 nm range of at least 30%, or at least 50%, or at least 70% or at least 80%.

In certain examples, the compositions described herein comprise rice bran oil in combination with one, two or three Type I oils or Group A oils. Where rice bran oil is present in combination with one, two or more Type I oils or Group A oils, the compositions desirably comprise a suitable amount of each oil to provide an average absorption of light over the 380-500 nm range or the 400-500 nm range of at least 30%, or at least 50%, or at least 70% or at least 80%.

In certain examples, the compositions described herein comprise hazelnut oil in combination with one, two or three Type I oils or Group A oils. Where hazelnut oil is present in combination with one, two or more Type I oils or Group A oils, the compositions desirably comprise a suitable amount of each oil to provide an average absorption of light over the 380-500 nm range or the 400-500 nm range of at least 30%, or at least 50%, or at least 70% or at least 80%.

In certain examples, the compositions described herein comprise marula oil in combination with one, two or three Type I oils or Group A oils. Where marula oil is present in combination with one, two or more Type I oils or Group A oils, the compositions desirably comprise a suitable amount of each oil to provide an average absorption of light over the 380-500 nm range or the 400-500 nm range of at least 30%, or at least 50%, or at least 70% or at least 80%.

In certain examples, the compositions described herein comprise meadowfoam oil in combination with one, two or three Type I oils or Group A oils. Where meadowfoam oil is present in combination with one, two or more Type I oils or Group A oils, the compositions desirably comprise a suitable amount of each oil to provide an average absorption of light over the 380-500 nm range or the 400-500 nm range of at least 30%, or at least 50%, or at least 70% or at least 80%.

In certain examples, the compositions described herein comprise coconut oil in combination with one, two or three Type I oils or Group A oils. Where coconut oil is present in combination with one, two or more Type I oils or Group A oils, the compositions desirably comprise a suitable amount of each oil to provide an average absorption of light over the 380-500 nm range or the 400-500 nm range of at least 30%, or at least 50%, or at least 70% or at least 80%.

In certain examples, the compositions described herein comprise chaga extract in combination with one, two or three Type I oils or Group A oils. Where chaga extract is present in combination with one, two or more Type I oils or Group A oils, the compositions desirably comprise a suitable amount of each oil to provide an average absorption of light over the 380-500 nm range or the 400-500 nm range of at least 30%, or at least 50%, or at least 70% or at least 80%.

In certain examples, the compositions described herein comprise chaga oil in combination with one, two or three Type I oils or Group A oils. Where chaga oil is present in combination with one, two or more Type I oils or Group A oils, the compositions desirably comprise a suitable amount of each oil to provide an average absorption of light over the 380-500 nm range or the 400-500 nm range of at least 30%, or at least 50%, or at least 70% or at least 80%.

In certain examples, the compositions described herein comprise oregano extract in combination with one, two or three Type I oils or Group A oils. Where oregano extract is present in combination with one, two or more Type I oils or Group A oils, the compositions desirably comprise a suitable amount of each oil to provide an average absorption of light over the 380-500 nm range or the 400-500 nm range of at least 30%, or at least 50%, or at least 70% or at least 80%.

In certain examples, the compositions described herein comprise oreganol in combination with one, two or three Type I oils or Group A oils. Where oreganol is present in combination with one, two or more Type I oils or Group A oils, the compositions desirably comprise a suitable amount of each oil to provide an average absorption of light over the 380-500 nm range or the 400-500 nm range of at least 30%, or at least 50%, or at least 70% or at least 80%.

In certain examples, the compositions described herein comprise soybean oil in combination with one, two or three Type I oils or Group A oils. Where soybean oil is present in combination with one, two or more Type I oils or Group A oils, the compositions desirably comprise a suitable amount of each oil to provide an average absorption of light over the 380-500 nm range or the 400-500 nm range of at least 30%, or at least 50%, or at least 70% or at least 80%.

In certain examples, the compositions described herein comprise castor oil in combination with one, two or three Type I oils or Group A oils. Where castor oil is present in combination with one, two or more Type I oils or Group A oils, the compositions desirably comprise a suitable amount of each oil to provide an average absorption of light over the 380-500 nm range or the 400-500 nm range of at least 30%, or at least 50%, or at least 70% or at least 80%.

In certain embodiments, the oils may be classified according to the absorption ratios where oils considered to be Type III oils generally have a 420/380 ratio less than 0.3 and a 460/380 ratio less than 0.1. FIG. 11 shows a list of Type III oils which include, but are not limited to, Helichrysum oil, ginger oil, cinnamon bark oil, turmeric oil, clove oil, grapefruit seed oil, frankincense oil, yellow marigold oil, Egyptian germanium oil, tea tree oil and eucalyptus oil. These Type III oils provide good absorption from 380-400 nm but substantially less or no absorption in the 400-500 nm range. Thus, Type III oils may desirably be combined with Type I oils, Type II oils, Group A oils or Group B oils (or combinations thereof) to provide an overall composition which has an average absorbance of at least 30%, or at least 50% over the 380-500 nm range or the 400-500 nm range.

In some examples, the compositions described herein comprise Helichrysum oil in combination with one, two or three Type I oils, Type II oils or Group A oils. Where Helichrysum oil is present in combination with one, two or more Type I oils, Type II oils or Group A oils, the compositions desirably comprise a suitable amount of each oil to provide an average absorption of light over the 380-500 nm range or the 400-500 nm range of at least 30%, or at least 50%, or at least 70% or at least 80%.

In some examples, the compositions described herein comprise ginger oil in combination with one, two or three Type I oils, Type II oils or Group A oils. Where ginger oil is present in combination with one, two or more Type I oils, Type II oils or Group A oils, the compositions desirably comprise a suitable amount of each oil to provide an average absorption of light over the 380-500 nm range or the 400-500 nm range of at least 30%, or at least 50%, or at least 70% or at least 80%.

In some examples, the compositions described herein comprise cinnamon bark oil in combination with one, two or three Type I oils, Type II oils or Group A oils. Where cinnamon bark oil is present in combination with one, two or more Type I oils, Type II oils or Group A oils, the compositions desirably comprise a suitable amount of each oil to provide an average absorption of light over the 380-500 nm range or the 400-500 nm range of at least 30%, or at least 50%, or at least 70% or at least 80%.

In some examples, the compositions described herein comprise turmeric oil in combination with one, two or three Type I oils, Type II oils or Group A oils. Where turmeric oil is present in combination with one, two or more Type I oils, Type II oils or Group A oils, the compositions desirably comprise a suitable amount of each oil to provide an average absorption of light over the 380-500 nm range or the 400-500 nm range of at least 30%, or at least 50%, or at least 70% or at least 80%.

In some examples, the compositions described herein comprise clove oil in combination with one, two or three Type I oils, Type II oils or Group A oils. Where clove oil is present in combination with one, two or more Type I oils, Type II oils or Group A oils, the compositions desirably comprise a suitable amount of each oil to provide an average absorption of light over the 380-500 nm range or the 400-500 nm range of at least 30%, or at least 50%, or at least 70% or at least 80%.

In some examples, the compositions described herein comprise grapefruit seed oil in combination with one, two or three Type I oils, Type II oils or Group A oils. Where grapefruit seed oil is present in combination with one, two or more Type I oils, Type II oils or Group A oils, the compositions desirably comprise a suitable amount of each oil to provide an average absorption of light over the 380-500 nm range or the 400-500 nm range of at least 30%, or at least 50%, or at least 70% or at least 80%.

In some examples, the compositions described herein comprise frankincense oil in combination with one, two or three Type I oils, Type II oils or Group A oils. Where frankincense oil is present in combination with one, two or more Type I oils, Type II oils or Group A oils, the compositions desirably comprise a suitable amount of each oil to provide an average absorption of light over the 380-500 nm range or the 400-500 nm range of at least 30%, or at least 50%, or at least 70% or at least 80%.

In some examples, the compositions described herein comprise yellow marigold oil in combination with one, two or three Type I oils, Type II oils or Group A oils. Where yellow marigold oil is present in combination with one, two or more Type I oils, Type II oils or Group A oils, the compositions desirably comprise a suitable amount of each oil to provide an average absorption of light over the 380-500 nm range or the 400-500 nm range of at least 30%, or at least 50%, or at least 70% or at least 80%.

In some examples, the compositions described herein comprise Egyptian germanium oil in combination with one, two or three Type I oils, Type II oils or Group A oils. Where Egyptian germanium oil is present in combination with one, two or more Type I oils, Type II oils or Group A oils, the compositions desirably comprise a suitable amount of each oil to provide an average absorption of light over the 380-500 nm range or the 400-500 nm range of at least 30%, or at least 50%, or at least 70% or at least 80%.

In some examples, the compositions described herein comprise tea tree oil in combination with one, two or three Type I oils, Type II oils or Group A oils. Where tea tree oil is present in combination with one, two or more Type I oils, Type II oils or Group A oils, the compositions desirably comprise a suitable amount of each oil to provide an average absorption of light over the 380-500 nm range or the 400-500 nm range of at least 30%, or at least 50%, or at least 70% or at least 80%.

In some examples, the compositions described herein comprise eucalyptus oil in combination with one, two or three Type I oils, Type II oils or Group A oils. Where eucalyptus oil is present in combination with one, two or more Type I oils, Type II oils or Group A oils, the compositions desirably comprise a suitable amount of each oil to provide an average absorption of light over the 380-500 nm range or the 400-500 nm range of at least 30%, or at least 50%, or at least 70% or at least 80%.

In addition to the various oils and oils combinations listed above, other ingredients can be added to provide specific functionality, e.g. fragrance, color-neutralizing compounds, butter (rhea butter, kokum seed butter, mango butter), waxes (beeswax), plant juices, extracts, propolis, powders (oat powder, colloidal oatmeal), petroleum jelly, menthol crystals, stabilizers, emulsifiers, alcohols, preservatives, emollients, colorants, viscosity modifiers, thixotropic agents, fibers, beads, liposomes, etc. In some examples, the compositions comprise an excipient, carrier, powder or other delivery agent to facilitate topical application of the compositions to the skin, hair and nails. If desired, particularly where applications to the nails may be performed, iontophoresis or other application of current or voltage can be used to drive the compositions into the nails and/or nail bed.

In certain examples, the oils selected for use in the compositions may also be selected based on fatty acid content. The various fatty acid content and/or ratios of the oils are shown in FIGS. 12 and 13. Fatty acids (FA) are necessary for the human body in many ways, but they are not synthesized by the body. Therefore, they can only be obtained through some external means like oil skin treatment. The FA usually have antioxidant and moisturizing properties. These essential FAs, which can be saturated (SFA), monounsaturated (MUFA) and polyunsaturated (PUFA), are all important for the regulation and maintenance of healthy skin and prevention of premature aging signs. Some of the essential oils are considered as the important sources for the natural antimicrobials.

Skin lipids play an essential role in skin barrier function and skin homeostasis. An imbalance in skin lipid composition is associated with disorders like atopic dermatitis. Lipids are a heterogeneous group of hydrophobic substances, including fats, free fatty acids, sterols, waxes, ceramides, triglyceride, fat soluble vitamins, phospholipids and others. Skin lipids are different from those of other tissues in that they are primarily synthesized in situ from glucose. In addition, the skin contains fatty acids (FAs), essential FAs (EFAs), squalene, wax and wax esters.

All mammals have a water permeability barrier in the epidermis of the skin that prevents water loss from the body. This barrier consists of dead skin cells surrounded by layers of lipids. The barrier lipids consist of a mixture of cholesterol, free fatty acids and special ceramides, among which is a unique ceramide containing linoleic acid. The traditional symptoms seen after prolonged dietary deficiency of (n-6)-fatty acids, e.g. increased trans-epidermal water loss, scaly skin, hair loss and poor growth, can all be ascribed to a lack of linoleic acid in special O-acylated ceramides, which constitute part of the lipid structure of the lamellar membranes between the cornocytes in stratum corneum of the epidermis. These extracellular lamellar membranes form together with the cornocytes a significant part of the water permeability barrier of the skin. Young growing rats would develop scaly skin, hair loss and poor growth due to lack of FAs in the diet and these deficiency symptoms could be cured by adding linoleic acid or other n-3 and n-6 fatty acids to the diet.

Essential fatty acids (EFAs) are essential for normal growth and maintaining good health. Characteristic for each EFA is the position and number of double bonds. Among the n-6 fatty acids are linoleic acid LA (18:2), γ-linolenic acid GLA (18:3), di-homo-γ-linolenic acid DHGLA (20:3) and arachidonic acid AA (20:4). Important n-3 fatty acids are α-linolenic acid ALA (18:3), eicosapentaenoic acid EPA (20:5) and docosahexaenoic acid DHA (22:6). The human organism is able to synthesize longer chain and higher desaturated fatty acids starting with ingested C18 EFAs in a multiple step reaction catalyzed by a set of desaturates and elongases, e.g. LA can be converted to GLA, DHGLA and AA. The same set of enzymes converts ALA into stearidonic acid and EPA. LA, an n-6 FA, and ALA, an n-3 FA, cannot be synthesized by humans and are considered essential. These EFAs, LA and ALA, are the precursors of the longer chain members in the n-6 and n-3 FA series, respectively. FAs are often abbreviated by their chemical designation, e.g. LA as 18:2n-6 where 18 indicates the length of the carbon chain; the 2, the number of cis double bonds; and the n-6 indicates that the first of these double bonds begins at the sixth carbon atom from the methyl end of the carbon chain. ALA is abbreviated as 18:3n-3, the n-3 indicates that the first double bond is at the third carbon from the methyl end of the chain. The longer chain FA, i.e. AA (20:4n-6), EPA (20:5n-3) and DHA (22:6n-3), can be synthesized in humans from their respective precursor EFA through a series of desaturation (addition of a double bond) and elongation (addition of two carbon atoms) enzymatic reactions. The (n-3) fatty acids and (n-6) fatty acids cannot be inter-converted in mammals. Polyunsaturated FAs, PUFAs, depending on the position of the first unsaturated double bond from the methyl end of the molecule are categorized into omega-3 (n-3), omega-6 (n-6) and omega-9 (n-9) families, as well as rare omega-5 (n-5) and omega-7 (n-7) fatty acids.

EFAs are needed for proper function of all tissues including the skin, e.g. linoleic acid (LA) deficiency results in impaired skin barrier function and scaling. The biochemical mechanisms underlying the effects of the oils on barrier function are not fully understood. It is believed that for n-6, the main protective activity at the skin level seems to be due to a long chain derivative of LA and DHGLA (20:3 n-6), which improves the cutaneous barrier as well as promoting hydration and retarding aging. One study showed that LA deficiency results in impaired barrier function and scaling, which might be due to the fact that LA is a constituent of ceramides, an important structural element of the skin barrier. Prolonged deficiency of LA results in a defective water permeability barrier of the skin, resulting in increased water loss over the skin. C20 fatty acids are important precursors of lipids which play a major role in the immune response of the skin.

It is important that the two series (n-6 and n-3) are present in a correct ratio, since they perform in various, and in many respects, contrasting actions. A correct ratio between the two series is therefore fundamental since EPA and DHA have an anti-inflammatory and immunoprotective action on the skin, as well as an anti-tumoral and cardioprotective one, in contrast to AA that has pro-inflammatory and immune suppressive effects. Therefore, PUFAs have the potential of a therapeutic effect on inflammatory skin disorders because of their effects on the fluidity and function of immune cell membranes, but also as precursors for the immune modulators eicosanoids. The presence of the longer chain derivatives of 20-22 carbon atoms, or LC-PUFA, as dihomo-gamma-linolenic, or DHGLA (20:3 n-6), arachidonic, or AA (20:4 n-6), eicosapentaenoic, or EPA (20:5 n-3) and docosaesaenoic, or DHA (22:6 n-3) in the skin and in the body is also very crucial. However, though it needs long chain derivatives (LC-PUFA), the skin does not possess elongase and desaturase enzymes, and therefore, it cannot form them from C18 EFAs, such as LA and ALA. Thus, LC-PUFA have to "arrive" in the skin already preformed. The skin, however, has cyclo-oxygenase and lipo-oxygenase, enzymes that form prostaglandins, thromboxanes and leukotrienes from LC-PUFA.

Therefore, to protect dermal cell integrity, it seems desirable to ensure an optimum PUFA n-6 amount; neither too little nor too much. PUFA n-3 is recommended for their resistance to peroxidation for their protective action on the body in general and on the skin in particular. It is very important both for the body and the skin that a balanced ratio between the n-6 and n-3 series (not greater than 10:1) is maintained. Many researchers recommend ratio around 5:1 for infants and elderly people. This balanced ratio can be maintained not only by increasing the n-3, but also by reducing the n-6, which can be obtained by preferring MUFA (oleic acid) highly resistant to peroxidative processes.

A sufficient topical and/or dietary intake of EFAs maintains skin homeostasis since these fatty acids play an important role as a barrier for the skin, promoting its hydration and preventing eventual skin disorders, such as atopic alterations, psoriasis, acne, and eczema. Therefore, certain formulations described herein are directed to topical formulations with the "right" composition and ratio of fatty acids needed for a good skin health while at the same time providing protection from HEV light. In additional formulations, compositions having the "right" ratio of fatty acids that provide HEV protection may also comprise one or more antioxidants (tocopherols, carotenoids and polyphenols) so the combination of the materials provides protection against HEV light as well as generation of reactive oxygen species or other harmful material within the cell.

Essential FAs are major components of all cell membranes, to which they provide permeability and elasticity. These acids play an essential role in the formation of ceramides—the most important lipids for the epidermis barrier—and are therefore, essential for the stability and function of the skin barrier. Emollients, such as lipids and oils, enhance skin flexibility and have moisturizing and soothing actions. These compounds repair the skin and influence skin permeability, thus improving the barrier function. The stearic, linoleic, oleic, linolenic and lauric acids are usually used as emollients in cosmetics. Because of their lipophilic nature, vegetable fats and oils are good emollients. These compounds efficiently prevent water loss through the epidermis because of their occlusive properties. Moreover, higher unsaturation degrees correspond to lower viscosities and larger penetration rates into the skin. Much research has been conducted in recent decades about the role of essential FAs in the formation and function of the barrier on the superficial skin layers. Some studies showed reduced transepidermal water loss (TEWL) after application of linoleic acid (LA) and γ-linoleic acid (GLA) for some days. Different LA or GLA treatments resulted in stable TEWL for several days. It was concluded that the action of LA and GLA on TEWL might be due to induced structural changes in the epidermis, in particular in the horny layer. These oils are used in dermatology and cosmetology for the treatment of dry and wrinkled skin, and to promote wound healing by stimulating tissue regeneration.

Various classifications of essential oils have been proposed. For instance, oils considered as in the MUFA class are almond, avocado, EVOO and argan oil. Grape seed, wheat germ, sunflower, linseed, walnut, sesame, soybean, and pumpkin oils, are considered as oils in the PUFA group. According to another classification, wheat germ, sunflower, sesame, soybean, and pumpkin oils are classified in the linoleic+MUFA subclass, since these oils, in addition to the important proportions of linoleic acid, also have high amounts of MUFA. The flax seed oil is the only one included in the linolenic+MUFA subclass, due to its exceptional content of 55.2% of linolenic acid. Sesame oil and argan oil have oleic and linoleic acids as major FAs. Soybean and pumpkin seed oils have very similar amounts of MUFA, but soybean showed higher PUFA, due to its special content of linolenic acid. When unsaturated oils are exposed to free radicals, they can create chain reactions of free radicals that spread the damage in the cell, and thus contribute to the cell's aging. In some instances, the composition may comprise at least one compound in Group FA-1, e.g., Group FA-1 either alone or in combination with one or more of a Group A oil, a Group B oil, a Type I oil, a Type II oil or a Type III oil. In some instances, the composition may comprise at least one compound in Group FA-2, e.g., Group FA-2 either alone or in combination with one or more of a Group A oil, a Group B oil, a Type I oil, a Type II oil or a Type III oil. In some instances, the composition may comprise at least one compound in Group FA-3, e.g., Group FA-3 either alone or in combination with one or more of a Group A oil, a Group B oil, a Type I oil, a Type II oil or a Type III oil. In additional instances, the composition may comprise at least one compound in Group FA-1 and at least one compound in Group FA-2, e.g., Group FA-1+Group FA-2 either alone or in combination with one or more of a Group A oil, a Group B oil, a Type I oil, a Type II oil or a Type III oil. In yet another instances, the composition may comprise at least one compound in Group FA-1 and at least one compound in Group FA-2 and at least one compound in Group FA-3, e.g., Group FA-1+Group FA-2+Group FA-3 either alone or in combination with one or more of a Group A oil, a Group B oil, a Type I oil, a Type II oil or a Type III oil.

Tocopherols (including Vitamin E) are excellent anti-free radical and antioxidant agents. Vitamin E protects the Vitamin A levels and essential fatty acids in the body. It prevents the evaporation of moisture from epidermis in skin; therefore, it can act as a barrier against aging of cells and promotes the nourishment of cells. With other words, vitamin E contributes to younger-looking skin, but also it has been seen to be very helpful against scarring from wounds and stretch marks. Total tocopherol (TP) content for various materials is shown in FIG. 14. In some instances, the composition may comprise at least one compound in Group X, e.g., Group X either alone or in combination with one or more of a Group A oil, a Group B oil, a Type I oil, a Type II oil or a Type III oil. In some instances, the composition may comprise at least one compound in Group Y, e.g., Group Y either alone or in combination with one or more of a Group A oil, a Group B oil, a Type I oil, a Type II oil or a Type III oil. In additional instances, the composition may comprise at least one compound in Group X and at least one compound in Group Y, e.g., Group X+Group Y either alone or in combination with one or more of a Group A oil, a Group B oil, a Type I oil, a Type II oil or a Type III oil.

Polyphenols or phenolic compounds present in the plant oils are natural components and have the long-lasting reputation of being anti-inflammatory, antiseptic, anti-aging, anti-allergic and antioxidant. Polyphenols prevent the penetration of UV radiation into the skin and can act as sunscreen, and thus, reduce inflammatory, oxidative stress and DNA damaging effects of UV radiation in the skin. The amount of total phenolics can be analyzed with Folin-Ciocalteu method; gallic acid or caffeic acid can be used as a standard. The results are expressed in terms of gallic acid equivalents (GAE) or caffeic acid equivalents (CAE). Total phenol content for various oils is shown in FIGS. 15 and 16.

Natural fat-soluble carotenoids protect the skin from the external radiation and free radical reactivity. Particularly, the photoprotective activity of carotenoids is related to their antioxidant properties, efficiently scavenging singlet molecular oxygen and peroxyl radicals. The carotenoid content for certain materials is shown in FIG. 17. Total sterol content is certain materials is shown in FIG. 18.

Trolox values and oxygen radical absorbance capacity (ORAC) values (expressed in units of mmol Trolox Equivalent per 100 grams) are listed in FIGS. 19A, 19B and—20. ORAC-values and Trolox equivalency are used as a benchmark for the antioxidant capacity. Trolox (6-hydroxy-2,5,7,8-tetrametmethylchroman-2-carboxylic acid), a water soluble vitamin E analog, is often used as the calibration standard. Various boosters/enhancers are shown in FIG. 21.

As noted herein, extra virgin olive oil (EVOO) is the oil obtained solely from the fruit of the olive tree (*Olea europaea* L.). It has been shown to be very effective against oxidative stress, which is defined as an imbalance between the oxidant and antioxidant systems of the body, in favor of the oxidants. Oxidative stress produced by free radicals has been linked to the development of several diseases such as cardiovascular, cancer, and neurodegenerative diseases. EVOO is rich in FAs as major components, especially monounsaturated fatty acids (MUFAs), e.g. the oleic acid, which prevent inflammation. EVOO also contains linoleic acid, a component that helps to prevent water from evaporation from the skin, and thus, promotes a youthful appearance of the skin.

Besides its richness in FAs, EVOO contains also minor components with multiple biological properties, providing antioxidant, anti-inflammatory, chemopreventive and anti-cancer benefits. Some of the minor components are phenolics, sterols, tocopherols, hydrocarbons and pigments. The phenolics, especially the hydrophilic and lipophilic phenols are the main antioxidants of EVOO, and they include a large variety of compounds. Among them, the most concentrated phenols are lignans and secoiridoids. The phenolic compounds present in olive oil are strong antioxidants and radical scavengers. Hydroxytyrosol and oleuropein have shown good antimicrobial activity against ATTC bacterial strains and clinical bacterial strains. Also, the healthy amount of tocopherols (including vitamin E) in EVOO efficiently neutralizes the free radicals and photoaging from harmful radiation. The levels of tocopherols in EVOO has shown that from the eight known "E-vitamers", the α-homologue comprises approx. 90% of the total tocopherol content. α-tocopherol is found in the free form. Moreover, among the hydrocarbons present in considerable amounts in EVOO are squalene and carotenoids (mainly β-carotene), the later possessing antioxidant capacities, and together with the pheophytins, are contributing to the EVOO color.

Argan oil is mainly produced in from the nut of the argan tree (*Argania spinosa*, L.). It is an excellent source of tocopherols (vitamin E) and unsaturated fatty acids, especially linoleic acid (Omega 6), which represents one third of the total composition of argan virgin oil. Alpha-tocopherol makes up 75% of the total tocopherols in the argan oil. Alpha-tocopherol and gamma-tocopherol are the two major forms of vitamin E in human plasma and the primary lipid-soluble antioxidants. Alpha-tocopherol has the ability to protect against nitrogen-based free radicals. Nitrogen free radicals play an important role in diseases associated with chronic inflammation, including cancer, heart disease and degenerative brain disorders. Besides tocopherols (vitamin E), the argan oil contains phenols, carotenes, squalene, and fatty acids, (80% unsaturated fatty acids). The main natural phenols in the argan oil are caffeic acid, oleuropein, vanillic acid, tyrosol, catechol, resorcinol, among the others.

The FAs present in argan Oil have antioxidant and moisturizing properties. These essential FAs are all important for the regulation and maintenance of healthy skin and skin elasticity, as well as prevention of premature aging signs. Furthermore, prostaglandins can be formed from fatty acids under enzyme action within the cells. They are anti-inflammatory and have a bearing on overall cell development and growth.

Furthermore, ferulic acid is the most abundant phenolic compound present in the argan oil. Its antioxidant potency increases on exposure to UV radiations, thus it is a very potent barrier against the damaging effects of Solar radiation. The natural fat soluble carotenoids protect the skin from ultra violet radiation and free radical reactivity. The chemical structure of argan sterols and human sterols is very similar, thus the argan oil sterols work in "great harmony" with the human skin. They perform a multitude of functions as part of Argan oil like keeping structural integrity of cell membrane, reducing inflammation, improving skin metabolism process and moisture retention.

Apricot kernel oil is pressed from the kernels of the *Prunus armeniaca* (apricots). Apricot kernels have an oil content of 40-50%. The seed cake is also used separately to extract an essential oil. The apricot oil (*Prunus armeniaca*

L.) consists mainly of unsaturated fatty acids, such as oleic and linoleic acid. Pharmacological studies demonstrated anti-asthmatic, anti-inflammatory, analgesic, anti-mutagenic, anti-cancer, antioxidant and anti-microbial effects of the apricot seed. The essential oil of apricot seed possesses antimicrobial activity against a range of bacteria and yeasts. For instance, it has inhibitory activities against *Staphylococcus aureus, Escherichia coli, Proteus mirabilis, Salmonella typhi* and *Candida albicans* among the others.

Rosehip seed oil is produced from the seeds of *Rosa* aff. *rubiginosa*. It contains a high percentage of poly-unsaturated essential fatty acids (PUFAs), such as linoleic and linolenic acids, known to be involved in prostaglandin synthesis, membrane generation, defense mechanisms, growth and other cell regeneration related processes. Therefore this oil is of great use to promote epithelization. It also contains other substances such as transretinoic acid, tannins, flavonoids, vitamin C and β-carotene, as well as natural Retinoic Acid (a Vitamin A derivative), which replenishes and helps rebuild skin tissue.

Rosehip seed oil is essential fatty acids-rich oil, which action is regulation of skin elasticity and restoring skin moisture. Additional to its effects on the outermost layers of the skin, rosehip oil also has invigorative activity on the innermost skin cell layers, fibroblasts and cells that produce collagen, elastin, hyaluronic acid and which are responsible for skin firmness and elasticity. Besides its firming action on deep skin layers, the rosehip seed oil prevents photoaging and skin disorders related to sunlight radiation, as well as to reduction of skin pores. The application of rosehip oil can help in attenuating scars, wrinkles and stretch marks, and in preventing premature aging and in regaining natural color and tone.

Linseed oil or flaxseed oil is an oil obtained from the dried, ripened seeds of the flax plant (*Linum usitatissimum*). Flaxseed is an oil seed that contains roughly 38-45% oil. α-Linolenic acid (ALA), an omega-3 fatty acid, accounts for 52% of the fatty acids in the oil, and therefore flaxseed oil is considered as one of the leading sources of ALA. Flaxseed is a rich source of different types of phenolics such as lignans, phenolic acids, flavonoids, phenylpropanoids and tannins. Linseed oil is a type of drying oil, meaning it can polymerize into a solid form. Due to its polymer-forming properties, it can be used to form protective coatings (films).

Jojoba Oil (*Simmondsia Chinensis*) which shows structural similarities to the human skin oil (sebum), has anti-inflammation action. Jojoba Oil is actually a liquid wax ester and not an oil. It is a natural emollient with good spreadability and can be used to provide a protective coating on the skin, nails or hair. It can be made as jojoba seed oil, jojoba seed wax, jojoba butter, or jojoba alcohol. In recent years, meadowfoam Seed Oil (*Limnanthes Alba*) has been proposed as an alternative to Jojoba Oil.

The active ingredients in green tea (*Camellia sinensis*) are the polyphenols, which possess antioxidant, anti-inflammatory and anti-carcinogenic properties. Green tea polyphenols (GTP) prevent ultraviolet (UV)-B-induced cyclobutane pyrimidine dimers, which are considered to be mediators of UVB-induced immune suppression and skin cancer induction. These in vivo observations suggest that GTPs are photoprotective, and can be used for the prevention of solar UVB light-induced skin disorders associated with immune suppression and DNA damage. The exact mechanism of preventing UV penetration into the skin is not established but it is known that GTPs absorb some of low wavelengths of UV spectrum (280-290 nm).

Wheat germ oil—certain skin conditions such as scarring and inflammation; Wheat germ oil is also very high in vitamin E (255 mg/100 g), and has the highest content of vitamin E of any food that has not undergone prior preparation or vitamin fortification Grapeseed oil contains lot of vitamin E, approximately twice as much as olive oil. It also has the highest concentration of omega-6 polyunsaturated fatty acids (PUFAs).

Coconut oil or Copra oil is an oil extracted from the kernel or meat of matured coconuts harvested from the coconut palm (*Cocos nucifera*). Virgin coconut oil have excellent antioxidant and anti-inflammatory properties. It is known for its main saturated fatty acids, such as lauric and myristic fatty acids.

Sunflower oil is the oil compressed from sunflower (*Helianthus annuus*) seeds. Sunflower oil is a monounsaturated (MUFA)/polyunsaturated (PUFA) fatty acid mixture of mostly oleic acid (omega-9)-linoleic acid (omega-6) group of oils.

Hemp oil or hempseed oil is obtained by pressing hemp seeds from varieties of hemps (*Cannabis sativa* L.). Hemp seed oil contains linoleic acids, omega-6 and omega-3 polyunsaturated fatty acids (PUFA).

Sesame oil (*Sesamum indicum* L.) is well known for its oxidative stability; one of the reasons for this extra-stability is attributed to its tocopherol content.

In certain embodiments, various Trolox value of oils are shown in FIGS. 19 and 20. Trolox values refer to the total antioxidant capacity of the various materials. A higher Trolox value in the overall composition is desirable to enhance the protective effects of the compositions.

In certain instances, the compositions described herein may comprise one or more booster or enhances which can be used in combination with the Group A oils, Group B oils, Type I-III oils or Group X or Group Y materials. Illustrative booster or enhancers are shown in FIG. 21 and include, but are not limited to, chaga mushroom extract, cumin oil, seabuckthorn oil or extract, pomegranate seed oil, turmeric oil, green tea extract, berry extracts or oils, rosehip oil, cranberry oil, broccoli oil, grape seed extract or oil or extra virgin olive oil (EVOO). When present, the boosters are typically present in small amounts, e.g., 10 weight percent or less. As can be seen in FIG. 21, there is some overlap in the boosters and the various Groups and Types of oils described herein. A booster may be added where the booster material is absent from the formulation. For example, where a formulation includes a Group A oil other than EVOO, the EVOO may be added in a minor amount, e.g., 5% by weight or less, to enhance the overall activity of the compositions. Another example is adding chaga extract to a certain combination of oils, which combination already strongly absorbs in HEV range, but the addition of chaga extract will "boost" the antioxidant activity of the final formulation with the SOD-enzymatic antioxidant and other nutrients. Yet another example is when grape seed extract is added to a strongly absorbing oil formulation in HEV spectral range and increases the final formulation's antioxidant activity (e.g. ORAC value) due its high content of proanthocyanidins.

Certain embodiments described herein use the visible light protective properties of these oils in addition to the UV protective and other properties of some of the oils. One illustrative embodiment in the present invention is that the skin, hair or nail care composition forms a barrier or protective layer that acts as a filter, i.e. blocks the harmful violet-blue visible (and UV) light rays to penetrate into the skin, hair and nail structure. In addition to the protective layer formation, some of the compositions in the present invention might partially penetrate into the skin, hair or nails, and thus, nourish, rejuvenate, regenerate, moisturize and/or heal the skin, hair and nails. In cases, where e.g. increased skin penetration is needed, alcohol(s) can be added, as well, which have been proven to provide good carrier (transfer) properties.

The compositions described herein can be used, for example, in the following forms: topical cream, ointment, skin care stick, lip balm, lip gloss, lip stick, serum, nourishing or conditioning day/night skin care kit, colloidal bath product, tonic, balsam, pomade, aerosol/spray, oil, corrective foundation, anti-aging kit, mask, mousse, foam, shaving cream, baby cream and lotion, nail polish, nail gloss, eye liner, mascara, eye shadow, suntan, sun screen, etc. Moreover, the compositions can be used in wet or dry cleansing wipes; the wipes can be infused or immersed in the proposed compositions, which after use leave a protective coating on the face, hands and the skin.

Depending on the particular materials which are present, the compositions can provide one or more of the following attributes: broad blue-violet protection, broad UVA+HEV protection, broad UVB+UVA+HEV protection, anti-inflammatory activity, anti-aging functionality, anti-wrinkle property, anti-oxidative function, softening action, nourishment, anti-microbial activity, soothing action, healing activity, rejuvenating action, regeneration function, restoration action, moisturizing action, barrier functionality, corrective functionality (skin toning, covering, brightening), dryness/eczema relief, anti-itching functionality, fragrance activity, etc.

In certain applications the product may be applied and/or reapplied to various areas of the body including, but not limited to, exposed skin including the body, face, lips, feet, hands, etc., to eye lids, to the hair and nails. In another embodiment, the compositions can also be used as veterinary care products to protect, moisturize and nourish the skin, fur and hair of animals (horses, cats, dogs, etc.)

In other embodiments, the compositions of this invention, besides the various oils and combinations thereof, may contain other compounds known in the art of various care products, e.g. TiO2 and/or ZnO2 nanoparticles, alcohols, emulsifiers, stabilizers, etc. These additional materials may be selected to absorb wavelengths below 380 nm so the overall composition may be effective to absorb light from about 300 nm to about 500 nm, e.g., at least about 50% of the light, on average, over the 300-500 nm range can be absorbed.

In yet another embodiment, some of the compositions may contain liposomes or micelle-structure delivery system for a controlled release of the components of interest. Some of the proposed compositions might be oil-in-water or water-in-oil formulations. In yet another embodiment, the compositions can have some additional functionality, such as polymer- or film-forming property to provide temporary barrier to the skin, nails and hair and or improve the skin roughness (wrinkles). For such functionality, flax seed oil and/or natural polymers, viz. collagen and collagen derivatives, gum arabic, chitin, pectin, hyaluronic acid, cellulose, polysaccharides can be used. A spectrum of synthetic materials (silicone and acrylate polymers) can be used for adding such functionality, as well. In yet another embodiment, "smart lotion compositions" are proposed. For instance, compositions with triggered action for delivery of the active ingredient is proposed. The active ingredients (UV-visible light blocking components) are "stored" in liposomes/micelles, for example, and under UV-visible light, or heat, or both, or under rubbing action (friction), the active ingredients can be delivered. Color-changing functionality of the lotion or cream can be added for fun in e.g. kids' skin care compositions or as a warning sign that another layer of skin care product needs to be applied.

In additional instances, the compositions can be used in combination with a smart watch or a fitness tracker, e.g., a Fitbit™ device, to track the user and/or determine whether the compositions need to be reapplied. For example, a smart watch may include a GPS which can track whether a user is outside or inside and for how long. Alternatively, the smart watch or fitness tracker may be able to measure the amount of UV or blue-violet light that a user is exposed to. This tracking and/or measurement can be used to inform the user that it may be time to apply or re-apply the compositions. For example, the smart watch or fitness tracker can be programmed to alert the user after 1 hour of blue-violet light exposure, 2 hours of blue-violet light exposure, etc. In another instance, the compositions can be used in combination with various UV index measuring skin patches. In another instances, the compositions can be used in combination with hats to be delivered to the hair in a controlled manner.

In certain instances, the compositions described herein may provide a blue-violet light protection factor (BPF) similar to the sun protection factors (SPF) commonly used for sunscreens. For example, the materials of the composition can be selected such that use of the composition on the skin permits a user to be exposed to the blue-violet light for longer periods without any substantial damage. If damage to the skin from exposure to blue-violet light occurs in about 15 minutes, then a BPF of 10 would permit 150 minutes of exposure to the blue-violet light for the same amount of damage if the user was not wearing any of the compositions. In certain instances, the BPF of the composition is selected such that it blocks about 95% or more of the blue-violet light (380-500 nm or 400-500 nm) over a period of about two hours (assuming the wearer is not sweating or swimming). In some instances, the oils and other materials of the compositions may be selected such that it blocks about 97% or more of the blue-violet light (380-500 nm or 400-500 nm) over a period of about two hours (assuming the wearer is not sweating or swimming). A user can reapply the compositions about every two hours to restore the BPF of the topically applied compositions. If a user is sweating or swimming, then the BPF may be reduced, and reapplication of the compositions at a frequency shorter than two hours may be needed.

In certain cases, the compositions described herein can be further developed for targeted applications. As an example only, vitamin-rich and other nutrients-rich oils can be used in night cream applications, where the UV- and HEV-light protection is not crucial. For day cream applications, oils and extracts containing UV-light and HEV-light blocking functionalities are more desired to protect the skin from the Sun and other light sources and displays. Moreover, the day creams can be further tailored into day creams for users that spend more time indoors, e.g. in front of the computers or other electronic devices. Such day creams for indoor use should contain active ingredients (oils) that have peak absorbance values in 400-500 nm, and especially peak absorbances around 460 nm, which is for example the peak of many white LED lights and backlights of many electronic devices. Day creams for use outdoors also should contain ingredients that strongly absorb 380-500 nm, and particularly will have peaks around 380-440 nm. Sunscreens would have ingredients that block efficiently in UV and HEV spectral range.

In another embodiments, the compositions disclosed herein, can be further tailored for use in products for baby care, teenage-care, adult skin-, nail and hair-care products, products for elderly skin, etc. Moreover, the compositions can be tailored for particular use, e.g. on face, hands, body, feet, lips, nails, etc., for daily use and protection, or for weekly- or monthly use, such as masks, boosters, serums, etc.

In certain embodiments, the compositions described herein can be used for pet skin- and fur-protection. By example only, creams or sprays for cats, dogs, birds and horses can be further developed from the proposed compositions.

Certain specific examples of the compositions and methods are described in more detail below.

Example 1

Various combinations of two or more oils from Group A, Group B, Type I, Type II and/or Type III oils are shown in FIG. 22A-22B. The absorbance spectra for the different oil combinations are shown in FIGS. 23A-23BV.

Figure 23A:
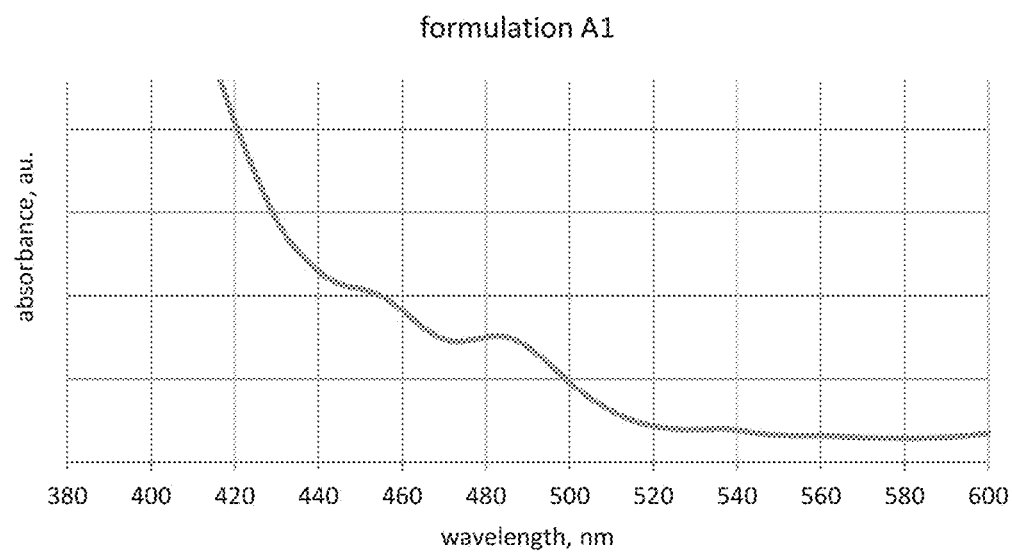
FIGS. 23A-23BV are absorbance spectra for the combinations listed in FIGS. 22A and 22B.
Figure 23B:
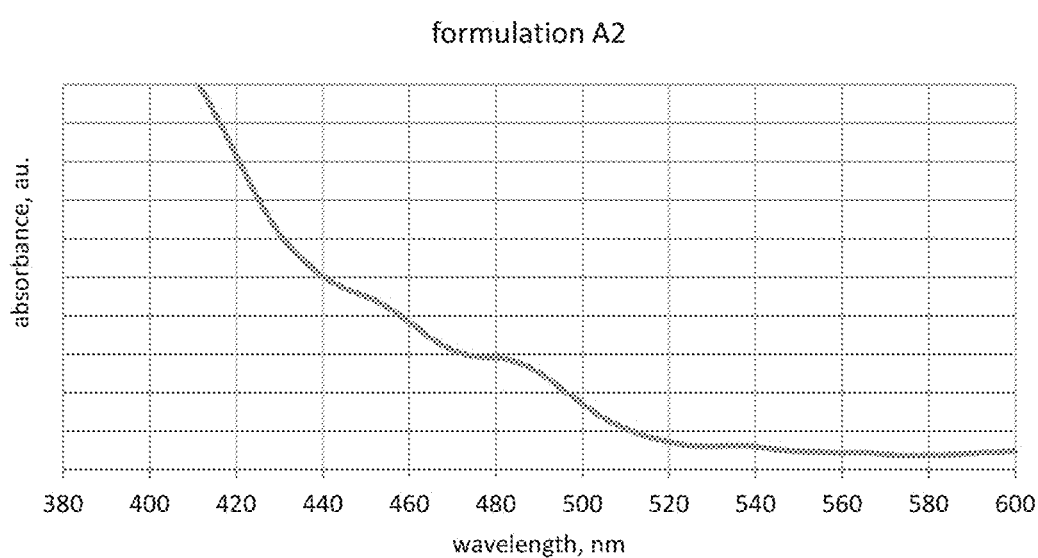
Figure 23C:
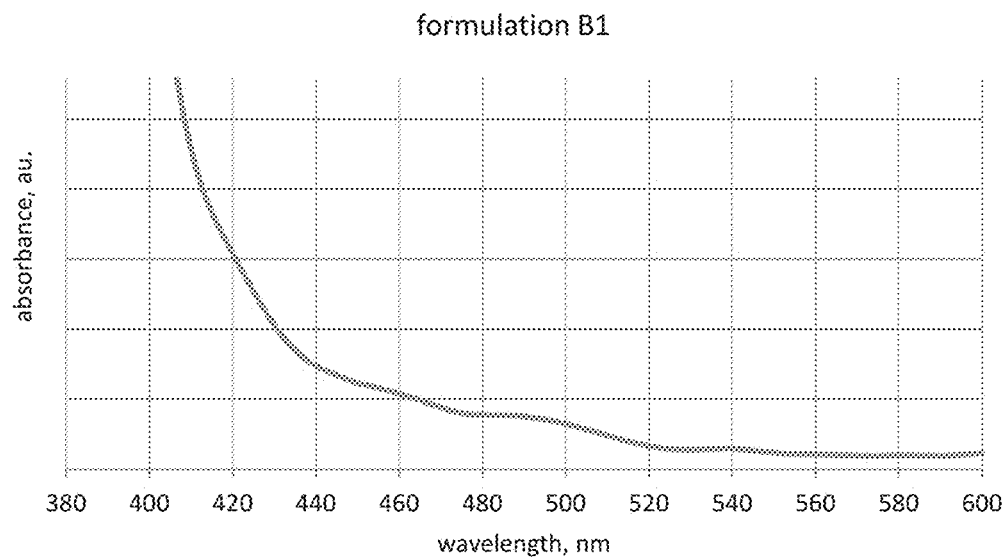
Figure 23D:
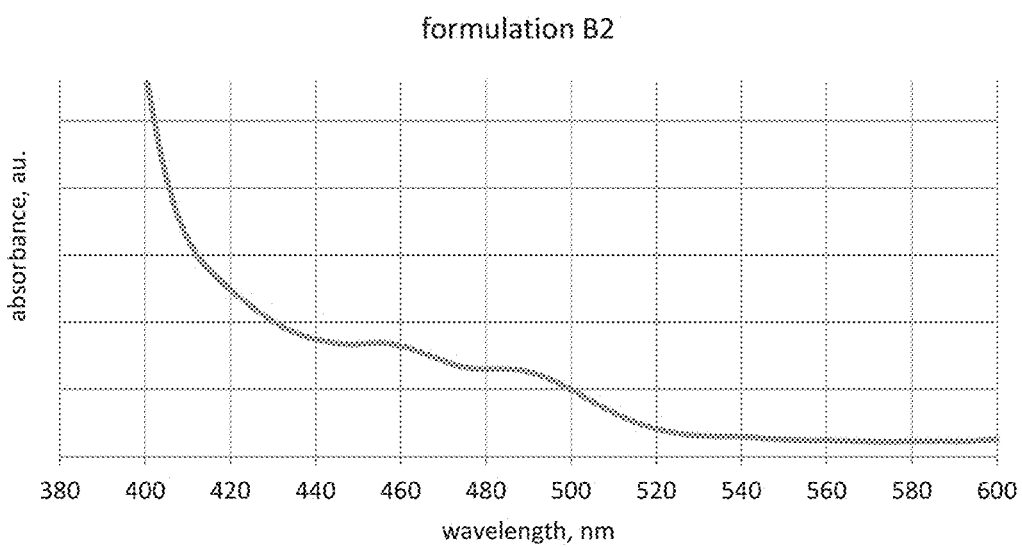

Referring to FIG. 23A-23B, which shows the absorbance spectra for formulations A1 and A2, respectively, the spectra for the two oil formulation provides some absorbance from 380-500 nm, but the absorbance is much higher closer to the 380 nm limit. When an addition oil is added (FIG. 23B), the absorbance spectrum flattens out from 440-500 nm. These results are consistent with the combinations of three or more oils providing more protection. A similar result is observed in comparing formulations B1 and B2 (FIGS. 23C-23D). Formulations A1, A2, B1 and B2 are good examples for oil combinations that can provide good UVA-protection, and to a certain extent, HEV-protection.

Figure 23E:
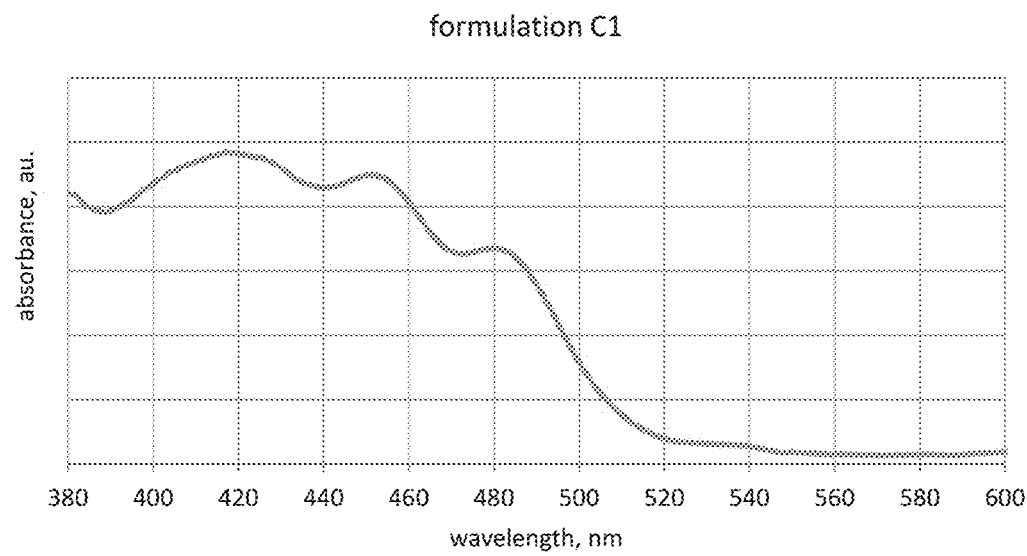
Figure 23F:
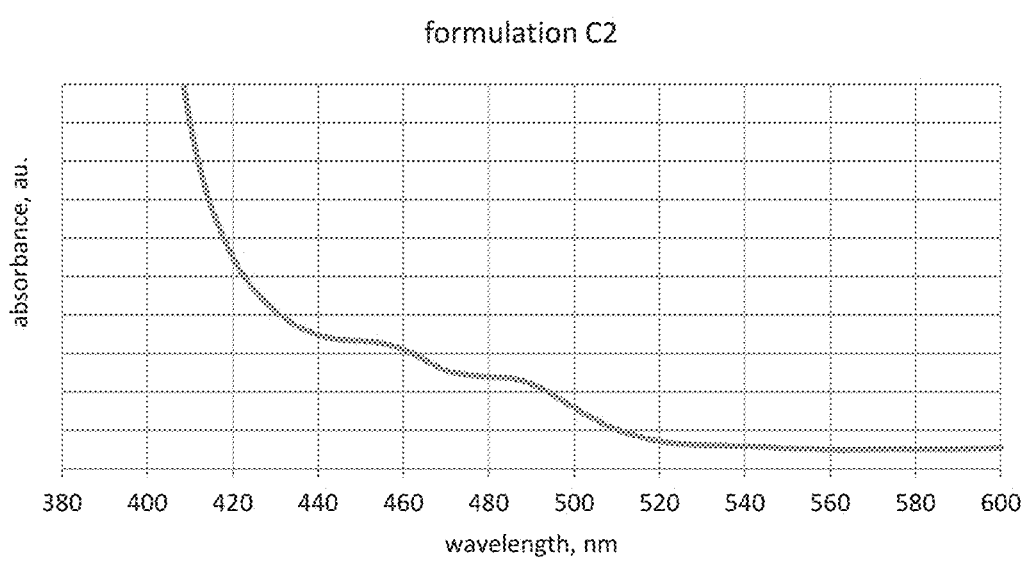

Comparing the spectra for formulations C1 and C2 (FIGS. 23E-23F), the absorbance spectrum for the C1 formulation is substantially flatter than that of the C2 formulation. Carrot seed oil and flax seed oil, the active ingredients in the C1 formulation, are strong absorbers in 400-500 nm range. The addition of cinnamon oil, which has very strong absorption around 400 nm and below, yielded a C2 formulation with strong absorption in UVA range in addition to the absorbance in high energy blue-violet visible range.

Figure 23G:
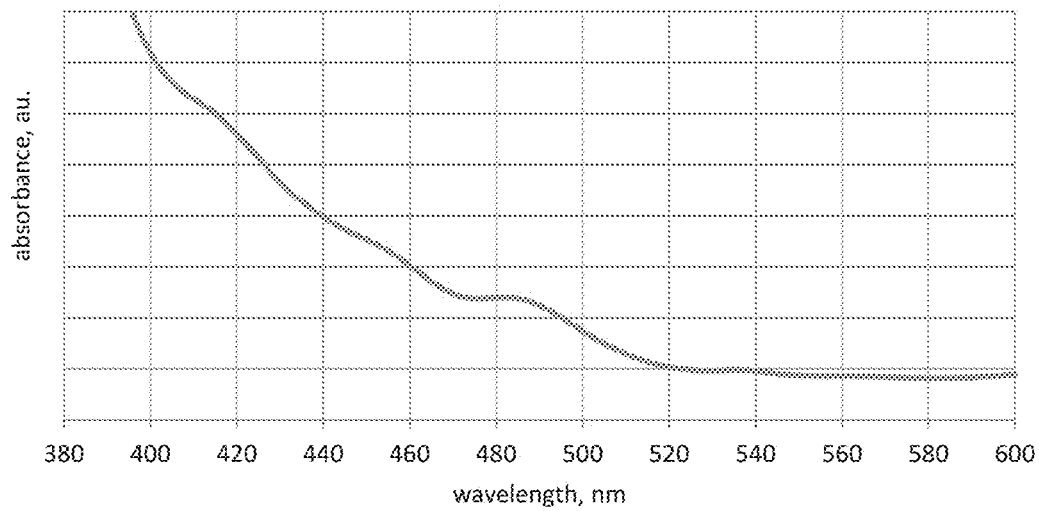
Figure 23H:
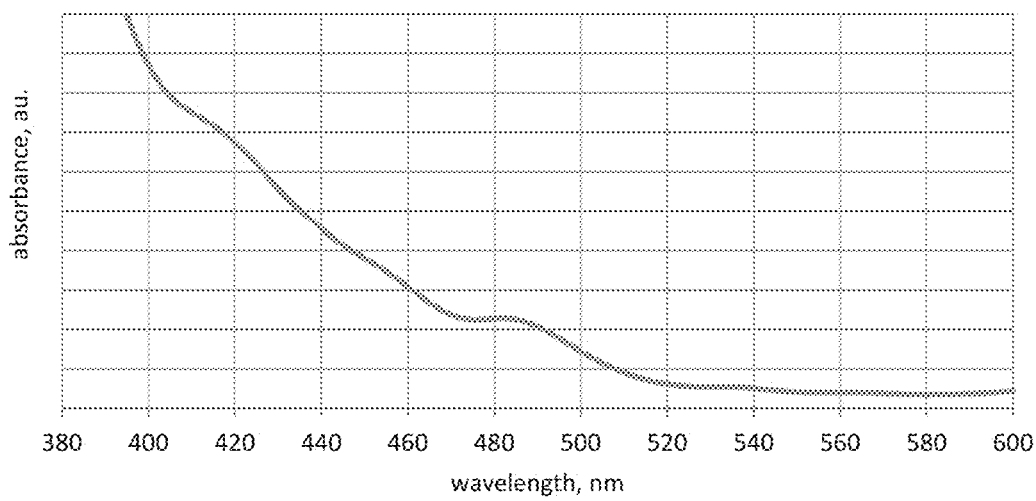

Comparing the spectra for formulations D1 and D2 (FIGS. 23G-23H), the absorbance spectra appear to be about the same. Thus, the addition of pumpkin seed oil to extra virgin olive oil and turmeric oil did not substantially alter the overall spectra appearance. Due to the very strong absorbance of one of the ingredients, turmeric oil, in the 400 nm range and below, formulations D1 and D2 provide are strong absorbers in this range and can provide good UVA protection, and to a certain extent, HEV protection.

Comparing the spectra for formulations E1 and E2 (FIGS. 23I-23J), the addition of pumpkin seed oil (FIG. 23J) flattened out the spectrum from 400-500 nm. Due to the very strong absorbance of one of the ingredients, turmeric oil, in the 400 nm range and below, formulations E1 and E2 are good examples for oil combinations that can provide good UVA protection, and to a certain extent, HEV protection.

Comparing the spectra for formulation F1 and F2 (FIGS. 23K-23L), the addition of Helichrysum oil results in very strong absorption in the 400 nm range and below in addition to the absorbance of rosehip oil and hemp seed oil in the 400-500 nm range.

Figure 23I:
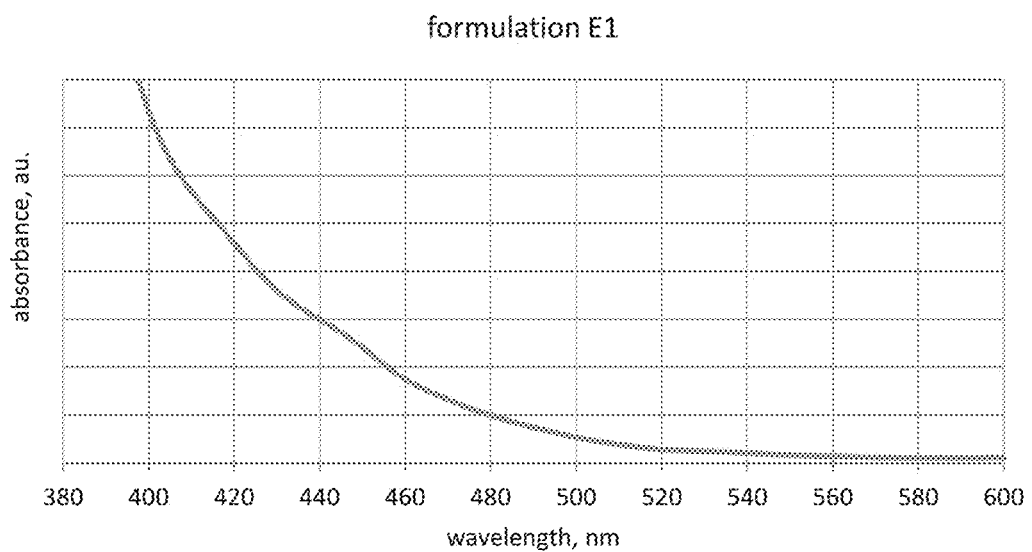
Figure 23J:
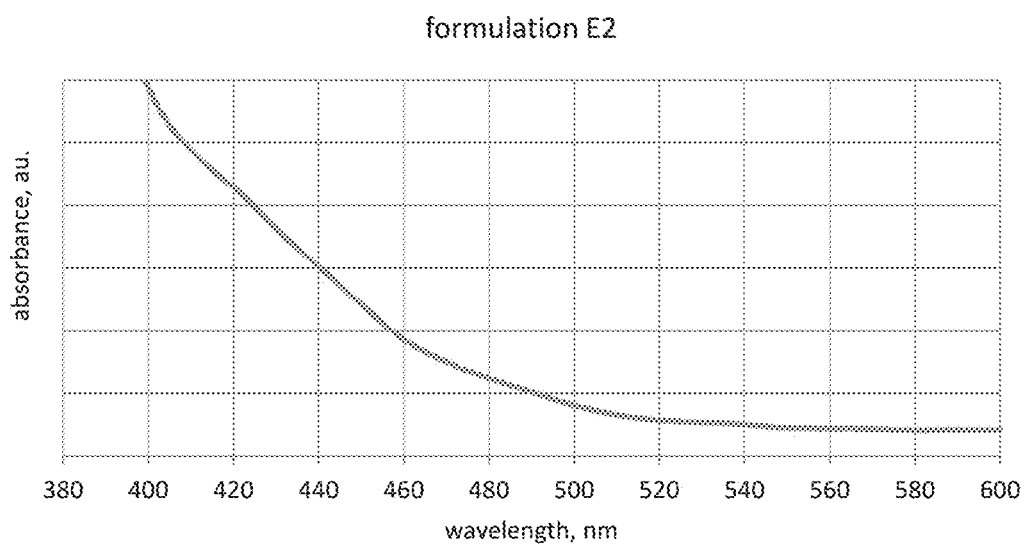
Figure 23K:
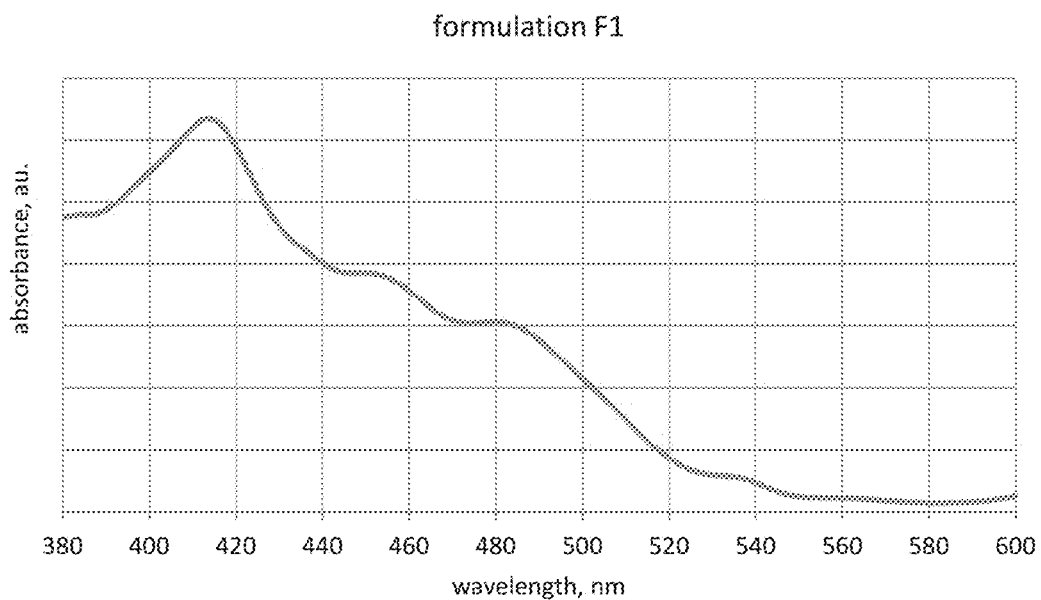
Figure 23L:
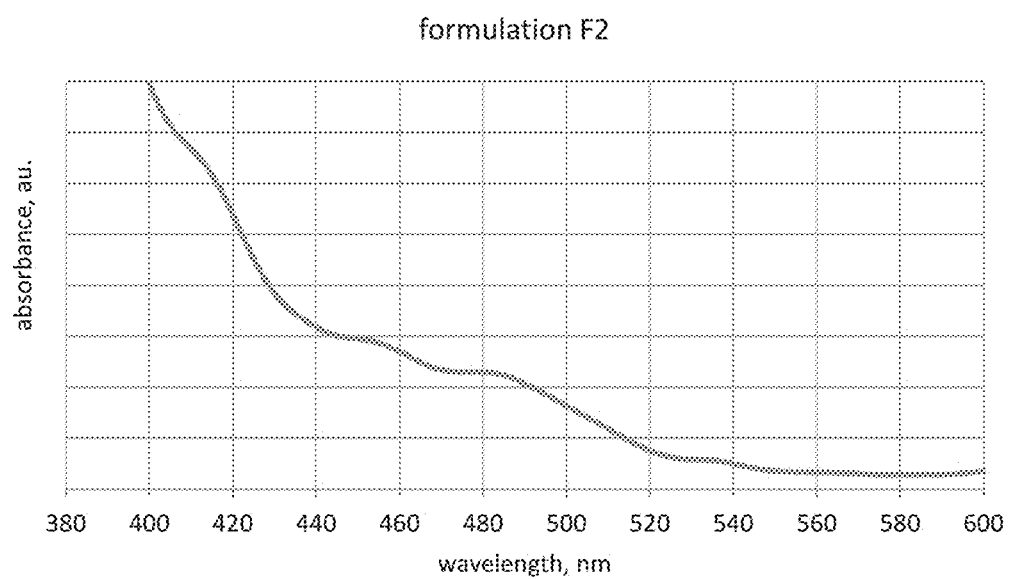
Figure 23M:
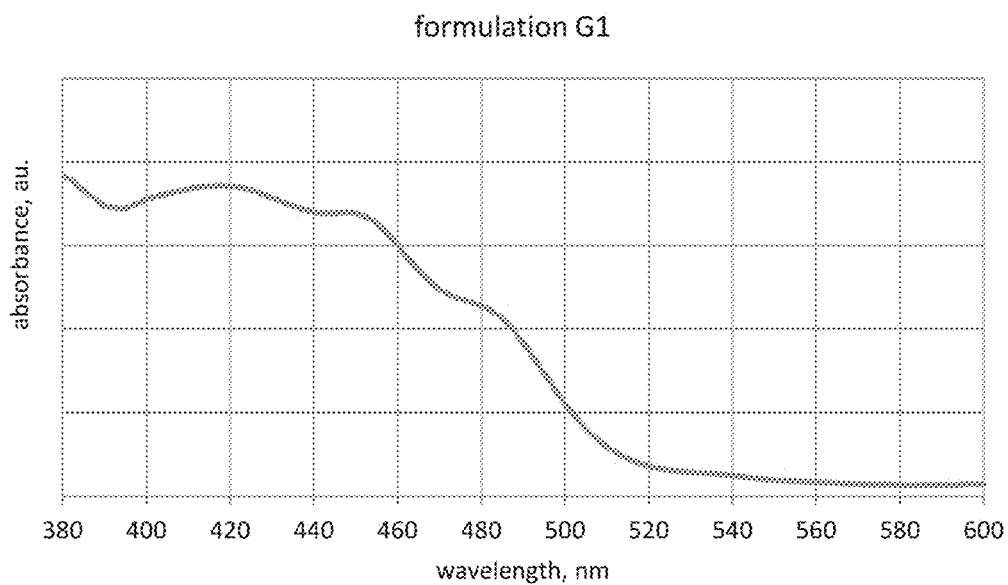
Figure 23N:
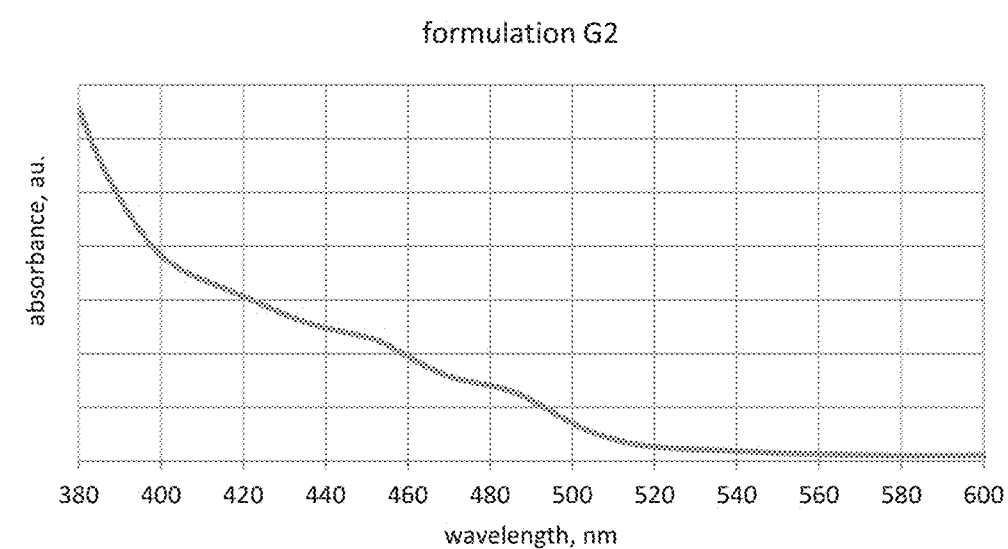

Comparing the spectra for formulations G1 and G2, the addition of turmeric oil to cumin oil/flax oil (FIG. 23M) seed does not improve the performance of the cumin oil/flax seed oil alone (FIG. 23N). This may be a result of diluting the cumin oil/flax seed oil proportions in the overall formulation. However, the addition of turmeric oil added a value—a stronger absorbance of the G2 formulation below 400 nm and made the formulation useful for UVA- and HEV-light protection.

Figure 23O:
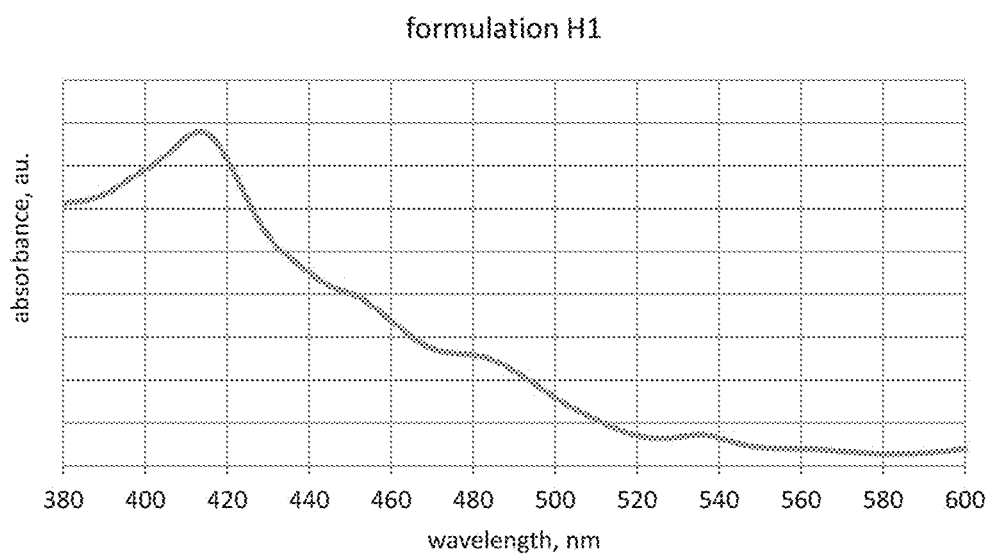
Figure 23P:
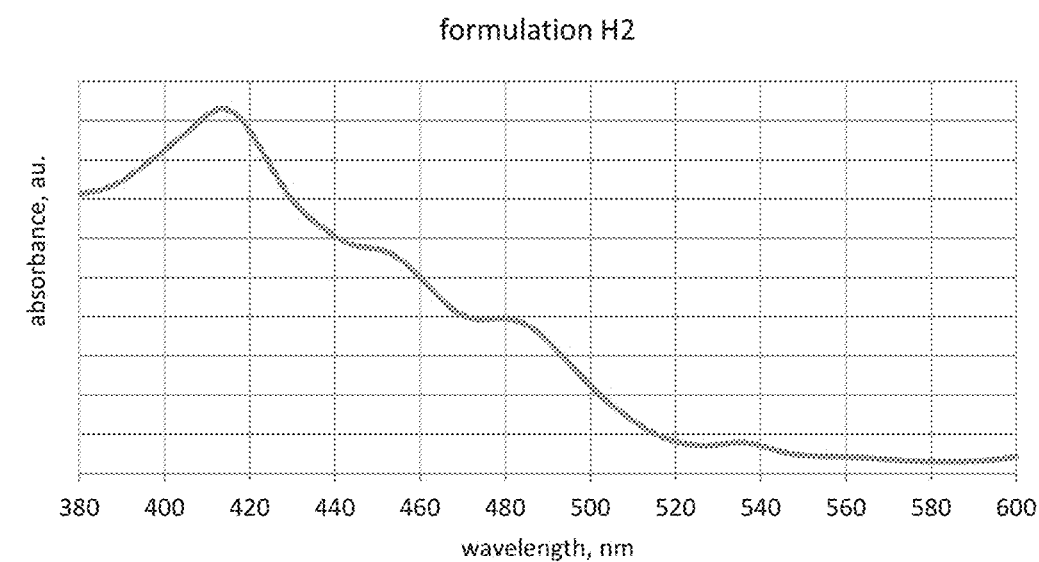
Figure 23Q:
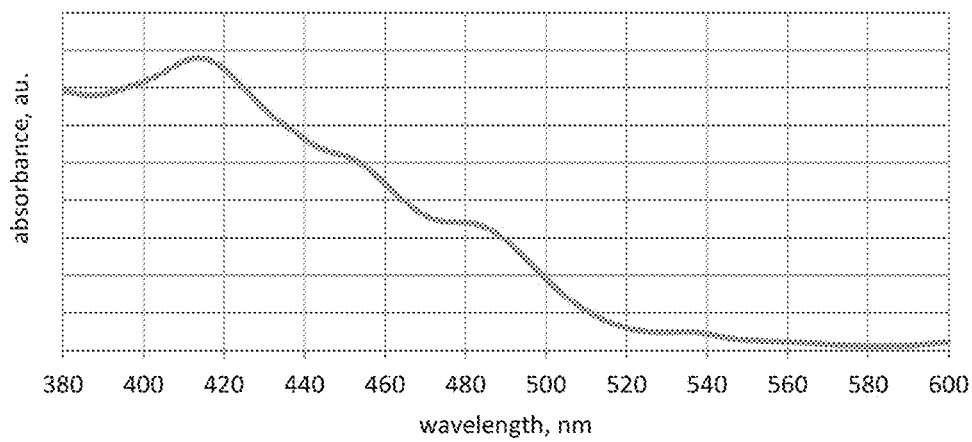
Figure 23R:
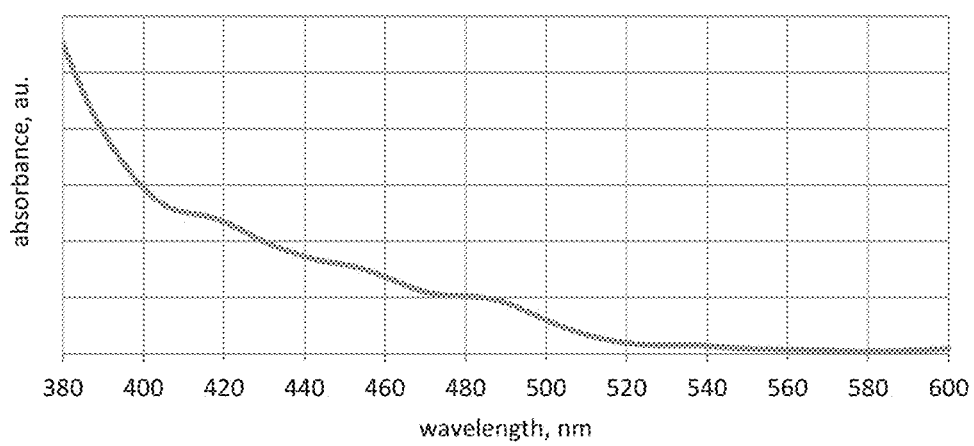

Comparing the spectra for formulations H1 and H2, the addition of flax seed oil to the cumin oil/hemp seed oil (FIG. 23O) does flatten out the absorbance spectrum from 400-500 nm compared to the two oils alone (FIG. 23P), meaning a broader absorbance profile, and thus, broader protection is provided in 400-500 nm, especially in 440-500 nm range In comparing the two spectra for formulations I1 and I2 (FIGS. 23Q-23R), the addition of cinnamon oil to the cumin oil/EVOO, which are good HEV-light absorbers, added a pronounced absorption in the range around 400 nm and below, which is characteristic of cinnamon oil.

Figure 23S:
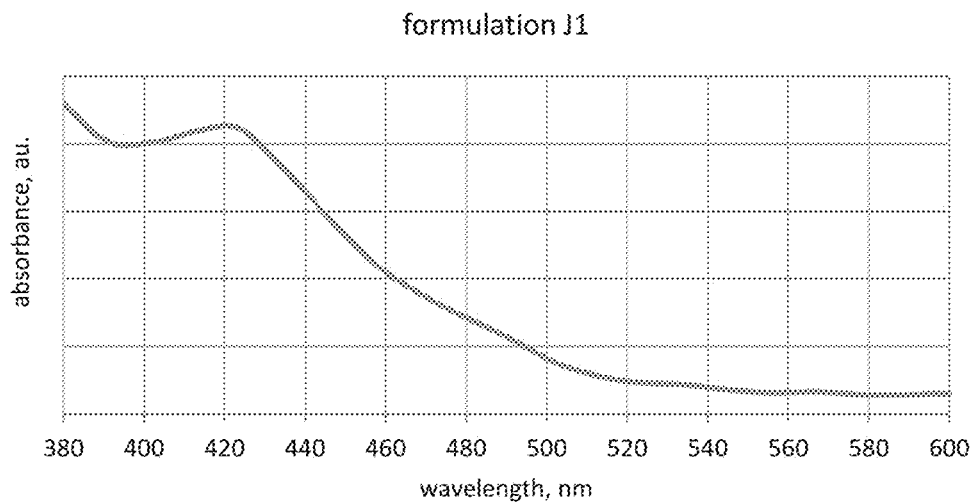
Figure 23T:
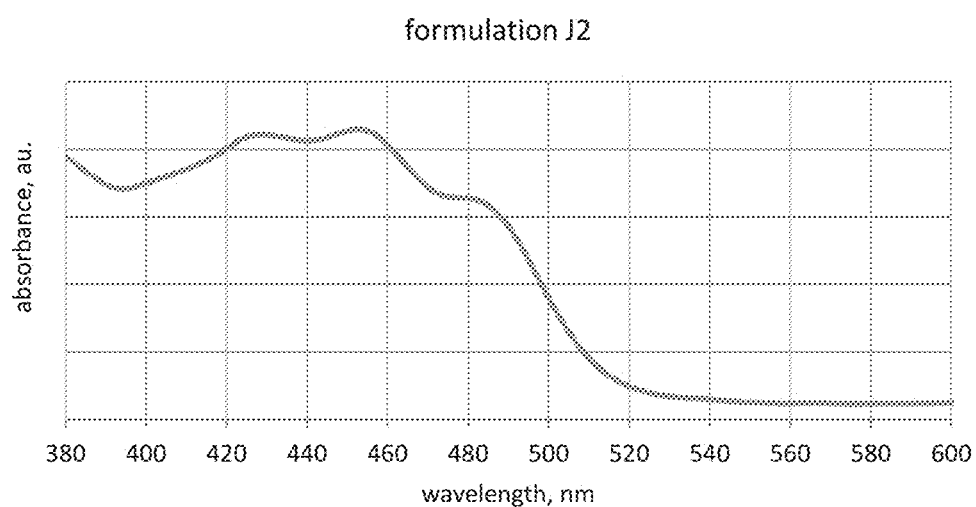

Comparing the spectra for formulations J1 and J2 (FIG. 23S-23T), there is a substantial flattening observed from 440-500 nm, when wheat germ oil is added to the cumin oil/pumpkin seed oil combination. This is expected as the wheat germ oil has pronounced absorbance peaks around 460 nm and 480 nm and is a good addition to the cumin oil and pumpkin oil which have strong absorption below 440 nm. Formulations J1 and J2 are good examples of oil combinations that yield strong high energy blue-violet light absorption, and thus, can provide good protection in this range (400-500 nm).

Figure 23U:
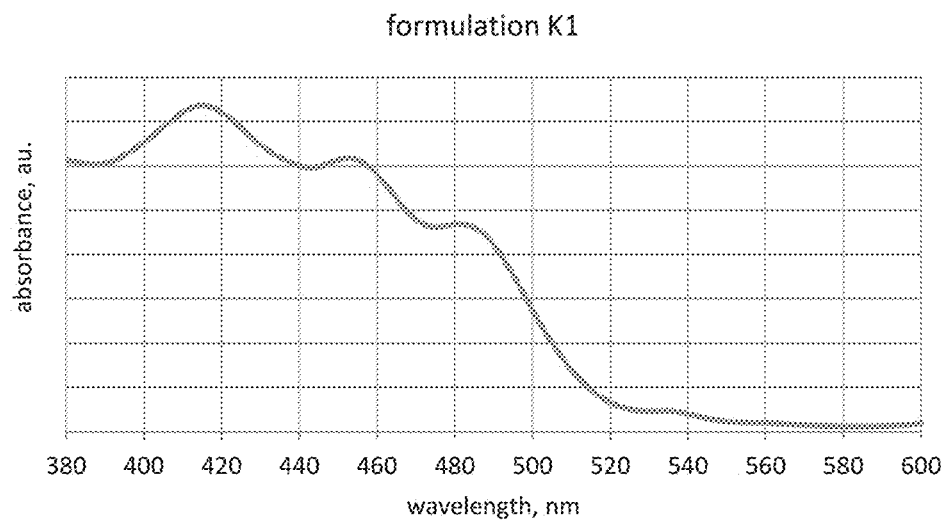
Figure 23V:
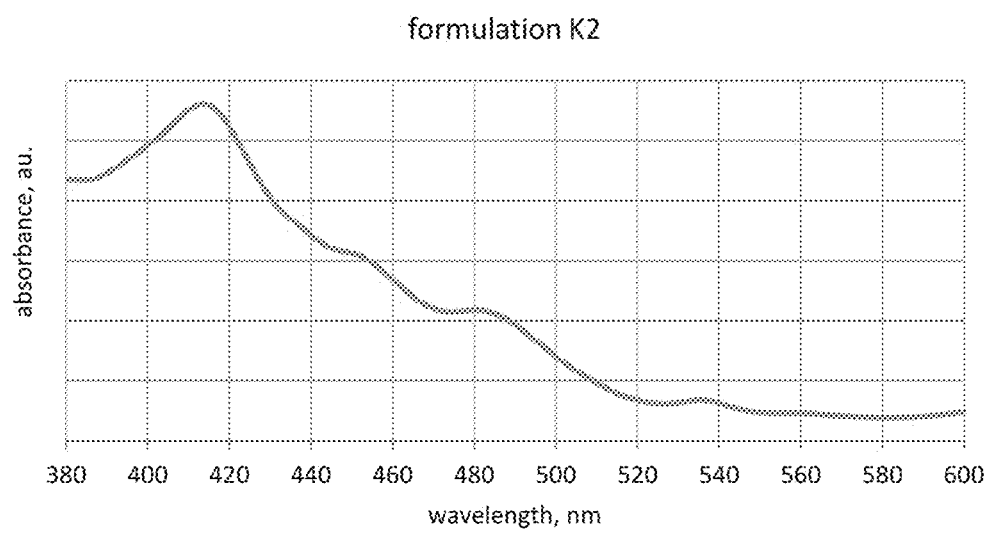
Figure 23W:
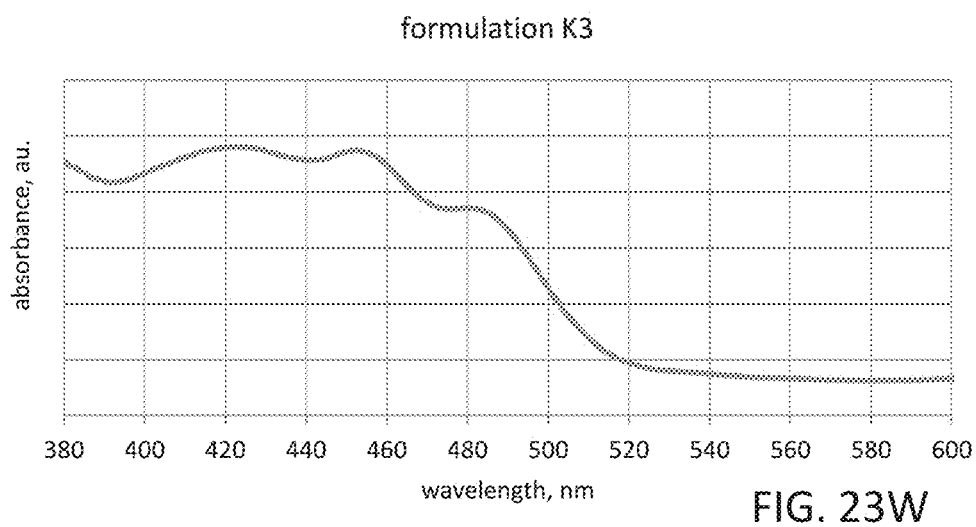
Figure 23X:
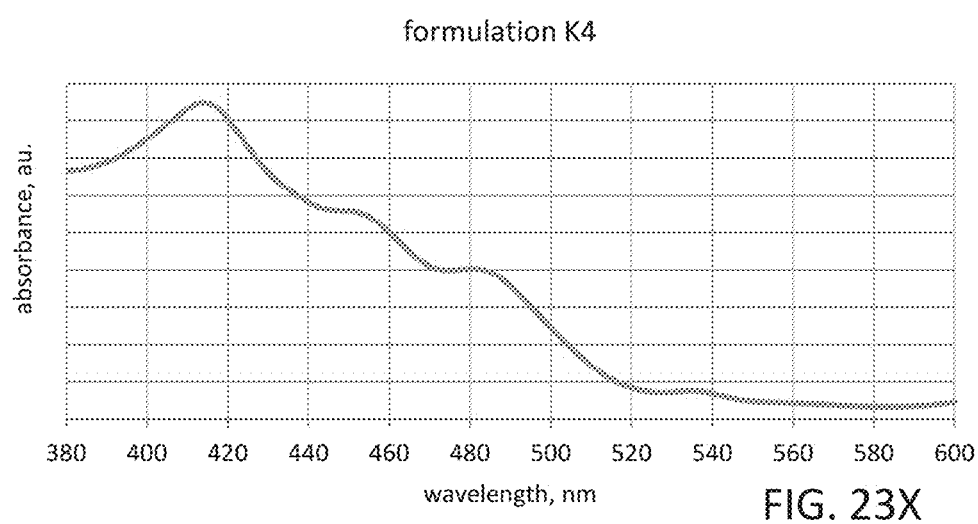
Figure 23Y:
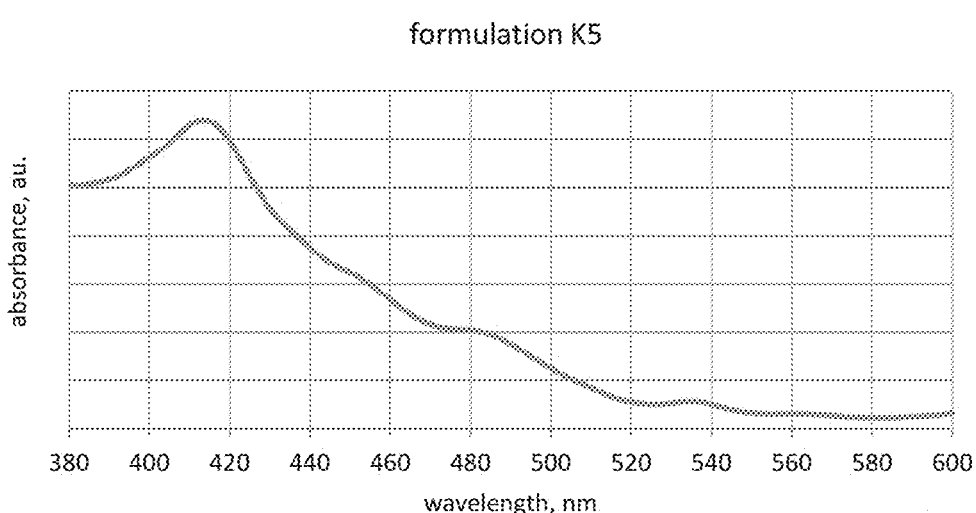

Comparing the spectra for formulations for K1-K5 (FIGS. 23U-23Y), the wheat germ oil in combination with the cumin oil/hemp oil (FIG. 23U) has a flatter absorbance curve than the cumin oil/hemp oil/EVOO combination (FIG. 23V). In comparing cumin oil/EVOO/wheat germ oil (FIG. 23W) vs cumin oil/hemp oil/wheat germ oil (FIG. 23U), the EVOO addition to the other two oils results in a flatter absorbance curve. Altering the amounts by adding a fourth oil (FIG. 23X) causes an increase in the slope from 440 nm to 500 nm. Replacing the wheat germ oil with pumpkin seed oil (FIG. 23Y), results in an increasing slope for the absorbance curve due to the strong absorbance peak of pumpkin seed oil at around 420 nm. Overall, K1-K5 formulations are good examples of tunability of the absorbance profile of various oil combinations; by selection of the type and fraction of HEV-absorbing oils, one can manipulate the absorbance profile and absorbance intensity in this range (400-500 nm).

Figure 23Z:
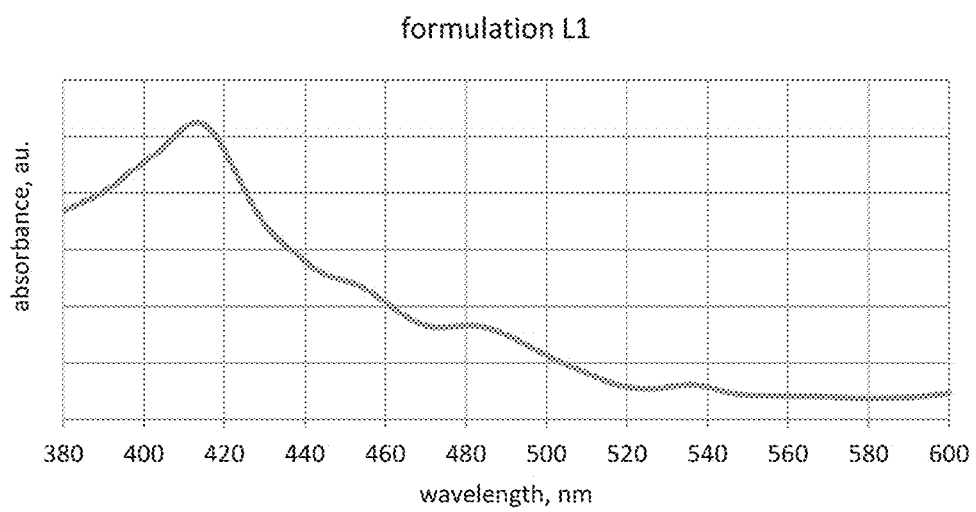
Figure 23A:
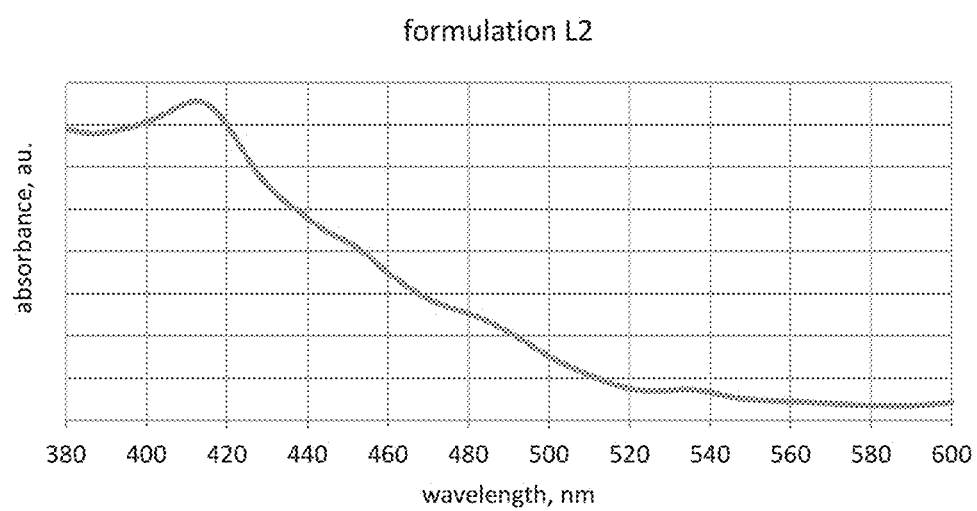
Figure 23A:
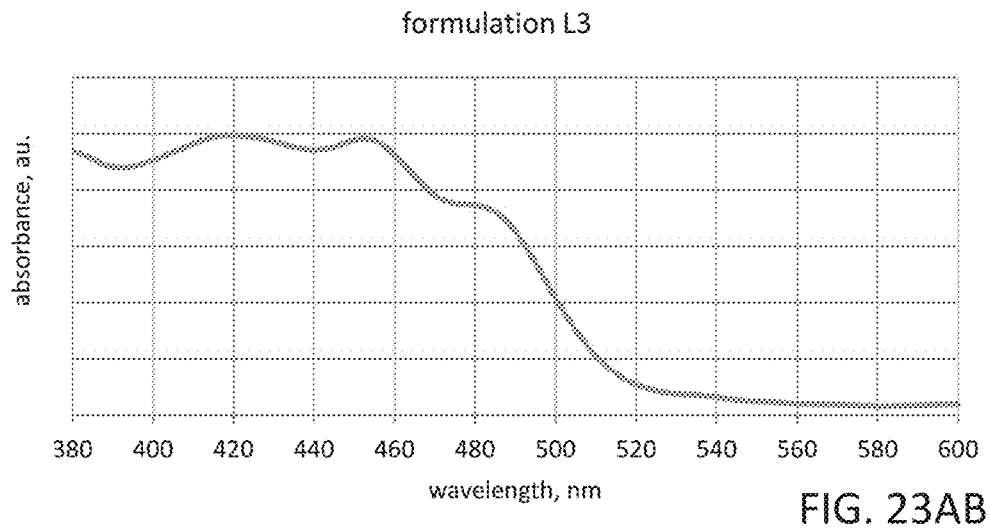
Figure 23A:
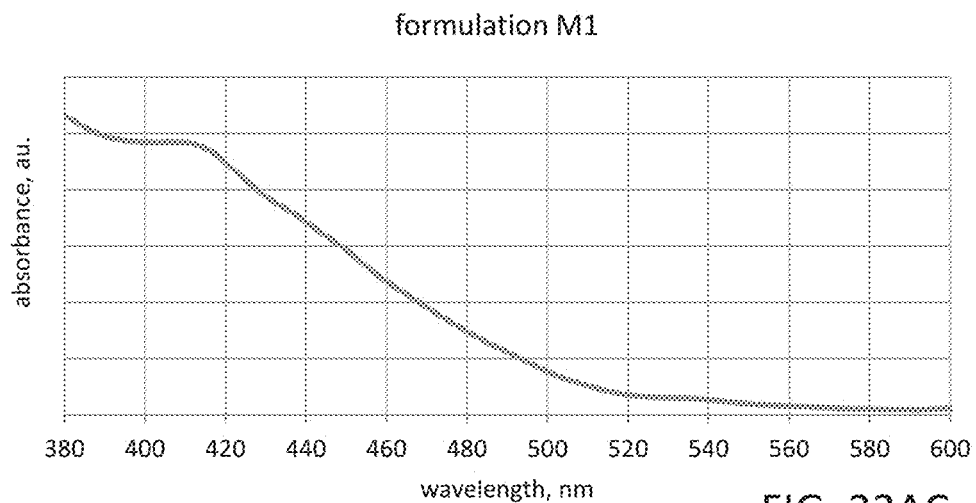
Figure 23A:
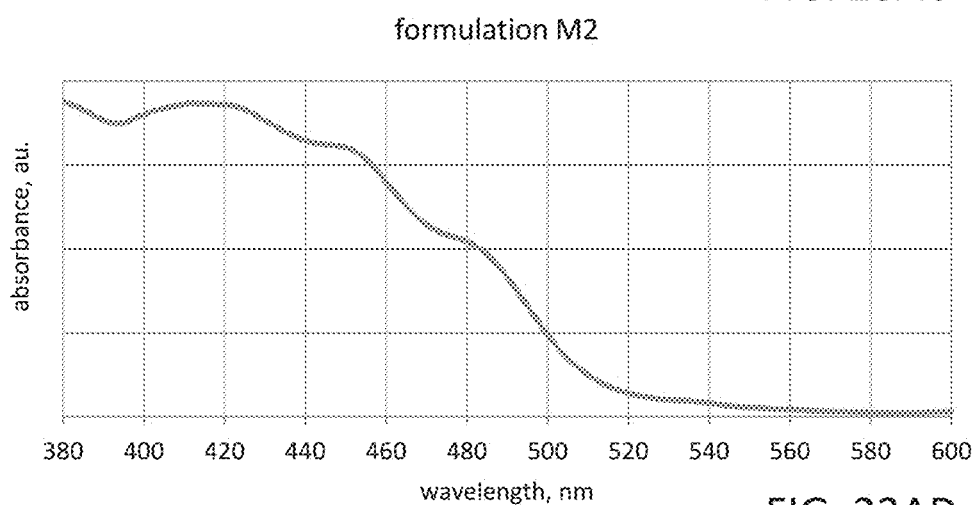
Figure 23A:
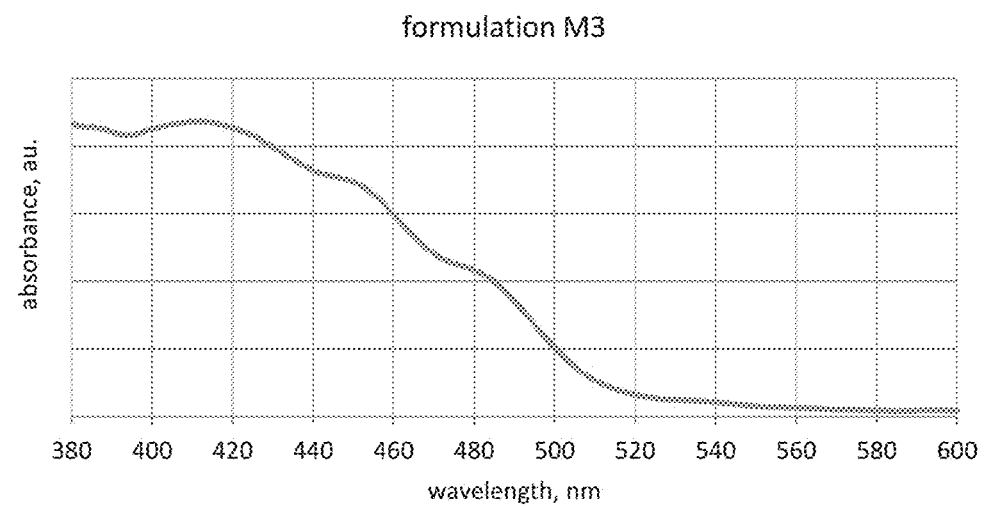
Figure 23A:
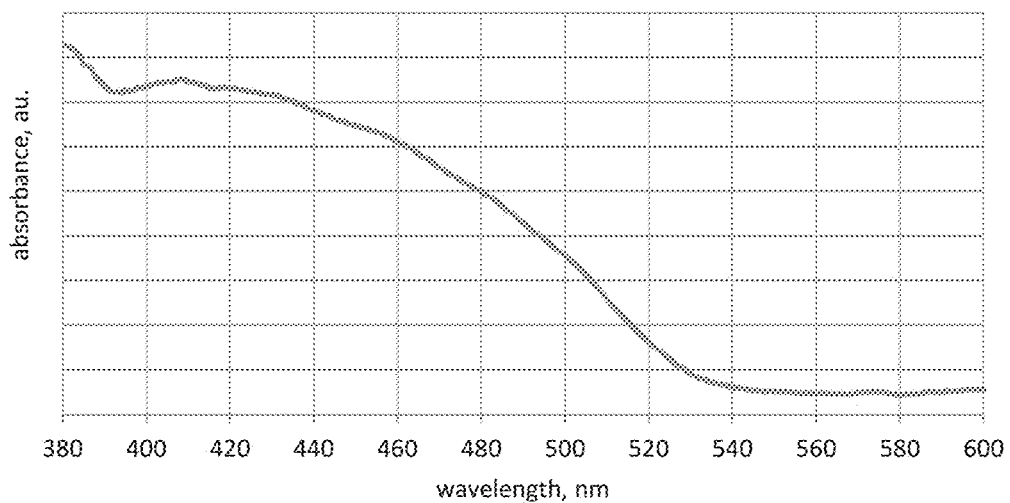
Figure 23A:
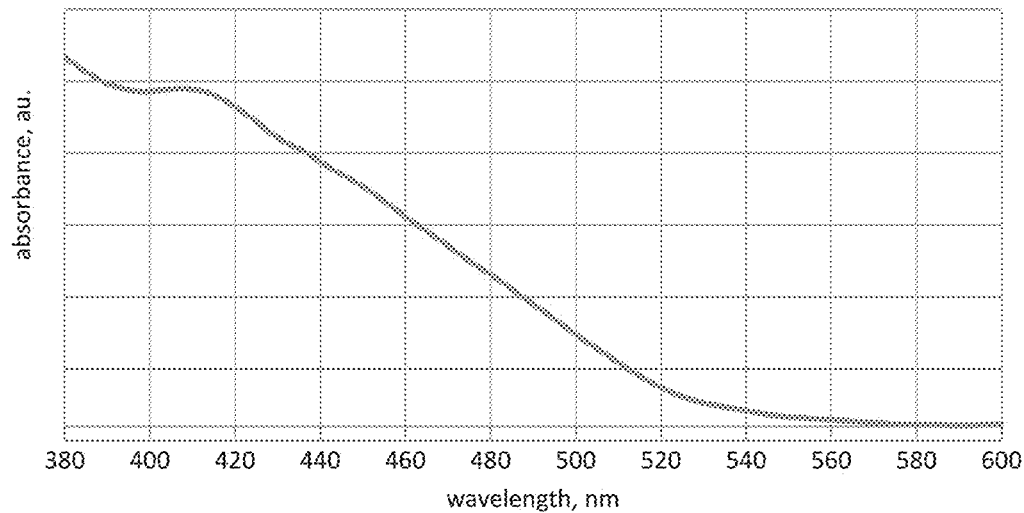
Figure 23A:
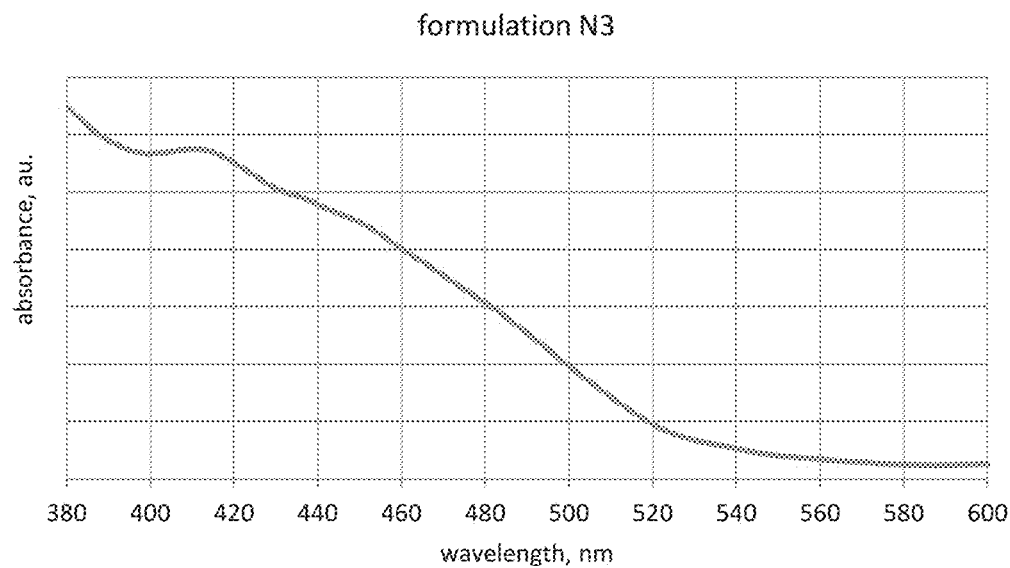
Figure 23A:
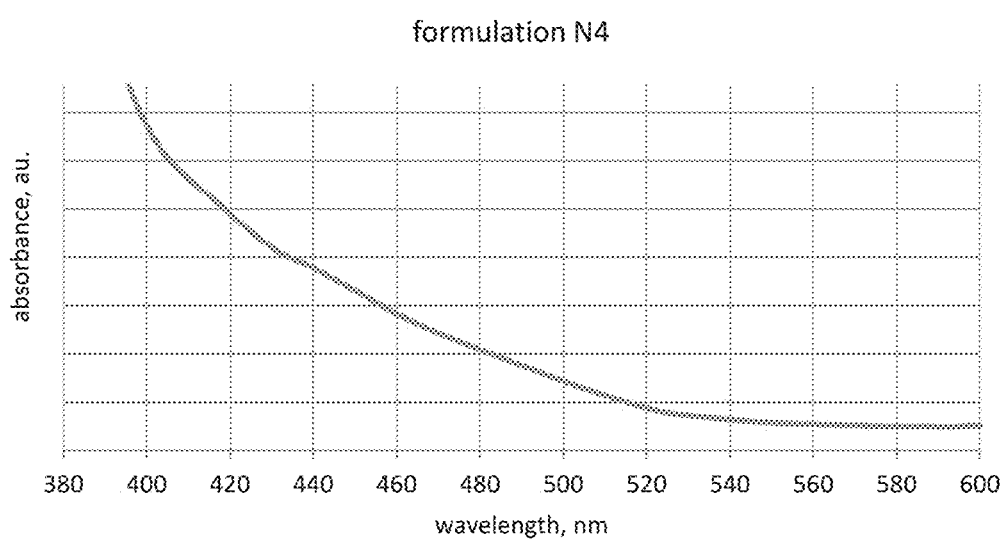
Figure 23A:
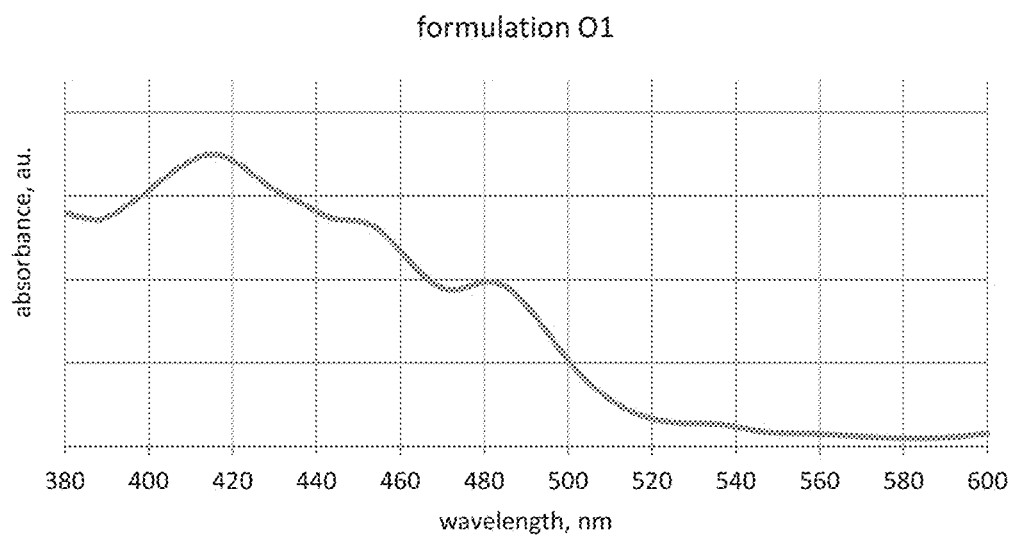
Figure 23A:
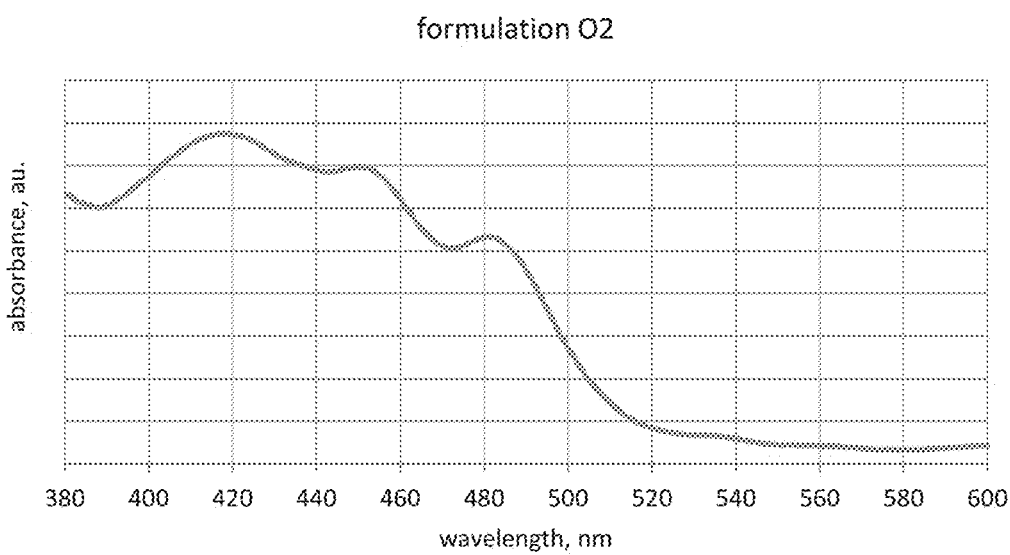
Figure 23A:
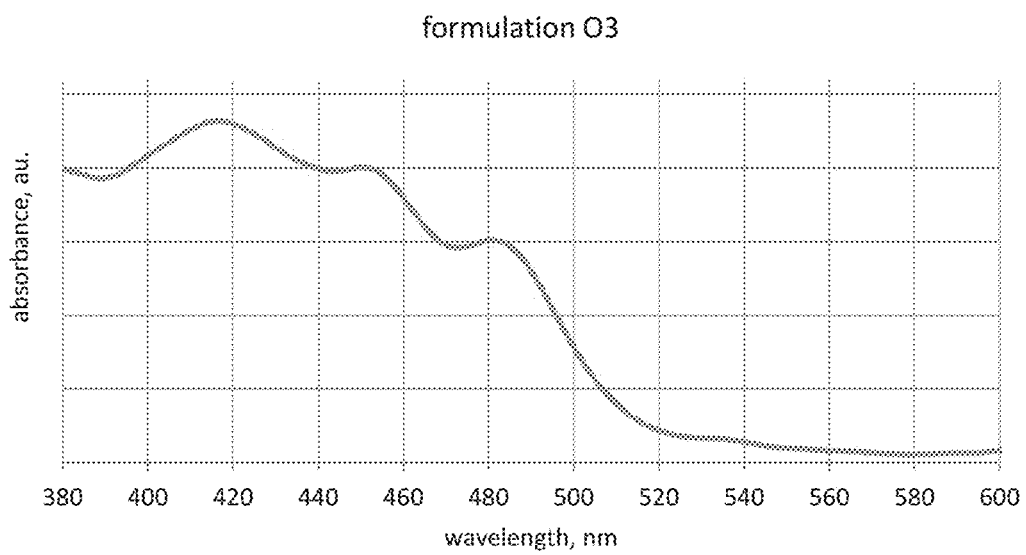
Figure 23A:
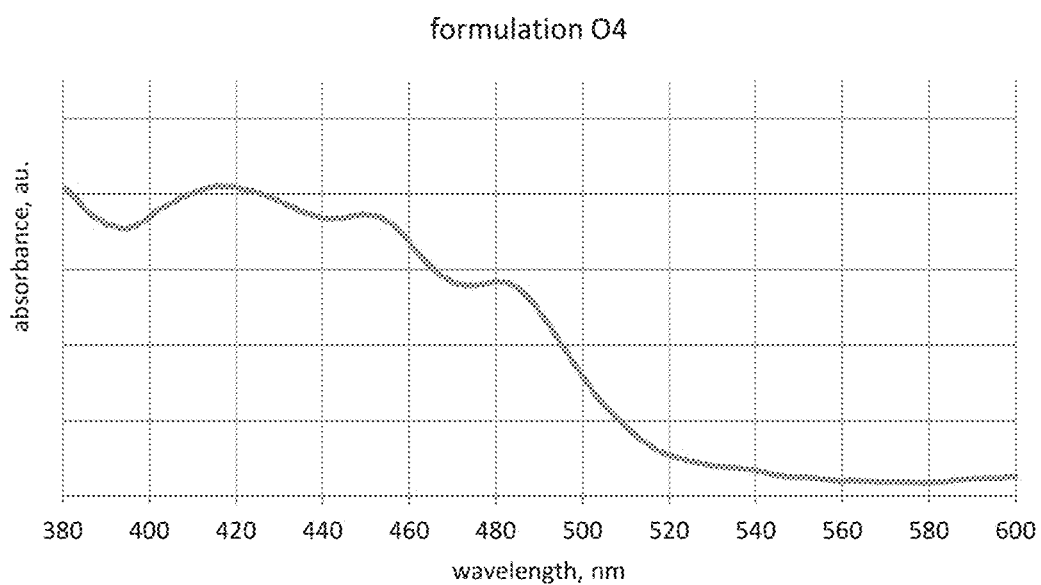
Figure 23A:
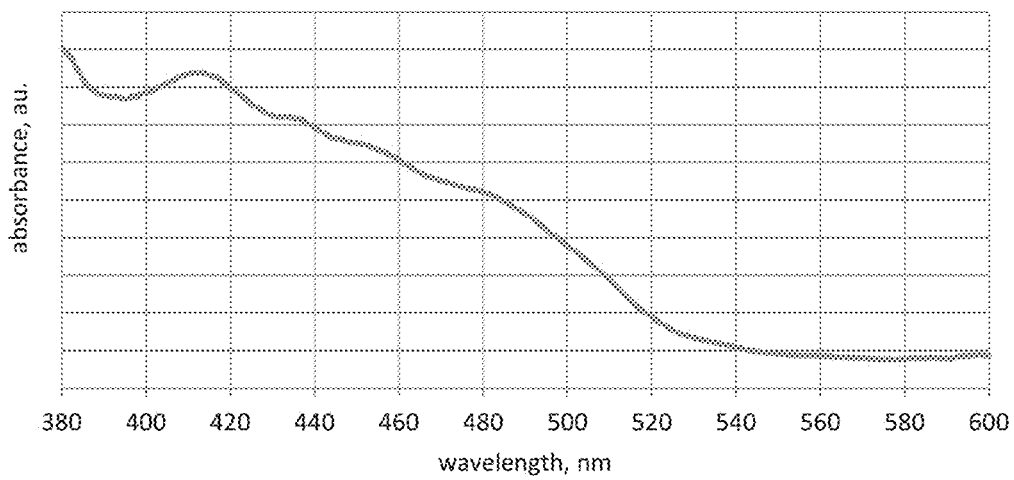
Figure 23A:
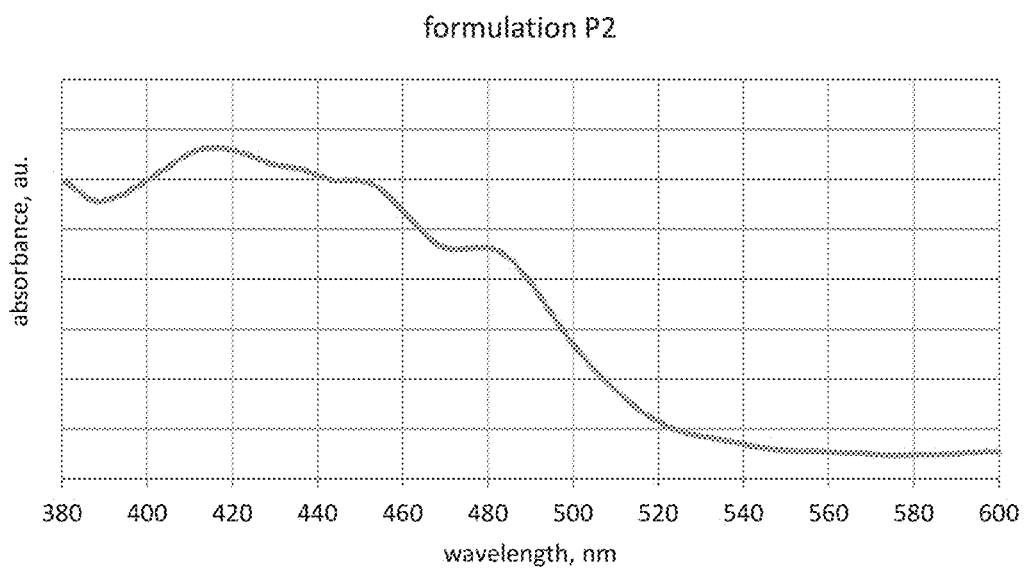
Figure 23A:
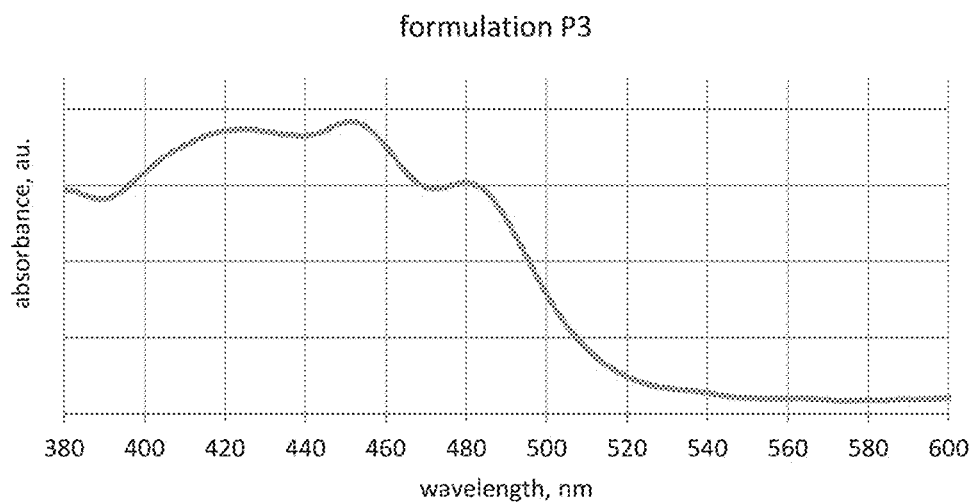
Figure 23A:
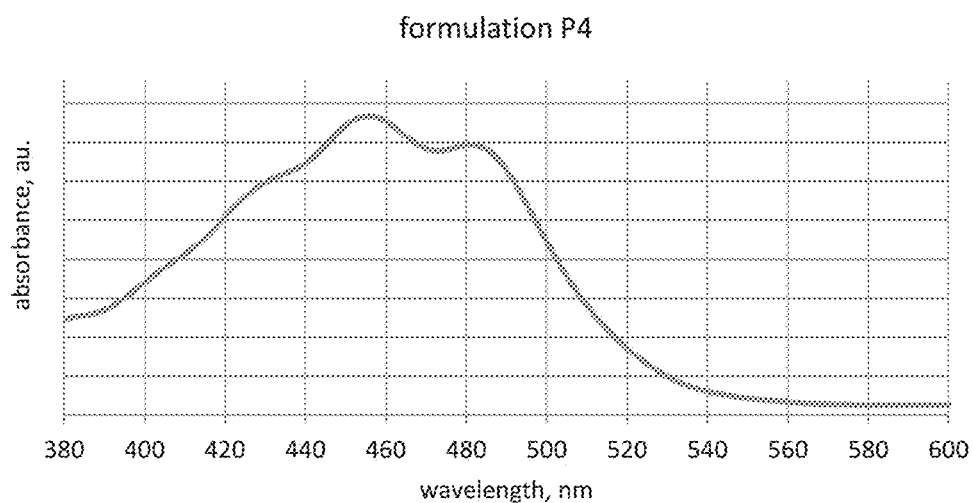
Figure 23A:
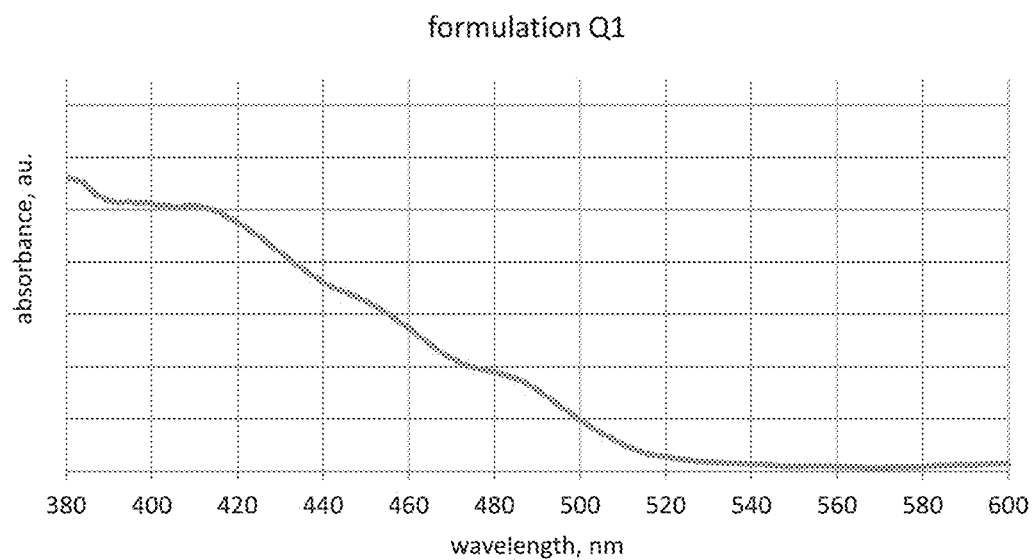
Figure 23A:
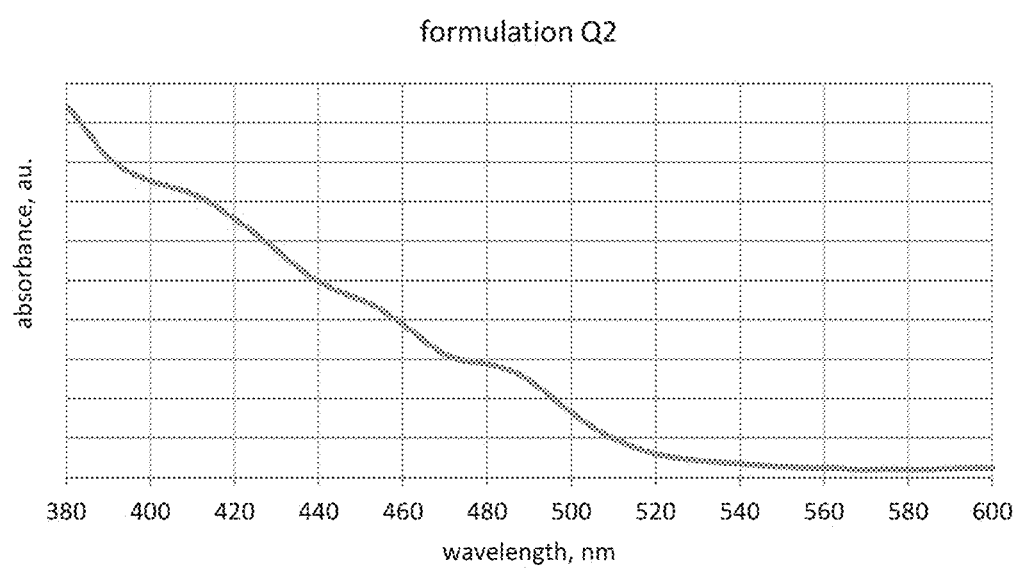
Figure 23A:
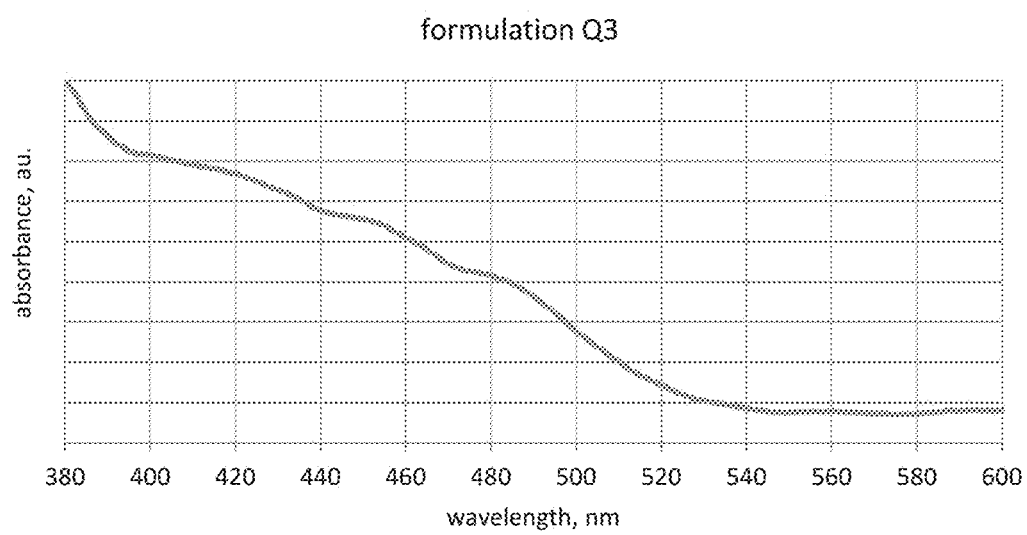
Figure 23A:
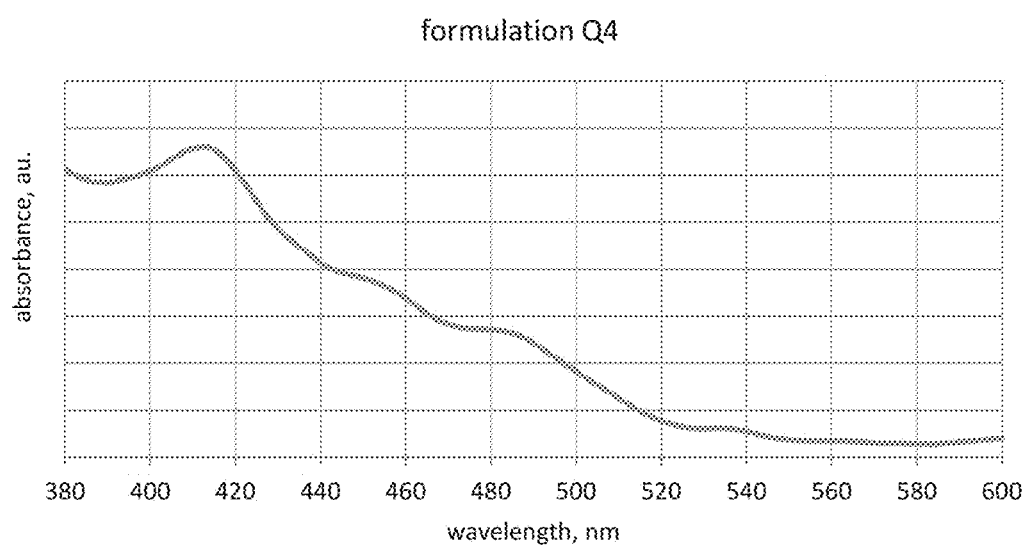
Figure 23A:
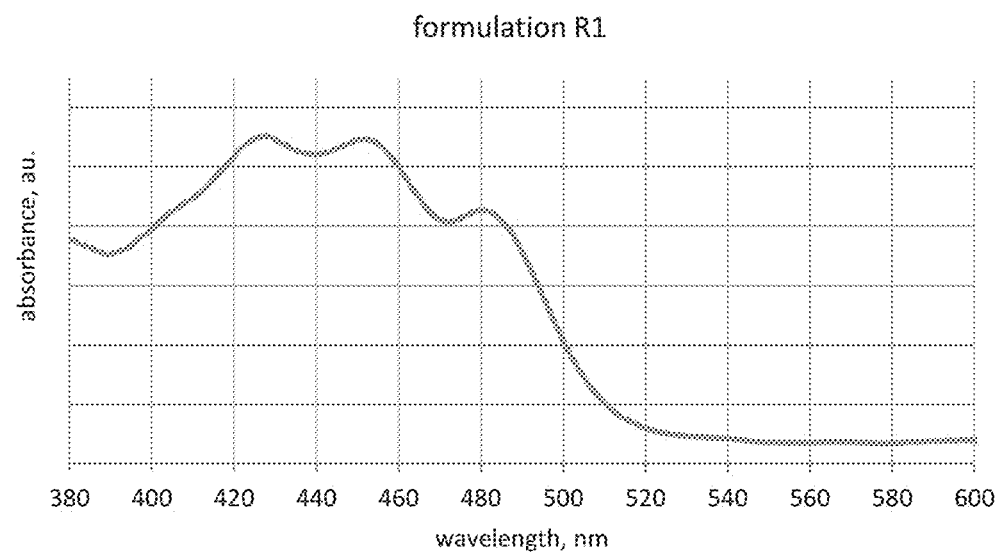
Figure 23A:
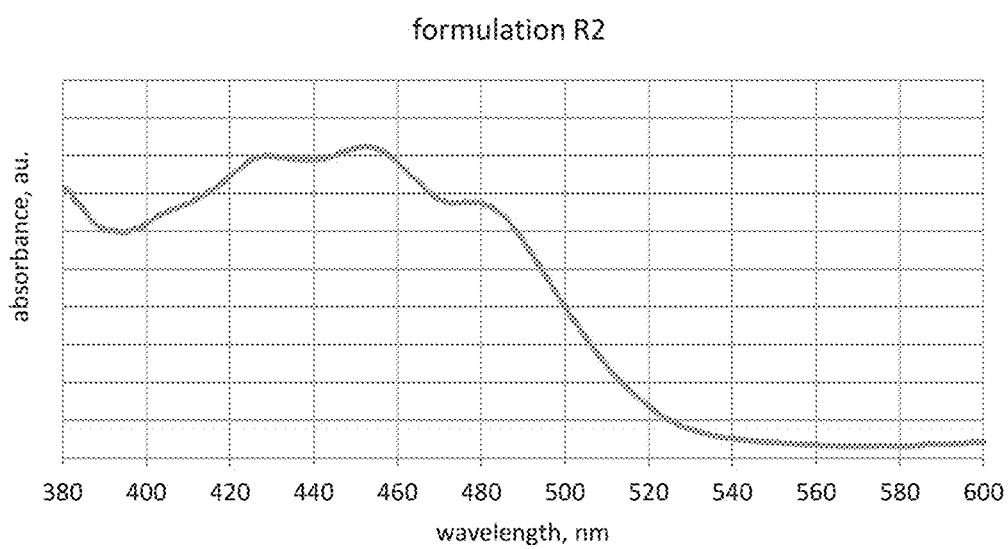
Figure 23A:
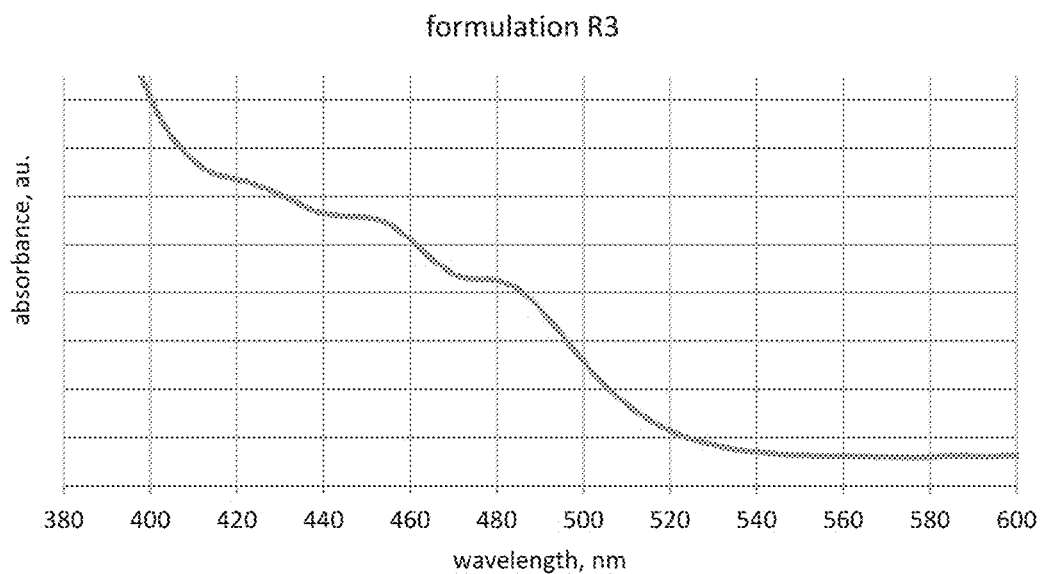
Figure 23A:
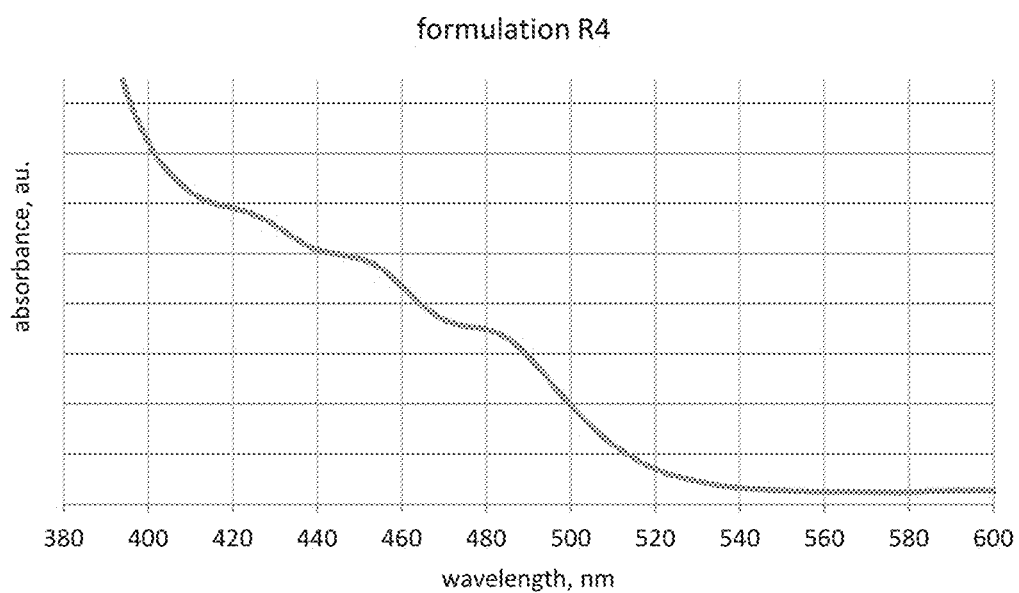
Figure 23A:
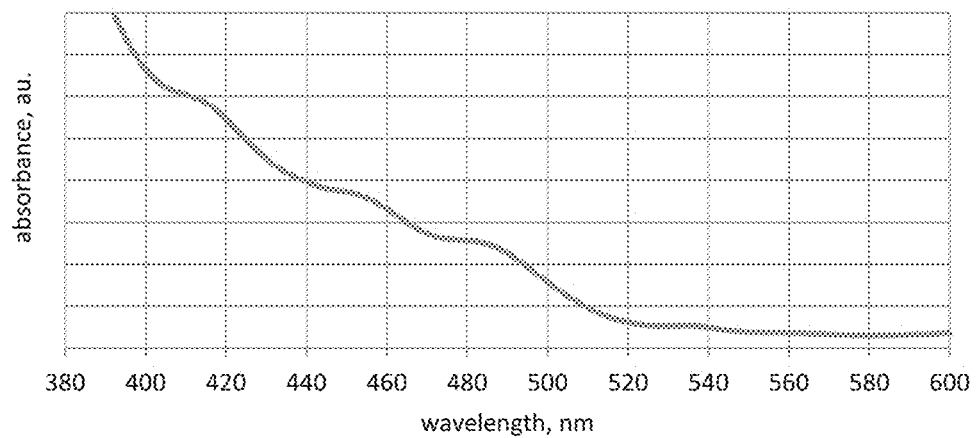
Figure 23B:
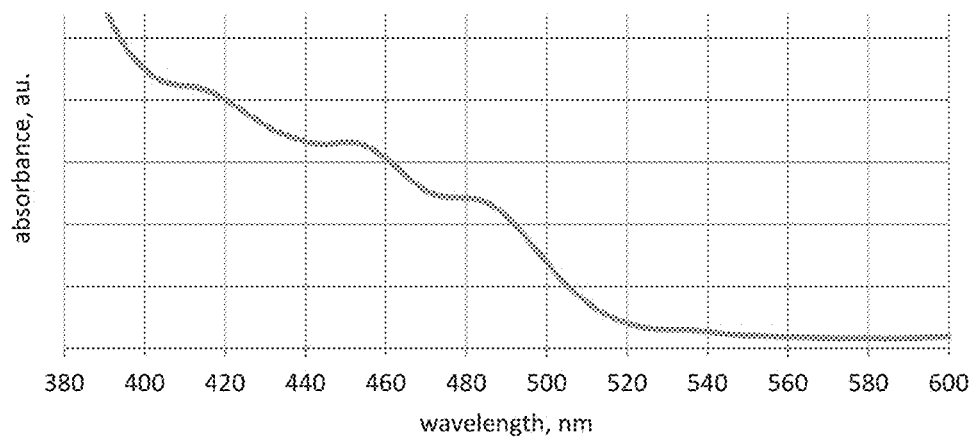
Figure 23B:
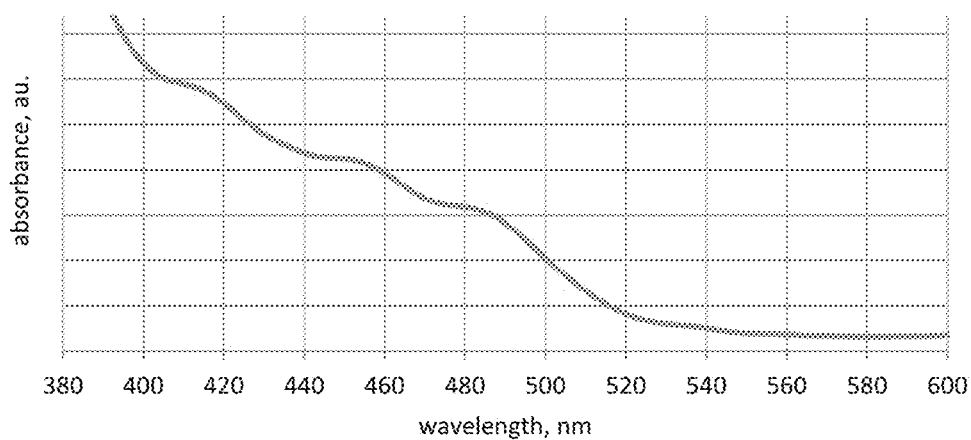
Figure 23B:
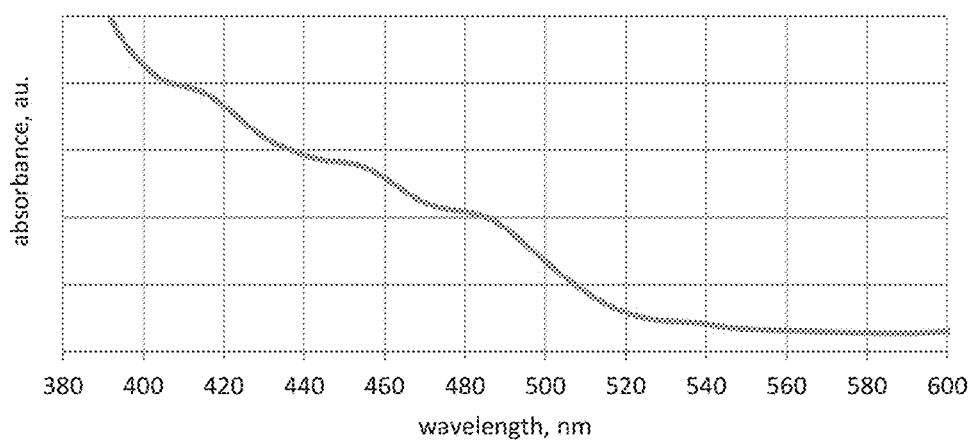
Figure 23B:
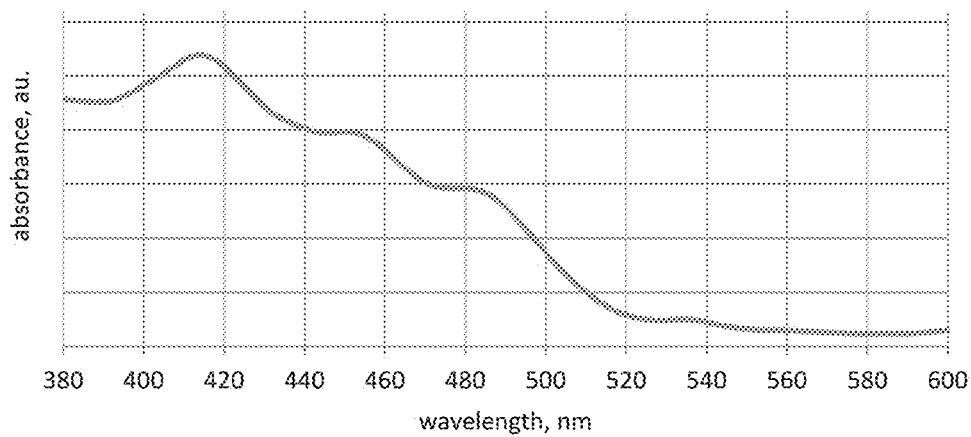
Figure 23B:
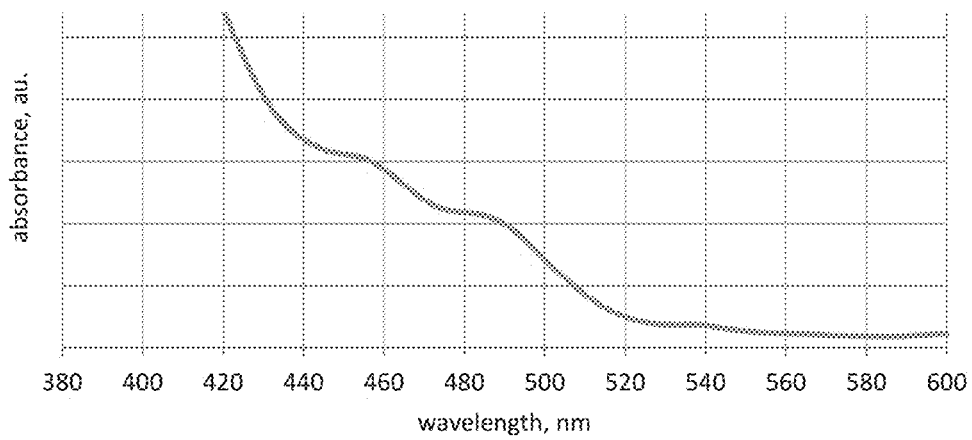
Figure 23B:
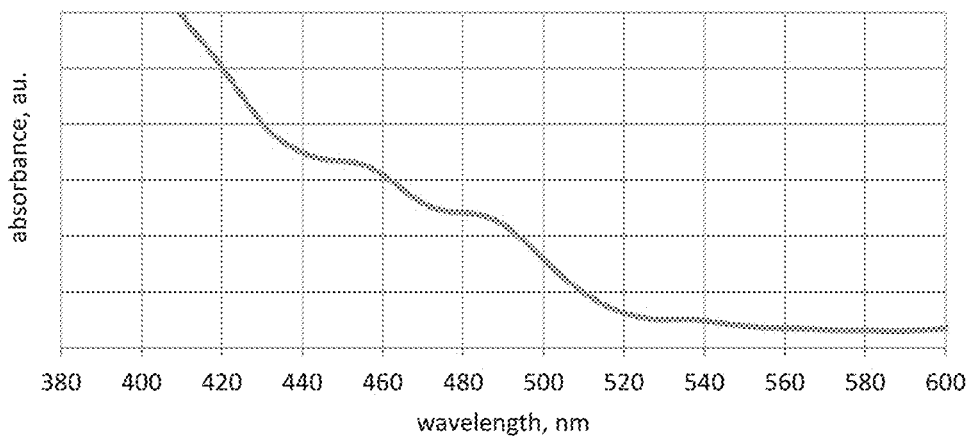
Figure 23B:
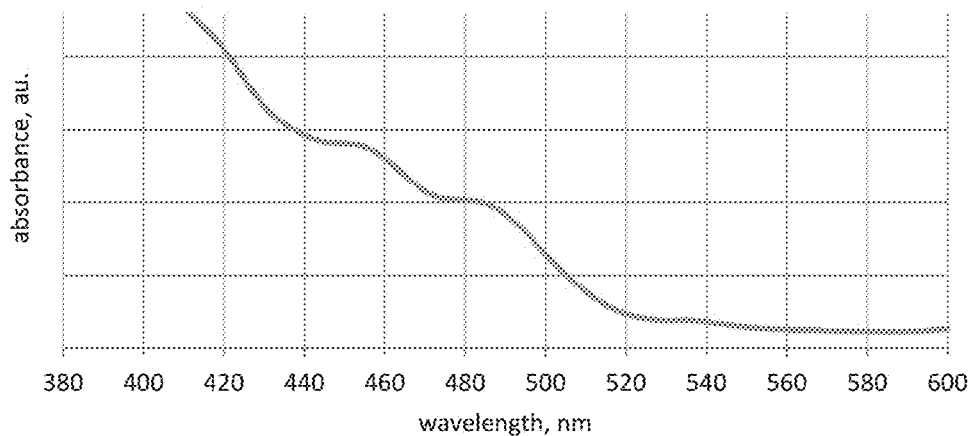
Figure 23B:
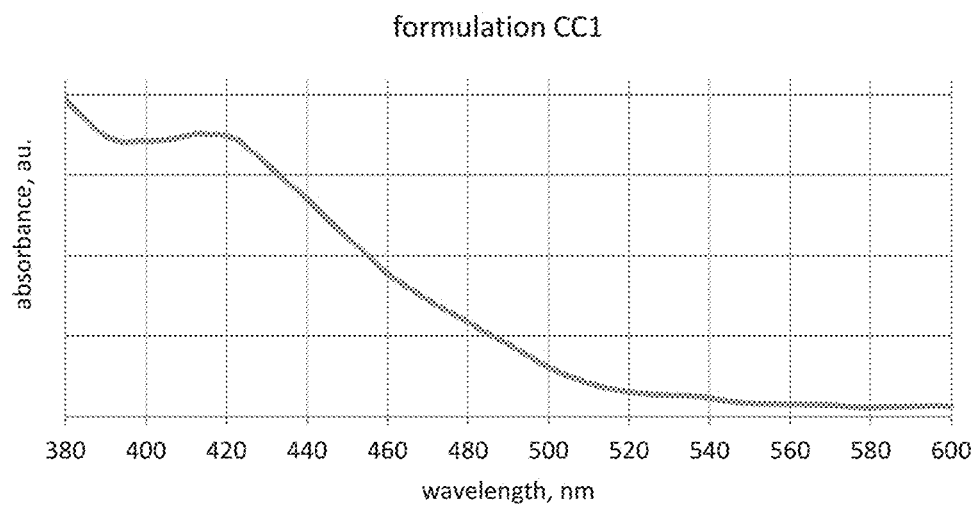
Figure 23B:
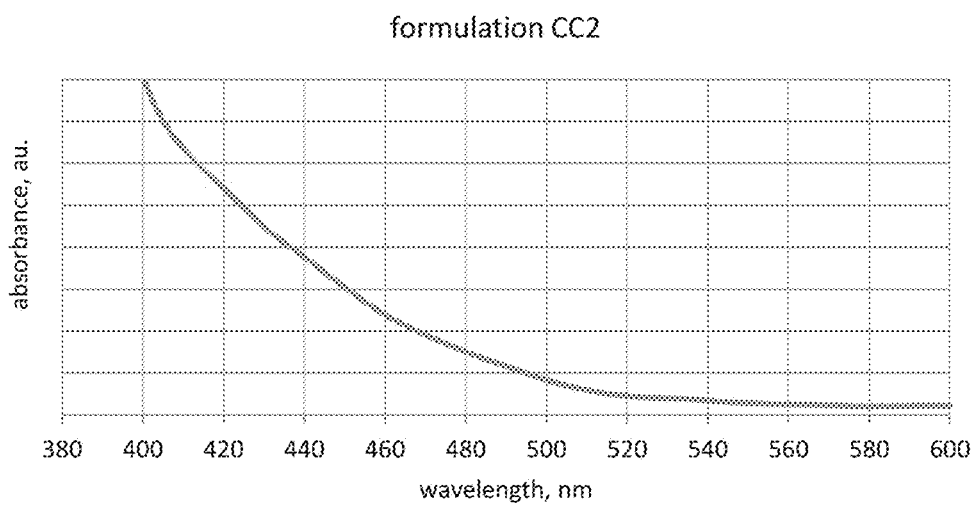
Figure 23B:
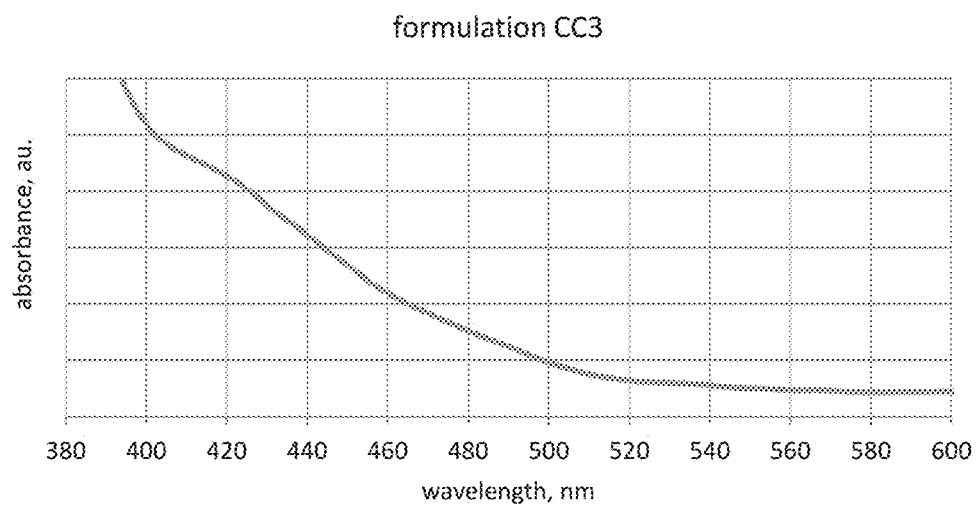
Figure 23B:
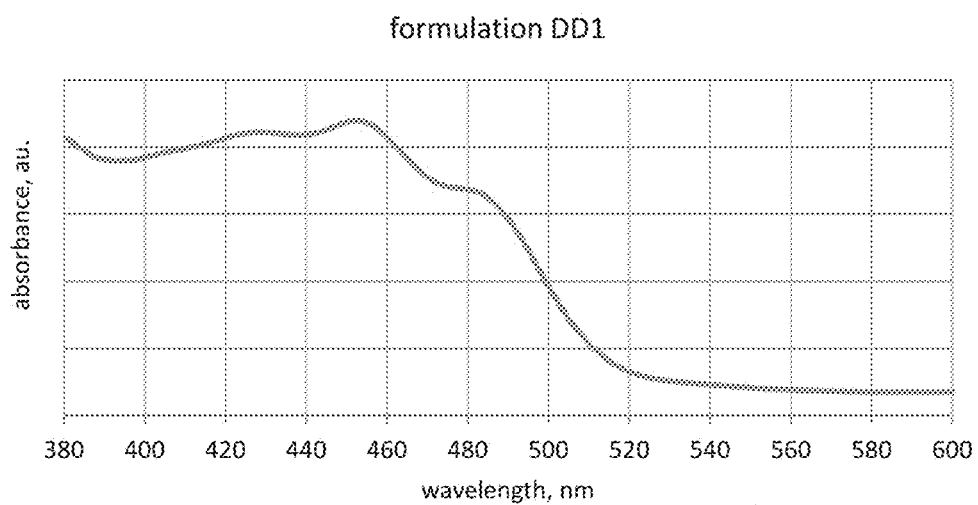
Figure 23B:
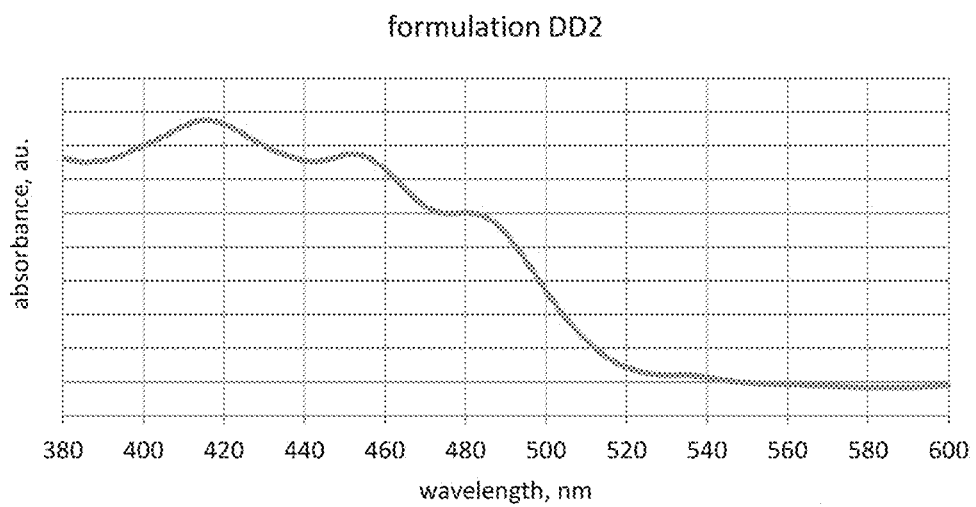
Figure 23B:
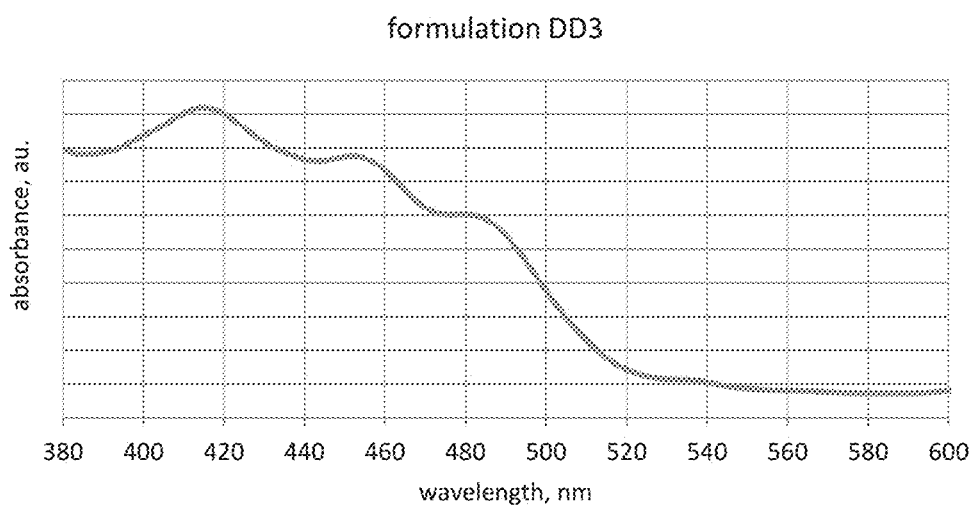
Figure 23B:
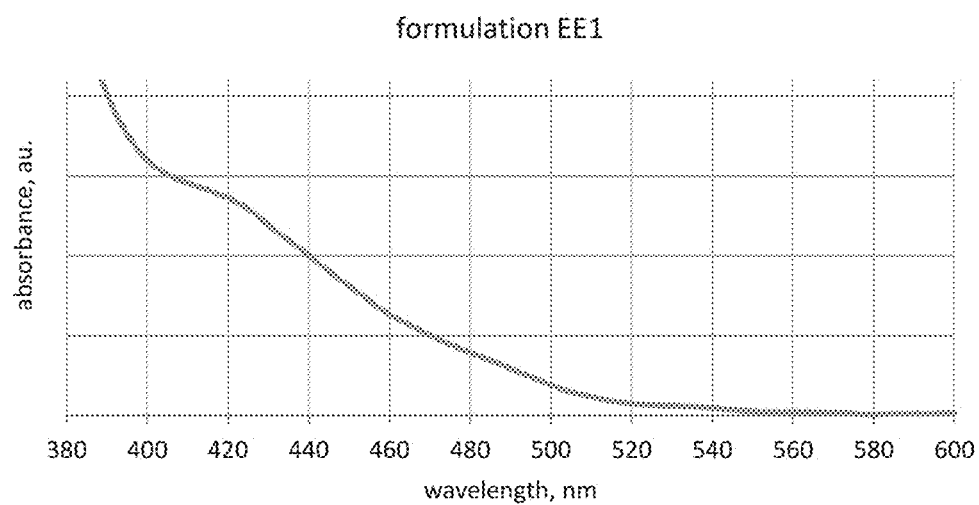
Figure 23B:
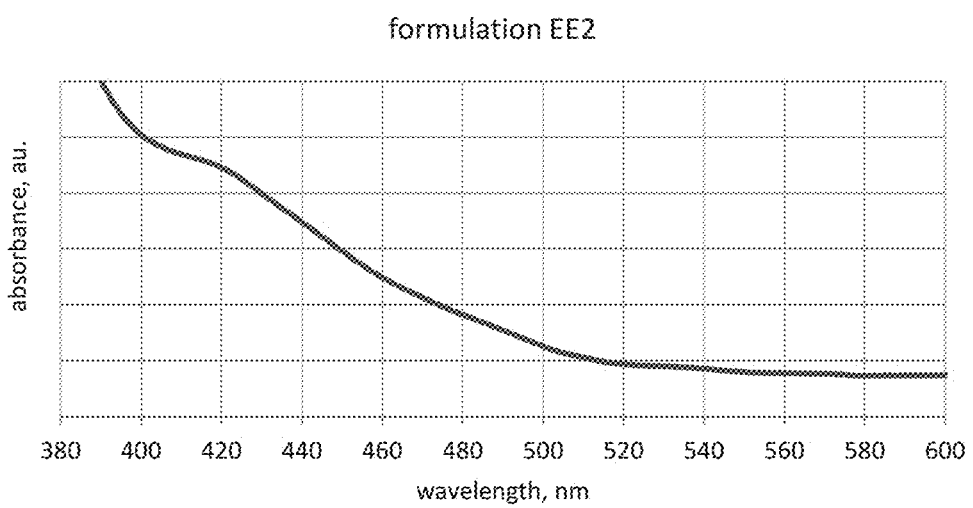
Figure 23B:
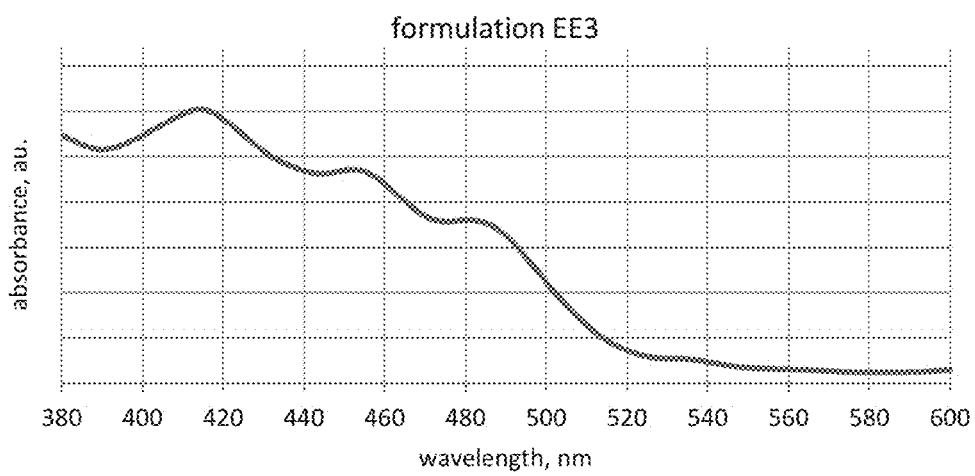
Figure 23B:
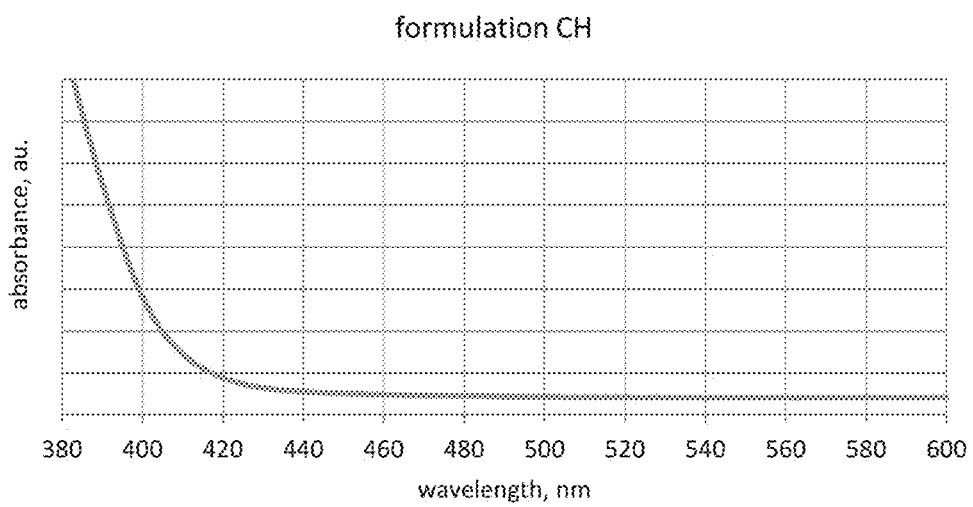
Figure 23B:
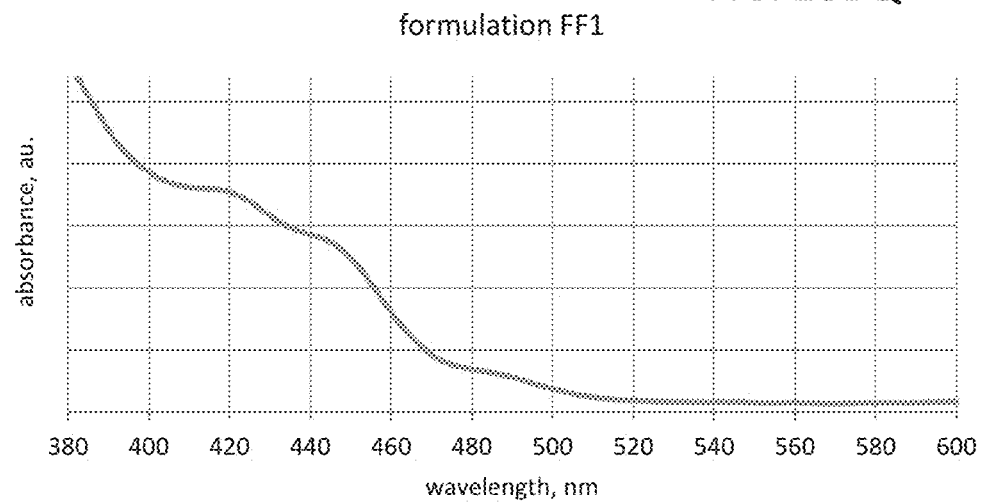
Figure 23B:
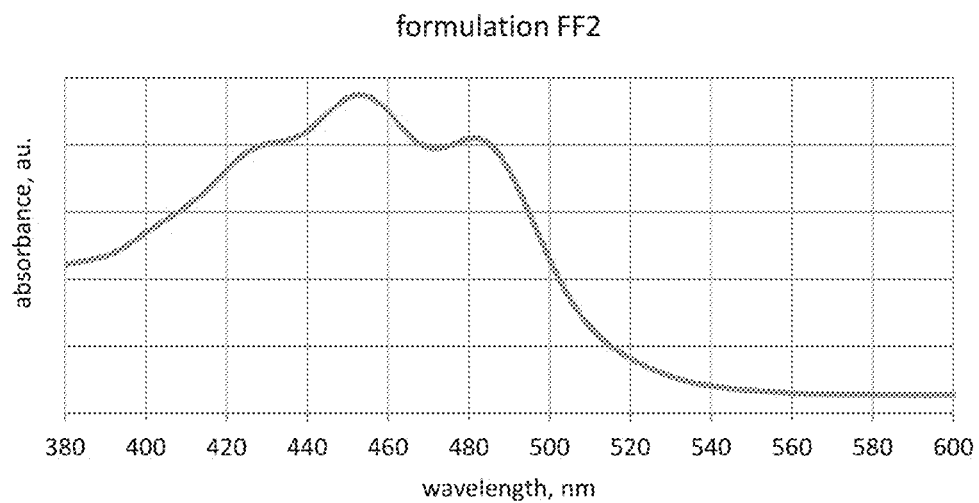
Figure 23B:
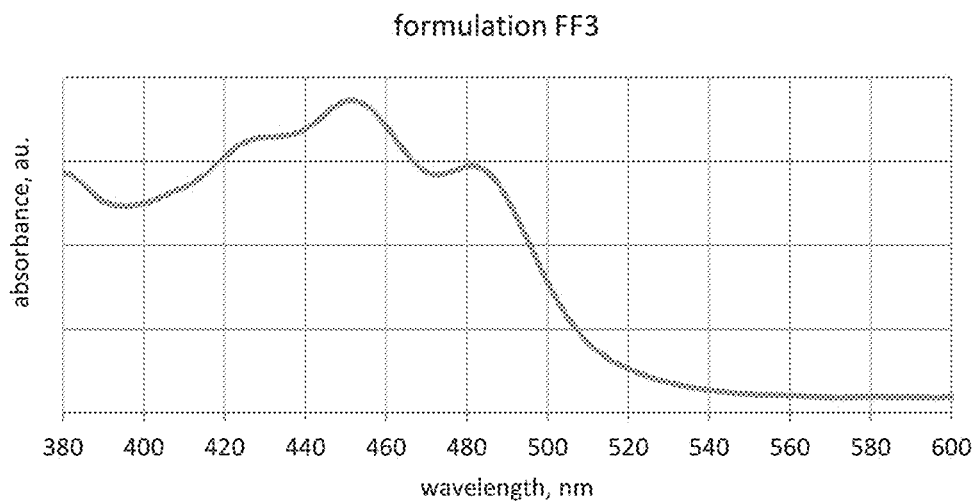
Figure 23B:
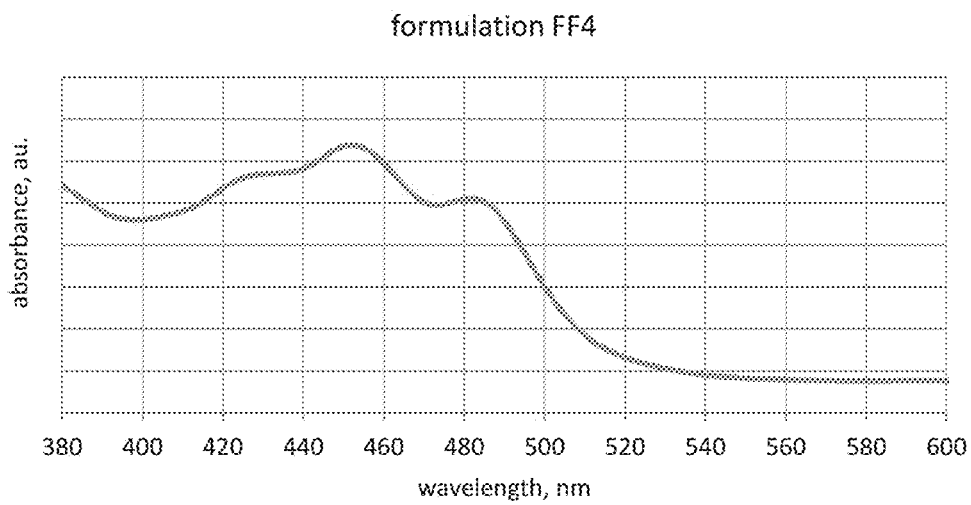
Figure 23B:
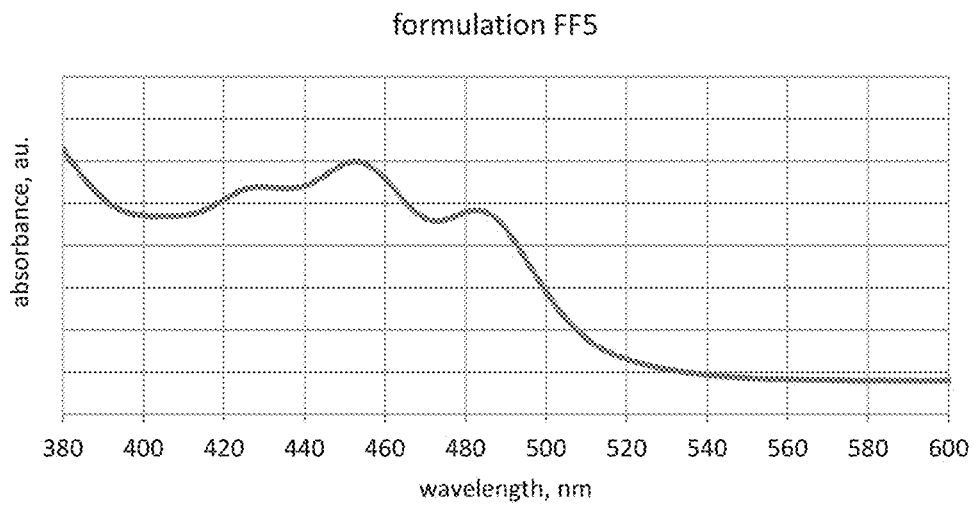
Figure 24A:
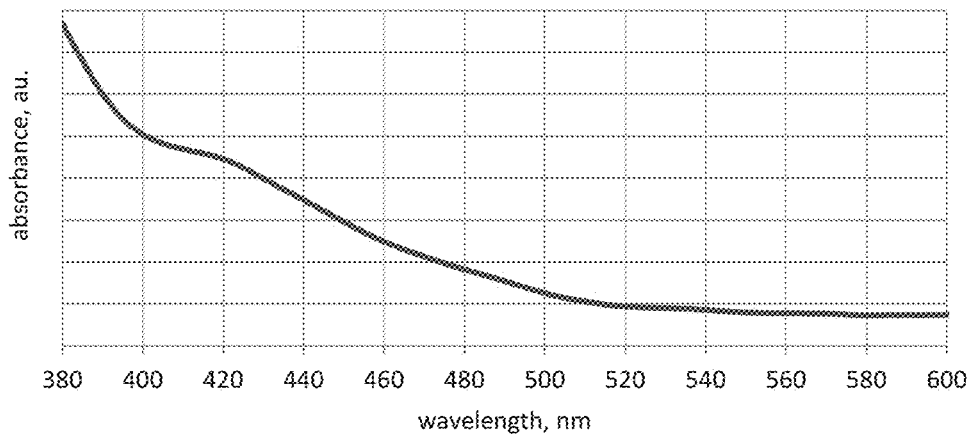
FIGS. 24A-24F are absorbance spectra for certain test formulations.
Figure 24B:
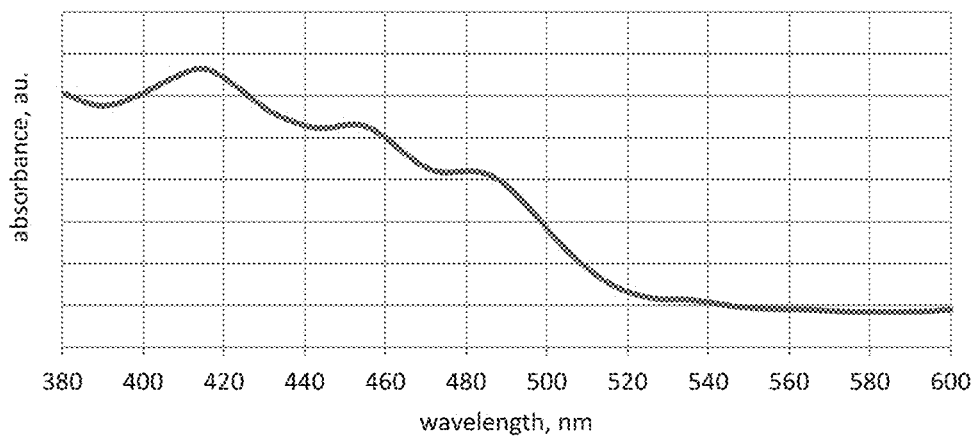
Figure 24C:
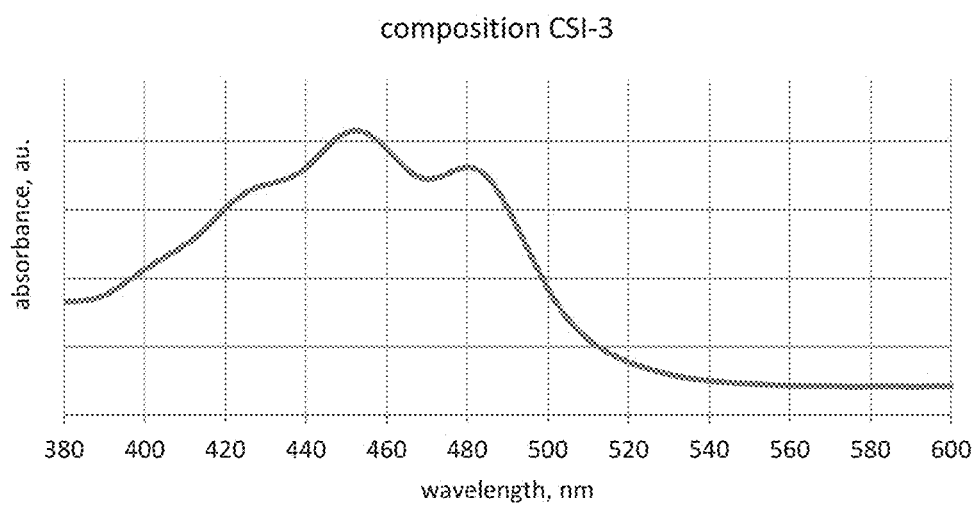
Figure 24D:
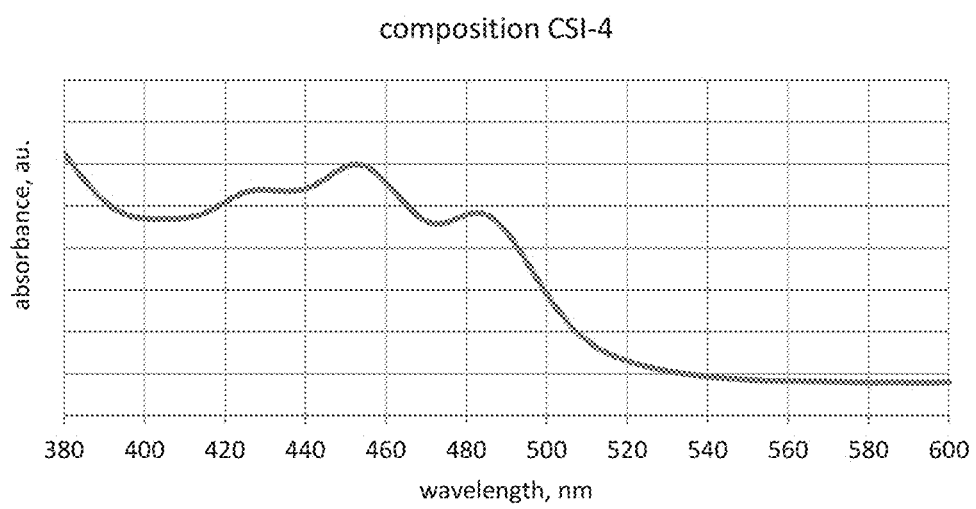
Figure 24E:
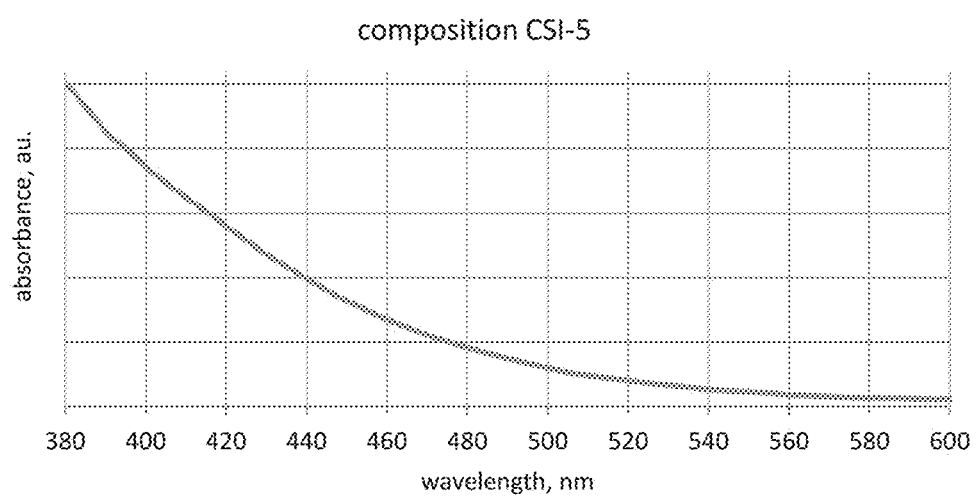
Figure 24F:
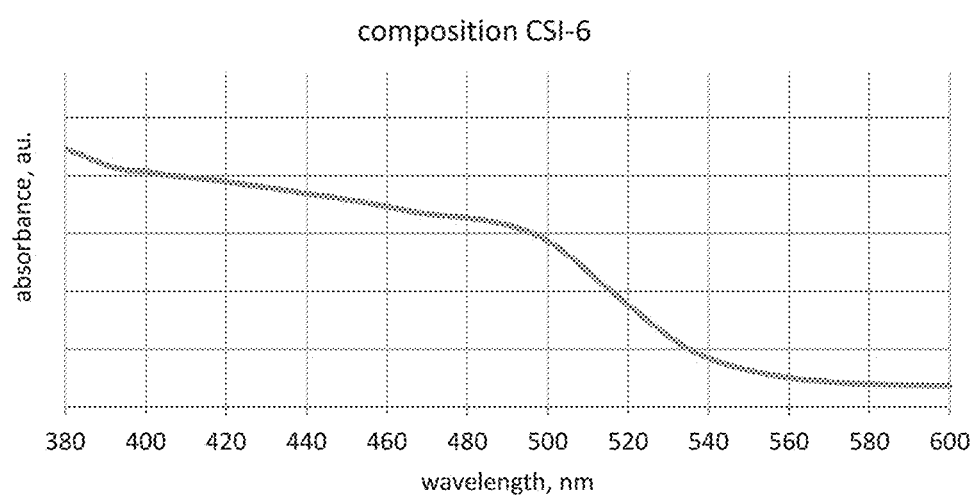

Comparing the spectra for formulations L1-L3 (FIGS. 23Z-23AB), the addition of cumin oil (FIG. 23AA) to jojoba oil/hemp oil flattens out the absorbance curve from 400-500 nm. The further addition of wheat germ oil (FIG. 23AB) to provide a four oil combination further flattens the curve from 380-500 nm. This is an example how the combination of oils with strong absorption around 400 nm and in 400-500 nm range can provide a tailored protection from high energy blue-violet light: while L1 formulation provides a good protection in 400-450 nm range, L2 and L3 formulations provide a broader protection than L1, i.e. protection in the whole 400-500 nm range.

Comparing the spectra for formulations M1-M3 (FIGS. 23AC-23AE), the addition of flax seed oil (FIG. 23AD) to jojoba oil/cumin oil in equal amounts flattens out the absorbance curve from 400-500 nm. The presence of more jojoba oil (FIG. 23AE) appears to provide a decreased slope from 440-500 nm due to a more pronounced absorption of jojoba oil in the range below 440 nm. M1-M3 formulations are good examples of high tunability of the absorption profile in 400-500 nm range by selecting certain types and amounts of oils that absorb in this range.

Comparing the spectra for formulations N1-N4 (FIGS. 23AF-23AI), the addition of cumin oil (FIG. 23AG) to jojoba oil/rosehip oil causes a decrease in the slope from 420-500 nm. A similar result is observed when turmeric oil is added to rosehip oil/cumin oil (FIG. 23I). These results are consistent with a reduction in the amount of cumin oil causing decreased absorbance from 420-500 nm.

Comparing the spectra for formulations O1-O4 (FIGS. 23AJ-23AM), the addition of broccoli seed oil to EVOO/cranberry oil flattens out the absorbance curve from 400-500 nm. Further additions of black raspberry and rosehip oils to EVOO/cranberry oil/broccoli oil insignificantly affect the absorption curve in 400-500 nm range, but these two oils add more antioxidants and other nutrients to the formulation. O1-O4 formulations are good examples for oil combinations with strong absorption in HEV spectral range, and thus, are representative of oil combinations that can provide a good light protection in this range.

Comparing the spectra for formulations P1-P4 (FIGS. 23AN-23AQ), the addition of cranberry oil to the carrot seed oil/rosehip oil flattens out the absorbance curve from 400-500 nm. The addition of broccoli seed oil to the carrot seed oil/rosehip oil/cranberry oil formulation further flattens the absorption curve in 400-500 nm range. Furthermore, the addition of strongly-HEV-absorbing seabuckthorn seed oil, which peak absorbance is around 450 nm, make the O4-absorption curve to have similar peak absorbance around 450 nm. P1-P4 formulations are another good examples for oil combinations with strong absorption in HEV spectral range, or with other words, oil combinations that can provide a good protection in HEV spectral range.

Comparing the spectra for formulations Q1-Q4 (FIGS. 23AR-23AU), the addition of red raspberry oil to black raspberry oil/jojoba oil formulation yielded a formulation with a similar slope of the absorption curve in 420-500 nm range. However, the Q2-formulation has more absorption around 400 nm range and below than Q1-formulation due to the UVA-absorbance of red raspberry oil. The addition of rosehip oil decreased the slope of the absorption curve in 420-500 nm range due to the broad absorption peak of rosehip oil in this range. Furthermore, when hemp seed oil was added, the slope slightly increased.

Comparing the spectra for formulations R1-R4 (FIGS. 23AV-23AY), the addition of rosehip oil to the pumpkin seed oil/broccoli oil flattens out the absorbance curve from 400-500 nm. The addition of turmeric oil and jojoba oil increase the slope of the absorption curve in 420-500 nm due to the stronger absorption of these two oils in the 400 nm range. While R1 and R2 formulations are good examples for oil combinations with strong absorption in 400-500 nm range, R3 and R4 formulations are good examples of oil combinations with good UVA and good HEV absorbance. These four examples are examples of tailoring the absorbance profile, and thus, adjusting the protection in HEV light spectral range only, or in both, UVA and HEV light spectral range by selection of the active ingredients (oils) and their fractions in the oil combination.

Comparing the spectra for formulations AA1-AA4 (FIGS. 23AZ-23BC), the alteration of the ratios of four oils (FIGS. 23AZ and 23BA) results in a change in the absorbance curve. In particular, decreasing the amounts of cumin oil, turmeric oil and EVOO causes an increase in the slope. A similar result (but to a lesser degree) is observed with rosehip oil is added to the mixture (FIGS. 23BB, 23BC).

These results are consistent with the presence of more oils permitting adjustment of the individual amounts of oils in the formulation without adversely affecting the performance.

Comparing the spectra for formulations BB1-BB4 (FIGS. 23BD-23BG), the addition of cinnamon oil and Helichrysum oil to cumin oil/wheat germ oil/hemp oil results in an increase in the slope (FIG. 23BE). This observation may be due to the cumin oil/wheat germ oil/hemp oil formulation being diluted, as well as due to the strong absorption of cinnamon oil and Helichrysum oil around 400 nm and below. Altering the amounts (FIG. 23BF and FIG. 23BG) did not substantially alter the overall spectra, but the presence of more cumin oil/wheat germ oil/hemp seed oil does appear to provide a flatter curve. This is an example of how from a strong HEV light absorbing oil combination (BB1 formulation), one can make oil combinations (BB2, BB3 and BB4 formulations) with strong UVA absorption and good HEV light absorption.

Comparing the spectra for formulations CC1-CC3 (FIGS. 23BH-23BJ), the addition of turmeric oil to cumin oil/pumpkin seed oil formulation increases the slope of the absorption curve in 420-500 nm range. This is due to the dilution of the cumin oil and pumpkin seed oil, but also due to the strong absorption of turmeric oil in 400 nm range and below. Changes in the amount of the active ingredients in the formulations can affect the slope in 420-500 nm range.

Comparting the spectra for formulations DD1-DD3 (FIGS. 23BK-23BM), the addition of hemp oil to cumin oil/wheat germ oil combination (FIG. 23BL) flattens out the absorbance curve from 380-440 nm. The addition of rosehip oil to the three oil combination did not substantially alter the overall absorbance curve (FIG. 23BM). All three formulations DD1-DD3 are examples of oil combinations with strong absorbance in 380-500 nm range, i.e. oil combinations that can provide good protection from the HEV light.

Comparing the spectra for formulations EE1-EE3 (FIGS. 23BN-23BP), a change in the overall amounts of cumin oil/pumpkin seed oil/turmeric oil did not substantially alter the overall absorbance curve of the spectra (FIGS. 23BN and 23BO). The four oil EE3-formulation did result in flattening of the absorbance spectrum from 400-500 nm (FIG. 23BP) and strong absorption in this spectral range An absorbance curve for a formulation including cinnamon oil/Helichrysum oil is shown in FIG. 23BQ. As can be seen, this formulation provides very strong absorbance from 380-400 nm but little or no absorbance above 400 nm, and thus, it is an example of oil combination with very good UVA protection The absorbance spectra for two formulations FF1 and FF2 including turmeric oil/broccoli oil/cranberry oil and seabuckthorn oil are shown in FIGS. 23BR-23BS. FIGS. 23BT-23BV show the addition of Helichrysum oil in various amounts. In comparing the five spectra, the addition of seabuckthorn oil (FIG. 23BS) to the three oil formulation results in a substantial absorbance increase in the 450-500 nm range. When Helichrysum oil is added to the four oil formulation, the new formulations FF3, FF4 and FF5 have the characteristics of strong UVA absorption due to the strong absorption of Helichrysum oil around 400 nm and below. All these formulations, especially FF3-FF5 formulations are examples of oil combinations with strong UVA and strong HEV light absorption.

Example 2

The absorbance spectra for several test formulations (CSI-1 to CSI-6) are shown in FIGS. 24A-24F. The formulations included: CSI-1—cumin oil/pumpkin oil/turmeric oil (51.4/45.7/2.9% by volume), CSI-2—cumin oil/hemp seed oil/wheat germ oil/rosehip oil (30.8/30.8/30.8/7.7% by volume); CSI-3—seabuckthorn berry oil (100% by volume), CSI-4—turmeric oil/broccoli seed oil/cranberry oil/seabuckthorn berry oil/Helichrysum oil (33.3/16.7/7.25/8.3/16.7% by volume), CSI-5—chaga extract in grain alcohol (100% by volume), CSI-6—chaga extract/seabuckthorn berry oil (77/23% by volume)

Example 3

The ability of the CSI-1 to CSI-4 formulations to reduce radical oxygen species in cells was studied using fish embryos.

Embryos of medaka fish were exposed to high-energy visible light (HEV or violet-blue visible light) to investigate the response of the cells to the induced oxidative stress and test the potential of two different compositions in preventing of ROS accumulation. Medaka embryos at the developmental stages 35-36 (5-6 days old) were used.

Four experimental replicates of 10 embryos/replicate were evaluated for ROS accumulation after exposure to HEV light. Each replicate was treated with CSI-1, CSI-2, CSI-3 or CSI-4 composition (without dilution) before irradiation during 5 minutes. Equally, four experimental replicates were prepared for "control" (untreated embryos) and for control irradiated ("control+HEV"), and treated embryos with the compositions and not irradiated (CSI-1, CSI-2, CSI-3 and CSI-4).

Embryos were irradiated in an excavated microscope slide, immersed in 100 microliters of Yamamoto medium, to avoid dehydration. The HEV light source (Lexman Blue Lamp GU10-12LED-BE-A) was placed at 6 cm from the embryos surface and the time of exposure was 4 hours (240 min), with an approximate intensity of 70 W/m2 at 460 nm. Immediately after irradiation, cells were incubated in ROS detection buffer for approximately 1 hr. The intracellular ROS accumulated reacted with a fluorogenic sensor localized in the cytoplasm, resulting in a fluorometric product in amounts proportional to the amount of ROS present. Fluorescence quantification was measured using an excitation wavelength of 490 nm and an emission wavelength of 525 nm.

All the data were normalized to the "control" and represented as mean±standard deviation, analyzed statistically comparing treated vs "control", and irradiated vs non-irradiated samples. The test applied for the analysis was the Student's t-test. Statistical significance was set at p<0.05, 95% of confidence. The data are presented in three forms of normalization. In the first normalization process, untreated "control" was used as the reference "control" and the data defined the antioxidant activity and the efficacy of the irradiation treatment (i.e. HEV exposure) inducing ROS. In the second case, the irradiated control, i.e. "control+HEV" was used as a reference control to detect the efficacy of the compound protecting from ROS accumulation. The third normalization used the difference between ROS levels at the "control+HEV" and the "control" as a reference, to determine the efficacy of the treatment upon the HEV-induced oxidative stress.

Fluorescence data collected from the assay was analyzed. The mean background of fluorescence was subtracted to each measure in each replicate. Then, the mean value for the four replicates in the control (untreated, non-irradiated) was calculated and this value was used to normalize each measure of absorbance of the replicates in all the samples and conditions. A bar graph was generated to represent graphically ROS accumulation in each of the conditions tested. Statistical analysis was performed to determinate the significance between the differences in the level of ROS detected among the samples and the treatments.

Figure 25:
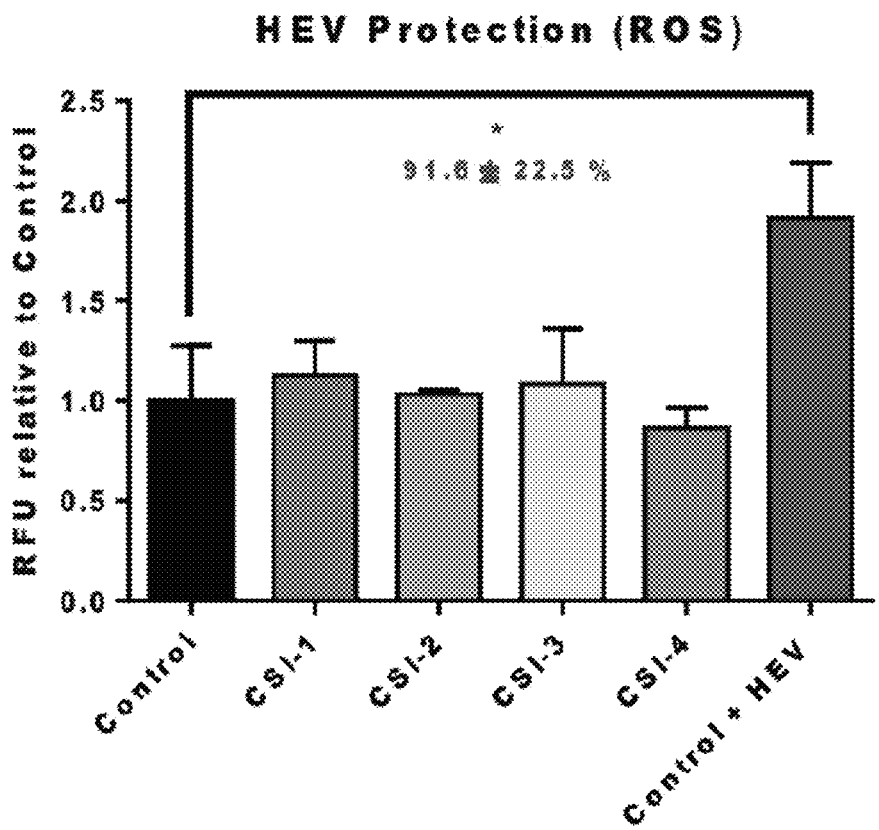
FIGS. 25-27 show graphs for certain test formulations in Example 3.
Figure 26:
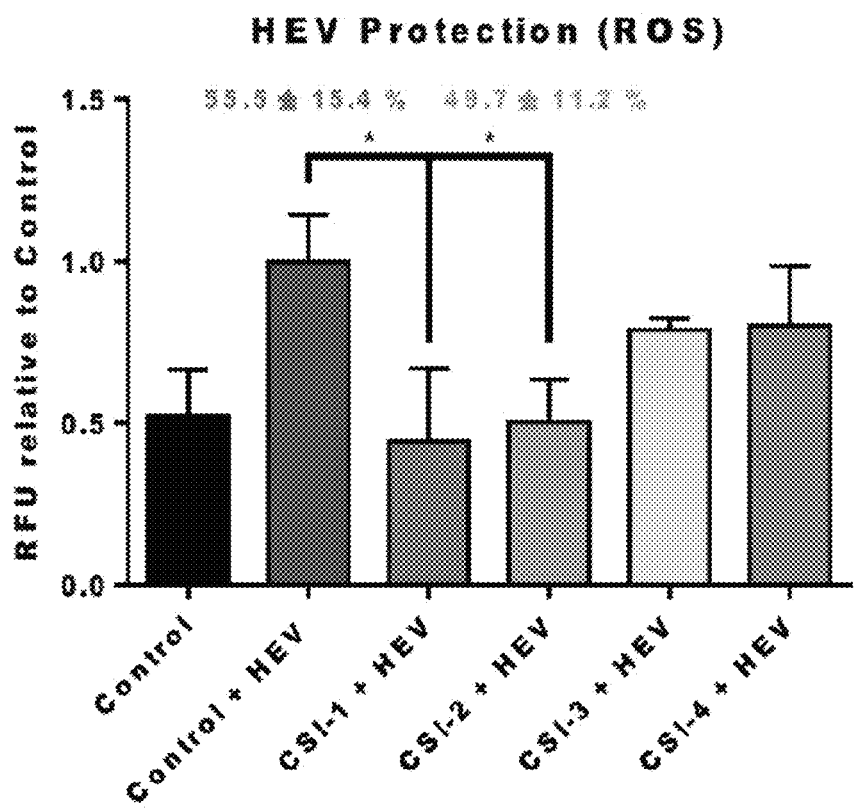

The results showed that HEV light (blue light) induced ROS levels in fish embryos by 91.6±22.5% compared to the control group. When embryos without being irradiated were treated with CSI-1, CSI-2, CSI-3 and CSI-4, ROS levels were not affected compared to the control group (FIG. 25 where p-value<0.05). When embryos were treated with the products and irradiated, results showed that CSI-1 and CSI-2 decreased ROS levels by 55.5±15.4% and 49.7±11.2%, respectively, when ROS were induced after HEV light exposure. The treatments with CSI-3 and CSI-4 showed a positive trend by decreasing ROS levels in 21.3±8.5% and 19.8±13.4%, respectively. The high oil content of products CSI-3 and CSI-4 compared with CSI-1 and CSI-2, make the embryo penetration difficult and explain the low HEV light protection provided by them (FIG. 26).

Figure 27:
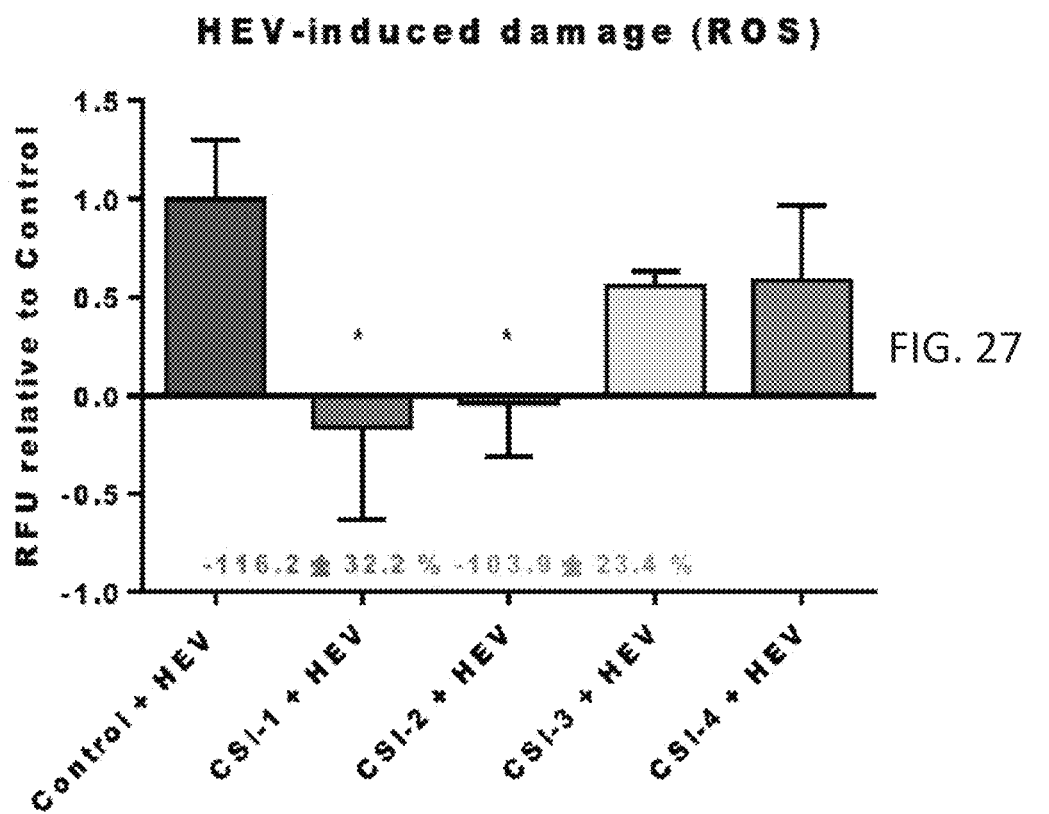

The basal level of ROS present in the untreated control is considered the background level of ROS endogenous to all cells. This way, the difference between ROS levels in the "control+HEV" and the "control" corresponds to the oxidative stress induced by HEV light. By subtracting the basal level (control) to all other samples, the effect of the treatment on the HEV-induced ROS accumulation was quantified. The results showed that the treatments with CSI-1 and CSI-2 significantly protected from HEV-induced oxidative stress (ROS accumulation) by 116.2±32.2% and 103.9±23.4%, respectively. The treatments with CSI-3 and CSI-4 showed a positive trend by decreasing ROS levels in 44.4±17.8% and 41.5±28.1%, respectively FIG. 27).

Results from HEV protection studies showed that HEV light (blue light) induced ROS levels in fish embryos by 91.6±22.5% compared to the control group, and the treatment with CSI-1 and CSI-2 decreased ROS levels by 55.5±15.4% and 49.7±11.2%, respectively. The treatments with CSI-3 and CSI-4 showed a positive trend by decreasing ROS levels in 21.3±8.5% and 19.8±13.4%, respectively. When analyzing only the HEV-induced oxidative stress (difference between ROS levels in the "Control+HEV" and the "Control"), results showed that the treatments with CSI-1 and CSI-2 significantly protected from HEV-induced damage (ROS accumulation) by 116.2±32.2% and 103.9±23.4%, respectively. The treatments with CSI-3 and CSI-4 showed a positive trend by decreasing ROS levels in 44.4±17.8% and 41.5±28.1%, respectively, but these results were not statistically significant. The high oil content of products CSI-3 and CSI-4, compared with CSI-1 and CSI-2, may render CSI-3 and CSI-4 substantially impermeable to dermal penetration and explain the small protection provided by them.

These results are consistent with the CSI-1 and CSI-2 formulations significantly protecting the cells from oxidative stress induced by high-energy visible (HEV) light. All the results are statistically analyzed and considered significant with a p value<0.05.

In summary, these results showed that CSI-1 and CSI-2 protected from HEV-induced damage in fish eleutheroembryos by 116.2±32.2% and 103.9±23.4%, respectively, compared to the control group, when oxidative stress was induced with HEV irradiation. The treatments with CSI-3 and CSI-4 showed a positive trend by decreasing ROS levels in 44.4±17.8% and 41.5±28.1%, respectively, but these results were not statistically significant. The high oil content of products CSI-3 and CSI-4, compared with CSI-1 and CSI-2, make the embryo penetration difficult and may explain the small HEV light protection provided by them.

Example 4

The ability of the CSI-5 and CSI-6 formulations to reduce radical oxygen species in cells was studied using fish embryos in a similar manner as used in Example 3.

Embryos of medaka fish were exposed to high-energy visible light (HEV or violet-blue visible light) to investigate the response of the cells to the induced oxidative stress and test the potential of the two different compositions (CSI-5 and CSI-6) in preventing of ROS accumulation. Medaka embryos at the developmental stages 35-36 (5-6 days old) were used. Four experimental replicates of 10 embryos/replicate were evaluated for ROS accumulation after exposure to HEV light. Each replicate was treated with CSI-5 or CSI-6 composition (without dilution) before irradiation during 5 minutes. Equally, four experimental replicates were prepared for "control" (untreated embryos) and for control irradiated ("control+HEV"), and treated embryos with the compositions and not irradiated (CSI-5 and CSI-6).

Embryos were irradiated in an excavated microscope slide, immersed in 100 microliters of Yamamoto medium, to avoid dehydration. The HEV light source (Lexman Blue Lamp GU10-12LED-BE-A) was placed at 6 cm from the embryos surface and the time of exposure was 4 hours (240 min), with an approximate intensity of 70 W/m2 at 460 nm. Immediately after irradiation, cells were incubated in ROS detection buffer for approximately 1 hr. The intracellular ROS accumulated reacted with a fluorogenic sensor localized in the cytoplasm, resulting in a fluorometric product in amounts proportional to the amount of ROS present. Fluorescence quantification was measured at an excitation wavelength of 490 nm and an emission wavelength of 525 nm.

All the data were normalized to the "control" and represented as mean±standard deviation, analyzed statistically comparing treated vs "control", and irradiated vs non-irradiated samples. The test applied for the analysis was the Student's t-test. Statistical significance was set at $p<0.05$, 95% of confidence. The data are presented in three forms of normalization. In the first normalization process, untreated "control" was used as the reference "control" and the data defined the antioxidant activity and the efficacy of the irradiation treatment (i.e. HEV exposure) inducing ROS. In the second case, the irradiated control, i.e. "control+HEV" was used as a reference control to detect the efficacy of the compound protecting from ROS accumulation. The third normalization used the difference between ROS levels at the "control+HEV" and the "control" as a reference, to determine the efficacy of the treatment upon the HEV-induced oxidative stress.

Fluorescence data collected from the assay was analyzed. The mean background of fluorescence was subtracted to each measure in each replicate. Then, the mean value for the four replicates in the control (untreated, non-irradiated) was calculated and this value was used to normalize each measure of absorbance of the replicates in all the samples and conditions. A bar graph was generated to represent graphically ROS accumulation in each of the conditions tested. Statistical analysis was performed to determinate the significance between the differences in the level of ROS detected among the samples and the treatments.

Figure 28:
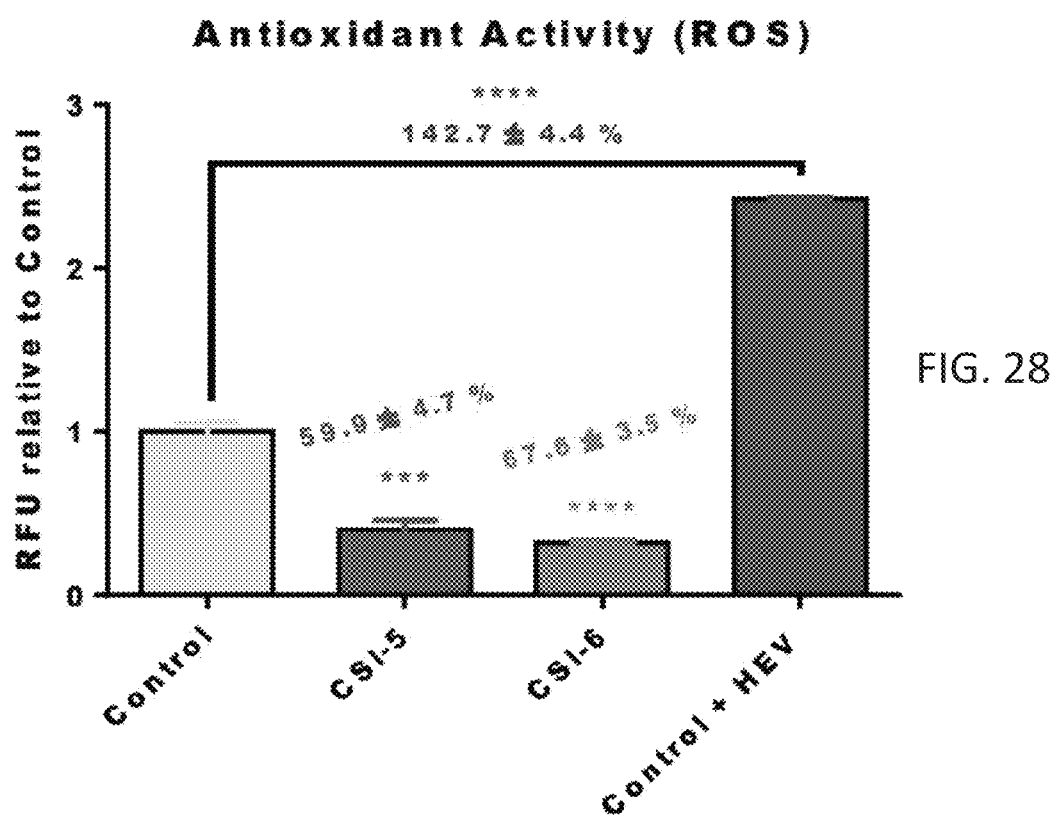
FIGS. 28-30 show graphs for certain test formulations in Example 4.

The results showed that HEV light (violet-blue light) significantly induced ROS levels in fish embryos by 142.7±4.4% compared to the control group. When embryos without being irradiated were treated with the CSI-5 and CSI-6 formulations, the results showed that CSI-5 and CSI-6 compositions displayed antioxidant activity, since they significantly decreased ROS accumulation by 59.9±4.7% and 67.6±3.5%, respectively, as shown in FIG. 28.

Figure 29:
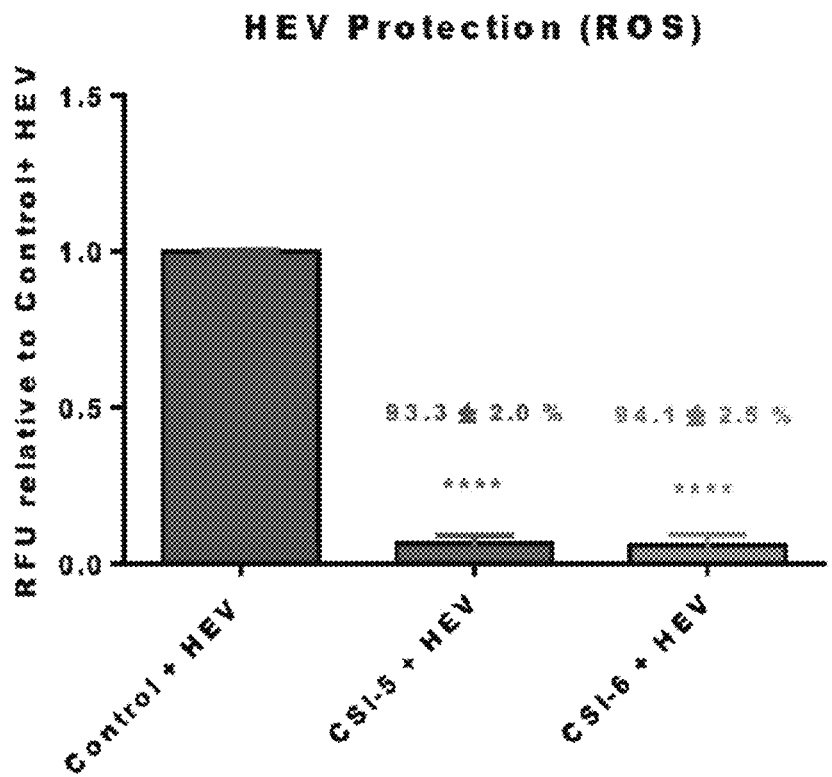

When embryos were treated with the CSI-5 and CSI-6 compositions and irradiated, the results showed that CSI-5 and CSI-6 decreased ROS levels by 93.3±2.0% and 94.1±2.5%, respectively, where ROS were induced after HEV light (FIG. 29).

Figure 30:
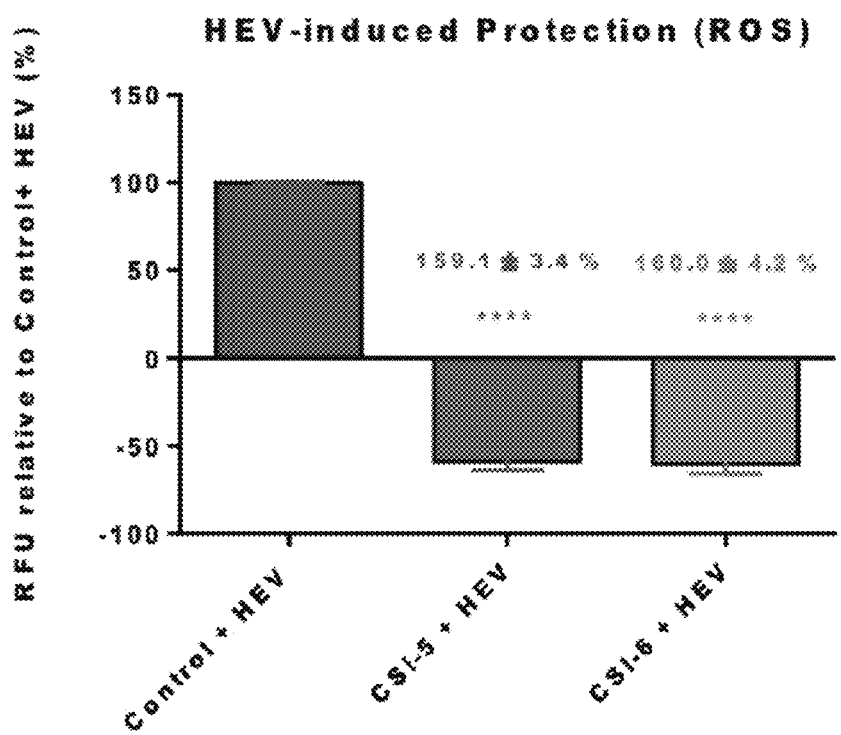

The basal level of ROS present in the untreated control is considered the background level of ROS endogenous to all cells. This way, the difference between ROS levels in the "control+HEV" and the "control" corresponds to the oxidative stress induced by HEV light. By subtracting the basal level (control) to all other samples, the effect of the treatment on the HEV-induced ROS accumulation was quantified. The results showed that the treatments with CSI-5 and CSI-6 significantly protected from HEV-induced damage (ROS accumulation) by 159.1±3.4% and 160.0±4.2%, respectively (FIG. 30).

Together, the results are consistent with the CSI-5 and CSI-6 displaying antioxidant activity, since they significantly decreased ROS accumulation by 59.9±4.7% and 67.6±3.5%, respectively, when topically applied on medaka eleutheroembryos without subsequent irradiation. When embryos were treated with the products and irradiated, results showed that CSI-5 and CSI-6 decreased ROS levels by 93.3±2.0% and 94.1±2.5%. When analyzing only the HEV-induced oxidative stress (difference between ROS levels in the "control+HEV" and the "control"), results showed that the treatments with CSI-5 and CSI-6 significantly protected from HEV-induced damage (ROS accumulation) by 159.1±3.4% and 160.0±4.2%, respectively. These results indicate that CSI-5 and CSI-6 present antioxidant activity and significantly protect from oxidative stress induced by high-energy visible (HEV) light. All the results are statistically analyzed and considered significant with a p value<0.05. In summary, the results showed that CSI-5 and CSI-6 displayed antioxidant activity, through decreasing ROS accumulation by 59.9±4.7% and 67.6±3.5%, respectively, when topically applied on medaka eleutheroembryos without subsequent irradiation. CSI-5 and CSI-6 also protected from HEV-induced damage by 159.1±3.4% and 160.0±4.2%, respectively, compared to the control group, when oxidative stress was induced with HEV irradiation.

Example 5

The absorbance spectra of various commercial sunscreen products were compared to the absorbance spectra of various oils. The results are shown in FIGS. 31A-31F.

Figure 31A:
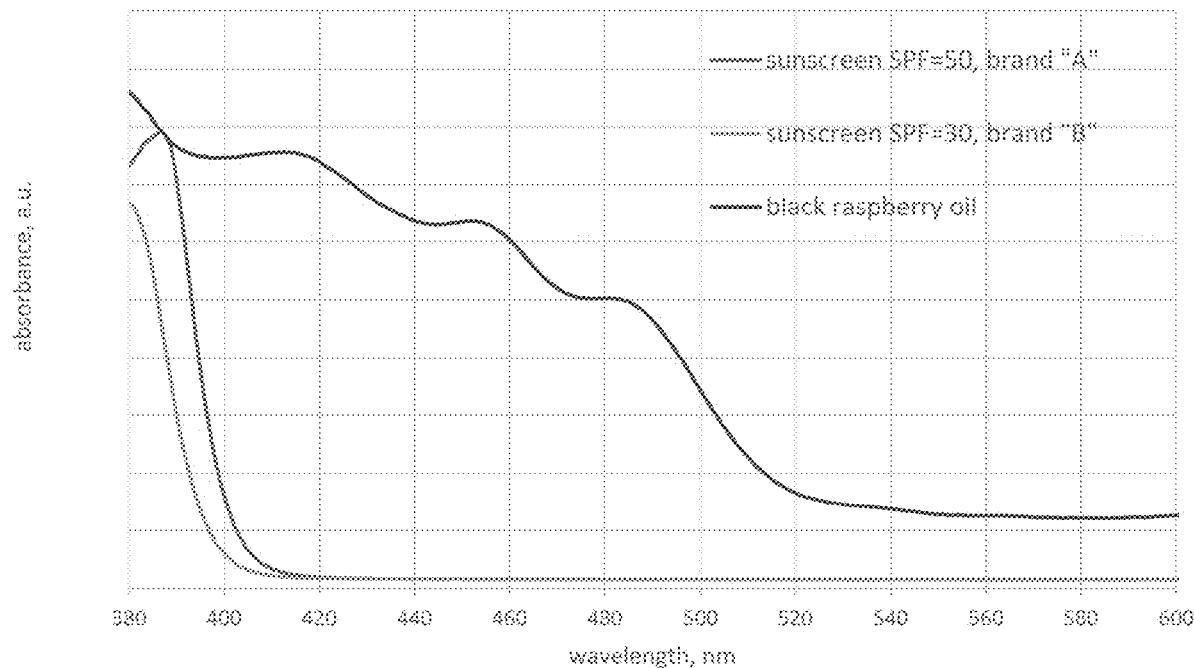
FIGS. 31A-31F are absorbance spectra comparing commercial sunscreens to certain formulations.

Referring to FIG. 31A, the absorbance spectrum of blackberry oil compared to SPF50 and SPF30 sunscreens shows that the two sunscreen formulations have little or no absorbance from 400-500 nm, whereas the blackberry oil has a high absorbance from 380-500 nm. Therefore, blackberry oil can be added to existing sunscreen formulations with broad UVB+UVA protection and extend the sunscreen's range of protection to 500 nm.

Figure 31B:
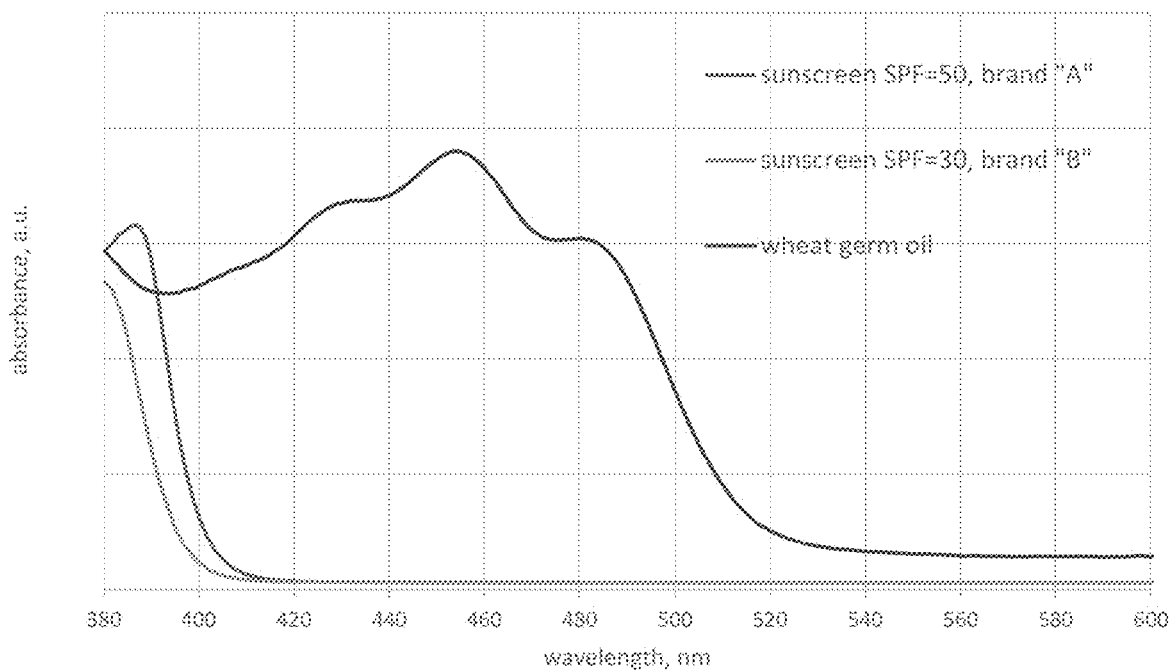

Referring to FIG. 31B, the absorbance spectrum of wheat germ oil compared to SPF50 and SPF30 sunscreen shows that the two sunscreen formulations have little or no absorbance from 400-500 nm, whereas the wheat germ oil has a high absorbance from 380-500 nm. Therefore, wheat germ oil can be added to existing sunscreen formulations with broad UVB+UVA protection and extend the sunscreen's range of protection to 500 nm.

Figure 31C:
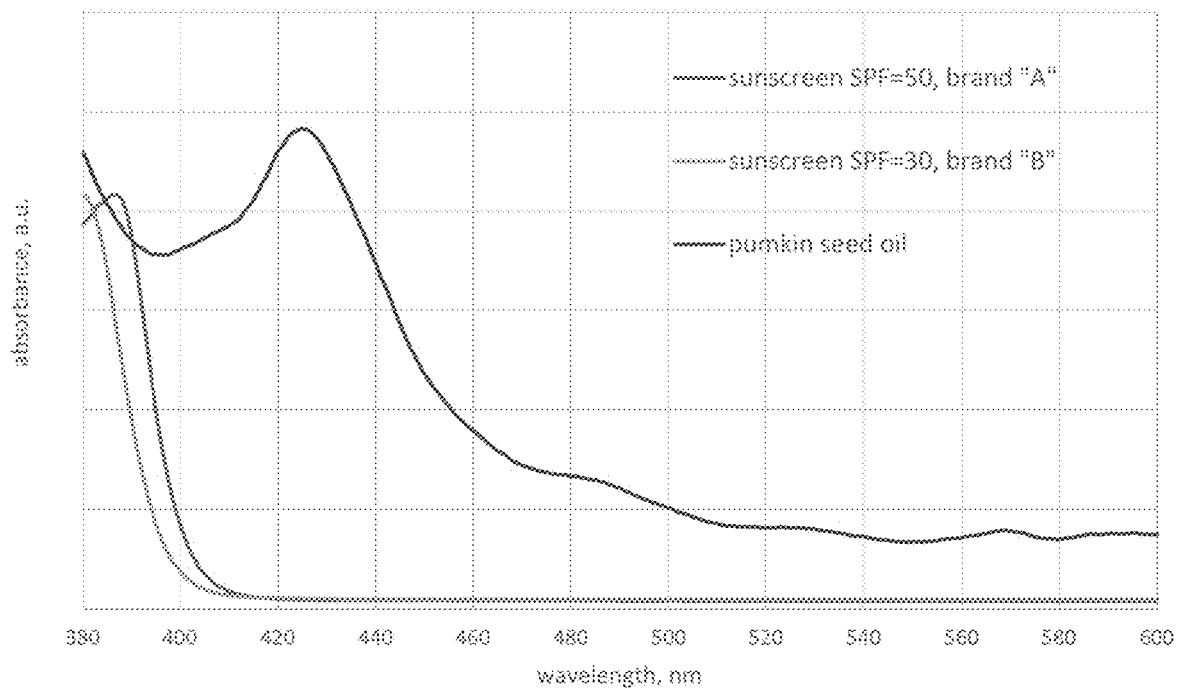

Referring to FIG. 31C, the absorbance spectrum of pumpkin seed oil compared to SPF50 and SPF30 sunscreen shows that the two sunscreen formulations have little or no absorbance from 400-500 nm, whereas the pumpkin seed oil has a high absorbance from 380-500 nm. Therefore, pumpkin seed oil can be added to existing sunscreen formulations with broad UVB+UVA protection and extend the sunscreen's range of protection to 500 nm.

Figure 31D:
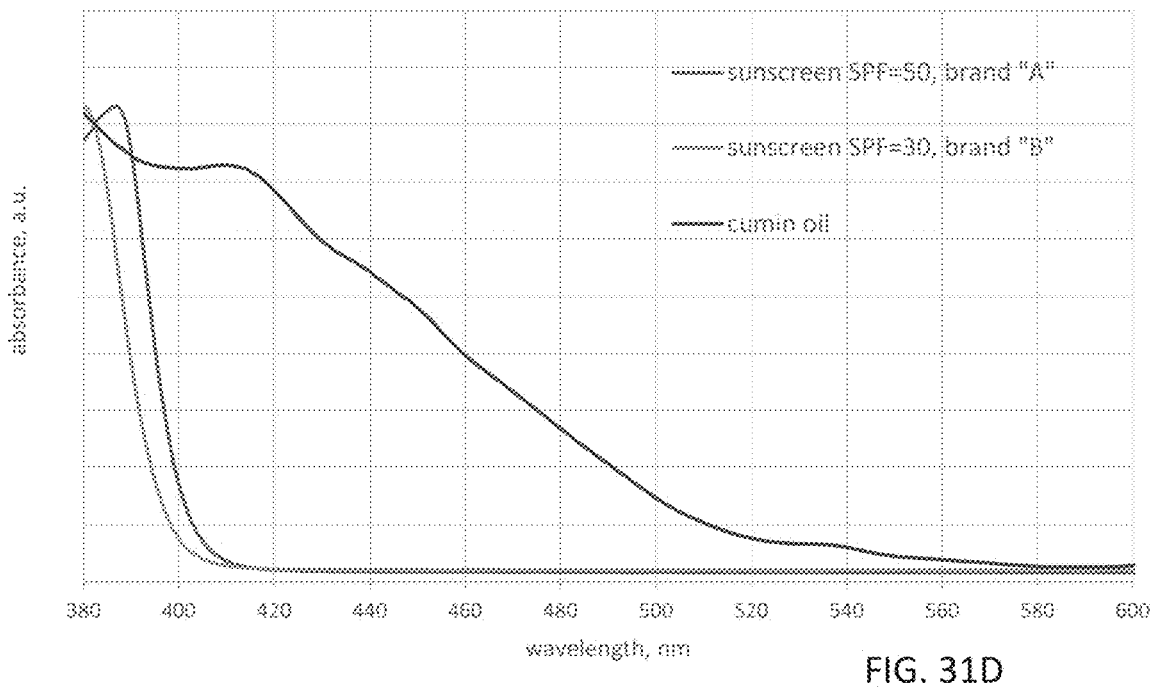

Referring to FIG. 31D, the absorbance spectrum of cumin oil compared to SPF50 and SPF30 sunscreen shows that the two sunscreen formulations have little or no absorbance from 400-500 nm, whereas the cumin oil has a high absorbance from 380-500 nm. Therefore, cumin (black seed) oil can be added to existing sunscreen formulations with broad UVB+UVA protection and extend the sunscreen's range of protection to 500 nm.

Figure 31E:
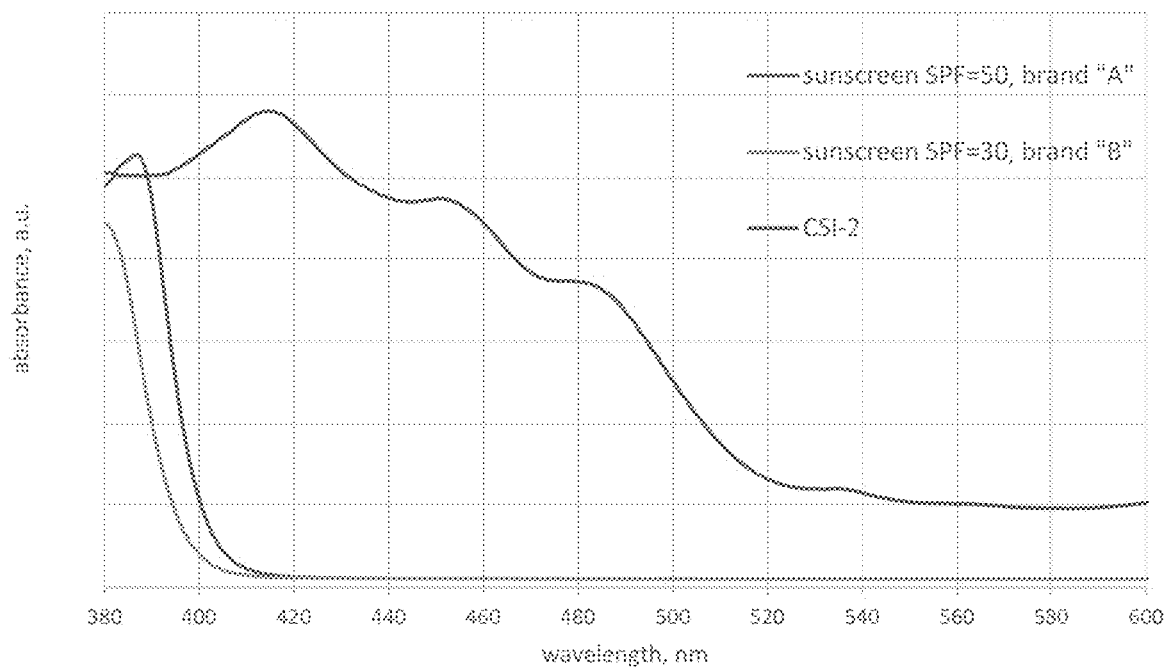

Referring to FIG. 31E, the absorbance spectrum of CSI-2 (cumin oil/hemp oil/wheat germ oil/rosehip oil at 30.8/30.8/30.8/7.7% by volume, respectively) compared to SPF50 and SPF30 sunscreens shows that the two sunscreen formulations have little or no absorbance from 400-500 nm, whereas the CSI-2 formulation has a high absorbance from 380-500 nm. Therefore, CSI-2 formulation can be added to existing sunscreen formulations with broad UVB+UVA protection and extend the sunscreen's range of protection to 500 nm.

Figure 31F:
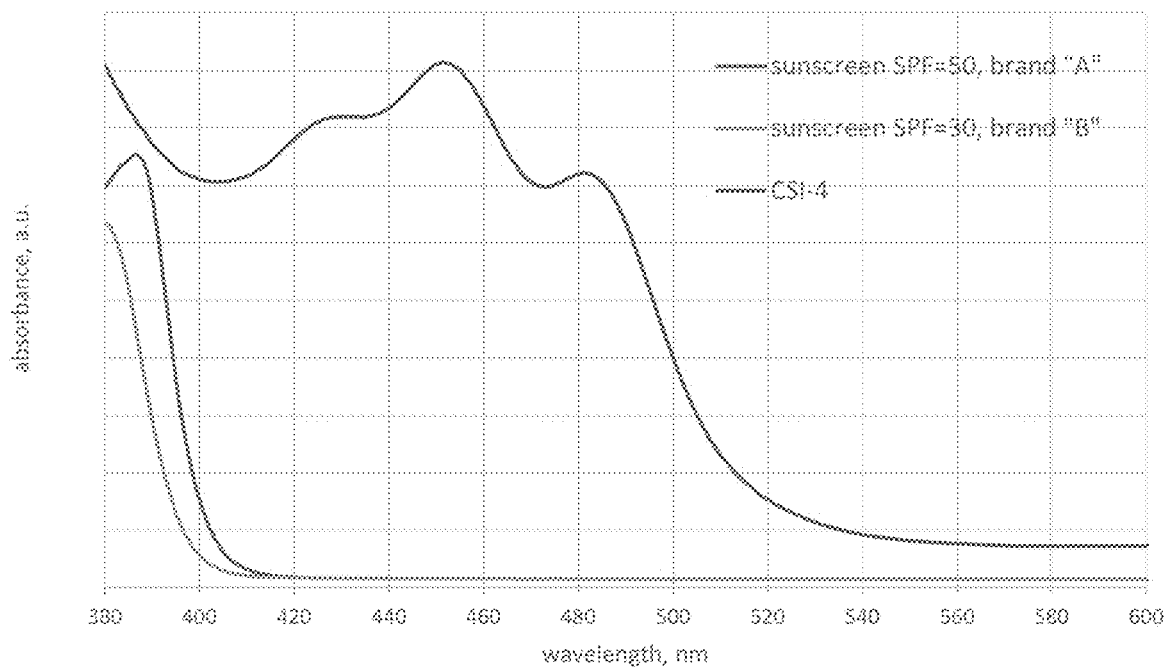

Referring to FIG. 31F, the absorbance spectrum of CSI-4 (turmeric oil/broccoli oil/cranberry oil/seabuckthorn berry oil/Helichrysum oil at 33.3/16.7/7.25/8.3/16.7% by volume, respectively) compared to SPF50 and SPF30 sunscreen shows that the two sunscreen formulations have little or no absorbance from 400-500 nm, whereas the CSI-4 formulation has a high absorbance from 380-500 nm. Therefore, CSI-4 formulation can be added to existing sunscreen formulations with broad UVB+UVA protection and extend the sunscreen's range of protection to 500 nm.

Example 6

Figure 32A:
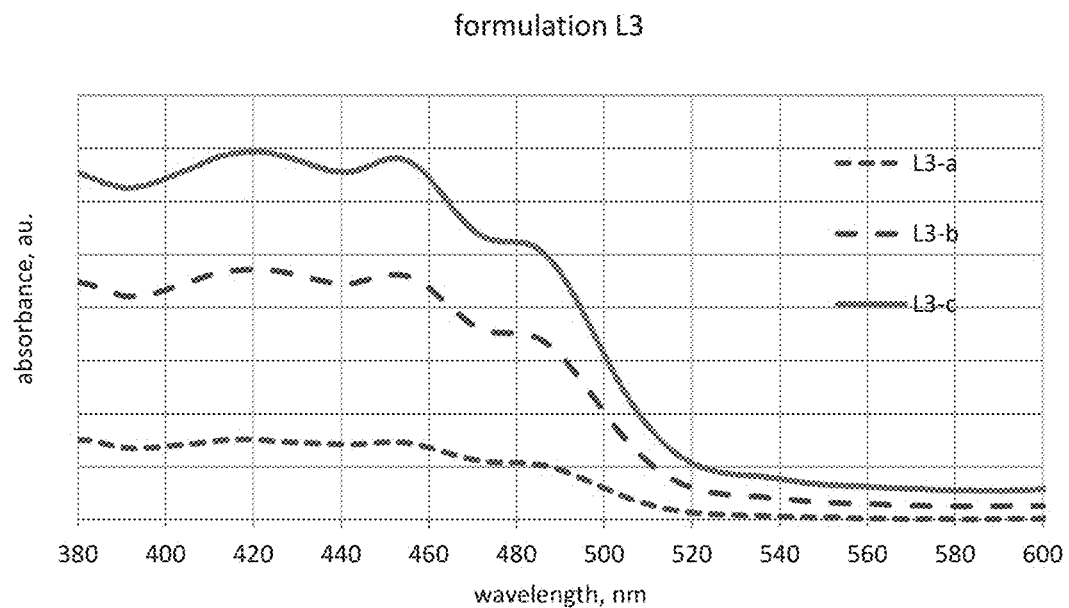
FIGS. 32A-32B are spectra taken of different thicknesses of formulations L3 and K5.
Figure 32B:
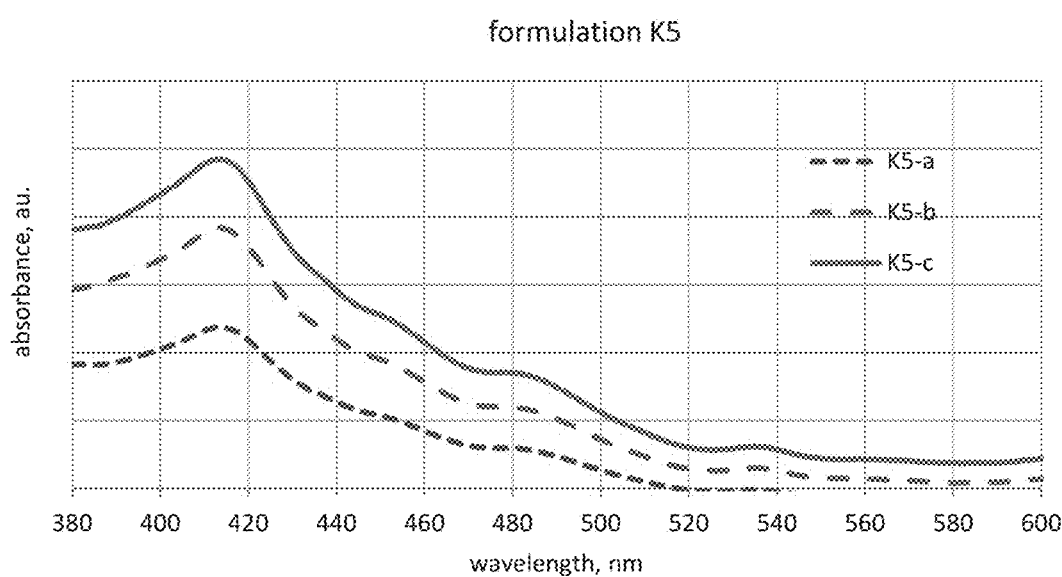

Absorbance spectra presented in FIGS. 32A and 32B are spectra taken of different thicknesses of formulations L3 and K5, respectively, where L3-a and K5-a are the absorption spectra of the thinnest samples of L3 and K5, followed by L3-b and K5-b samples, while samples L3-c and K5-c are the thickest samples among all three measured samples of both formulations. The absorption spectra presented in FIGS. 32A and 32B are examples of tunability of the absorbance intensity (amplitude) by adjusting the optical path in accordance with the Beer's law: $A=Ecl$, where A is the absorbance, E is the extinction coefficient, c is the concentration and l is the optical path (thickness). In a topically applied composition, this optical path (i.e. the thickness of the active ingredients) can be easily controlled by the delivery method, viz. film-forming ability of the final compositions and the thickness of the applied topical film, or by the size of the liposomes or other carriers or delivery agents where the active ingredients are incorporated, etc. Also, the intensity of the absorbance can be easily tuned by the concentration of the active ingredients (oils) in the final formulation in accordance with the Beer's law.

Example 7

HEV/VIS ratios were calculated for various oils. The HEV value was based on the average absorbance in the 400-500 nm range, and the VIS value was based on the average absorbance in the 380-750 nm range. As shown in FIGS. 33A-33C, the oils are grouped according to their HEV/VIS ratio with oils having a HEV/VIS ratio greater than or equal to 1.5 being HEV-1 group oils, those oils having a HEV/VIS ratio in the range 1.0-1.5 being HEV-2 group oils, and those oils having a HEV/VIS ratio of less than or equal to 1.0 being UVA group oils. The higher the HEV/VIS ratio, the better the ability to protect within the 400-500 nm wavelength range.

Example 8

The HEV/VIS ratio of the oil formulations of Example 1 were calculated to assess the relative ability of the various formulations to protect from HEV light. As shown in FIG. 34, those formulations with HEV/VIS ratios of about 1.5 or above should provide more protection to the skin, hair and nails than those formulations with a HEV/VIS ratio below 1.5. Certain formulations provide a HEV/VIS ratio of over 2.0 or 2.5. These formulations may be particularly desirable since they should absorb substantial amounts of HEV light over the 400-500 nm range or the 380-500 nm range.

When introducing elements of the examples disclosed herein, the articles "a," "an," "the" and "said" are intended to mean that there are one or more of the elements. The terms "comprising," "including" and "having" are intended to be open-ended and mean that there may be additional elements other than the listed elements. It will be recognized by the person of ordinary skill in the art, given the benefit of this disclosure, that various components of the examples can be interchanged or substituted with various components in other examples.

Although certain aspects, examples and embodiments have been described above, it will be recognized by the person of ordinary skill in the art, given the benefit of this disclosure, that additions, substitutions, modifications, and alterations of the disclosed illustrative aspects, examples and embodiments are possible.

What is claimed is:

1. A method of protecting cellular damage of an animal skin from exposure to incident high energy visible light from an artificial light source or the sun comprising a wavelength of about 400 nm to about 500 nm, the method comprising topically administering a composition to the animal skin comprising at least one natural oil present in an effective amount to provide a HEV/VIS ratio of greater than or equal to 1.5 at an area of the animal cell where the composition has been topically administered.

2. The method of claim 1, further comprising configuring the composition to comprise the at least one natural oil and at least one additional natural oil or extract present together in an effective amount to provide a HEV/VIS ratio of greater than or equal to 1.5 at an area of the animal skin where the composition has been topically administered.

3. The method of claim 1, further comprising configuring the composition to comprise the at least one natural oil, a second natural oil or extract, and a third natural oil or extract present together in an effective amount to provide a HEV/VIS ratio of greater than or equal to 1.5 at an area of the animal skin where the composition has been topically administered.

4. The method of claim 1, further comprising configuring the composition to comprise the at least one natural oil, a second natural oil or extract, a third natural oil or extract, and a fourth natural oil or extract present together in an effective amount to provide a HEV/VIS ratio of greater than or equal to 1.5 at an area of the animal skin where the composition has been topically administered.

5. The method of claim 1, further comprising configuring the composition to comprise at least one Group A natural oil and at least one Group B natural oil, wherein the at least one natural oil is the at least one Group A natural oil or the at least one Group B natural oil.

6. The method of claim 1, wherein the at least one natural oil comprises at least one Type I oils.

7. The method of claim 1, wherein the at least one natural oil comprises at least one Type III oil.

8. The method of claim 1, further comprising configuring the composition with at least one carrier effective to permit topical administration of the composition on the skin.

9. The method of claim 1, wherein the composition comprises a first natural oil that absorbs at least 30% of the incident high energy light having a wavelength of about 380-400 nm that is incident on the area of the animal skin where the composition has been topically administered.

10. The method of claim 9, wherein the composition comprises a second natural oil that absorbs at least 30% of the incident high energy light having a wavelength of about 400-440 nm that is incident on the area of the animal skin where the composition has been topically administered.

11. The method of claim 10, wherein the composition comprises a third natural oil that absorbs at least 30% of the incident high energy light having a wavelength of about 440-500 nm that is incident on the area of the animal skin where the composition has been topically administered.

12. The method of claim 1, wherein the composition partially penetrates into the skin.

13. The method of claim 12, wherein the composition comprises an alcohol to increase penetration of the composition into the skin.

14. The method of claim 1, wherein the amount of the composition topically administered to the animal skin is selected to absorb substantially all light emitted from the artificial light source or the sun comprising a wavelength of about 400 nm to about 500 nm at areas of the animal skin where the composition has been topically administered.

15. The method of claim 1, wherein the composition partially penetrates into the skin, and wherein the amount of composition topically administered to the animal skin is selected to absorb substantially all light emitted from the artificial light source or the sun comprising a wavelength of about 400 nm to about 500 nm, during an exposure period to the artificial light source or sun of 4 to 6 hours, at areas of the animal skin where the composition has been topically administered.

16. The method of claim 1, wherein the composition comprises turmeric oil, broccoli seed oil, cranberry oil, sea buckthorn oil and Helichrysum oil.

* * * * *